United States Patent
Wang

(10) Patent No.: US 11,001,859 B2
(45) Date of Patent: *May 11, 2021

(54) RECOMBINANTLY-MODIFIED ADENO-ASSOCIATED VIRUS HELPER VECTORS AND THEIR USE TO IMPROVE THE PACKAGING EFFICIENCY OF RECOMBINANTLY-MODIFIED ADENO-ASSOCIATED VIRUS

(71) Applicant: Vigene Biosciences Inc., Rockville, MD (US)

(72) Inventor: Qizhao Wang, Rockville, MD (US)

(73) Assignee: Vigene Biosciences, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/705,831

(22) Filed: Dec. 6, 2019

(65) Prior Publication Data

US 2021/0017538 A1    Jan. 21, 2021

Related U.S. Application Data

(63) Continuation of application No. 16/512,194, filed on Jul. 15, 2019, now Pat. No. 10,557,149.

(51) Int. Cl.
| | |
|---|---|
| *C12N 15/864* | (2006.01) |
| *C12N 15/63* | (2006.01) |
| *C12N 15/71* | (2006.01) |
| *C12N 15/86* | (2006.01) |
| *C12N 5/071* | (2010.01) |
| *C12N 5/07* | (2010.01) |

(52) U.S. Cl.
CPC .......... *C12N 15/86* (2013.01); *C12N 5/0601* (2013.01); *C12N 5/0686* (2013.01)

(58) Field of Classification Search
None
See application file for complete search history.

(56) References Cited

U.S. PATENT DOCUMENTS

| | | | |
|---|---|---|---|
| 6,566,118 B1 | 5/2003 | Atkinson et al. | |
| 6,723,551 B2 | 4/2004 | Kotin et al. | |
| 6,733,757 B2 | 5/2004 | Patel et al. | |
| 6,753,419 B1 | 6/2004 | Toniatti et al. | |
| 6,759,050 B1 | 7/2004 | Sista et al. | |
| 6,764,845 B2 | 7/2004 | Sista et al. | |
| 6,821,511 B2 | 11/2004 | Kotin et al. | |
| 6,841,357 B1 | 1/2005 | Vaillancourt et al. | |
| 6,846,665 B1 | 1/2005 | Horer et al. | |
| 6,962,815 B2 | 11/2005 | Bartlett | |
| 6,984,517 B1 | 1/2006 | Chiorini et al. | |
| 6,989,264 B2 | 1/2006 | Atkinson et al. | |
| 6,995,006 B2 | 2/2006 | Atkinson et al. | |
| 7,105,345 B2 | 9/2006 | Wilson et al. | |
| 7,115,391 B1 | 10/2006 | Chen et al. | |
| 7,122,348 B2 | 10/2006 | Wong et al. | |
| 7,186,552 B2 | 3/2007 | Wilson et al. | |
| 7,208,315 B2 | 4/2007 | Miller et al. | |
| 7,271,002 B2 | 9/2007 | Kotin et al. | |
| 7,419,817 B2 | 9/2008 | Chiorini et al. | |
| 7,439,065 B2 | 10/2008 | Ferrari et al. | |
| 7,479,554 B2 | 1/2009 | Chiorini et al. | |
| 7,598,070 B2 | 10/2009 | Sista et al. | |
| 7,625,570 B1 | 12/2009 | Schaffer et al. | |
| 7,906,111 B2 | 3/2011 | Wilson et al. | |
| 8,163,543 B2 | 4/2012 | Urabe et al. | |
| 8,192,975 B2 | 6/2012 | Sista et al. | |
| 8,507,267 B2 | 8/2013 | Chiorini et al. | |
| 8,697,359 B1 | 4/2014 | Zhang | |
| 8,846,389 B2 | 9/2014 | Chiorini et al. | |
| 8,852,607 B2 | 10/2014 | Sista et al. | |
| 8,945,918 B2 | 2/2015 | Chen | |
| 9,193,956 B2 | 11/2015 | Schaffer et al. | |
| 9,441,206 B2 | 9/2016 | Grieger et al. | |
| 9,441,244 B2 | 9/2016 | Schaffer et al. | |
| 9,457,103 B2 | 10/2016 | Schaffer et al. | |
| 9,458,517 B2 | 10/2016 | Schaffer et al. | |

(Continued)

FOREIGN PATENT DOCUMENTS

WO    WO 2017/112948    6/2017

OTHER PUBLICATIONS

Vigene Biosciences, Tripling Down On Efficient Gene Therapy Production, downloaeded Jan. 21, 2020, p. 1.*
Adamson-Small, L. et al. (2017) "*Sodium Chloride Enhances Recombinant Adeno-Associated Virus Production in a Serum-Free Suspension Manufacturing Platform Using the Herpes Simplex Virus System*," Hum. Gene Ther. Meth. 28(1):1-14.
Auricchio, A. et al. (2001) "*Isolation of Highly Infectious and Pure Adeno-Associated Virus Type 2 Vectors With a Single-Step Gravity-Flow Column*," Hum. Gene Ther. 12:71-76.

(Continued)

*Primary Examiner* — Maria Marvich
(74) *Attorney, Agent, or Firm* — Jeffrey I. Auerbach; AuerbachSchrot LLC

(57) ABSTRACT

The present invention is directed to recombinantly-modified adeno-associated virus (AAV) helper vectors that are capable of increasing the packaging efficiency of recombinantly-modified adeno-associated virus (rAAV) and their use to improve the packaging efficiency of such rAAV. The present invention is particularly directed to recombinantly-modified adeno-associated virus (AAV) helper vectors that have been further modified to replace (or augment) the P5 and/or P40 promoter sequences that are natively associated with the Rep proteins encoded by such rAAV with AAV P5 and/or P40 promoters that are associated with the Rep proteins of an rAAV of different serotype. The use of such substitute or additional promoter sequences causes increased production of recombinantly-modified adeno-associated virus.

28 Claims, 16 Drawing Sheets

Specification includes a Sequence Listing.

(56) References Cited

U.S. PATENT DOCUMENTS

| | | | |
|---|---|---|---|
| 9,598,703 | B2 | 3/2017 | Garcia et al. |
| 9,677,089 | B2 | 6/2017 | Gao et al. |
| 9,737,618 | B2 | 8/2017 | Wilson et al. |
| 9,856,539 | B2 | 1/2018 | Schaffer et al. |
| 9,879,279 | B2 | 1/2018 | Chen |
| 9,879,282 | B2 | 1/2018 | Chen |
| 9,884,071 | B2 | 2/2018 | Wilson et al. |
| 10,000,772 | B2 | 6/2018 | Doudna et al. |
| 10,017,746 | B2 | 7/2018 | Sheldon et al. |
| 10,046,016 | B2 | 8/2018 | Schaffer et al. |
| 10,113,167 | B2 | 10/2018 | Doudna et al. |
| 10,161,011 | B2 | 12/2018 | Akashika et al. |
| 10,202,657 | B2 | 2/2019 | Schaffer et al. |
| 10,214,566 | B2 | 2/2019 | Schaffer et al. |
| 10,214,730 | B2 | 2/2019 | Bahou et al. |
| 10,214,785 | B2 | 2/2019 | Schaffer et al. |
| 10,227,611 | B2 | 3/2019 | Doudna et al. |
| 10,265,417 | B2 | 4/2019 | Wilson et al. |
| 10,266,846 | B2 | 4/2019 | Gao et al. |
| 10,294,452 | B2 | 5/2019 | He |
| 10,301,650 | B2 | 5/2019 | Gao et al. |
| 10,557,149 | B1* | 2/2020 | Wang ............... C12N 15/86 |
| 2005/0266567 | A1 | 12/2005 | Atkinson et al. |
| 2015/0238550 | A1* | 8/2015 | McCown ............ C12N 15/86 424/93.2 |

OTHER PUBLICATIONS

Ayuso, E. (2016) "Manufacturing of Recombinant Adeno-Associated Viral Vectors: New Technologies Are Welcome," Methods & Clinical Development 3: 15049 (pp. 1-3).

Balakrishnan, B. et al. (2014) "Basic Biology of Adeno-Associated Virus (AAV) Vectors Used in Gene Therapy," Curr. Gene Ther. 14(2):86-100.

Ben-Israel, H. et al. (2002) "Adenovirus and Cell Cycle Control," Front. Biosci. 7:d1369-d1395.

Berns, K. I. et al. (2017) "AAV: An Overview of Unanswered Questions," Human Gene Ther. 28(4):308-313.

Berry, G.E. et al. (2016) "Cellular Transduction Mechanisms of Adeno-Associated Viral Vectors," Curr. Opin. Virol. 21:54-60.

Blessing, D. et al. (2016) "Adeno Associated Virus and Lentivirus Vectors: A Refined Toolkit for The Central Nervous System," 21:61-66.

Brument, N. et al. (2002) "A Versatile and Scalable Two-Step Ion-Exchange Chromatography Process for the Purification of Recombinant Adeno-Associated Virus Serotypes-2 and -5," Mol. Ther. 6:678-686.

Büning, H. et al. (2019) "Capsid Modifications for Targeting and Improving the Efficacy of AAV Vectors," Mol. Ther. Meth. Clin. Devel. 12:P248-P265.

Cao, M. et al. (2014) "The X Gene of Adeno-Associated Virus 2 (AAV2) Is Involved in Viral DNA Replication," PLoS One 9, e104596:1-10.

Chiorini, J.A. et al. (1997) "Cloning of Adeno-Associated Virus Type 4 (AAV4) and Generation of Recombinant AAV4 Particles," J. Virol. 71(9):6823-6833.

Chopra, A. (2007) "Recombinant Adenovirus With Enhanced Green Fluorescent Protein," In: Molecular Imaging and Contrast Agent Database (MICAD) [Internet]. Bethesda (MD): National Center for Biotechnology Information (pp. 1-5).

Cinelli, R.A. et al. (2000) "The Enhanced Green Fluorescent Protein As a Tool for the Analysis of Protein Dynamics and Localization: Local Fluorescence Study At the Single Molecule Level," Photochem. Photobiol. 71(6):771-776.

Clément, N. et al. (2016) "Manufacturing of Recombinant Adeno-Associated Viral Vectors for Clinical Trials," Meth. Clin. Develop. 3:16002:1-7.

Colella, P. et al. (2018) "Emerging Issues in AAV-Mediated in Vivo Gene Therapy," Molec. Ther. Meth. Clin. Develop. 8:87-104.

Davidoff, A.M. et al. (2004) "Purification of Recombinant Adeno-Associated Virus Type 8 Vectors by Ion Exchange Chromatography Generates Clinical Grade Vector Stock," J. Virol. Methods 121:209-215.

Duan, D. (2016) "Systemic Delivery of Adeno-Associated Viral Vectors," Curr. Opin. Virol. 21:16-25.

During, M.J. et al. (1998) "In Vivo Expression of Therapeutic Human Genes for Dopamine Production in the Caudates of MPTP-Treated Monkeys Using an AAV Vector," Gene The. 5:820-827.

Durocher, Y. et al. (2007) "Scalable Serum-Free Production of Recombinant Adeno-Associated Virus Type 2 by Transfection of 293 Suspension Cells," J. Virol. Meth. 144:32-40.

Eddy, J. et al. (2006) "Gene Function Correlates With Potential for G4 DNA Formation in the Human Genome," Nucleic Acids Res. 34:3887-3896.

Egelie, K.J. et al. (2016) "The Emerging Patent Landscape of CRISPR—Cas Gene Editing Technology," Nature Biotechnol. 34(10):1025-1031.

Ferreira, V. et al. (2014) "Immune Responses to AAV-Vectors, The Glybera Example From Bench to Bedside" Front. Immunol. 5(82):1-15.

Francois, A. et al. (2018) "Accurate Titration of Infectious AAV Particles Requires Measurement of Biologically Active Vector Genomes and Suitable Controls," Molec. Ther. Meth. Clin. Develop. 10:223-236.

Gambotto, A. et al. (2000) "Immunogenicity of Enhanced Green Fluorescent Protein (EGFP) In BALB/C Mice: Identification of An H2-Kd-Restricted CTL Epitope," Gene Ther. 7(23):2036-2040.

Gao, G.P. et al. (2002) "Novel Adeno-Associated Viruses From Rhesus Monkeys as Vectors for Human Gene Therapy," Proc. Natl. Acad. Sci. (U.S.A.) 99(18):11854-11859.

Ghosh, A. et al. (2007) "Expanding Adeno-Associated Viral Vector Capacity: A Tale of Two Vectors," Biotechnol. Genet. Eng. Rev. 24:165-177.

Grieger, J.C. et al. (2012) "Adeno-Associated Virus Vectorology, Manufacturing, and Clinical Applications," Meth. Enzymol. 507:229-254.

Grimm, D. et al. (1998) "Novel Tools for Production and Purification of Recombinant Adeno-Associated Virus Vectors," Hum. Gene Ther. 9:2745-2760.

Guggino, W.B. et al. (2017) "AAV Gene Therapy for Cystic Fibrosis: Current Barriers and Recent Developments," Expert Opin Biol Ther. 17(10): 1265-1273.

Hastie, E. et al. (2015) "Adeno-Associated Virus at 50: A Golden Anniversary of Discovery, Research, and Gene Therapy Success—A Personal Perspective," Human Gene Ther. 26:257-265.

Hauck, B. et al. (2003) "Generation and Characterization of Chimeric Recombinant AAV Vectors," Mol. Ther. 7:419-425.

Hocquemiller, M. et al. (2016) "Adeno-Associated Virus-Based Gene Therapy for CNS Diseases," Hum. Gene Ther. 27(7):478-496.

Hoeben, R.C. et al. (2013) "Adenovirus DNA Replication," Cold Spring Harb. Perspect. Biol. 5:a013003 (pp. 1-11).

Johnson, F.B. et al. (1972) "Immunological Reactivity of Antisera Prepared Against the Sodium Dodecyl Sulfate-Treated Structural Polypeptides of Adenovirus-Associated Virus," J. Virol. 9(6):1017-1026.

Kay, M. et al. (2017) "Future of rAAV Gene Therapy: Platform for RNAi, Gene Editing and Beyond," Human Gene Ther. 28:361-372.

Kotterman, M.A. et al. (2014) "Engineering Adeno-Associated Viruses for Clinical Gene Therapy," Nat. Rev. Genet. 15(7):445-451.

Kwon, I. et al. (2007) "Designer Gene Delivery Vectors: Molecular Engineering and Evolution of Adeno-Associated Viral Vectors for Enhanced Gene Transfer," Pharm. Res. 25(3):489-499.

Lackner, D.F. et al. (2002) "Studies of the Mechanism of Transactivation of the Adeno-Associated Virus p19 Promoter by Rep Protein," J. Virol. 76(16):8225-8235.

Le, H.T. et al. (2005) "Utility of Pegylated Recombinant Adeno-Associated Viruses for Gene Transfer," J. Control. Release 108:161-177.

Lee, G.K. et al. (2005) "PEG Conjugation Moderately Protects Adeno-Associated Viral Vectors Against Antibody Neutralization," Biotechnol. Bioeng. 92:24-34.

Lino, C.A. et al. (2018) "Delivering CRISPR: A Review of the Challenges and Approaches," Drug Deliv. 25(1):1234-1237.

Lisowski, L. et al. (2015) "Adeno-Associated Virus Serotypes for Gene Therapeutics," 24:59-67.

(56) References Cited

OTHER PUBLICATIONS

Liu, Q. et al. (2014) "*Neutralizing Antibodies Against AAV2, AAV5 and AAV8 in Healthy and HIV-1-Infected Subjects in China: Implications for Gene Therapy Using AAV Vectors*," Gene Ther. 21:732-738.

Lock, M. et al. (2010) "*Rapid, Simple, and Versatile Manufacturing of Recombinant Adeno-Associated Viral Vectors at Scale*," Hum. Gene Ther. 21:1259-1271.

Lykken, E.A. et al. (2018) "*Recent Progress and Considerations for AAV Gene Therapies Targeting the Central Nervous System*," J. Neurodevelop. Dis. 10:16:1-10.

Matsushita, T. et al. (1998) "*Adeno-Associated Virus Vectors Can Be Efficiently Produced Without Helper Virus*," Gene Ther. 5:938-945.

McClements, M.E. et a. (2017) "*Adeno-associated Virus (AAV) Dual Vector Strategies for Gene Therapy Encoding Large Transgenes*," Yale J. Biol. Med. 90:611-623.

Monahan, P.E. et al. (2000) "*AAV Vectors: Is Clinical Success on the Horizon?*," Gene Ther. 7:24-30.

Murphy, M. et al. (2007) "*Adeno-Associated Virus Type 2 p5 Promoter: a Rep-Regulated DNA Switch Element Functioning in Transcription, Replication, and Site-Specific Integration*," J. Virol. 81(8):3721-3730.

Nash, K. et al. (2009) "*Identification of Cellular Proteins That Interact With the Adeno-Associated Virus Rep Protein*," J. Virol. 83(1):454-469.

Naso, M.F. et al. (2017) "*Adeno-Associated Virus (AAV) as a Vector for Gene Therapy*," BioDrugs 31:317-334.

Ni, T.H. et al. (1998) "*Cellular Proteins Required for Adeno-Associated Virus DNA Replication in the Absence of Adenovirus Coinfection*," J. Virol. 72(4):2777-2787.

Nicolas, A. et al. (2012) "*Factors Influencing Helper-Independent Adeno-Associated Virus Replication*," Virology 432(1):1-9.

Ogasawara, Y. et al. (1998) "*The Use of Heterologous Promoters for Adeno-Associated Virus (AAV) Protein Expression in AAV Vector Production*," Microbiol. Immunol. 42(3):177-185.

Penaud-Budloo, M. et al. (2018) "*Pharmacology of Recombinant Adeno-associated Virus Production*," Molec. Ther. Meth. Clin. Develop. 8:166-180.

Rabinowitz, J.E. et al. (2004) "*Crossdressing the Virion: The Transcapsidation of Adeno-Associated Virus Serotypes Functionally Defines Subgroups*," J. Virol. 78:4421-4432.

Rastall, D.P.W. (2017) "*Current and Future Treatments for Lysosomal Storage Disorders*," Curr. Treat Options Neurol. 19(12):45.

Salganik, M. et al. (2015) "*Adeno-Associated Virus as a Mammalian DNA Vector*," Microbiol. Spectr. 3(4):1-32.

Santiago-Ortiz, J.L. (2016) "*Adeno Associated Virus (AAV) Vectors in Cancer Gene Therapy*," J. Control Release 240:287-301.

Satkunanathan, S. et al. (2017) "*The Function of DNA Binding Protein Nucleophosmin in AAV Replication*," Virol. 510:46-54.

Sharma, A. et al. (2010) "*Transduction Efficiency Of AAV 2/6, 2/8 and 2/9 Vectors for Delivering Genes in Human Corneal Fibroblasts*," Brain Res. Bull. 81(2-3):273-278.

Smith, J.K. et al. (2018) "*Creating an Arsenal of Adeno-Associated Virus (AAV) Gene Delivery Stealth Vehicles*," PLoS Pathog. 14(5):1-6.

Smith, R.H. et al. (2009) "*A Simplified Baculovirus-AAV Expression Vector System Coupled With One-Step Affinity Purification Yields High-Titer rAAV Stocks From Insect Cells*," Mol. Ther. 17:1888-1896.

Tsien, R.Y. (1998) "*The Green Fluorescent Protein*," Annu. Rev. Biochem. 67:509-544.

Van Vliet K.M. et al. (2008) *The Role of the Adeno-Associated Virus Capsid in Gene Transfer.* In: Drug Delivery Systems, Jain, K.K. (eds.), Meth. Molec. Biol. 437:51-91.

Vandamme, C. et al. (2017) "*Unraveling the Complex Story of Immune Responses to AAV Vectors Trial After Trial*," Hum. Gene. Ther. 28(11):1061-1074.

Weitzman, M.D. (2005) "*Functions of the Adenovirus E4 Proteins and Their Impact on Viral Vectors*," Front. Biosci. 10:1106-1117.

Weitzman, M.D. (2006) "*The Parvovirus Life Cycle: An Introduction to Molecular Interactions Important for Infection*," In: Kerr, J.R. et al. (Eds.) Parvoviruses, Hodder Arnold, London, UK (pp. 143-156).

Wu, Z. et al. (2010) "*Effect of Genome Size on AAV Vector Packaging*," Molec. Ther. 18:80-86.

Yao, T et al. (2017) "*Animal-Cell Culture Media: History, Characteristics, and Current Issues*," Reproduc. Med. Biol. 16(2): 99-117.

Zen, Z. et al. (2004) "*Infectious Titer Assay for Adeno-Associated Virus Vectors With Sensitivity Sufficient to Detect Single Infectious Events*," Hum. Gene Ther. 15:709-715.

Zinn, E. et al. (2014) "*Adeno-Associated Virus: Fit to Serve*," Curr. Opin. Virol. 0:90-97.

Zolotukhin, S. et al. (1999) "*Recombinant Adeno-Associated Virus Purification Using Novel Methods Improves Infectious Titer and Yield*," Gene Ther. 6:973-985.

Zolotukhin, S. et al. (2002) "*Production and Purification of Serotype 1, 2, and 5 Recombinant Adeno Associated Viral Vectors*," Methods 28:158-167.

\* cited by examiner

RECOMBINANTLY-MODIFIED ADENO-ASSOCIATED VIRUS HELPER VECTORS AND THEIR USE TO IMPROVE THE PACKAGING EFFICIENCY OF RECOMBINANTLY-MODIFIED ADENO-ASSOCIATED VIRUS

CROSS-REFERENCE TO RELATED APPLICATIONS

This application is a continuation application of U.S. patent application Ser. No. 16/512,194, which was filed on Jul. 15, 2019, and which issued as U.S. Pat. No. 10,577,149 on Feb. 11, 2020, which application is hereby incorporated by reference in its entirety.

FIELD OF THE INVENTION

The present invention is directed to recombinantly-modified adeno-associated virus (AAV) helper vectors that are capable of increasing the packaging efficiency of recombinantly-modified adeno-associated virus (rAAV) and their use to improve the packaging efficiency of such rAAV. The present invention is particularly directed to recombinantly-modified adeno-associated virus (AAV) helper vectors that have been further modified to replace (or augment) the P5 and/or P40 promoter sequences that are natively associated with the Rep proteins encoded by such rAAV with AAV P5 and/or P40 promoters that are associated with the Rep proteins of an rAAV of different serotype. The use of such substitute or additional promoter sequences causes increased production of recombinantly-modified adeno-associated virus.

REFERENCE TO SEQUENCE LISTING

This application includes one or more Sequence Listings pursuant to 37 C.F.R. 1.821 et seq., which are disclosed in computer-readable media (file name: 2650-0004US2_ST25.txt, created on Dec. 6, 2019, and having a size of 84,145 bytes), which file is herein incorporated by reference in its entirety.

BACKGROUND OF THE INVENTION

I. Adeno-Associated Virus (AAV)

Adeno-Associated Virus (AAV) is a small, naturally-occurring, non-pathogenic virus belonging to the *Dependovirus* genus of the Parvoviridae (Balakrishnan, B. et al. (2014) "*Basic Biology of Adeno Associated Virus (AAV) Vectors Used in Gene Therapy,*" Curr. Gene Ther. 14(2):86-100; Zinn, E. et al. (2014) "*Adeno-Associated Virus: Fit To Serve,*" Curr. Opin. Virol. 0:90-97). Despite not causing disease, AAV is known to be able to infect humans and other primates and is prevalent in human populations (Johnson, F. B. et al. (1972) "*Immunological Reactivity of Antisera Prepared Against the Sodium Dodecyl Sulfate-Treated Structural Polypeptides of Adenovirus-Associated Virus,*" J. Virol. 9(6):1017-1026). AAV infect a broad range of different cell types (e.g., cells of the central nervous system, heart, kidney, liver, lung, pancreas, retinal pigment epithelium or photoreceptor cells, or skeletal muscle cells). Twelve serotypes of the virus (e.g., AAV2, AAV5, AAV6, etc.), exhibiting different tissue infection capabilities ("tropisms"), have been identified (Colella, P. et al. (2018) "*Emerging Issues in AAV-Mediated In Vivo Gene Therapy,*" Molec. Ther. Meth. Clin. Develop. 8:87-104; Hocquemiller, M. et al. (2016) "*Adeno-Associated Virus-Based Gene Therapy for CNS Diseases,*" Hum. Gene Ther. 27(7):478-496; Lisowski, L. et al. (2015) "*Adeno-Associated Virus Serotypes For Gene Therapeutics,*" 24:59-67).

AAV is a single-stranded DNA virus that is composed of approximately 4,800 nucleotides. The viral genome may be described as having a 5' half and a 3' half which together comprise the genes that encode the virus' proteins (FIG. 1). The 5' half of the AAV genome comprises the AAV rep gene, which, through the use of multiple reading frames, staggered initiating promoters (P5, P19 and P40) and alternate splicing, encodes four non-structural Rep proteins (Rep40, Rep52, Rep68 and Rep78) that are required for viral transcription control and replication and for the packaging of viral genomes into the viral capsule (Lackner, D. F. et al. (2002) "*Studies of the Mechanism of Transactivation of the Adeno-Associated Virus p19 Promoter by Rep Protein,*" J. Virol. 76(16):8225-8235). In the presence of viral proteins (such as Ad proteins), the P5 promoter becomes activated and mediates the transcription of the Rep68 and Rep78 proteins, which are involved in transcriptional control, in latency, in rescue, and in viral DNA replication and thus function as master controllers of the AAV life cycle (Murphy, M. et al. (2007) "*Adeno Associated Virus Type 2 p5 Promoter: a Rep-Regulated DNA Switch Element Functioning in Transcription, Replication, and Site-Specific Integration,*" J. Virol. 81(8):3721-3730). Expression of the Rep68 and Rep78 proteins activates the P19 promoter, which is responsible for the transcription of the Rep40 and Rep52 proteins (Lackner, D. F. et al. (2002) "*Studies of the Mechanism of Transactivation of the Adeno-Associated Virus p19 Promoter by Rep Protein,*" J. Virol. 76(16):8225-8235; Ogasawara, Y. et al. (1998) "*The Use of Heterologous Promoters for Adeno-Associated Virus (AAV) Protein Expression in AAV Vector Production,*" Microbiol. Immunol. 42(3):177-185). The 3' half the AAV genome comprises the AAV capsid gene (cap), which encodes three capsid proteins (VP): VP1, VP2 and VP3. The three capsid proteins are translated from a single mRNA transcript that is controlled by a single promoter (P40 in case of AAV2). The 3' half of the AAV genome also comprises the AAP gene, which encodes the AAV assembly-activating protein (AAP). Sixty VP monomers (comprising approximately 5 copies of VP1, 5 copies of VP2, and 50 copies of VP3) self-assemble around the AAV genome to form the icosahedral protein shell (capsid) of the mature viral particle (Büning, H. et al. (2019) "*Capsid Modifications for Targeting and Improving the Efficacy of AAV Vectors,*" Mol. Ther. Meth. Clin. Devel. 12:P248-P265; Van Vliet K. M. et al. (2008) *The Role of the Adeno-Associated Virus Capsid in Gene Transfer.* In: DRUG DELIVERY SYSTEMS, Jain, K. K. (eds.), Meth. Molec. Biol. 437:51-91). The AAV AAP protein is believed to be required for stabilizing and transporting newly produced VP proteins from the cytoplasm into the cell nucleus. The 3' half of the AAV genome also comprises the AAV X gene, which is believed to encode a protein that supports genome replication (Colella, P. et al. (2018) "*Emerging Issues in AAV-Mediated In Vivo Gene Therapy,*" Molec. Ther. Meth. Clin. Develop. 8:87-104; Büning, H. et al. (2019) "*Capsid Modifications for Targeting and Improving the Efficacy of AAV Vectors,*" Mol. Ther. Meth. Clin. Devel. 12:P248-P265; Cao, M. et al. (2014) "*The X Gene Of Adeno-Associated Virus 2 (AAV2) Is Involved In Viral DNA Replication,*" PLoS ONE 9, e104596:1-10).

The above-described AAV gene-coding sequences are flanked by two AAV-specific palindromic inverted terminal repeated sequences (ITR) of 145 nucleotides (Balakrishnan, B. et al. (2014) "*Basic Biology of Adeno-Associated Virus (AAV) Vectors Used in Gene Therapy*," Curr. Gene Ther. 14(2):86-100; Colella, P. et al. (2018) "*Emerging Issues in AAV-Mediated In Vivo Gene Therapy*," Molec. Ther. Meth. Clin. Develop. 8:87-104).

AAV is an inherently defective virus, lacking the capacity to perform at least two critical functions: the ability to initiate the synthesis of viral-specific products and the ability to assemble such products to form the icosahedral protein shell (capsid) of the mature infectious viral particle. It thus requires a co-infecting "helper" virus, such as adenovirus (Ad), herpes simplex virus (HSV), cytomegalovirus (CMV), vaccinia virus or human papillomavirus to provide the viral-associated (VA) RNA that is not encoded by the genes of the AAV genome. Such VA RNA is not translated, but plays a role in regulating the translation of other viral genes. Similarly, the AAV genome does not include genes that encode the viral proteins E1a, E1b, E2a, and E4; thus, these proteins must also be provided by a co-infecting "helper" virus. The E1a protein greatly stimulate viral gene transcription during the productive infection. The E1b protein block apoptosis in adenovirus-infected cells, and thus allow productive infection to proceed. The E2a protein plays a role in the elongation phase of viral strand displacement replication by unwinding the template and enhancing the initiation of transcription. The E4 protein has been shown to affect transgene persistence, vector toxicity and immunogenicity (see, Grieger, J. C. et al. (2012) "*Adeno-Associated Virus Vectorology, Manufacturing, and Clinical Applications*," Meth. Enzymol. 507:229-254; Dyson, N. et al. (1992) "*Adenovirus E1A Targets Key Regulators Of Cell Proliferation*," Canc. Surv. 12:161-195; Jones N. C. (1990) "*Transformation By The Human Adenoviruses*," Semin. Cancer Biol. 1(6):425-435; Ben-Israel, H. et al. (2002) "*Adenovirus and Cell Cycle Control*," Front. Biosci. 7:d1369-d1395; Hoeben, R. C. et al. (2013) "*Adenovirus DNA Replication*," Cold Spring Harb. Perspect. Biol. 5:a013003 (pages 1-11); Berk, A. J. (2013) "*Adenoviridae: The Viruses And Their Replication*, In: FIELDS VIROLOGY, 6*th* Edition (Knipe, D. M. et al., Eds.), Vol. 2., Lippincott Williams & Wilkins, Philadelphia, pages 1704-1731; Weitzman, M. D. (2005) "*Functions Of The Adenovirus E4 Proteins And Their Impact On Viral Vectors*," Front. Biosci. 10:1106-1117).

AAV viruses infect both dividing and non-dividing cells, and persist as circular episomal molecules or can be integrated into the DNA of a host cell at specific chromosomic loci (Adeno-Associated Virus Integration Sites or AAVS) (Duan, D. (2016) "*Systemic Delivery Of Adeno-Associated Viral Vectors*," Curr. Opin. Virol. 21:16-25; Grieger, J. C. et al. (2012) "*Adeno-Associated Virus Vectorology, Manufacturing, and Clinical Applications*," Meth. Enzymol. 507: 229-254). AAV remains latent in such infected cells unless a helper virus is present to provide the functions needed for AAV replication and maturation.

II. rAAV and Their Use in Gene Therapy

In light of AAV's properties, recombinantly-modified versions of AAV (rAAV) have found substantial utility as vectors for gene therapy (see, Naso, M. F. et al. (2017) "*Adeno-Associated Virus (AAV) as a Vector for Gene Therapy*," BioDrugs 31:317-334; Berns, K. I. et al. (2017) "*AAV: An Overview of Unanswered Questions*," Human Gene Ther. 28(4):308-313; Berry, G. E. et al. (2016) "*Cellular Transduction Mechanisms Of Adeno-Associated Viral Vectors*," Curr. Opin. Virol. 21:54-60; Blessing, D. et al. (2016) "*Adeno-Associated Virus And Lentivirus Vectors: A Refined Toolkit For The Central Nervous System,*" 21:61-66; Santiago-Ortiz, J. L. (2016) "*Adeno-Associated Virus (AAV) Vectors in Cancer Gene Therapy*," J. Control Release 240: 287-301; Salganik, M. et al. (2015) "*Adeno-Associated Virus As A Mammalian DNA Vector*," Microbiol. Spectr. 3(4):1-32; Hocquemiller, M. et al. (2016) "*Adeno-Associated Virus-Based Gene Therapy for CNS Diseases*," Hum. Gene Ther. 27(7):478-496; Lykken, E. A. et al. (2018) "*Recent Progress And Considerations For AAV Gene Therapies Targeting The Central Nervous System*," J. Neurodevelop. Dis. 10:16:1-10; Büning, H. et al. (2019) "*Capsid Modifications for Targeting and Improving the Efficacy of AAV Vectors*," Mol. Ther. Meth. Clin. Devel. 12:P248-P265; During, M. J. et al. (1998) "*In Vivo Expression Of Therapeutic Human Genes For Dopamine Production In The Caudates Of MPTP-Treated Monkeys Using An AAV Vector*," Gene The. 5:820-827; Grieger, J. C. et al. (2012) "*Adeno-Associated Virus Vectorology, Manufacturing, and Clinical Applications*," Meth. Enzymol. 507:229-254; Kotterman, M. A. et al. (2014) "*Engineering Adeno-Associated Viruses For Clinical Gene Therapy*," Nat. Rev. Genet. 15(7):445-451; Kwon, I. et al. (2007) "*Designer Gene Delivery Vectors: Molecular Engineering and Evolution of Adeno-Associated Viral Vectors for Enhanced Gene Transfer*," Pharm. Res. 25(3):489-499; U.S. Pat. Nos. 10,266,845; 10,081,659; 9,890,396; 9,840,719; 9,839,696; 9,834,789; 9,803,218; 9,783,825; 9,777,291; 9,540,659; 9,527,904; 8,236,557; 7,972,593 and 7,943,374).

rAAV are typically produced using circular plasmids ("rAAV plasmid vector"). The AAV rep and cap genes are typically deleted from such constructs and replaced with a promoter, a β-globin intron, a cloning site into which a therapeutic gene of choice (transgene) has been inserted, and a poly-adenylation ("polyA") site. The inverted terminal repeated sequences (ITR) of the rAAV are, however, retained, so that the transgene expression cassette of the rAAV plasmid vector is flanked by AAV ITR sequences (Colella, P. et al. (2018) "*Emerging Issues in AAV-Mediated In Vivo Gene Therapy*," Molec. Ther. Meth. Clin. Develop. 8:87-104; Büning, H. et al. (2019) "*Capsid Modifications for Targeting and Improving the Efficacy of AAV Vectors*," Mol. Ther. Meth. Clin. Devel. 12:P248-P265). Thus, in the 5' to 3' direction, the rAAV comprises a 5' ITR, the transgene expression cassette of the rAAV, and a 3' ITR.

rAAV have been used to deliver a transgene to patients suffering from any of a multitude of genetic diseases (e.g., hereditary lipoprotein lipase deficiency (LPLD), Leber's congenital amaurosis (LCA), aromatic L-amino acid decarboxylase deficiency (AADC), choroideremia and hemophilia), and have utility in new clinical modalities, such as in interfering RNA (RNAi) therapy and gene-modifying strategies such as Crispr/Cas9 (U.S. Pat. Nos. 8,697,359, 10,000,772, 10,113,167, 10,227,611; Lino, C. A. et al. (2018) "*Delivering CRISPR: A Review Of The Challenges And Approaches*," Drug Deliv. 25(1):1234-1237; Ferreira, V. et al. (2014) "*Immune Responses To AAV-Vectors, The Glybera Example From Bench To Bedside*" Front. Immunol. 5(82):1-15), Büning, H. et al. (2019) "*Capsid Modifications for Targeting and Improving the Efficacy of AAV Vectors*," Mol. Ther. Meth. Clin. Devel. 12:P248-P265; Rastall, D. P. W. (2017) "*Current and Future Treatments for Lysosomal Storage Disorders*," Curr. Treat Options Neurol. 19(12):45; Kay, M. et al. (2017) "*Future Of rAAV Gene Therapy: Platform For RNAi, Gene Editing And Beyond*," Human Gene Ther. 28:361-372); Berns, K. I. et al. (2017) "*AAV: An Overview of Unanswered Questions*," Human Gene Ther. 28(4):308-313). More than 150 clinical trials involving rAAV have been instituted (Büning, H. et al. (2019) "*Capsid Modifications for Targeting and Improving the Efficacy of*

*AAV Vectors*," Mol. Ther. Meth. Clin. Devel. 12:P248-P265; Clément, N. et al. (2016) "*Manufacturing Of Recombinant Adeno-Associated Viral Vectors For Clinical Trials*," Meth. Clin. Develop. 3:16002:1-7). The most commonly used AAV serotype for such recombinantly-modified AAV is AAV2, which is capable of infecting cells of the central nervous system, kidney, retinal pigment epithelium and photoreceptor cells. AAV serotype is AAV9, which infects muscle cells, also has been widely used (Duan, D. (2016) "*Systemic Delivery Of Adeno-Associated Viral Vectors*," Curr. Opin. Virol. 21:16-25). AAV serotypes are described in U.S. Pat. Nos. 10,301,650; 10,266,846; 10,265,417; 10,214,785; 10,214,566; 10,202,657; 10,046,016; 9,884,071; 9,856,539; 9,737,618; 9,677,089; 9,458,517; 9,457,103; 9,441,244; 9,193,956; 8,846,389; 8,507,267; 7,906,111; 7,479,554; 7,186,552; 7,105,345; 6,984,517; 6,962,815; and 6,733,757.

III. Methods of rAAV Production rAAV containing a desired transgene expression cassette are typically produced by human cells (such as HEK293) grown in suspension. Since, as described above, rAAV are defective viruses, additional functions must be provided in order to replicate and package rAAV.

rAAV can be produced by transiently transfecting cells with an rAAV plasmid vector and a second plasmid vector that comprises an AAV helper function-providing polynucleotide that provides the Rep52 and Rep78 genes that are required for vector transcription control and replication, and for the packaging of viral genomes into the viral capsule (Rep40 and Rep68 are not required for rAAV production) and the cap genes that were excised from the AAV in order to produce the rAAV. The second plasmid vector may additionally comprise a non-AAV helper function-providing polynucleotide that encodes the viral transcription and translation factors (E1a, E1b, E2a, VA and E4) required for AAV proliferation, so as to comprise, in concert with the rAAV, a double plasmid transfection system (Grimm, D. et al. (1998) "*Novel Tools For Production And Purification Of Recombinant Adeno-Associated Virus Vectors*," Hum. Gene Ther. 9:2745-2760; Penaud-Budloo, M. et al. (2018) "*Pharmacology of Recombinant Adeno-associated Virus Production*," Molec. Ther. Meth. Clin. Develop. 8:166-180).

However, it has become increasingly common to clone the AAV helper function-providing polynucleotide (which provides the required rep and cap genes) into an AAV helper plasmid, and to clone the non-AAV helper function-providing polynucleotide (which provides the genes that encode the viral transcription and translation factors) on a different plasmid (e.g., an "Ad helper plasmid"), so that such plasmids, in concert with an rAAV plasmid vector, comprise a triple plasmid transfection system (FIG. 2). Use of the triple plasmid transfection system has the advantage of permitting one to easily switch one cap gene for another, thereby facilitating changes in the rAAV's serotype. The use of helper plasmids, rather than helper viruses, permits rAAV to be produced without additionally producing particles of the helper virus (François, A. et al. (2018) "*Accurate Titration of Infectious AAV Particles Requires Measurement of Biologically Active Vector Genomes and Suitable Controls*," Molec. Ther. Meth. Clin. Develop. 10:223-236; Matsushita, T. et al. (1998) "*Adeno-Associated Virus Vectors Can Be Efficiently Produced Without Helper Virus*," Gene Ther. 5:938-945).

The transient transfection of plasmid DNAs comprising the rAAV plasmid vector, the AAV rep and cap genes, and the trans-acting AAD helper genes into HEK293 cells by calcium phosphate coprecipitation has become the standard method to produce rAAV in the research laboratory (Grimm, D. et al. (1998) "*Novel Tools For Production And Purification Of Recombinant Adeno-Associated Virus Vectors*," Hum. Gene Ther. 9:2745-2760). However, the use of such a calcium phosphate-mediated transfection process with suspension-cultured transfected mammalian cells requires media exchanges, and is thus not considered ideal for the large-scale rAAV production that is required in order to produce therapeutic doses of rAAV (Lock, M. et al. (2010) "*Rapid, Simple, and Versatile Manufacturing of Recombinant Adeno-Associated Viral Vectors at Scale*," Hum. Gene Ther. 21:1259-1271). For this reason, polyethylenimine (PEI), has been used as a transfection reagent and has been found to provide yields of virus that are similar to those obtained using calcium phosphate-mediated transfection (Durocher, Y. et al. (2007) "*Scalable Serum-Free Production Of Recombinant Adeno-Associated Virus Type 2 By Transfection Of 293 Suspension Cells*," J. Virol. Meth. 144:32-40).

rAAV may alternatively be produced in insect cells (e.g., sf9 cells) using baculoviral vectors (see, e.g., U.S. Pat. Nos. 9,879,282; 9,879,279; 8,945,918; 8,163,543; 7,271,002 and 6,723,551), or in HSV-infected baby hamster kidney (BHK) cells (e.g., BHK21) (François, A. et al. (2018) "*Accurate Titration of Infectious AAV Particles Requires Measurement of Biologically Active Vector Genomes and Suitable Controls*," Molec. Ther. Meth. Clin. Develop. 10:223-236). Methods of rAAV production are reviewed in Grieger, J. C. et al. (2012) "*Adeno-Associated Virus Vectorology, Manufacturing, and Clinical Applications*," Meth. Enzymol. 507:229-254, and in Penaud-Budloo, M. et al. (2018) "*Pharmacology of Recombinant Adeno-associated Virus Production*," Molec. Ther. Meth. Clin. Develop. 8:166-180.

IV. Methods of rAAV Purification and Recovery

After production, rAAV are typically collected and purified by one or more overnight CsCl gradient centrifugations (Zolotukhin, S. et al. (1999) "*Recombinant Adeno-Associated Virus Purification Using Novel Methods Improves Infectious Titer And Yield*," Gene Ther. 6:973-985), followed by desalting to form a purified rAAV production stock. Titers of $10^{12}$-$10^{13}$ infectious rAAV capsids/mL are obtainable.

Because rAAV infection does not cause a cytopathic effect, plaque assays cannot be used to determine the infectious titer of an rAAV preparation. Infectious titer is thus typically measured as the median tissue culture infective dose (TCID50). In this method, a HeLa-derived AAV2 rep- and cap-expressing cell line is grown in a 96-well plate and infected with replicate 10-fold serial dilutions of the rAAV preparation, in the presence of adenovirus of serotype 5. After infection, vector genome replication is determined by quantitative PCR (qPCR) (Zen, Z. et al. (2004) "*Infectious Titer Assay For Adeno-Associated Virus Vectors With Sensitivity Sufficient To Detect Single Infectious Events*," Hum. Gene Ther. 15:709-715). Alternatively, the infectious titer of an rAAV preparation can be measured using the infectious center assay (ICA). This assay uses HeLa rep-cap cells and Ad, but, after incubation, involves transferring the cells to a membrane. A labeled probe that is complementary to a portion of the employed transgene is used to detect infectious centers (representing individual infected cells) via hybridization. Although more widely used, the TCID50 assay has been reported to lead to a higher background than the ICA and to overestimate vector infectivity relative to the ICA (François, A. et al. (2018) "*Accurate Titration of Infectious AAV Particles Requires Measurement of Biologically Active Vector Genomes and Suitable Controls*," Molec.

Ther. Meth. Clin. Develop. 10:223-236). Methods of producing and purifying rAAV are described inter alia in U.S. Pat. Nos. 10,294,452; 10,161,011; 10,017,746; 9,598,703; 7,625,570; 7,439,065; 7,419,817; 7,208,315; 6,995,006; 6,989,264; 6,846,665 and 6,841,357.

Despite all such prior advances, a need remains to develop methods capable of addressing problems that presently limit the applicability of rAAV to gene therapy (Grieger, J. C. et al. (2012) "*Adeno-Associated Virus Vectorology, Manufacturing, and Clinical Applications*," Meth. Enzymol. 507: 229-254; Kotterman, M. A. et al. (2014) "*Engineering Adeno-Associated Viruses For Clinical Gene Therapy*," Nat. Rev. Genet. 15(7):445-451; Kwon, I. et al. (2007) "*Designer Gene Delivery Vectors: Molecular Engineering and Evolution of Adeno-Associated Viral Vectors for Enhanced Gene Transfer*," Pharm. Res. 25(3):489-499; Naso, M. F. et al. (2017) "*Adeno-Associated Virus (AAV) as a Vector for Gene Therapy*," BioDrugs 31:317-334).

The present invention is directed to improved methods for increasing the efficiency of AAV and rAAV packaging through regulation of the expression of the AAV rep and cap genes.

SUMMARY OF THE INVENTION

The present invention is directed to recombinantly-modified adeno-associated virus (AAV) helper vectors that are capable of increasing the packaging efficiency of recombinantly-modified adeno-associated virus (rAAV) and their use to improve the packaging efficiency of such rAAV. The present invention is particularly directed to recombinantly-modified adeno-associated virus (AAV) helper vectors that have been further modified to replace (or augment) the P5 and/or P40 promoter sequences that are natively associated with the Rep proteins encoded by such rAAV with AAV P5 and/or P40 promoters that are associated with the Rep proteins of an rAAV of different serotype. The use of such substitute or additional promoter sequences causes increased production of recombinantly-modified adeno-associated virus.

In detail, the invention provides a recombinantly-modified adeno-associated virus (AAV) helper vector that comprises an AAV helper function-providing polynucleotide, and especially an AAV helper function-providing polynucleotide that is a plasmid vector, wherein the polynucleotide comprises a non-native AAV serotype P5 or P40 promoter sequence.

The invention particularly includes the embodiment of such recombinantly-modified adeno-associated virus (AAV) helper vector wherein the AAV helper function-providing polynucleotide vector comprises a non-native AAV serotype P5 promoter sequence and/or a non-native AAV serotype P40 promoter sequence.

The invention also particularly includes the embodiment of such recombinantly-modified adeno-associated virus (AAV) helper vector wherein the non-native AAV serotype P5 or P40 promoter sequence replaces a native AAV serotype promoter sequence.

The invention also particularly includes the embodiment of such recombinantly-modified adeno-associated virus (AAV) helper vector wherein the vector additionally comprises a non-AAV helper function-providing polynucleotide.

The invention additionally provides a method for increasing the production titer of a recombinantly-modified adeno-associated virus (rAAV) that comprises a transgene cassette, wherein the method comprises culturing cells that have been transfected with:
  (1) an rAAV plasmid vector that comprises the transgene cassette flanked by the inverted terminal repeated sequences;
  (2) the above-described recombinantly-modified adeno-associated virus (AAV) helper vector that additionally comprises a non-AAV helper function-providing polynucleotide;
wherein the culturing is conducted in a culture medium under conditions sufficient to permit the production of the rAAV, and wherein the presence of the non-native AAV serotype P5 or P40 promoter sequence causes the cells to produce the rAAV at an increased production titer relative to that which would be attained if the AAV helper function-providing polynucleotide contained native serotype P5 and P40 promoters.

The invention additionally provides a method for increasing the production titer of recombinantly-modified adeno-associated virus (rAAV) that comprises a transgene cassette, wherein the method comprises culturing cells that have been transfected with:
  (1) an rAAV plasmid vector that comprises the transgene cassette flanked by the inverted terminal repeated sequences;
  (2) any of the above-described recombinantly-modified adeno-associated virus (AAV) helper vectors; and
  (3) an additional vector, especially a plasmid vector, that comprises a non-AAV helper function-providing polynucleotide;
wherein the culturing is conducted in a culture medium under conditions sufficient to permit the production of the rAAV, and wherein the presence of the non-native AAV serotype P5 or P40 promoter sequence causes the cells to produce the rAAV at an increased production titer relative to that which would be attained if the AAV helper function-providing polynucleotide contained native serotype P5 and P40 promoters.

The invention particularly includes the embodiment of such methods, wherein the transgene cassette encodes a protein, or comprises a transcribed nucleic acid, that is therapeutic for a genetic or heritable disease or condition.

The invention also particularly includes the embodiment of such methods, wherein:
  (A) the AAV helper function-providing polynucleotide of the vector encodes an AAV1 Cap protein, and the non-native AAV serotype promoter sequence is a promoter sequence of an AAV of serotype AAV3, AAV4, AAV5, AAV6, AAV7 or AAV8, or a hybrid of one or more of the serotypes;
  (B) the AAV helper function-providing polynucleotide of the vector encodes an AAV2 Cap protein, and the non-native AAV serotype promoter sequence is a promoter sequence of an AAV of serotype AAV1, AAV3, AAV4, AAV5, AAV6, AAV7 or AAV8, or a hybrid of one or more of the serotypes;
  (C) the AAV helper function-providing polynucleotide of the vector encodes an AAV3 Cap protein, and the non-native AAV serotype promoter sequence is a promoter sequence of an AAV of serotype AAV1, AAV4, AAV5, AAV6, AAV7 or AAV8, or a hybrid of one or more of the serotypes;
  (D) the AAV helper function-providing polynucleotide of the vector encodes an AAV4 Cap protein, and the non-native AAV serotype promoter sequence is a promoter sequence of an AAV of serotype AAV1, AAV3, AAV5, AAV6, AAV7 or AAV8, or a hybrid of one or more of the serotypes;

(E) the AAV helper function-providing polynucleotide of the vector encodes an AAV5 Cap protein, and the non-native AAV serotype promoter sequence is a promoter sequence of an AAV of serotype AAV1, AAV3, AAV4, AAV6, AAV7 or AAV8, or a hybrid of one or more of the serotypes;

(F) the AAV helper function-providing polynucleotide of the vector encodes an AAV6 Cap protein, and the non-native AAV serotype promoter sequence is a promoter sequence of an AAV of serotype AAV1, AAV3, AAV4, AAV5, AAV7 or AAV8, or a hybrid of one or more of the serotypes;

(G) the AAV helper function-providing polynucleotide of the vector encodes an AAV7 Cap protein, and the non-native AAV serotype promoter sequence is a promoter sequence of an AAV of serotype AAV1, AAV3, AAV4, AAV5, AAV6 or AAV8, or a hybrid of one or more of the serotypes;

(H) the AAV helper function-providing polynucleotide of the vector encodes an AAV8 Cap protein, and the non-native AAV serotype promoter sequence is a promoter sequence of an AAV of serotype AAV1, AAV3, AAV4, AAV5, AAV6 or AAV7, or a hybrid of one or more of the serotypes.

The invention also particularly includes the embodiment of such methods, wherein the cells are human embryonic kidney cells, baby hamster kidney cells or sf9 insect cells.

The invention additionally provides a pharmaceutical composition that comprises the recombinantly-modified adeno-associated virus (rAAV) produced by any of the above-listed methods, and a pharmaceutically acceptable carrier.

P5-RC constructs are derivatives of parental plasmid AAV RC that have been modified to direct expression of the AAV rep gene using a non-native P5 promoter (i.e., an AAV P5 promoter that is not natively present within the AAV rep gene of the vector (downward striped box)) in lieu of the native AAV serotype P5 promoter (solid black box); P5-RC constructs direct expression of the AAV rep and cap genes using the native AAV serotype P19 and P40 promoter sequences (solid black boxes) of the parent vector. P40-RC constructs are derivatives of parental plasmid AAV RC that have been modified to direct expression of the AAV cap gene using a non-native P40 promoter (i.e., an AAV P40 promoter that is not natively present within the AAV rep gene (upward striped box)) of the vector in lieu of the native AAV serotype P40 promoter (solid black box); P40-RC constructs direct expression of the AAV rep gene using the native AAV serotype P5 and P19 promoter sequences (solid black boxes) of the parent vector. P5/P40-RC constructs are derivatives of parental plasmid AAV RC that have been modified to direct expression of the AAV rep gene using a non-native P5 promoter (i.e., an AAV P5 promoter that is not natively present within the AAV rep gene of the vector (downward striped box)) in lieu of the native AAV serotype P5 promoter (solid black box). P5/P40-RC constructs have additionally been modified to direct expression to direct expression of the AAV cap gene using a non-native P40 promoter (i.e., an AAV P40 promoter that is not natively present within the AAV rep gene (upward striped box)) of the vector in lieu of the native AAV serotype P40 promoter (solid black box). P40-RC constructs direct expression of the AAV rep gene using the native AAV serotype P19 promoter sequences (solid black boxes) of the parent vector. The sequences of the promoter regions are shown in Table 1.

Figure 11:
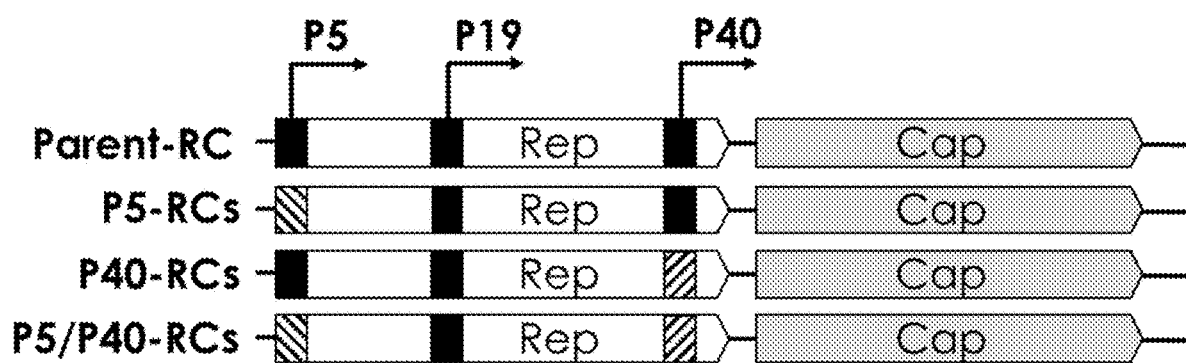
FIG. 11 shows the overall structure and approach followed for the development of the exemplary AAV helper constructs described herein. The parent construct (pAAV-RC2; Parent-RC) comprises AAV2 serotype promoter sequences for the P5 and P19 promoters (solid black boxes) that direct expression of the native AAV2 rep gene (white boxed gene), which encodes the Rep proteins, as well as the AAV2 serotype promoter sequence of the P40 promoter (solid black box) that directs expression of the native AAV2 cap gene (gray boxed gene), which encodes the Cap proteins.
Figure 12A:
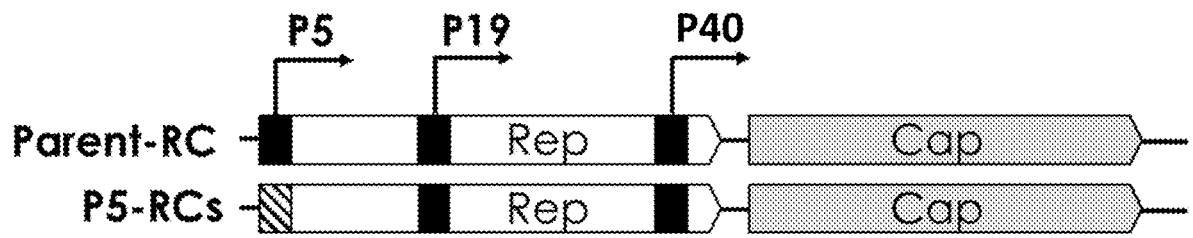
Figure 12B:
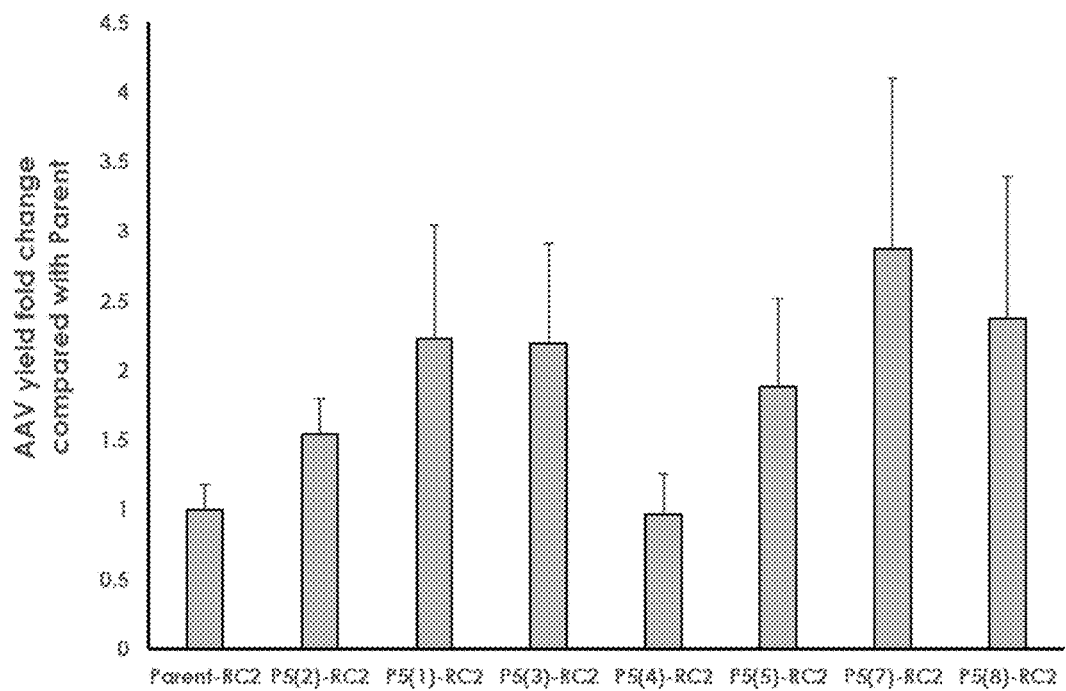

FIGS. 12A-12B show the production titers of rAAV obtained by modifying a parental RC2 vector to comprise a non-native P5 promoter sequence (FIG. 11; FIG. 12A; downward striped rectangle) in lieu of the AAV2 P5 promoter that is natively associated with the rep gene of such vector. The P19 and P40 promoters are both native AAV2 serotype promoter sequences (solid black rectangles). FIG. 12B shows the production titers of rAAV obtained using such AAV helper plasmid vectors. The following constructs were employed: Parent-RC2, P5(2)-RC2, P5(1)-RC2, P5(3)-RC2, P5(4)-RC2, P5(5)-RC2, P5(7)-RC2, and P5(8)-RC2. The sequences of the promoter regions are shown in Table 1. The production titers of rAAV were obtained using a triple plasmid transfection system with an rAAV, and an Ad helper plasmid that provided the required adenoviral functions.

Figure 13A:
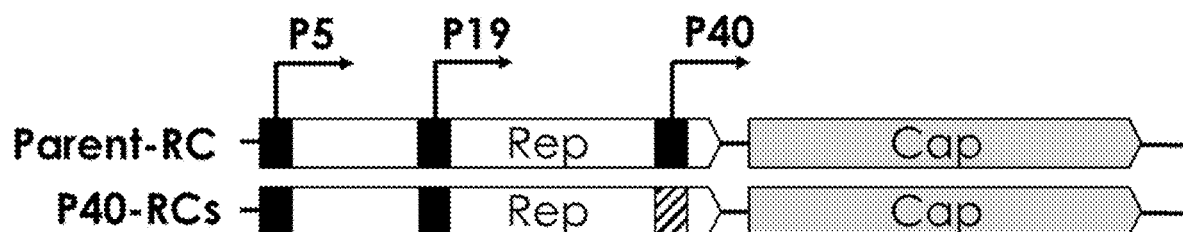
Figure 13B:
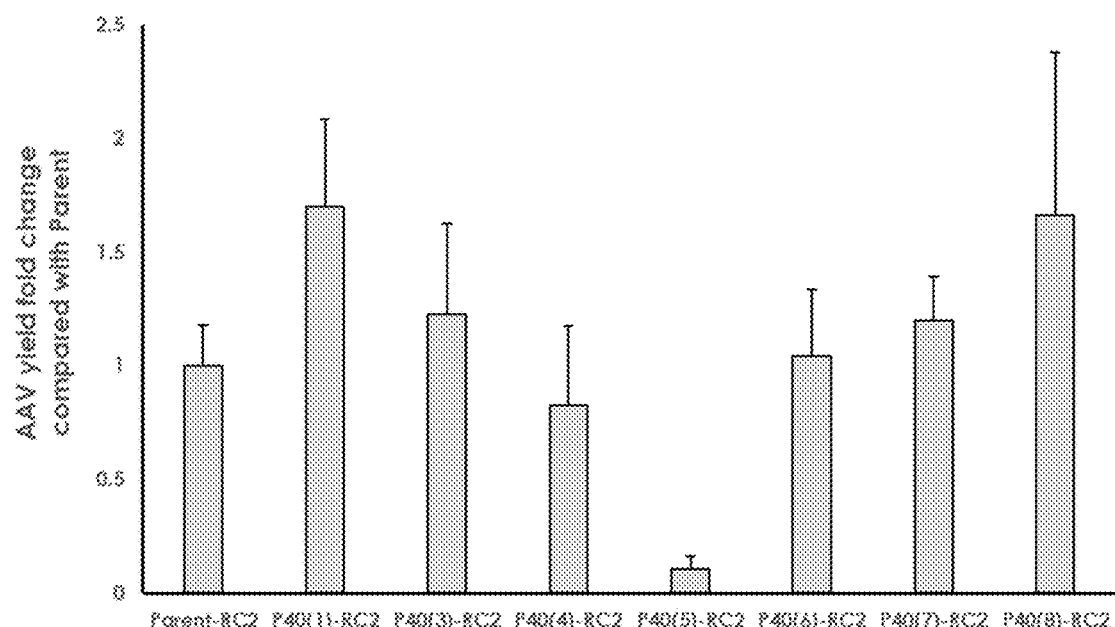

FIGS. 13A-13B show the production titers of rAAV obtained by modifying a parental RC2 vector to comprise a non-native P40 promoter sequence (FIG. 11; FIG. 13A; upward striped rectangle) in lieu of the AAV2 serotype P40 promoter of the parental vector. The P5 and P19 promoters are both native AAV2 serotype promoter sequences (solid black rectangle). FIG. 13B shows the production titers of rAAV obtained using such AAV helper plasmid vectors. The following constructs were employed: Parent-RC2, P40(1)-RC2, P40(3)-RC2, P40(4)-RC2, P40(5)-RC2, P40(6)-RC2, P40(7)-RC2, and P40(8)-RC2. The sequences of the promoter regions are shown in Table 1. The production titers of rAAV were obtained using a triple plasmid transfection system with an rAAV, and an Ad helper plasmid that provided the required adenoviral functions.

Figure 14A:
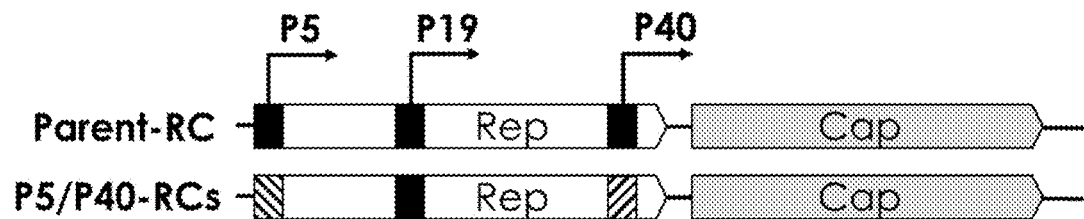
Figure 14B:
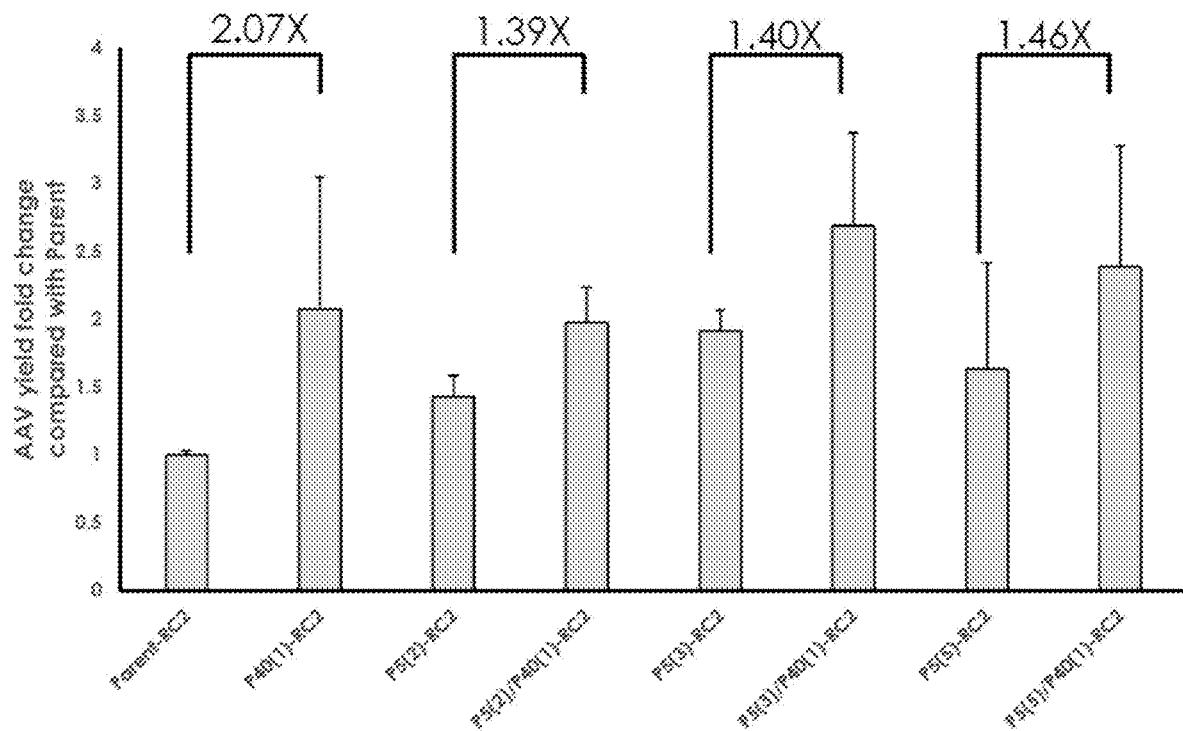

FIGS. 14A-14B show the production titers of rAAV obtained by modifying a parental RC2 vector to comprise a non-native P5 promoter sequence and/or a non-native P40 promoter sequence (FIG. 11; FIG. 14A; P5, downward striped rectangle; P40, upward striped rectangle) in lieu of the AAV2 serotype P5 and P40 promoters of the parental vector. The P19 promoter is a native AAV2 serotype promoter sequences (solid black rectangle). The following constructs were employed: Parent-RC2, P5(2)-RC2, P5(3)-RC2, P5(5)-RC2, P40(1)-RC2, P5(2)/P40(1)-RC2, P5(3)/P40(1)-RC2, and P5(5)/P40(1)-RC2. The sequences of the promoter regions are shown in Table 1. FIG. 14B shows the production titers of rAAV obtained using such AAV helper plasmid vectors. The production titers of rAAV were obtained using a triple plasmid transfection system with an rAAV, and an Ad helper plasmid that provided the required adenoviral functions.

Figure 15A:
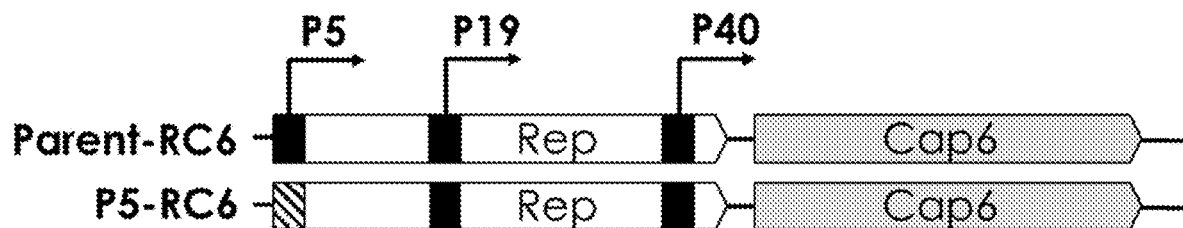
Figure 15B:
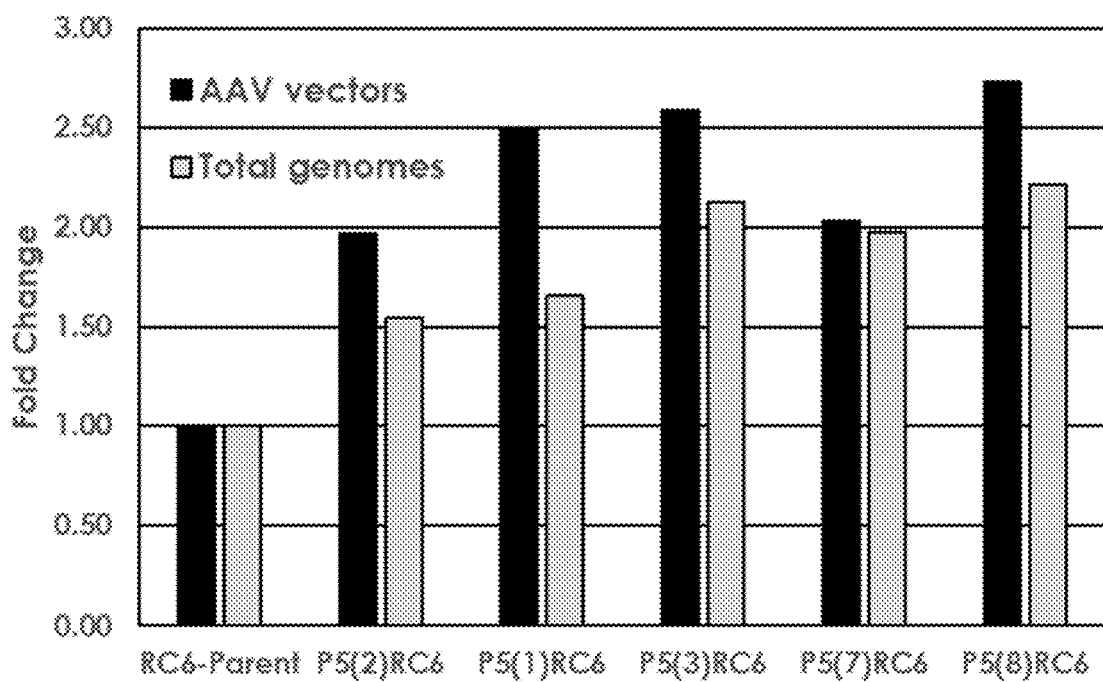
Figure 15C:
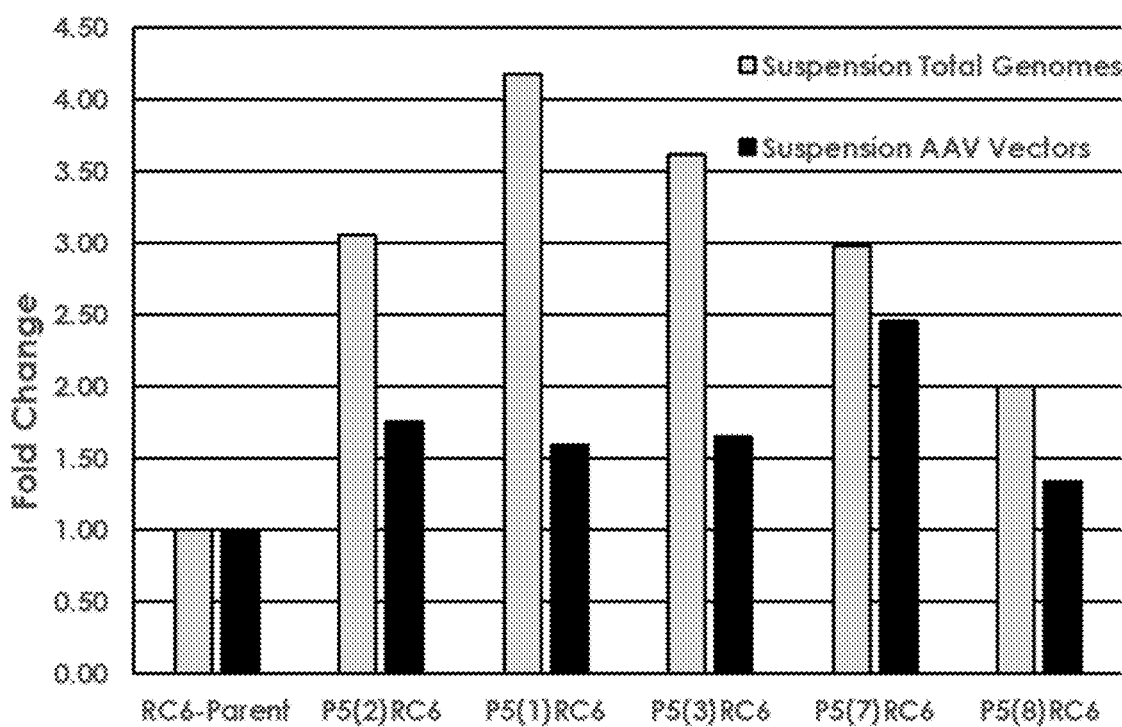

FIGS. 15A-15C show the production titers of rAAV obtained by modifying a parental RC6 vector to comprise a non-native P5 promoter sequence (FIG. 11; FIG. 15A; downward striped rectangle) in lieu of the AAV2 serotype P5 promoter that is natively associated with the rep gene of such vector. The P19 and P40 promoters are both native AAV2 serotype promoter sequences (solid black rectangles). The following constructs were employed: Parent-RC6, P5(1)-RC6, P5(2)-RC6, P5(3)-RC6, P5(7)-RC6 and P5(8)-RC6. The sequences of the promoter regions are shown in Table 1. The production titers of rAAV were obtained (FIGS. 15B-15C) using a triple plasmid transfection system with an rAAV, and an Ad helper plasmid that provided the required adenoviral functions.

Figure 16A:
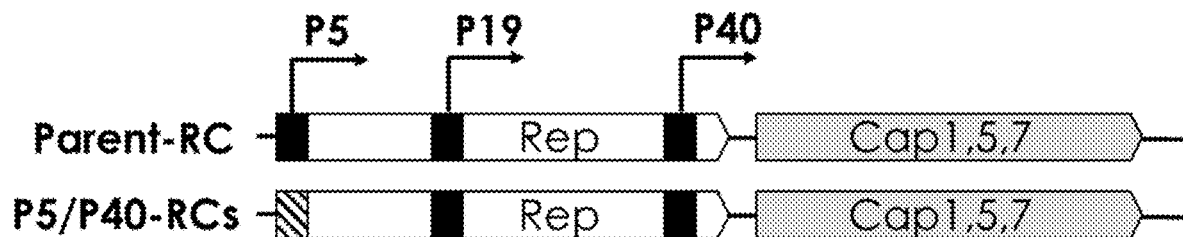
Figure 16B:
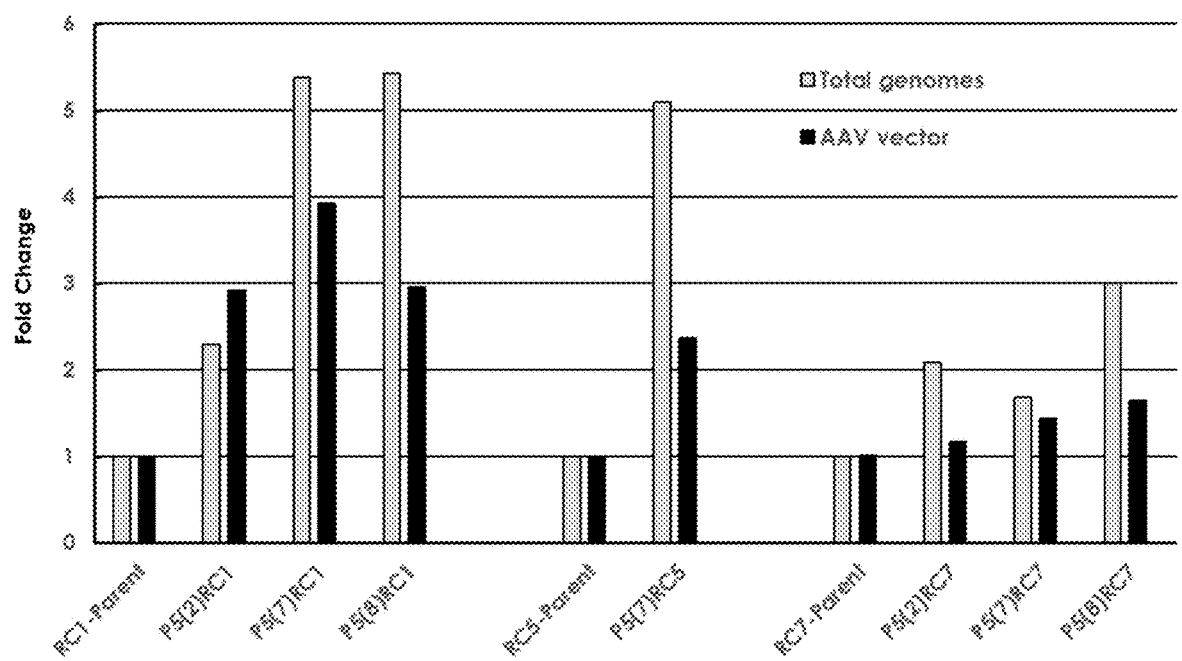

FIGS. 16A-16B show the production titers of rAAV obtained by modifying a parental RC1, RC5, or RC7 vector to comprise a non-native P5 promoter sequence (FIG. 11; FIG. 16A; downward striped rectangle) in lieu of the AAV2 serotype P5 promoter that is natively associated with the rep gene of such vectors. The P19 and P40 promoters are both native AAV2 serotype promoter sequences (solid black rectangles). The following constructs were employed: Parent-RC1, Parent-RC5, Parent-RC7, P5(2)-RC1, P5(7)-RC1, P5(8)-RC1, P5(7)-RC5, P5(2)-RC7, P5(7)-RC7 and P5(8)-RC7. The sequences of the promoter regions are shown in Table 1. The production titers of rAAV (FIG. 16B) were obtained using a triple plasmid transfection system with an rAAV, and an Ad helper plasmid that provided the required adenoviral functions.

DETAILED DESCRIPTION OF THE INVENTION

I. The Methods of the Present Invention

The present invention is directed to recombinantly-modified adeno-associated virus (AAV) helper vectors that are capable of increasing the packaging efficiency of recombinantly-modified adeno-associated virus (rAAV) and their use to improve the packaging efficiency of such rAAV. The present invention is particularly directed to recombinantly-modified adeno-associated virus (AAV) helper vectors that have been further modified to replace (or augment) the P5 and/or P40 promoter sequences that are natively associated with the Rep proteins encoded by such rAAV with AAV P5 and/or P40 promoters that are associated with the Rep proteins of an rAAV of different serotype. The use of such substitute or additional promoter sequences causes increased production of recombinantly-modified adeno-associated virus.

The present invention is based in part on the recognition that high levels of Rep and Cap proteins increase the amount of rAAV genomes particles produced and, consequently, the efficiency of rAAV packaging, and thus result in high production titers of rAAV stocks. It has been unexpectedly found that by replacing the AAV P5 and/or P40 promoters that direct the expression of the Cap proteins with different AAV P5 and/or P40 promoters, or by adding such different AAV P5 and/or P40 promoters in addition to those initially present, causes the desired high levels of rAAV to be attained. AAV Rep proteins are described in U.S. Pat. Nos. 10,214,730; 7,122,348; 6,821,511; 6,753,419; 9,441,206; and 7,115,391.

As discussed above, AAV and rAAV are characterized based on their serotype, which is determined by their capsid proteins (Colella, P. et al. (2018) "*Emerging Issues in AAV-Mediated In Vivo Gene Therapy,*" Molec. Ther. Meth. Clin. Develop. 8:87-104; Hocquemiller, M. et al. (2016) "*Adeno Associated Virus-Based Gene Therapy for CNS Diseases,*" Hum. Gene Ther. 27(7):478-496; Lisowski, L. et al. (2015) "*Adeno-Associated Virus Serotypes For Gene Therapeutics,*" 24:59-67; U.S. Pat. Nos. 10,301,650; 10,266,846; 10,265,417; 10,214,785; 10,214,566; 10,202,657; 10,046,016; 9,884,071; 9,856,539; 9,737,618; 9,677,089; 9,458,517; 9,457,103; 9,441,244; 9,193,956; 8,846,389; 8,507,267; 7,906,111; 7,479,554; 7,186,552; 7,105,345; 6,984,517; 6,962,815; and 6,733,757). By forming AAV and rAAV in the presence of AAV helper function-providing polynucleotides that encode two or more capsid proteins of different serotype, one can produce AAV and rAAV having "hybrid" serotypes. Such AAV and rAAV exhibit the combined trophism of AAV and rAAV having each of such capsid proteins.

The Rep proteins of the different AAV serotypes differ, however, since such proteins are not structural proteins, the differences do not contribute to the observed serotype of an AAV.

Figure 1:
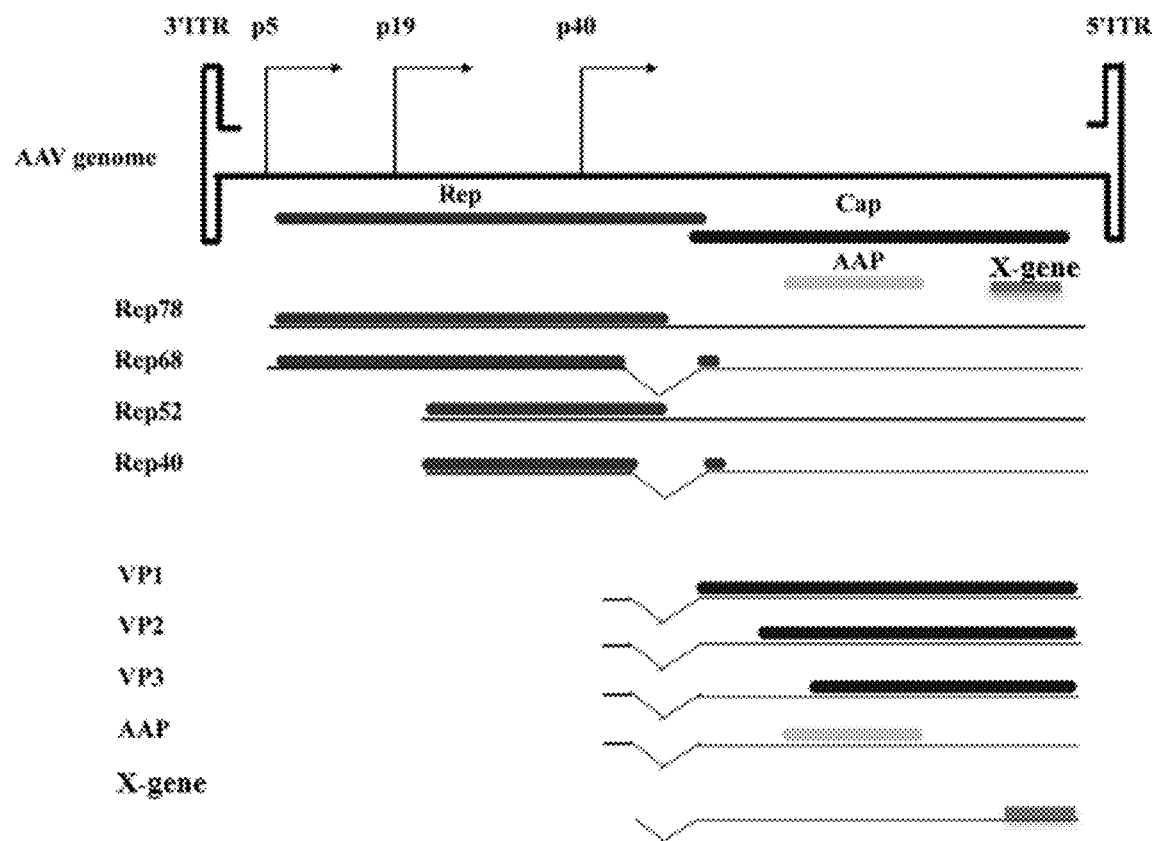
FIG. 1 provides a schematic genetic map of the wild-type (Wt) AAV genome.
Figure 2:
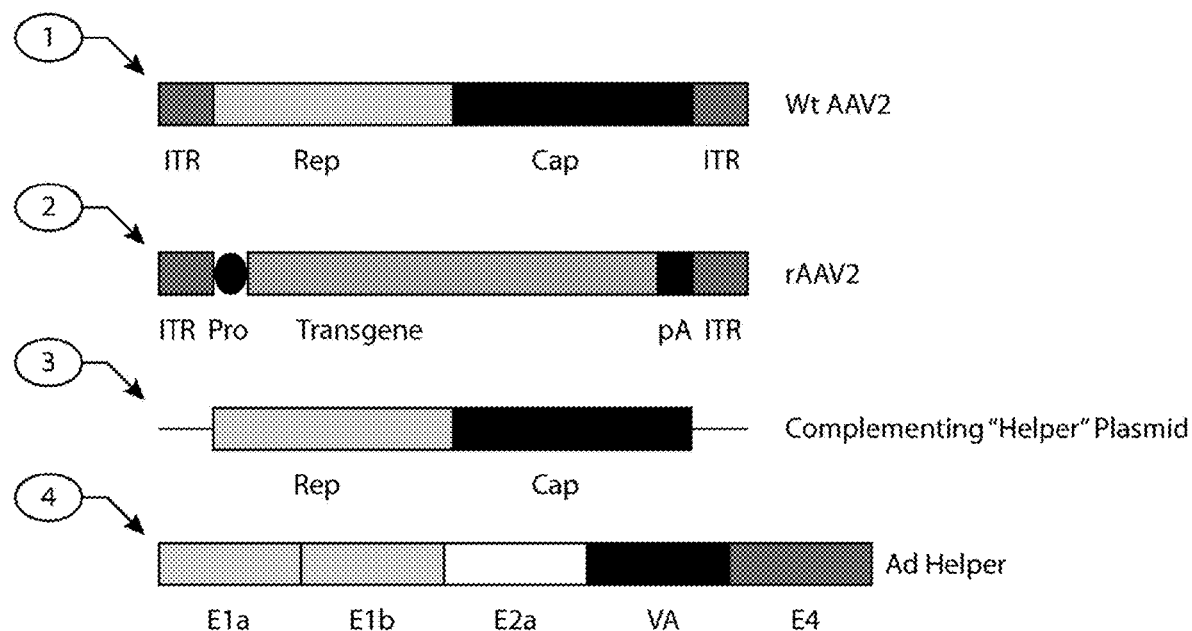
FIG. 2 provides a schematic of the structural domain of the wild-type AAV2 genome (1), a recombinant AAV (rAAV) (2), complementing "AAV helper plasmid" (3) and an adenovirus helper plasmid ("Ad helper plasmid") (4). The wild-type (Wt) AAV2 (1) is composed of AAV-specific palindromic inverted terminal repeated sequences (ITR), a 5' half containing genes that encode the Rep proteins and a 3' half containing genes that encode the Cap proteins. The rAAV (2) is formed by replacing the Rep- and Cap-encoding genes of the wild-type (Wt) AAV2 (1) with a transgene cassette that comprises a promoter (Pro), the exogenous transgene of interest, and a polyadenylation site (pA). In order to produce the rAAV (2), a complementing "AAV helper" plasmid vector (3) and an adenovirus helper plasmid vector (Ad helper plasmid) (4) are provided. The complementing AAV helper plasmid (3) provides Rep and Cap proteins. The Ad helper plasmid (4) provides adenovirus proteins E1a, E1b, E2a, VA and E4.

As used herein, the term "AAV" is intended to denote adeno-associated virus, and may be used to refer to the virus itself or derivatives thereof. The term covers all subtypes and both naturally-occurring and recombinant forms. As used herein, the term "rAAV" is intended to denote a recombinantly-modified version of AAV that comprises a polynucleotide sequence not of AAV origin (i.e., a polynucleotide heterologous to AAV). The rAAV may be single-stranded or double-stranded, and may be composed of deoxyribonucleotides or ribonucleotides. As discussed above, rAAV typically lack certain AAV genes and thus are produced using a double plasmid transfection system, or more preferably a triple plasmid transfection system that comprises a plasmid vector that comprises an AAV helper function-providing polynucleotide, a plasmid vector that comprises a non-AAV helper function-providing polynucleotide, and the rAAV plasmid vector (FIG. 2). In one embodiment, the AAV helper function-providing polynucleotide of such double or triple transfection systems may comprise more than one rep and/or cap gene, so as to be capable of forming rAAV having hybrid serotypes. In another embodiment, a second or additional AAV helper function-providing polynucleotide (for example on a second or additional plasmid vector) may be provided to permit the formation of rAAV having hybrid serotypes.

A. Illustrative AAV Helper Function-Providing Polynucleotides

As used herein, the term "AAV helper functions" denotes AAV proteins (e.g., Rep and Cap) and/or polynucleotides of AAV that are required for the replication and packaging of an rAAV. Such AAV helper functions are provided by an "AAV helper function-providing polynucleotide," which as such term is used herein is a virus, plasmid vector, a non-plasmid vector, or a polynucleotide that has been integrated into a cellular chromosome, that provides AAV helper functions. AAV helper plasmids that may be used in accordance with the present invention to provide AAV helper functions include pAAV-RC (Agilent; Addgene; Cell Biolabs), pAAV-RC1, pAAV-RC2, pAAV-RC5, pAAV-RC6, and pAAV-RC7.

1. Plasmid pAAV-RC1

Figure 3:
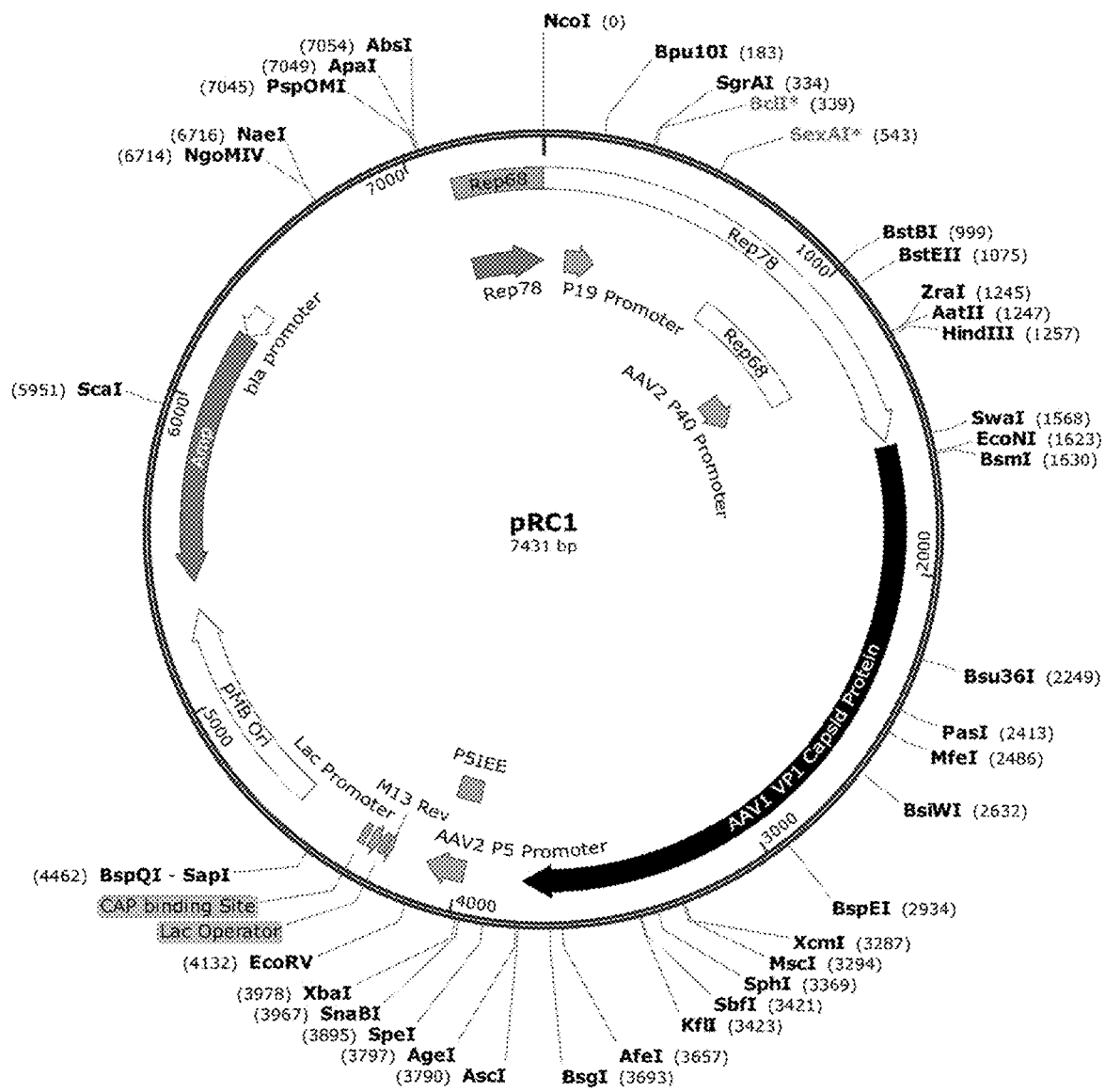
FIG. 3 shows a map of the AAV helper plasmid vector pAAV-RC1 (SEQ ID NO:1).

Plasmid pAAV-RC1 (SEQ ID NO:1; FIG. 3) is an AAV helper plasmid that expresses AAV1 serotype capsid proteins that may be used in accordance with the present invention to provide AAV helper functions. The P5 and P40 promoters of pAAV-RC1 are AAV2 serotype promoters (SEQ ID NO:10 and SEQ ID NO:18, respectively).

```
Coding Strand of Plasmid pAAV-RC1
(SEQ ID NO: 1):
catggttttg ggacgtttcc tgagtcagat tcgcgaaaaa ctgattcaga gaatttaccg cgggatcgag ccgactttgc caaactggtt cgcggtcaca aagaccagaa atggcgccgg aggcgggaac aaggtggtgg atgagtgcta catcccaat tacttgctcc ccaaaaccca gcctgagctc cagtgggcgt ggactaatat ggaacagtat ttaagcgcct gtttgaatct cacggagcgt aaacggttgg tggcgcagca tctgacgcac gtgtcgcaga cgcaggagca gaacaaagag aatcagaatc ccaattctga tgcgccggtg atcagatcaa aaacttcagc caggtacatg gagctggtcg ggtggctcgt ggacaagggg attacctcgg agaagcagtg gatccaggag gaccaggcct catacatctc cttcaatgcg gcctccaact cgcggtccca aatcaaggct gccttggaca atgcgggaaa gattatgagc ctgactaaaa ccgccccga ctacctggtg ggccagcagc ccgtggagga catttccagc aatcggattt ataaaatttt ggaactaaac gggtacgatc cccaatatgc ggcttccgtc tttctgggat gggccacgaa aaagttcggc aagaggaaca
```

```
ccatctggct gtttgggcct gcaactaccg ggaagaccaa catcgcggag gccatagccc acactgtgcc cttctacggg tgcgtaaact ggaccaatga aactttccc ttcaacgact gtgtcgacaa gatggtgatc tggtgggagg aggggaagat gaccgccaag gtcgtggagt cggccaaagc cattctcgga ggaagcaagg tgcgcgtgga ccagaaatgc aagtcctcgg cccagataga cccgactccc gtgatcgtca cctccaacac caacatgtgc gccgtgattg acgggaactc aacgaccttc gaacaccagc agccgttgca agaccggatg ttcaaatttg aactcacccg ccgtctggat catgactttg ggaaggtcac caagcaggaa gtcaaagact ttttccggtg ggcaaaggat cacgtggttg aggtggagca tgaattctac gtcaaaaagg gtggagccaa gaaaagaccc gccccagtg acgcagatat aagtgagccc aaacgggtgc gcgagtcagt tgcgcagcca tcgacgtcag acgcggaagc ttcgatcaac tacgcagaca ggtaccaaaa caaatgttct cgtcacgtgg gcatgaatct gatgctgttt ccctgcagac aatgcgagag aatgaatcag aattcaaata tctgcttcac tcacggacag aaagactgtt tagagtgctt tcccgtgtca gaatctcaac ccgtttctgt cgtcaaaaag gcgtatcaga aactgtgcta cattcatcat atcatgggaa aggtgccaga cgcttgcact gcctgcgatc tggtcaatgt ggatttggat gactgcatct ttgaacaata aatgatttaa atcaggtatg gctgccgatg gttatcttcc agattggctc gaggacaacc tctctgaggg cattcgcgag tggtgggact tgaaacctgg agccccgaag cccaaagcca accagcaaaa gcaggacgac ggccggggtc tggtgcttcc tggctacaag tacctcggac ccttcaacgg actcgacaag ggggagcccg tcaacgcggc ggacgcagcg gccctcgagc acgacaaggc ctacgaccag cagctcaaag cgggtgacaa tccgtacctg cggtataacc acgccgacgc cgagtttcag gagcgtctgc aagaagatac gtcttttggg ggcaacctcg ggcgagcagt cttccaggcc aagaagcggg ttctcgaacc tctcggtctg gttgaggaag cgctaagac ggctcctgga aagaaacgtc cggtagagca gtcgccacaa gagccagact cctcctcggg catcggcaag acaggccagc agcccgctaa aaagagactc aattttggtc agactggcga ctcagagtca gtccccgatc cacaacctct cggagaacct ccagcaaccc ccgctgctgt gggacctact acaatggctt caggcggtgg cgcaccaatg gcagacaata acgaaggcgc cgacggagtg ggtaatgcct caggaaattg gcattgcgat tccacatggc
```

-continued

```
tgggcgacag agtcatcacc accagcaccc gcacctgggc
cttgcccacc tacaataacc acctctacaa gcaaatctcc
agtgcttcaa cgggggccag caacgacaac cactacttcg
gctacagcac ccctgggg tattttgatt tcaacagatt
ccactgccac ttttcaccac gtgactggca gcgactcatc
aacaacaatt ggggattccg gcccaagaga ctcaacttca
aactcttcaa catccaagtc aaggaggtca cgacgaatga
tggcgtcaca accatcgcta ataaccttac cagcacggtt
caagtcttct cggactcgga gtaccagctt ccgtacgtcc
tcggctctgc gcaccagggc tgcctccctc cgttcccggc
ggacgtgttc atgattccgc aatacgcta cctgacgctc
aacaatggca gccaagccgt gggacgttca tcctttact
gcctggaata tttcccttct cagatgctga gaacgggcaa
caactttacc ttcagctaca cctttgagga agtgcctttc
cacagcagct acgcgcacag ccagagcctg gaccggctga
tgaatcctct catcgaccaa tacctgtatt acctgaacag
aactcaaaat cagtccgaa gtgcccaaaa caaggacttg
ctgtttagcc gtgggtctcc agctggcatg tctgttcagc
ccaaaaactg gctacctgga ccctgttatc ggcagcagcg
cgtttctaaa acaaaaacag acaacaacaa cagcaatttt
acctggactg gtgcttcaaa atataacctc aatgggcgtg
aatccatcat caaccctggc actgctatgg cctcacacaa
agacgacgaa gacaagtct ttcccatgag cggtgtcatg
attttggaa aagagagcgc cggagcttca aacactgcat
tggacaatgt catgattaca acgaagagg aaattaaagc
cactaaccct gtggccaccg aaagatttgg gaccgtggca
gtcaatttcc agagcagcag cacagaccct gcgaccggag
atgtgcatgc tatgggagca ttacctggca tggtgtggca
agatagagac gtgtacctgc agggtcccat ttgggccaaa
attcctcaca cagatggaca cttcaccccg tctcctctta
tgggcggctt tggactcaag aacccgcctc ctcagatcct
catcaaaaac acgcctgttc ctgcgaatcc tccggcggag
ttttcagcta caagttttgc ttcattcatc acccaatact
ccacaggaca agtgagtgtg aaattgaat gggagctgca
gaaagaaaac agcaagcgct ggaatcccga agtgcagtac
acatccaatt atgcaaaatc tgccaacgtt gatttactg
tggacaacaa tggactttat actgagcctc gccccattgg
caccgtttac cttacccgtc ccctgtaagg cgccgccacg
gttgcttgtt aatcaataaa ccgtttaatt cgtttcagtt
gaactttggt ctctgcgtat ttcttttctta tctagtttcc
atgctctagg atccactagt aacgccgcc agtgtgctgg
```

-continued

```
aattcggctt tgtagttaat gattaacccg ccatgctact
tatctacgta gccatgctct agaggtcctg tattagaggt
cacgtgagtg ttttgcgaca ttttgcgaca ccatgtggtc
acgctgggta tttaagcccg agtgagcacg cagggtctcc
attttgaagc gggaggtttg aacgcgcagc cgccaagccg
aattctgcag atatccaaac actggcggcc gctcgactag
agcggccgcc accgcggtgg agctccagct tttgttccct
ttagtgaggg ttaattgcgc gcttggcgta atcatggtca
tagctgtttc ctgtgtgaaa ttgttatccg ctcacaattc
cacacaacat acgagccgga agcataaagt gtaaagcctg
gggtgcctaa tgagtgagct aactcacatt aattgcgttg
cgctcactgc ccgctttcca gtcgggaaac ctgtcgtgcc
agctgcatta tgaatcggc caacgcgcgg ggagaggcgg
tttgcgtatt gggcgctctt ccgcttcctc gctcactgac
tcgctgcgct cggtcgttcg gctgcggcga gcggtatcag
ctcactcaaa ggcggtaata cggttatcca cagaatcagg
ggataacgca ggaaagaaca tgtgagcaaa aggccagcaa
aaggccagga accgtaaaaa ggccgcgttg ctggcgtttt
tccataggct ccgcccccct gacgagcatc acaaaaatcg
acgctcaagt cagaggtggc gaaacccgac aggactataa
agataccagg cgtttccccc tggaagctcc ctcgtgcgct
ctcctgttcc gaccctgccg cttaccggat acctgtccgc
cttttctccct tcgggaagcg tggcgctttc tcatagctca
cgctgtaggt atctcagttc ggtgtaggtc gttcgctcca
agctgggctg tgtgcacgaa ccccccgttc agcccgaccg
ctgcgcctta tccggtaact atcgtcttga gtccaacccg
gtaagacacg acttatcgcc actggcagca gccactggta
acaggattag cagagcgagg tatgtaggcg gtgctacaga
gttcttgaag tggtggccta actacggcta cactagaaga
acagtatttg gtatctgcgc tctgctgaag ccagttacct
tcggaaaaag agttggtagc tcttgatccg gcaaacaaac
caccgctggt agcggtggtt ttttgtttg caagcagcag
attacgcgca gaaaaaaagg atctcaagaa gatcctttga
tcttttctac ggggtctgac gctcagtgga acgaaaactc
acgttaaggg attttggtca tgagattatc aaaaaggatc
ttcacctaga tcctttttaaa ttaaaaatga agttttaaat
caatctaaag tatatatgag taaacttggt ctgacagtta
ccaatgctta atcagtgagg cacctatctc agcgatctgt
ctatttcgtt catccatagt tgcctgactc cccgtcgtgt
agataactac gatacgggag ggcttaccat ctggccccag
```

-continued

```
tgctgcaatg ataccgcgag acccacgctc accggctcca gatttatcag caataaacca gccagccgga agggccgagc gcagaagtgg tcctgcaact ttatccgcct ccatccagtc tattaattgt tgccgggaag ctagagtaag tagttcgcca gttaatagtt tgcgcaacgt tgttgccatt gctacaggca tcgtggtgtc acgctcgtcg tttggtatgg cttcattcag ctccggttcc caacgatcaa ggcgagttac atgatccccc atgttgtgca aaaaagcggt tagctccttc ggtcctccga tcgttgtcag aagtaagttg gccgcagtgt tatcactcat ggttatggca gcactgcata attctcttac tgtcatgcca tccgtaagat gcttttctgt gactggtgag tactcaacca agtcattctg agaatagtgt atgcggcgac cgagttgctc ttgcccggcg tcaatacggg ataataccgc gccacatagc agaactttaa aagtgctcat cattggaaaa cgttcttcgg ggcgaaaact ctcaaggatc ttaccgctgt tgagatccag ttcgatgtaa cccactcgtg cacccaactg atcttcagca tcttttactt tcaccagcgt ttctgggtga gcaaaaacag gaaggcaaaa tgccgcaaaa aagggaataa gggcgacacg gaaatgttga atactcatac tcttcctttt tcaatattat tgaagcattt atcagggtta ttgtctcatg agcggataca tatttgaatg tatttagaaa aataaacaaa taggggttcc gcgcacattt ccccgaaaag tgccacctaa attgtaagcg ttaatatttt gttaaaattc gcgttaaatt tttgttaaat cagctcattt tttaaccaat aggccgaaat cggcaaaatc ccttataaat caaaagaata gaccgagata gggttgagtg ttgttccagt ttggaacaag agtccactat taaagaacgt ggactccaac gtcaaagggc gaaaaaccgt ctatcagggc gatggcccac tacgtgaacc atcaccctaa tcaagttttt tggggtcgag gtgccgtaaa gcactaaatc ggaaccctaa agggagcccc cgatttagag cttgacgggg aaagccggcg aacgtggcga aaggaaggaa gaagaaagcg aaaggagcgg gcgctagggc gctggcaagt gtagcggtca cgctgcgcgt aaccaccaca cccgccgcgc ttaatgcgcc gctacagggc gcgtcccatt cgccattcag gctgcgcaac tgttgggaag ggcgatcggt gcgggcctct tcgctattac gccagctggc gaaaggggga tgtgctgcaa ggcgattaag ttgggtaacg ccagggtttt cccagtcacg acgttgtaaa acgacggcca gtgagcgcgc gtaatacgac tcactatagg gcgaattggg taccgggccc cccctcgagg tcgacggtat cggggggagct cgcagggtct ccattttgaa gcgggaggtt tgaacgcgca gccgccatgc cggggtttta cgagattgtg attaaggtcc
```

-continued

```
ccagcgacct tgacgagcat ctgcccggca tttctgacag ctttgtgaac tgggtggccg agaaggaatg ggagttgccg ccagattctg acatggatct gaatctgatt gagcaggcac ccctgaccgt ggccgagaag ctgcagcgcg actttctgac ggaatggcgc cgtgtgagta aggccccgga ggctcttttc tttgtgcaat ttgagaagga gagagctac ttccacatgc acgtgctcgt ggaaaccacc ggggtgaaat c
```

In SEQ ID NO:1, residues 1-1561 of pAAV-RC1 encode the Rep protein, Rep78 (with residues 95-221 corresponding to the AAV2 P19 promoter and residues 1075-1254 corresponding to the AAV2 P40 promoter (SEQ ID NO:18)); residues 1578-3788 encode the AAV1 VP1 capsid protein; residues 7127-7431 encode a portion of the Rep68 protein; residues 3984-4114 correspond to AAV2 P5 promoter sequences (SEQ ID NO:10); residues 4237-4253 are M13 Rev sequences; residues 4261-4277 are Lac operator sequences; 4285-4315 are Lac promoter sequences; residues 4578-5302 correspond to pMB ori sequences, residues 5398-6258 encode an ampicillin resistance determinant; and residues 6259-6357 are bla promoter sequences (FIG. 3).

2. Plasmid pAAV-RC2

Figure 4:
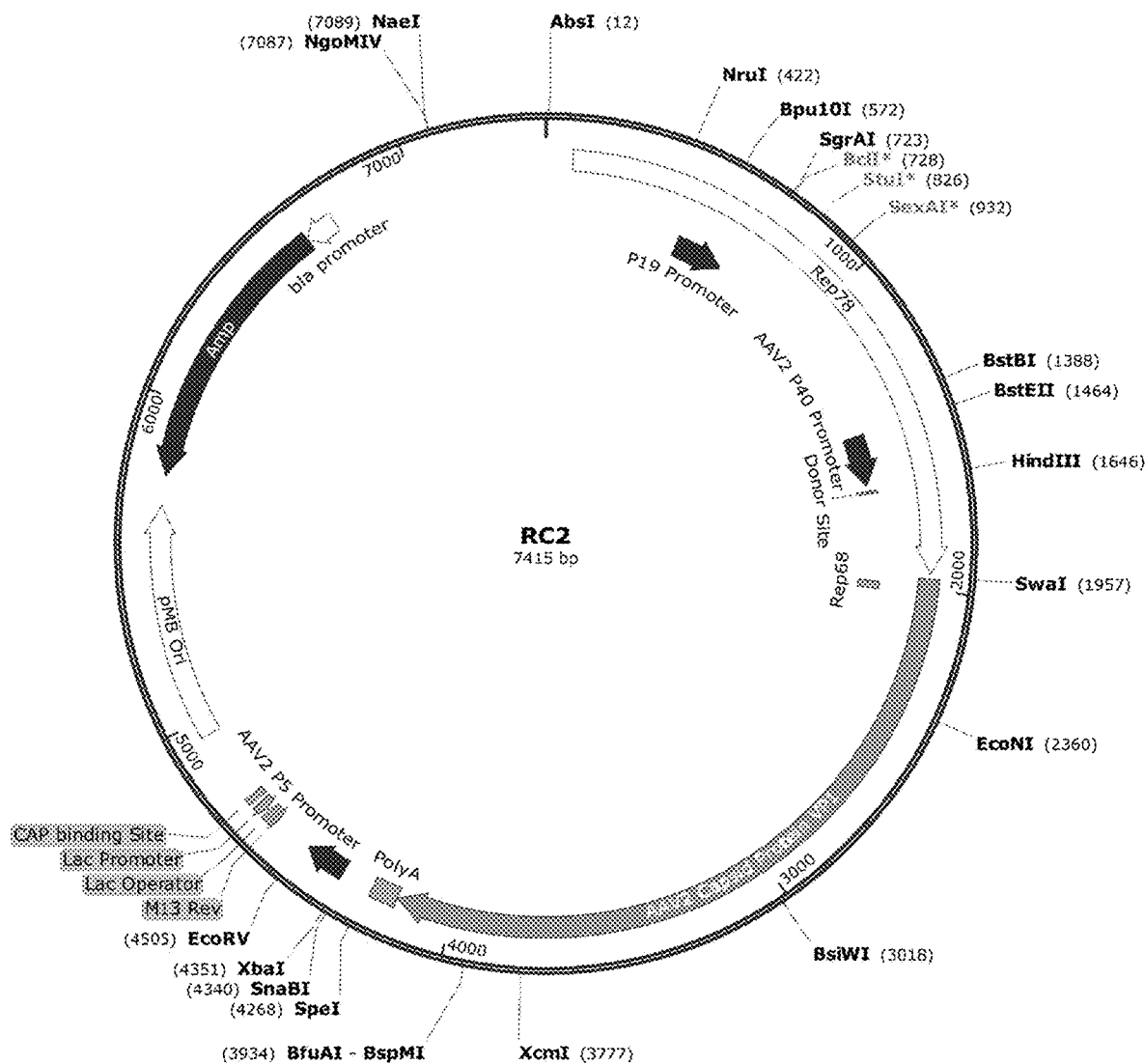
FIG. 4 shows a map of the AAV helper plasmid vector pAAV-RC2 (SEQ ID NO:2).

Plasmid pAAV-RC2 (SEQ ID NO:2; FIG. 4) is an AAV helper plasmid that expresses AAV2 serotype capsid proteins that may be used in accordance with the present invention to provide AAV helper functions. The P5 and P40 promoters of pAAV-RC2 are AAV2 serotype promoters (SEQ ID NO:10 and SEQ ID NO:18, respectively).

```
Coding Strand of Plasmid pAAV-RC2
(SEQ ID NO: 2):
ccgggccccc cctcgaggtc gacggtatcg ggggagctcg cagggtctcc attttgaagc gggaggtttg aacgcgcagc cgccatgccg gggttttacg agattgtgat taaggtcccc agcgaccttg acgagcatct gcccggcatt tctgacagct ttgtgaactg ggtggccgag aaggaatggg agttgccgcc agattctgac atggatctga atctgattga gcaggcaccc ctgaccgtgg ccgagaagct gcagcgcgac tttctgacgg aatggcgccg tgtgagtaag gccccggagg ctcttttctt tgtgcaattt gagaaggag agagctactt ccacatgcac gtgctcgtgg aaaccaccgg ggtgaaatcc atggttttgg gacgtttcct gagtcagatt cgcgaaaaac tgattcagag aatttaccgc gggatcgagc gactttgcc aaactggttc gcggtcacaa agaccagaaa tggcgccgga ggcgggaaca aggtggtgga tgagtgctac atccccaatt acttgctccc caaaaccag cctgagctcc agtgggcgtg gactaatatg gaacagtatt taagcgcctg tttgaatctc acggagcgta aacggttggt ggcgcagcat ctgacgcacg tgtcgcagac gcaggagcag aacaaagaga atcagaatcc caattctgat
```

-continued

```
gcgccggtga tcagatcaaa aacttcagcc aggtacatgg
agctggtcgg gtggctcgtg gacaaggggg ttacctcgga
gaagcagtgg atccaggagg accaggcctc atacatctcc
ttcaatgcgg cctccaactc gcggtcccaa atcaaggctg
ccttggacaa tgcgggaaag attatgagcc tgactaaaac
cgcccccgac tacctggtgg ccagcagcc gtggaggac
atttccagca atcggattta taaattttg gaactaaacg
ggtacgatcc ccaatatgcg gcttccgtct ttctgggatg
ggccacgaaa aagttcggca agaggaacac catctggctg
tttgggcctg caactaccgg gaagaccaac atcgcggagg
ccatagccca cactgtgccc ttctacgggt gcgtaaactg
gaccaatgag aactttccct tcaacgactg tgtcgacaag
atggtgatct ggtgggagga ggggaagatg accgccaagg
tcgtggagtc ggccaaagcc attctcggag gaagcaaggt
gcgcgtggac cagaaatgca agtcctcggc ccagatagac
ccgactcccg tgatcgtcac ctccaacacc aacatgtgcg
ccgtgattga cgggaactca acgaccttcg aacaccagca
gccgttgcaa gaccggatgt tcaaatttga actcacccgc
cgtctggatc atgactttgg aaggtcacc aagcaggaag
tcaaagactt tttccggtgg gcaaaggatc acgtggttga
ggtggagcat gaattctacg tcaaaaaggg tggagccaag
aaaagacccg cccccagtga cgcagatata agtgagccca
aacgggtgcg cgagtcagtt gcgcagccat cgacgtcaga
cgcggaagct tcgatcaact acgcagacag gtaccaaaac
aaatgttctc gtcacgtggg catgaatctg atgctgtttc
cctgcagaca atgcgagaga atgaatcaga attcaaatat
ctgcttcact cacggacaga aagactgttt agagtgcttt
cccgtgtcag aatctcaacc cgtttctgtc gtcaaaaagg
cgtatcagaa actgtgctac attcatcata tcatgggaaa
ggtgccagac gcttgcactg cctgcgatct ggtcaatgtg
gatttggatg actgcatctt tgaacaataa atgatttaaa
tcaggtatgg ctgccgatgg ttatcttcca gattggctcg
aggacactct ctctgaagga ataagacagt ggtggaagct
caaacctggc ccaccaccac caaagcccgc agagcggcat
aaggacgaca gcaggggtct tgtgcttcct gggtacaagt
acctcggacc cttcaacgga ctcgacaagg gagagccggt
caacgaggca gacgccgcgg ccctcgagca cgacaaagcc
tacgaccggc agctcgacag cggagacaac ccgtacctca
agtacaacca cgccgacgcg gagtttcagg agcgccttaa
agaagatacg tcttttgggg gcaacctcgg acgagcagtc
ttccaggcga aaaagagggt tcttgaacct ctgggcctgg
```

-continued

```
ttgaggaacc tgttaagacg gctccgggaa aaagaggcc
ggtagagcac tctcctgtgg agccagactc ctcctcggga
accggaaagg cgggccagca gcctgcaaga aaagattga
attttggtca gactggagac gcagactcag tacctgaccc
ccagcctctc ggacagccac cagcagcccc ctctggtctg
ggaactaata cgatggctac aggcagtggc gcaccaatgg
cagacaataa cgagggcgcc gacggagtgg gtaattcctc
gggaaattgg cattgcgatt ccacatggat gggcgacaga
gtcatcacca ccagcacccg aacctgggcc ctgcccacct
acaacaacca cctctacaaa caaatttcca gccaatcagg
agcctcgaac gacaatcact actttggcta cagcacccct
tggggtatt ttgacttcaa cagattccac tgccactttt
caccacgtga ctggcaaaga ctcatcaaca caaactgggg
attccgaccc aagagactca acttcaagct ctttaacatt
caagtcaaag aggtcacgca gaatgacggt acgacgacga
ttgccaataa ccttaccagc acggttcagg tgtttactga
ctcggagtac cagctcccgt acgtcctcgg ctcggcgcat
caaggatgcc tcccgccgtt cccagcagac gtcttcatgg
tgccacagta tggataccte accctgaaca cgggagtca
ggcagtagga cgctcttcat tttactgcct ggagtacttt
ccttctcaga tgctgcgtac cggaaacaac tttaccttca
gctacacttt tgaggacgtt cctttccaca gcagctacgc
tcacagccag agtctggacc gtctcatgaa tcctctcatc
gaccagtacc tgtattactt gagcagaaca aacactccaa
gtggaaccac cacgcagtca aggcttcagt tttctcaggc
cggagcgagt gacattcggg accagtctag gaactggctt
cctggaccct gttaccgcca gcagcgagta tcaaagacat
ctgcggataa caacaacagt gaatactcgt ggactggagc
taccaagtac cacctcaatg gcagagactc tctggtgaat
ccgggcccgg ccatggcaag ccacaaggac gatgaagaaa
agttttttcc tcagagcggg gttctcatct ttgggaagca
aggctcagag aaaacaaatg tggacattga aaggtcatg
attacagacg aagaggaaat caggacaacc aatcccgtgg
ctacggagca gtatggttct gtatctacca acctccagag
aggcaacaga caagcagcta ccgcagatgt caacacacaa
ggcgttcttc aggcatggt ctggcaggac agagatgtgt
accttcaggg gcccatctgg gcaaagattc cacacacgga
cggacatttt caccccctct ccctcatggg tggattcgga
cttaaacacc ctcctccaca gattctcatc aagaacaccc
cggtacctgc gaatccttcg accaccttca gtgcggcaaa
```

```
gtttgcttcc ttcatcacac agtactccac gggacaggtc
agcgtggaga tcgagtggga gctgcagaag gaaaacagca
aacgctggaa tcccgaaatt cagtacactt ccaactacaa
caagtctgtt aatgtggact ttactgtgga cactaatggc
gtgtattcag agcctcgccc cattggcacc agatacctga
ctcgtaatct gtaattgctt gttaatcaat aaaccgttta
attcgtttca gttgaacttt ggtctctgcg tatttctttc
ttatctagtt tccatgtctc aggatccact agtaacggcc
gccagtgtgc tggaattcgg ctttgtagtt aatgattaac
ccgccatgct acttatctac gtagccatgc tctagaggtc
ctgtattaga ggtcacgtga gtgttttgcg acattttgcg
acaccatgtg gtcacgctgg gtatttaagc ccgagtgagc
acgcagggtc tccatttga agcgggaggt ttgaacgcgc
agccgccaag ccgaattctg cagatatcca aacactggcg
gccgctcgac tagagcggcc gccaccgcgg tggagctcca
gcttttgttc cctttagtga gggttaattg cgcgcttggc
gtaatcatgg tcatagctgt ttcctgtgtg aaattgttat
ccgctcacaa ttccacacaa catacgagcc ggaagcataa
agtgtaaagc ctggggtgcc taatgagtga gctaactcac
attaattgcg ttgcgctcac tgcccgcttt ccagtcggga
aacctgtcgt gccagctgca ttaatgaatc ggccaacgcg
cggggagagg cggtttgcgt attgggcgct cttccgcttc
ctcgctcact gactcgctgc gctcggtcgt tcggctgcgg
cgagcggtat cagctcactc aaaggcggta atacggttat
ccacagaatc aggggataac gcaggaaaga acatgtgagc
aaaaggccag caaaaggcca ggaaccgtaa aaaggccgcg
ttgctggcgt ttttccatag gctccgcccc cctgacgagc
atcacaaaaa tcgacgctca agtcagaggt ggcgaaaccc
gacaggacta taaagatacc aggcgtttcc ccctggaagc
tccctcgtgc gctctcctgt tccgaccctg ccgcttaccg
gatacctgtc cgcctttctc ccttcgggaa gcgtggcgct
ttctcatagc tcacgctgta ggtatctcag ttcggtgtag
gtcgttcgct ccaagctggg ctgtgtgcac gaaccccccg
ttcagcccga ccgctgcgcc ttatccggta actatcgtct
tgagtccaac ccggtaagac acgacttatc gccactggca
gcagccactg gtaacaggat tagcagagcg aggtatgtag
gcggtgctac agagttcttg aagtggtggc ctaactacgg
ctacactaga agaacagtat ttggtatctg cgctctgctg
aagccagtta ccttcggaaa aagagttggt agctcttgat
ccggcaaaca aaccaccgct ggtagcggtg gtttttttgt
ttgcaagcag cagattacgc gcagaaaaaa aggatctcaa
```

```
gaagatcctt tgatcttttc tacggggtct gacgctcagt
ggaacgaaaa ctcacgttaa gggattttgg tcatgagatt
atcaaaaagg atcttcacct agatcctttt aaattaaaaa
tgaagtttta atcaatcta aagtatatat gagtaaactt
ggtctgacag ttaccaatgc ttaatcagtg aggcacctat
ctcagcgatc tgtctatttc gttcatccat agttgcctga
ctccccgtcg tgtagataac tacgatacgg gagggcttac
catctggccc cagtgctgca atgataccgc gagacccacg
ctcaccggct ccagatttat cagcaataaa ccagccagcc
ggaagggccg agcgcagaag tggtcctgca actttatccg
cctccatcca gtctattaat tgttgccggg aagctagagt
aagtagttcg ccagttaata gtttgcgcaa cgttgttgcc
attgctacag gcatcgtggt gtcacgctcg tcgtttggta
tggcttcatt cagctccggt tcccaacgat caaggcgagt
tacatgatcc cccatgttgt gcaaaaaagc ggttagctcc
ttcggtcctc cgatcgttgt cagaagtaag ttggccgcag
tgttatcact catggttatg gcagcactgc ataattctct
tactgtcatg ccatccgtaa gatgcttttc tgtgactggt
gagtactcaa ccaagtcatt ctgagaatag tgtatgcggc
gaccgagttg ctcttgcccg gcgtcaatac gggataatac
cgcgccacat agcagaactt taaaagtgct catcattgga
aaacgttctt cggggcgaaa actctcaagg atcttaccgc
tgttgagatc cagttcgatg taacccactc gtgcacccaa
ctgatcttca gcatctttta ctttcaccag cgtttctggg
tgagcaaaaa caggaaggca aaatgccgca aaaaagggaa
taagggcgac acggaaatgt tgaatactca tactcttcct
ttttcaatat tattgaagca tttatcaggg ttattgtctc
atgagcggat acatatttga atgtatttag aaaaataaac
aaataggggt tccgcgcaca tttccccgaa aagtgccacc
taaattgtaa gcgttaatat tttgttaaaa ttcgcgttaa
attttttgtta aatcagctca ttttttaacc aataggccga
aatcggcaaa atcccttata atcaaaagaa atagaccgag
ataggttga gtgttgttcc agtttggaac aagagtccac
tattaaagaa cgtggactcc aacgtcaaag ggcgaaaaac
cgtctatcag ggcgatggcc cactacgtga accatcaccc
taatcaagtt ttttggggtc gaggtgccgt aaagcactaa
atcggaaccc taaagggagc cccgatttta gagcttgacg
gggaaagccg gcgaacgtgg cgagaaagga agggaagaaa
gcgaaaggag cgggcgctag ggcgctggca agtgtagcgg
tcacgctgcg cgtaaccacc acacccgccg cgcttaatgc
```

-continued
```
gccgctacag ggcgcgtccc attcgccatt caggctgcgc aactgttggg aagggcgatc ggtgcgggcc tcttcgctat tacgccagct ggcgaaaggg ggatgtgctg caaggcgatt aagttgggta acgccagggt tttcccagtc acgacgttgt aaaacgacgg ccagtgagcg cgcgtaatac gactcactat agggcgaatt gggta
```

In SEQ ID NO:2, residues 85-1950 of pAAV-RC2 encode the Rep protein, Rep78 (with residues 484-663 corresponding to the AAV2 P19 promoter, residues 1464-1643 corresponding to the AAV2 P40 promoter (SEQ ID NO:18) and residues 1668-1676 being a donor site); residues 1967-4174 encode the AAV2 VP1 capsid protein; residues 1992-2016 encode a portion of the Rep68 protein; residues 4175-4256 encode a polyA sequence; residues 4357-4487 correspond to the AAV2 P5 promoter sequences of SEQ ID NO:10); residues 4610-4626 are M13 Rev sequences; residues 4634-4650 are Lac operator sequences; 4658-4688 are Lac promoter sequences; residues 4951-5675 correspond to pMB ori sequences, residues 5771-6631 encode an ampicillin resistance determinant; and residues 6632-6730 are bla promoter sequences (FIG. 4).

3. Plasmid pAAV-RC5

Figure 5:
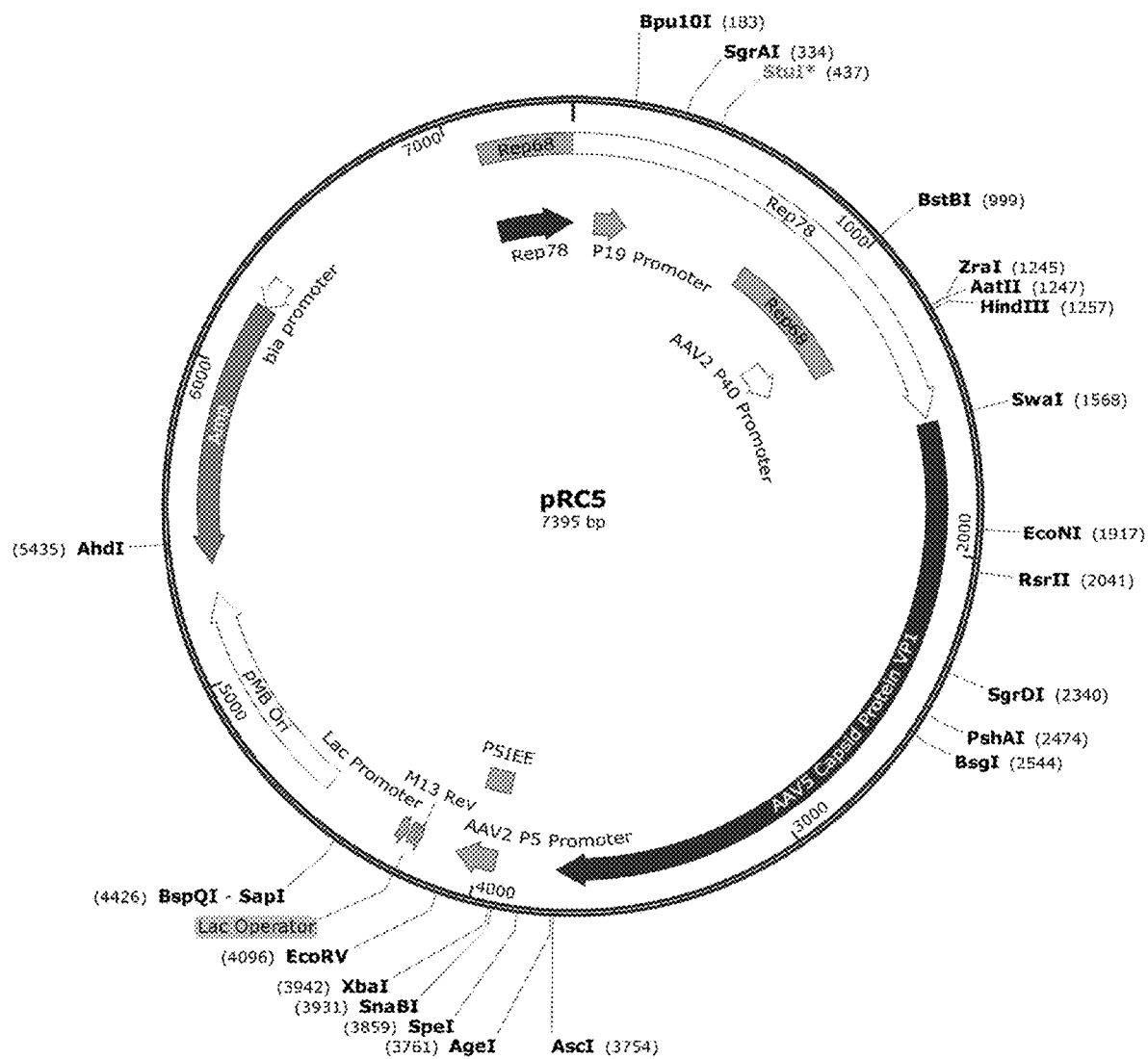
FIG. 5 shows a map of the AAV helper plasmid vector pAAV-RC5 (SEQ ID NO:3).

Plasmid pAAV-RC5 (SEQ ID NO:3; FIG. 5) is an AAV helper plasmid that expresses AAV5 serotype capsid proteins that may be used in accordance with the present invention to provide AAV helper functions. The P5 and P40 promoters of pAAV-RC5 are AAV2 serotype promoters (SEQ ID NO:10 and SEQ ID NO:18, respectively).

```
Coding Strand of Plasmid pAAV-RC5 (SEQ ID NO: 3):
catggttttg ggacgtttcc tgagtcagat tcgcgaaaaa ctgattcaga gaatttaccg cgggatcgag ccgactttgc caaactggtt cgcggtcaca aagaccagaa atggcgccgg aggcgggaac aaggtggtgg atgagtgcta catccccaat tacttgctcc ccaaaaccca gcctgagctc cagtgggcgt ggactaatat ggaacagtat ttaagcgcct gtttgaatct cacggagcgt aaacggttgg tggcgcagca tctgacgcac gtgtcgcaga cgcaggagca gaacaaagag aatcagaatc ccaattctga tgcgccggtg atcagatcaa aaacttcagc caggtacatg gagctggtcg ggtggctcgt ggacaagggg attacctcgg agaagcagtg gatccaggag gaccaggcct catacatctc cttcaatgcg gcctccaact cgcggtccca aatcaaggct gccttggaca atgcgggaaa gattatgagc ctgactaaaa ccgcccccga ctacctggtg ggccagcagc ccgtggagga catttccagc aatcggattt ataaaatttt ggaactaaac gggtacgatc cccaatatgc ggcttccgtc tttctgggat gggccacgaa aaagttcggc aagaggaaca ccatctggct gtttgggcct gcaactaccg ggaagaccaa catcgcggag gccatagccc acactgtgcc cttctacggg tgcgtaaact ggaccaatga gaactttccc ttcaacgact gtgtcgacaa gatggtgatc tggtgggagg aggggaagat gaccgccaag gtcgtggagt cggccaaagc cattctcgga ggaagcaagg tgcgcgtgga ccagaaatgc aagtcctcgg cccagataga cccgactccc gtgatcgtca cctccaacac caacatgtgc gccgtgattg acgggaactc aacgaccttc gaacaccagc agccgttgca agaccggatg ttcaaatttg aactcacccg ccgtctggat catgactttg ggaaggtcac caagcaggaa gtcaaagact ttttccggtg ggcaaaggat cacgtggttg aggtggagca tgaattctac gtcaaaaagg gtggagccaa gaaaagaccc gcccccagtg acgcagatat aagtgagccc aaacgggtgc gcgagtcagt tgcgcagcca tcgacgtcag acgcggaagc ttcgatcaac tacgcagaca ggtaccaaaa caaatgttct cgtcacgtgg gcatgaatct gatgctgttt ccctgcagac aatgcgagag aatgaatcag aattcaaata tctgcttcac tcacggacag aaagactgtt tagagtgctt tccccgtgtca gaatctcaac ccgtttctgt cgtcaaaaag
```

-continued

```
gcgtatcaga aactgtgcta cattcatcat atcatgggaa aggtgccaga
cgcttgcact gcctgcgatc tggtcaatgt ggatttggat gactgcatct
ttgaacaata aatgatttaa atcaggtatg tcttttgttg atcaccctcc
agattggttg gaagaagttg gtgaaggtct tcgcgagttt ttgggccttg
aagcgggccc accgaaacca aaacccaatc agcagcatca agatcaagcc
cgtggtcttg tgctgcctgg ttataactat ctcggacccg gaaacggtct
cgatcgagga gagcctgtca cagggcaga cgaggtcgcg cgagagcacg
acatctcgta caacgagcag cttgaggcgg gagacaaccc ctacctcaag
tacaaccacg cggacgccga gtttcaggag aagctcgccg acgacacatc
cttcggggga aacctcggaa aggcagtctt tcaggccaag aaaagggttc
tcgaaccttt tggcctggtt gaagagggtg ctaagacggc ccctaccgga
aagcggatag acgaccactt tccaaaaaga aagaaggctc ggaccgaaga
ggactccaag ccttccacct cgtcagacgc cgaagctgga cccagcggat
cccagcagct gcaaatccca gcccaaccag cctcaagttt gggagctgat
acaatgtctg cgggaggtgg cggcccattg ggcgacaata accaaggtgc
cgatggagtg ggcaatgcct cgggagattg gcattgcgat tccacgtgga
tgggggacag agtcgtcacc aagtccaccc gaacctgggt gctgcccagc
tacaacaacc accagtaccg agagatcaaa agcggctccg tcgacggaag
caacgccaac gcctactttg gatacagcac cccctggggg tactttgact
ttaaccgctt ccacagccac tggagccccc gagactggca aagactcatc
aacaactact ggggcttcag accccggtcc ctcagagtca aaatcttcaa
cattcaagtc aaagaggtca cggtgcagga ctccaccacc accatcgcca
acaacctcac ctccaccgtc caagtgttta cggacgacga ctaccagctg
ccctacgtcg tcggcaacgg gaccgaggga tgcctgccgg ccttccctcc
gcaggtcttt acgctgccgc agtacggtta cgcgacgctg aaccgcgaca
acacagaaaa tcccaccgag aggagcagct tcttctgcct agagtacttt
cccagcaaga tgctgagaac gggcaacaac tttgagttta cctacaactt
tgaggaggtg cccttccact ccagcttcgc tcccagtcag aacctgttca
agctggccaa cccgctggtg gaccagtact tgtaccgctt cgtgagcaca
aataacactg gcggagtcca gttcaacaag aacctggccg ggagatacgc
caacacctac aaaaactggt tcccggggcc catgggccga acccagggct
ggaacctggg ctccggggtc aaccgcgcca gtgtcagcgc cttcgccacg
accaatagga tggagctcga gggcgcgagt taccaggtgc cccgcagcc
gaacggcatg accaacaacc tccagggcag caacacctat gccctggaga
acactatgat cttcaacagc agccggcga acccgggcac caccgccacg
tacctcgagg gcaacatgct catcaccagc gagagcgaga cgcagccggt
gaaccgcgtg gcgtacaacg tcggcgggca gatggccacc aacaaccaga
gctccaccac tgcccccgcg accggcacgt acaacctcca ggaaatcgtg
cccggcagcg tgtggatgga gagggacgtg tacctccaag gacccatctg
ggccaagatc ccagagacgg gggcgcactt tcacccctct ccggccatgg
gcggattcgg actcaaacac ccaccgccca tgatgctcat caagaacacg
```

```
cctgtgcccg gaaatatcac cagcttctcg gacgtgcccg tcagcagctt
catcacccag tacagcaccg ggcaggtcac cgtggagatg gagtgggagc
tcaagaagga aaactccaag aggtggaacc cagagatcca gtacacaaac
aactacaacg accccagtt tgtggacttt gccccggaca gcaccgggga
atacagaacc accagaccta tcggaacccg ataccttacc cgaccccttt
aaggcgcgcc accggttgct tgttaatcaa taaaccgttt aattcgtttc
agttgaactt tggtctctgc gtatttcttt cttatctagt ttccatgctc
taggatccac tagtaacggc cgccagtgtg ctggaattcg ctttgtagt
taatgattaa cccgccatgc tacttatcta cgtagccatg ctctagaggt
cctgtattag aggtcacgtg agtgttttgc gacattttgc gacaccatgt
ggtcacgctg ggtatttaag cccgagtgag cacgcagggt ctccattttg
aagcgggagg tttgaacgcg cagccgccaa gccgaattct gcagatatcc
aaacactggc ggccgctcga ctagagcggc cgccaccgcg gtggagctcc
agcttttgtt ccctttagtg agggttaatt gcgcgcttgg cgtaatcatg
gtcatagctg tttcctgtgt gaaattgtta tccgctcaca attccacaca
acatacgagc cggaagcata agtgtaaag cctggggtgc ctaatgagtg
agctaactca cattaattgc gttgcgctca ctgcccgctt tccagtcggg
aaacctgtcg tgccagctgc attaatgaat cggccaacgc gcggggagag
gcggtttgcg tattgggcgc tcttccgctt cctcgctcac tgactcgctg
cgctcggtcg ttcggctgcg gcgagcggta tcagctcact caaaggcggt
aatacggtta tccacagaat caggggataa cgcaggaaag aacatgtgag
caaaaggcca gcaaaaggcc aggaaccgta aaaaggccgc gttgctggcg
tttttccata ggctccgccc ccctgacgag catcacaaaa atcgacgctc
aagtcagagg tggcgaaacc cgacaggact ataaagatac caggcgtttc
ccccctggaag ctccctcgtg cgctctcctg ttccgaccct gccgcttacc
ggatacctgt ccgcctttct cccttcggga agcgtggcgc tttctcatag
ctcacgctgt aggtatctca gttcggtgta ggtcgttcgc tccaagctgg
gctgtgtgca cgaacccccc gttcagcccg accgctgcgc cttatccggt
aactatcgtc ttgagtccaa cccggtaaga cacgacttat cgccactggc
agcagccact ggtaacagga ttagcagagc gaggtatgta ggcggtgcta
cagagttctt gaagtggtgg cctaactacg gctacactag aagaacagta
tttggtatct gcgctctgct gaagccagtt accttcggaa aaagagttgg
tagctcttga tccggcaaac aaaccaccgc tggtagcggt ggtttttttg
tttgcaagca gcagattacg cgcagaaaaa aaggatctca agaagatcct
ttgatctttt ctacggggtc tgacgctcag tggaacgaaa actcacgtta
agggatttg gtcatgagat tatcaaaaag gatcttcacc tagatccttt
taaattaaaa atgaagtttt aaatcaatct aaagtatata tgagtaaact
tggtctgaca gttaccaatg cttaatcagt gaggcaccta tctcagcgat
ctgtctattt cgttcatcca tagttgcctg actccccgtc gtgtagataa
ctacgatacg ggagggctta ccatctggcc ccagtgctgc aatgataccg
```

```
cgagacccac gctcaccggc tccagattta tcagcaataa accagccagc cggaagggcc gagcgcagaa gtggtcctgc aactttatcc gcctccatcc agtctattaa ttgttgccgg gaagctagag taagtagttc gccagttaat agtttgcgca acgttgttgc cattgctaca ggcatcgtgg tgtcacgctc gtcgtttggt atggcttcat tcagctccgg ttcccaacga tcaaggcgag ttacatgatc ccccatgttg tgcaaaaaag cggttagctc cttcggtcct ccgatcgttg tcagaagtaa gttggccgca gtgttatcac tcatggttat ggcagcactg cataattctc ttactgtcat gccatccgta agatgctttt ctgtgactgg tgagtactca accaagtcat tctgagaata gtgtatgcgg cgaccgagtt gctcttgccc ggcgtcaata cgggataata ccgcgccaca tagcagaact ttaaaagtgc tcatcattgg aaaacgttct cggggcgaa aactctcaag gatcttaccg ctgttgagat ccagttcgat gtaacccact cgtgcaccca actgatcttc agcatctttt actttcacca gcgtttctgg gtgagcaaaa acaggaaggc aaaatgccgc aaaaaaggga ataagggcga cacggaaatg ttgaatactc atactcttcc ttttttcaata ttattgaagc atttatcagg gttattgtct catgagcgga tacatatttg aatgtattta gaaaaataaa caaataggggg ttccgcgcac atttccccga aaagtgccac ctaaattgta agcgttaata ttttgttaaa attcgcgtta aattttttgtt aaatcagctc attttttaac caataggccg aaatcggcaa atcccttat aaatcaaaag aatagaccga gatagggttg agtgttgttc cagtttggaa caagagtcca ctattaaaga acgtggactc caacgtcaaa gggcgaaaaa ccgtctatca gggcgatggc ccactacgtg aaccatcacc ctaatcaagt tttttgggt cgaggtgccg taaagcacta atcggaacc ctaaagggag cccccgattt agagcttgac ggggaaagcc ggcgaacgtg gcgagaaagg aagggaagaa agcgaaagga gcgggcgcta gggcgctggc aagtgtagcg gtcacgctgc gcgtaaccac cacacccgcc gcgcttaatg cgccgctaca gggcgcgtcc cattcgccat tcaggctgcg caactgttgg gaagggcgat cggtgcgggc ctcttcgcta ttacgccagc tggcgaaagg gggatgtgct gcaaggcgat taagttgggt aacgccaggg ttttcccagt cacgacgttg taaaacgacg gccagtgagc gcgcgtaata cgactcacta tagggcgaat tgggtaccgg gccccccctc gaggtcgacg gtatcggggg agctcgcagg gtctccattt tgaagcggga ggtttgaacg cgcagccgcc atgccggggt tttacgagat tgtgattaag gtccccagcg accttgacga gcatctgccc ggcatttctg acagctttgt gaactgggtg gccgagaagg aatgggagtt gccgccagat tctgacatgg atctgaatct gattgagcag gcacccctga ccgtggccga aagctgcag cgcgactttc tgacggaatg gcgccgtgtg agtaaggccc cggaggctct tttctttgtg caatttgaga agggagagag ctacttccac atgcacgtgc tcgtggaaac caccggggtg aaatc
```

In SEQ ID NO:3, residues 1-1561 of pAAV-RC5 encode the Rep protein, Rep78 (with residues 91-221 corresponding to the AAV2 P19 promoter, and residues 1075-1254 corresponding to the P40 promoter (SEQ ID NO:18)); residues 1578-3749 encode the AAV5 VP1 capsid protein; residues 7091-7395 encode a portion of the Rep68 protein; residues 3948-4078 correspond to the AAV2 P5 promoter sequences of SEQ ID NO:10); residues 4201-4217 are M13 Rev sequences; residues 4225-4241 are Lac operator sequences; 4249-4279 are Lac promoter sequences; residues 4542-5266 correspond to pMB ori sequences, residues 5362-6222 encode an ampicillin resistance determinant; and residues 6223-6321 are bla promoter sequences (FIG. 5).

4. Plasmid pAAV-RC6

Figure 6:
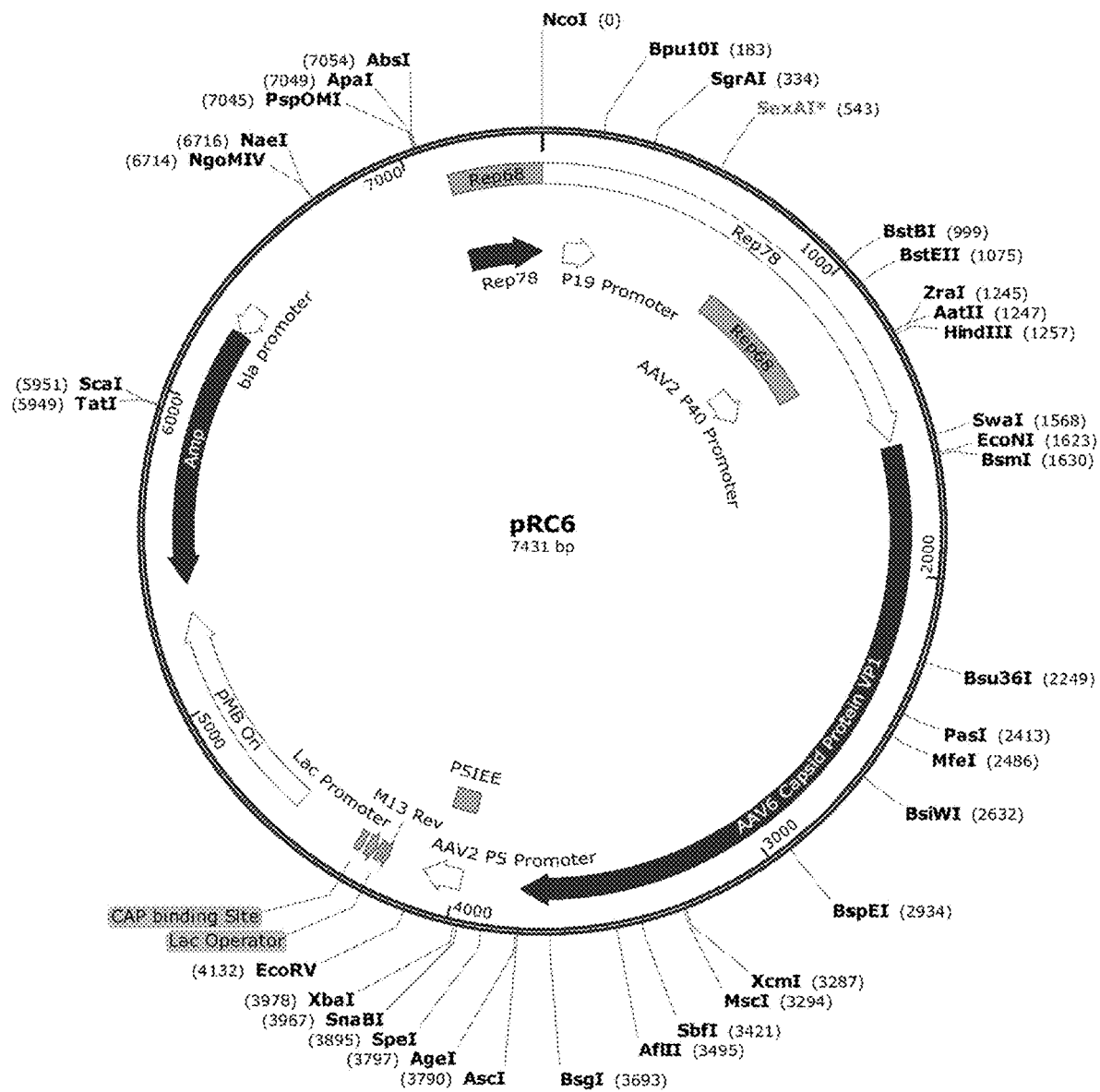
FIG. 6 shows a map of the AAV helper plasmid vector pAAV-RC6 (SEQ ID NO:4).

Plasmid pAAV-RC6 (SEQ ID NO:4; FIG. 6) is an AAV helper plasmid that expresses AAV6 serotype capsid proteins that may be used in accordance with the present invention to provide AAV helper functions. The P5 and P40 promoters of pAAV-RC6 are AAV2 serotype promoters (SEQ ID NO:10 and SEQ ID NO:18, respectively).

```
Coding Strand of Plasmid pAAV-RC6 (SEQ ID NO: 4):
catggttttg ggacgtttcc tgagtcagat tcgcgaaaaa ctgattcaga gaatttaccg cgggatcgag ccgactttgc caaactggtt cgcggtcaca aagaccagaa atggcgccgg aggcgggaac aaggtggtgg atgagtgcta catccccaat tacttgctcc ccaaaaccca gcctgagctc cagtgggcgt ggactaatat ggaacagtat ttaagcgcct gtttgaatct cacggagcgt aaacggttgg tggcgcagca tctgacgcac gtgtcgcaga cgcaggagca gaacaaagag aatcagaatc ccaattctga tgcgccggtg atcagatcaa aaacttcagc caggtacatg gagctggtcg ggtggctcgt ggacaagggg attacctcgg agaagcagtg gatccaggag gaccaggcct catacatctc cttcaatgcg gcctccaact cgcggtccca aatcaaggct gccttggaca atgcgggaaa gattatgagc ctgactaaaa ccgcccccga ctacctggtg ggccagcagc ccgtggagga catttccagc aatcggattt ataaaatttt ggaactaaac gggtacgatc cccaatatgc ggcttccgtc tttctgggat gggccacgaa aaagttcggc aagaggaaca ccatctggct gtttgggcct gcaactaccg ggaagaccaa catcgcggag gccatagccc acactgtgcc cttctacggg tgcgtaaact ggaccaatga gaactttccc ttcaacgact gtgtcgacaa gatggtgatc tggtgggagg aggggaagat gaccgccaag gtcgtggagt cggccaaagc cattctcgga ggaagcaagg tgcgcgtgga ccagaaatgc aagtcctcgg cccagataga cccgactccc gtgatcgtca cctccaacac caacatgtgc gccgtgattg acgggaactc aacgaccttc gaacaccagc agccgttgca agaccggatg ttcaaatttg aactcacccg ccgtctggat catgactttg gaaggtcac caagcaggaa gtcaaagact ttttccggtg ggcaaaggat cacgtggttg aggtggagca tgaattctac gtcaaaaagg gtggagccaa gaaaagaccc gcccccagtg acgcagatat aagtgagccc aaacgggtgc gcgagtcagt tgcgcagcca tcgacgtcag acgcggaagc ttcgatcaac tacgcagaca ggtaccaaaa caaatgttct cgtcacgtgg gcatgaatct gatgctgttt ccctgcagac aatgcgagag aatgaatcag aattcaaata tctgcttcac tcacggacag aaagactgtt tagagtgctt tcccgtgtca gaatctcaac ccgtttctgt cgtcaaaaag gcgtatcaga aactgtgcta cattcatcat atcatgggaa aggtgccaga cgcttgcact gcctgcgatc tggtcaatgt ggatttggat gactgcatct ttgaacaata aatgatttaa atcaggtatg gctgccgatg gttatcttcc agattggctc gaggacaacc tctctgaggg cattcgcgag tggtgggact tgaaacctgg agccccgaaa cccaaagcca accagcaaaa gcaggacgac
```

-continued

```
ggccggggtc tggtgcttcc tggctacaag tacctcggac ccttcaacgg
actcgacaag ggggagcccg tcaacgcggc ggatgcagcg gccctcgagc
acgacaaggc ctacgaccag cagctcaaag cgggtgacaa tccgtacctg
cggtataacc acgccgacgc cgagtttcag gagcgtctgc aagaagatac
gtcttttggg ggcaacctcg ggcgagcagt cttccaggcc aagaagaggg
ttctcgaacc ttttggtctg gttgaggaag gtgctaagac ggctcctgga
aagaaacgtc cggtagagca gtcgccacaa gagccagact cctcctcggg
cattggcaag acaggccagc agcccgctaa aaagagactc aattttggtc
agactggcga ctcagagtca gtccccgacc cacaacctct cggagaacct
ccagcaaccc ccgctgctgt gggacctact acaatggctt caggcggtgg
cgcaccaatg gcagacaata acgaaggcgc cgacggagtg ggtaatgcct
caggaaattg gcattgcgat tccacatggc tgggcgacag agtcatcacc
accagcaccc gaacatgggc cttgcccacc tataacaacc acctctacaa
gcaaatctcc agtgcttcaa cgggggccag caacgacaac cactacttcg
gctacagcac ccctgggggg tattttgatt tcaacagatt ccactgccat
ttctcaccac gtgactggca gcgactcatc aacaacaatt ggggattccg
gcccaagaga ctcaacttca agctcttcaa catccaagtc aaggaggtca
cgacgaatga tggcgtcacg accatcgcta ataaccttac cagcacggtt
caagtcttct cggactcgga gtaccagttg ccgtacgtcc tcggctctgc
gcaccagggc tgcctccctc cgttcccggc ggacgtgttc atgattccgc
agtacggcta cctaacgctc aacaatggca gccaggcagt gggacggtca
tccttttact gcctggaata tttcccatcg cagatgctga gaacgggcaa
taactttacc ttcagctaca ccttcgagga cgtgcctttc cacagcagct
acgcgcacag ccagagcctg gaccggctga tgaatcctct catcgaccag
tacctgtatt acctgaacag aactcagaat cagtccggaa gtgcccaaaa
caaggacttg ctgtttagcc gggggtctcc agctggcatg tctgttcagc
ccaaaaactg gctacctgga ccctgttacc ggcagcagcg cgtttctaaa
acaaaaacag acaacaacaa cagcaacttt acctggactg gtgcttcaaa
atataacctt aatgggcgtg aatctataat caaccctggc actgctatgg
cctcacacaa agacgacaaa gacaagttct ttcccatgag cggtgtcatg
attttggaa aggagagcgc cggagcttca aacactgcat ggacaatgt
catgatcaca gacgaagagg aaatcaaagc cactaaccc gtggccaccg
aaagatttgg gactgtggca gtcaatctcc agagcagcag cacagaccct
gcgaccggag atgtgcatgt tatgggagcc ttacctggaa tggtgtggca
agacagagac gtatacctgc agggtcctat ttgggccaaa attcctcaca
cggatggaca ctttcacccg tctcctctca tgggcggctt tggacttaag
cacccgcctc ctcagatcct catcaaaaac acgcctgttc ctgcgaatcc
tccggcagag ttttcggcta caaagtttgc ttcattcatc acccagtatt
ccacaggaca agtgagcgtg gagattgaat gggagctgca gaaagaaaac
agcaaacgct ggaatcccga agtgcagtat acatctaact atgcaaaatc
```

-continued

```
tgccaacgtt gatttcactg tggacaacaa tggactttat actgagcctc gccccattgg cacccgttac ctcacccgtc cctgtaagg cgcgccaccg gttgcttgtt aatcaataaa ccgtttaatt cgtttcagtt gaactttggt ctctgcgtat ttcttcctta tctagtttcc atgctctagg atccactagt aacggccgcc agtgtgctgg aattcggctt tgtagttaat gattaacccg ccatgctact tatctacgta gccatgctct agaggtcctg tattagaggt cacgtgagtg ttttgcgaca ttttgcgaca ccatgtggtc acgctgggta tttaagcccg agtgagcacg cagggtctcc atttgaagc gggaggtttg aacgcgcagc cgccaagccg aattctgcag atatccaaac actggcggcc gctcgactag agcggccgcc accgcggtgg agctccagct tttgttccct ttagtgaggg ttaattgcgc gcttggcgta atcatggtca tagctgtttc ctgtgtgaaa ttgttatccg ctcacaattc cacacaacat acgagccgga agcataaagt gtaaagcctg gggtgcctaa tgagtgagct aactcacatt aattgcgttg cgctcactgc ccgctttcca gtcgggaaac ctgtcgtgcc agctgcatta atgaatcggc caacgcgcgg ggagaggcgg tttgcgtatt gggcgctctt ccgcttcctc gctcactgac tcgctgcgct cggtcgttcg gctgcggcga gcggtatcag ctcactcaaa ggcggtaata cggttatcca cagaatcagg ggataacgca ggaaagaaca tgtgagcaaa aggccagcaa aaggccagga accgtaaaaa ggccgcgttg ctggcgtttt tccataggct ccgcccccct gacgagcatc acaaaaatcg acgctcaagt cagaggtggc gaaacccgac aggactataa agataccagg cgtttccccc tggaagctcc ctcgtgcgct ctcctgttcc gaccctgccg cttaccggat acctgtccgc ctttctccct tcgggaagcg tggcgctttc tcatagctca cgctgtaggt atctcagttc ggtgtaggtc gttcgctcca agctgggctg tgtgcacgaa ccccccgttc agcccgaccg ctgcgcctta tccggtaact atcgtcttga gtccaacccg gtaagacacg acttatcgcc actggcagca gccactggta acaggattag cagagcgagg tatgtaggcg gtgctacaga gttcttgaag tggtggccta actacggcta cactagaaga acagtatttg gtatctgcgc tctgctgaag ccagttacct tcggaaaaag agttggtagc tcttgatccg gcaaacaaac caccgctggt agcggtggtt tttttgtttg caagcagcag attacgcgca gaaaaaaagg atctcaagaa gatcctttga tcttttctac ggggtctgac gctcagtgga acgaaaactc acgttaaggg attttggtca tgagattatc aaaaaggatc ttcacctaga tccttttaaa ttaaaaatga agttttaaat caatctaaag tatatatgag taaacttggt ctgacagtta ccaatgctta atcagtgagg cacctatctc agcgatctgt ctatttcgtt catccatagt tgcctgactc cccgtcgtgt agataactac gatacgggag ggcttaccat ctggccccag tgctgcaatg ataccgcgag acccacgctc accggctcca gatttatcag caataaacca gccagccgga agggccgagc gcagaagtgg tcctgcaact ttatccgcct ccatccagtc tattaattgt tgccgggaag ctagagtaag tagttcgcca gttaatagtt tgcgcaacgt tgttgccatt gctacaggca tcgtggtgtc acgctcgtcg tttggtatgg
```

```
cttcattcag ctccggttcc caacgatcaa ggcgagttac atgatccccc atgttgtgca aaaaagcggt tagctccttc ggtcctccga tcgttgtcag aagtaagttg gccgcagtgt tatcactcat ggttatggca gcactgcata attctcttac tgtcatgcca tccgtaagat gcttttctgt gactggtgag tactcaacca agtcattctg agaatagtgt atgcggcgac cgagttgctc ttgcccggcg tcaatacggg ataataccgc gccacatagc agaactttaa aagtgctcat cattggaaaa cgttcttcgg ggcgaaaact ctcaaggatc ttaccgctgt tgagatccag ttcgatgtaa cccactcgtg cacccaactg atcttcagca tcttttactt tcaccagcgt ttctgggtga gcaaaaacag gaaggcaaaa tgccgcaaaa aagggaataa gggcgacacg gaaatgttga atactcatac tcttcctttt tcaatattat tgaagcattt atcagggtta ttgtctcatg agcggataca tatttgaatg tatttagaaa aataaacaaa tagggttcc gcgcacattt ccccgaaaag tgccacctaa attgtaagcg ttaatatttt gttaaaattc gcgttaaatt tttgttaaat cagctcattt tttaaccaat aggccgaaat cggcaaaatc ccttataaat caaaagaata gaccgagata gggttgagtg ttgttccagt ttggaacaag agtccactat taaagaacgt ggactccaac gtcaaagggc gaaaaaccgt ctatcagggc gatggcccac tacgtgaacc atcaccctaa tcaagttttt tggggtcgag gtgccgtaaa gcactaaatc ggaacccaa agggagcccc cgatttagag cttgacgggg aaagccggcg aacgtggcga gaaaggaagg gaagaaagcg aaaggagcgg gcgctagggc gctggcaagt gtagcggtca cgctgcgcgt aaccaccaca cccgccgcgc ttaatgcgcc gctacagggc gcgtcccatt cgccattcag gctgcgcaac tgttgggaag ggcgatcggt gcgggcctct tcgctattac gccagctggc gaaagggga tgtgctgcaa ggcgattaag ttgggtaacg ccagggtttt cccagtcacg acgttgtaaa acgacggcca gtgagcgcgc gtaatacgac tcactatagg gcgaattggg taccgggccc cccctcgagg tcgacggtat cggggagct cgcagggtct ccattttgaa gcgggaggtt tgaacgcgca gccgccatgc cggggtttta cgagattgtg attaaggtcc ccagcgacct tgacgagcat ctgcccggca tttctgacag ctttgtgaac tgggtggccg agaaggaatg ggagttgccg ccagattctg acatggatct gaatctgatt gagcaggcac ccctgaccgt ggccgagaag ctgcagcgcg actttctgac ggaatggcgc cgtgtgagta aggccccgga ggctcttttc tttgtgcaat ttgagaaggg agagagctac ttccacatgc acgtgctcgt ggaaaccacc ggggtgaaat c
```

In SEQ ID NO:4, residues 1-1561 of pAAV-RC6 encode the Rep protein, Rep78 (with residues 91-221 corresponding to the AAV2 P19 promoter, and residues 1075-1254 corresponding to the P40 promoter (SEQ ID NO:18)); residues 1578-3788 encode the AAV6 VP1 capsid protein; residues 736-1281 encode a portion of the Rep68 protein; residues 3984-4114 correspond to the AAV2 P5 promoter sequences of SEQ ID NO:10); residues 4237-4253 are M13 Rev sequences; residues 4261-4277 are Lac operator sequences; 4285-4315 are Lac promoter sequences; residues 4578-5302 correspond to pMB ori sequences, residues 5398-6258 encode an ampicillin resistance determinant; and residues 6259-6357 are bla promoter sequences (FIG. 6).

5. Plasmid pAAV-RC7

Figure 7:
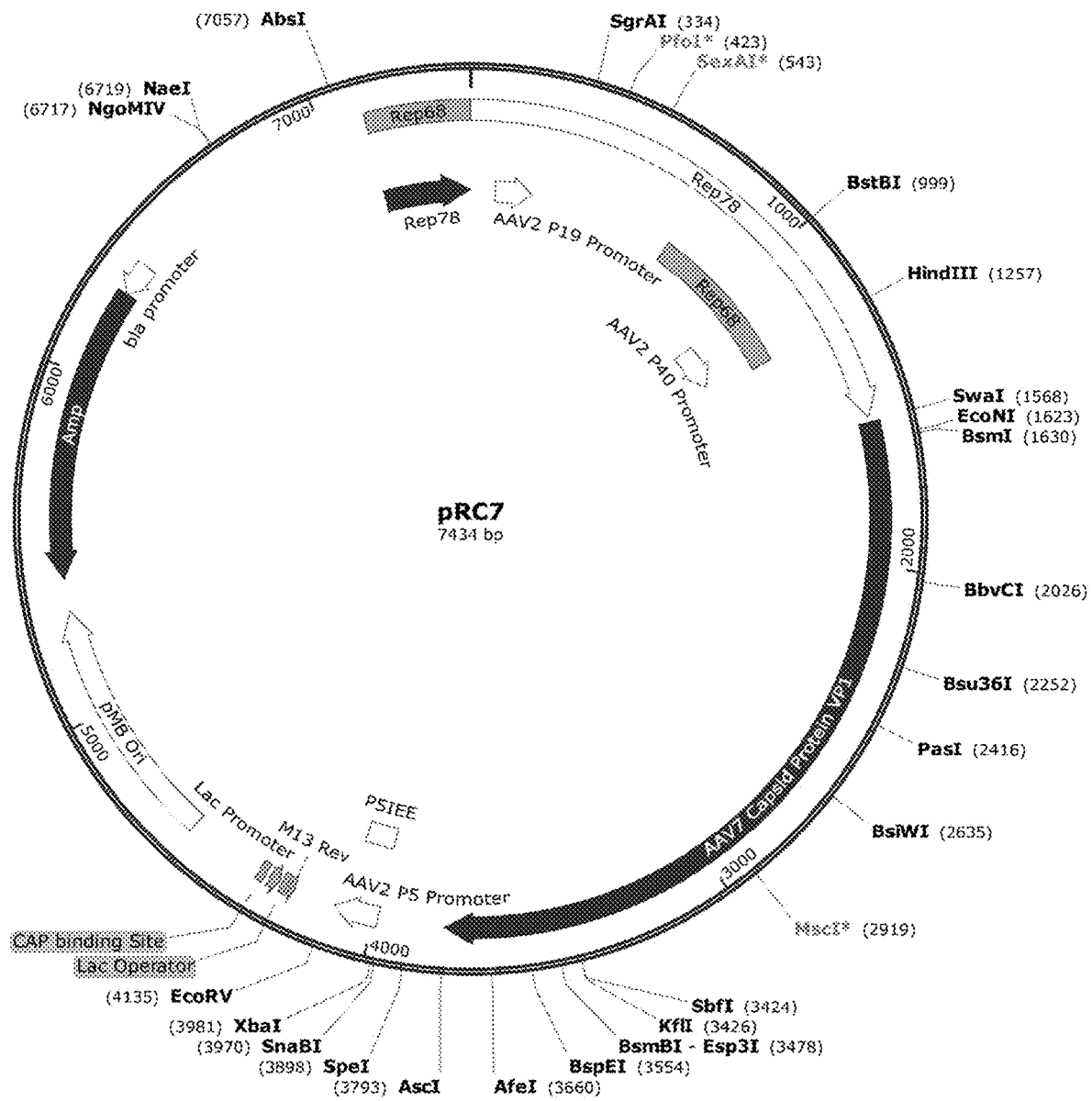
FIG. 7 shows a map of the AAV helper plasmid vector pAAV-RC7 (SEQ ID NO:5).

Plasmid pAAV-RC7 (SEQ ID NO:5; FIG. 7) is an AAV helper plasmid that expresses AAV6 serotype capsid proteins that may be used in accordance with the present invention to provide AAV helper functions. The P5 and P40 promoters of pAAV-RC7 are AAV2 serotype promoters (SEQ ID NO:10 and SEQ ID NO:18, respectively).

Coding Strand of Plasmid pAAV-RC7 (SEQ ID NO: 5):
catggttttg gacgtttcc tgagtcagat tcgcgaaaaa ctgattcaga
gaatttaccg cgggatcgag ccgactttgc caaactggtt cgcggtcaca
aagaccagaa atggcgccgg aggcgggaac aaggtggtgg atgagtgcta
catccccaat tacttgctcc ccaaaaccca gcctgagctc agtgggcgt
ggactaatat ggaacagtat ttaagcgcct gtttgaatct cacggagcgt
aaacggttgg tggcgcagca tctgacgcac gtgtcgcaga cgcaggagca
gaacaaagag aatcagaatc ccaattctga tgcgccggtg atcagatcaa
aaacttcagc caggtacatg agctggtcg ggtggctcgt ggacaagggg
attacctcgg agaagcagtg gatccaggag gaccaggcct catacatctc
cttcaatgcg gcctccaact cgcggtccca atcaaggct gccttggaca
atgcgggaaa gattatgagc ctgactaaaa ccgcccccga ctacctggtg
ggccagcagc ccgtggagga catttccagc aatcggattt ataaaatttt
ggaactaaac gggtacgatc cccaatatgc ggcttccgtc tttctgggat
gggccacgaa aaagttcggc aagaggaaca ccatctggct gtttgggcct
gcaactaccg ggaagaccaa catcgcggag gccatagccc acactgtgcc
cttctacggg tgcgtaaact ggaccaatga aactttccc ttcaacgact
gtgtcgacaa gatggtgatc tggtgggagg aggggaagat gaccgccaag
gtcgtggagt cggccaaagc cattctcgga ggaagcaagg tgcgcgtgga
ccagaaatgc aagtcctcgg cccagataga cccgactccc gtgatcgtca
cctccaacac caacatgtgc gccgtgattg acgggaactc aacgaccttc
gaacaccagc agccgttgca agaccggatg ttcaaatttg aactcacccg
ccgtctggat catgactttg gaaggtcac caagcaggaa gtcaaagact
ttttccggtg ggcaaaggat cacgtggttg aggtggagca tgaattctac
gtcaaaaagg gtggagccaa gaaaagaccc gccccagtg acgcagatat
aagtgagccc aaacgggtgc gcgagtcagt tgcgcagcca tcgacgtcag
acgcggaagc ttcgatcaac tacgcagaca ggtaccaaaa caaatgttct
cgtcacgtgg gcatgaatct gatgctgttt ccctgcagac aatgcgagag
aatgaatcag aattcaaata tctgcttcac tcacggacag aaagactgtt
tagagtgctt tcccgtgtca gaatctcaac ccgtttctgt cgtcaaaaag
gcgtatcaga aactgtgcta cattcatcat atcatgggaa aggtgccaga
cgcttgcact gcctgcgatc tggtcaatgt ggatttggat gactgcatct
ttgaacaata aatgatttaa atcaggtatg gctgccgatg gttatcttcc
agattggctc gaggacaacc tctctgaggg cattcgcgag tggtgggacc
tgaaacctgg agccccgaaa cccaaagcca accagcaaaa gcaggacaac
ggccgggtc tggtgcttcc tggctacaag tacctcggac ccttcaacgg
actcgacaag ggggagcccg tcaacgcggc ggacgcagcg gccctcgagc
acgacaaggc ctacgaccag cagctcaaag cgggtgacaa tccgtacctg
cggtataacc acgccgacgc cgagtttcag gagcgtctgc aagaagatac
gtcatttggg ggcaacctcg gcgagcagt cttccaggcc aagaagcggg
ttctcgaacc tctcggtctg gttgaggaag cgctaagac ggctcctgca -continued

```
aagaagagac cggtagagcc gtcacctcag cgttccccg actcctccac gggcatcggc aagaaaggcc agcagcccgc cagaaagaga ctcaatttcg gtcagactgg cgactcagag tcagtccccg accctcaacc tctcggagaa cctccagcag cgccctctag tgtgggatct ggtacagtgg ctgcaggcgg tggcgcacca atggcagaca ataacgaagg tgccgacgga gtgggtaatg cctcaggaaa ttggcattgc gattccacat ggctgggcga cagagtcatt accaccagca cccgaacctg ggccctgccc acctacaaca accacctcta caagcaaatc tccagtgaaa ctgcaggtag taccaacgac aacacctact tcggctacag cacccctgg gggtattttg actttaacag attccactgc cacttctcac cacgtgactg gcagcgactc atcaacaaca actggggatt ccggcccaag aagctgcggt tcaagctctt caacatccag gtcaaggagg tcacgacgaa tgacggcgtt acgaccatcg ctaataacct taccagcacg attcaggtat tctcggactc ggaataccag ctgccgtacg tcctcggctc tgcgcaccag ggctgcctgc ctccgttccc ggcggacgtc ttcatgattc ctcagtacgg ctacctgact ctcaacaatg cagtcagtc tgtgggacgt tcctccttct actgcctgga gtacttcccc tctcagatgc tgagaacggg caacaacttt gagttcagct acagcttcga ggacgtgcct ttccacagca gctacgcaca cagccagagc ctggaccggc tgatgaatcc cctcatcgac cagtacttgt actacctggc cagaaacacag agtaacccag gaggcacagc tggcaatcgg gaactgcagt tttaccaggg cgggccttca actatggccg aacaagccaa gaattggtta cctggaccctt gcttccggca acaaagagtc tccaaaacgc tggatcaaaa caacaacagc aactttgctt ggactggtgc caccaaatat cacctgaacg gcagaaactc gttggttaat cccggcgtcg ccatggcaac tcacaaggac gacgaggacc gcttttccc atccagcgga gtcctgattt ttgaaaaaac tggagcaact aacaaaacta cattggaaaa tgtgttaatg acaaatgaag aagaaattcg tcctactaat cctgtagcca cggaagaata cgggatagtc agcagcaact acaagcggc taatactgca gcccagacac aagttgtcaa caaccaggga gccttacctg gcatggtctg gcagaaccgg gacgtgtacc tgcagggtcc catctgggcc aagattcctc acacggatgg caactttcac ccgtctcctt tgatgggcgg cttttggactt aaacatccgc ctcctcagat cctgatcaag aacactcccg ttcccgctaa tcctccggag gtgtttactc ctgccaagtt tgcttcgttc atcacacagt acagcaccgg acaagtcagc gtggaaatcg agtgggagct gcagaaggaa aacagcaagc gctggaaccc ggagattcag tacacctcca ctttgaaaa gcagactggt gtggactttg ccgttgacag ccagggtgtt tactctgagc ctcgccctat tggcactcgt tacctcaccc gtaatctgta aggcgcgcca ccggttgctt gttaatcaat aaaccgttta attcgtttca gttgaactttt ggtctctgcg tatttctttc ttatctagtt tccatgctct aggatccact agtaacggcc gccagtgtgc tggaattcgg cttttgtagtt aatgattaac ccgccatgct acttatctac gtagccatgc tctagaggtc ctgtattaga ggtcacgtga gtgttttgcg acattttgcg acaccatgtg gtcacgctgg
```

-continued

```
gtatttaagc ccgagtgagc acgcagggtc tccattttga agcgggaggt ttgaacgcgc agccgccaag ccgaattctg cagatatcca aacactggcg gccgctcgac tagagcggcc gccaccgcgg tggagctcca gcttttgttc cctttagtga gggttaattg cgcgcttggc gtaatcatgg tcatagctgt ttcctgtgtg aaattgttat ccgctcacaa ttccacacaa catacgagcc ggaagcataa agtgtaaagc ctggggtgcc taatgagtga gctaactcac attaattgcg ttgcgctcac tgcccgcttt ccagtcggga aacctgtcgt gccagctgca ttaatgaatc ggccaacgcg cgggagagg cggtttgcgt attgggcgct cttccgcttc ctcgctcact gactcgctgc gctcggtcgt tcggctgcgg cgagcggtat cagctcactc aaaggcggta atacggttat ccacagaatc agggggataac gcaggaaaga acatgtgagc aaaaggccag caaaaggcca ggaaccgtaa aaaggccgcg ttgctggcgt ttttccatag gctccgcccc cctgacgagc atcacaaaaa tcgacgctca agtcagaggt ggcgaaaccc gacaggacta taaagatacc aggcgtttcc ccctggaagc tccctcgtgc gctctcctgt tccgaccctg ccgcttaccg gatacctgtc cgcctttctc ccttcgggaa gcgtggcgct ttctcatagc tcacgctgta ggtatctcag ttcggtgtag gtcgttcgct ccaagctggg ctgtgtgcac gaaccccccg ttcagcccga ccgctgcgcc ttatccggta actatcgtct tgagtccaac ccggtaagac acgacttatc gccactggca gcagccactg gtaacaggat tagcagagcg aggtatgtag gcggtgctac agagttcttg aagtggtggc ctaactacgg ctacactaga agaacagtat ttggtatctg cgctctgctg aagccagtta ccttcggaaa aagagttggt agctcttgat ccggcaaaca aaccaccgct ggtagcggtg gtttttttgt ttgcaagcag cagattacgc gcagaaaaaa aggatctcaa gaagatcctt tgatcttttc tacggggtct gacgctcagt ggaacgaaaa ctcacgttaa gggattttgg tcatgagatt atcaaaaagg atcttcacct agatcctttt aaattaaaaa tgaagtttta atcaatcta aagtatatat gagtaaactt ggtctgacag ttaccaatgc ttaatcagtg aggcacctat ctcagcgatc tgtctatttc gttcatccat agttgcctga ctccccgtcg tgtagataac tacgatacgg gagggcttac catctggccc cagtgctgca atgataccgc gagacccacg ctcaccggct ccagatttat cagcaataaa ccagccagcc ggaagggccg agcgcagaag tggtcctgca actttatccg cctccatcca gtctattaat tgttgccggg aagctagagt aagtagttcg ccagttaata gtttgcgcaa cgttgttgcc attgctacag gcatcgtggt gtcacgctcg tcgtttggta tggcttcatt cagctccggt tcccaacgat caaggcgagt tacatgatcc cccatgttgt gcaaaaaagc ggttagctcc ttcggtcctc cgatcgttgt cagaagtaag ttggccgcag tgttatcact catggttatg gcagcactgc ataattctct tactgtcatg ccatccgtaa gatgcttttc tgtgactggt gagtactcaa ccaagtcatt ctgagaatag tgtatgcggc gaccgagttg ctcttgcccg gcgtcaatac gggataatac cgcgccacat agcagaactt
```

-continued
```
taaaagtgct catcattgga aaacgttctt cggggcgaaa actctcaagg atcttaccgc tgttgagatc cagttcgatg taacccactc gtgcacccaa ctgatcttca gcatcttta ctttcaccag cgtttctggg tgagcaaaaa caggaaggca aaatgccgca aaaaaggaa taagggcgac acggaaatgt tgaatactca tactcttcct ttttcaatat tattgaagca tttatcaggg ttattgtctc atgagcggat acatatttga atgtatttag aaaaataaac aaatagggt tccgcgcaca tttccccgaa aagtgccacc taaattgtaa gcgttaatat tttgttaaaa ttcgcgttaa atttttgtta aatcagctca ttttttaacc aataggccga aatcggcaaa atcccttata aatcaaaaga ataccgag atagggttga gtgttgttcc agtttggaac aagagtccac tattaaagaa cgtggactcc aacgtcaaag ggcgaaaaac cgtctatcag ggcgatggcc cactacgtga accatcaccc taatcaagtt ttttggggtc gaggtgccgt aaagcactaa atcggaaccc taaagggagc ccccgattta gagcttgacg gggaaagccg gcgaacgtgg cgagaagga agggaagaaa gcgaaaggag cgggcgctag ggcgctggca agtgtagcgg tcacgctgcg cgtaaccacc acacccgccg cgcttaatgc gccgctacag ggcgcgtccc attcgccatt caggctgcgc aactgttggg aagggcgatc ggtgcgggcc tcttcgctat tacgccagct ggcgaaaggg ggatgtgctg caaggcgatt aagttgggta acgccagggt tttcccagtc acgacgttgt aaaacgacgg ccagtgagcg cgcgtaatac gactcactat agggcgaatt gggtaccggg cccccctcg aggtcgacgg tatcggggga gctcgcaggg tctccatttt gaagcgggag gtttgaacgc gcagccgcca tgccggggtt ttacgagatt gtgattaagg tccccagcga ccttgacgag catctgcccg gcatttctga cagctttgtg aactgggtgg ccgagaagga atgggagttg ccgccagatt ctgacatgga tctgaatctg attgagcagg caccctgac cgtggccgag aagctgcagc gcgactttct gacggaatgg cgccgtgtga gtaaggcccc ggaggctctt ttctttgtgc aatttgagaa gggagagagc tacttccaca tgcacgtgct cgtggaaacc accggggtga aatc
```

In SEQ ID NO:5, residues 1-1561 of pAAV-RC7 encode the Rep protein, Rep78 (with residues 91-221 corresponding to the AAV2 P19 promoter, and residues 1075-1254 corresponding to the P40 promoter (SEQ ID NO:18)); residues 1578-3791 encode the AAV7 VP1 capsid protein; residues 736-1281 encode a portion of the Rep68 protein; residues 3987-4117 correspond to the AAV2 P5 promoter sequences of SEQ ID NO:10); residues 4240-4256 are M13 Rev sequences; residues 4264-4280 are Lac operator sequences; 4288-4318 are Lac promoter sequences; residues 4581-5305 correspond to pMB ori sequences, residues 5401-6261 encode an ampicillin resistance determinant; and residues 6262-6360 are bla promoter sequences (FIG. 7).

B. Illustrative Non-AAV Helper Function-Providing Polynucleotides

As used herein, the term "non-AAV helper functions" denotes proteins of Ad, CMV, HSV or other non-AAD viruses (e.g., E1a, E1b, E2a, VA and E4) and/or polynucleotides of Ad, CMV, HSV or other non-AAD viruses that are required for the replication and packaging of an rAAV. Such non-AAV helper functions are provided by a "non-AAV helper function-providing polynucleotide," which as such term is used herein is a virus, plasmid vector, a non-plasmid vector, or a polynucleotide that has been integrated into a cellular chromosome, that provides non-AAV helper functions. The vector, pHelper, and derivatives thereof (such as those commercially available from Cell Biolabs, Inc., Invitrogen, Stratagene and other sources), are suitable non-AAV helper function-providing polynucleotide (see, e.g., Matsushita, T. et al. (1998) "*Adeno-Associated Virus Vectors Can Be Efficiently Produced Without Helper Virus*," Gene Ther. 5:938-945; Sharma, A. et al. (2010) "*Transduction Efficiency Of AAV 2/6, 2/8 And 2/9 Vectors For Delivering Genes In Human Corneal Fibroblasts*," Brain Res. Bull. 81(2-3):273-278).

Figure 8:
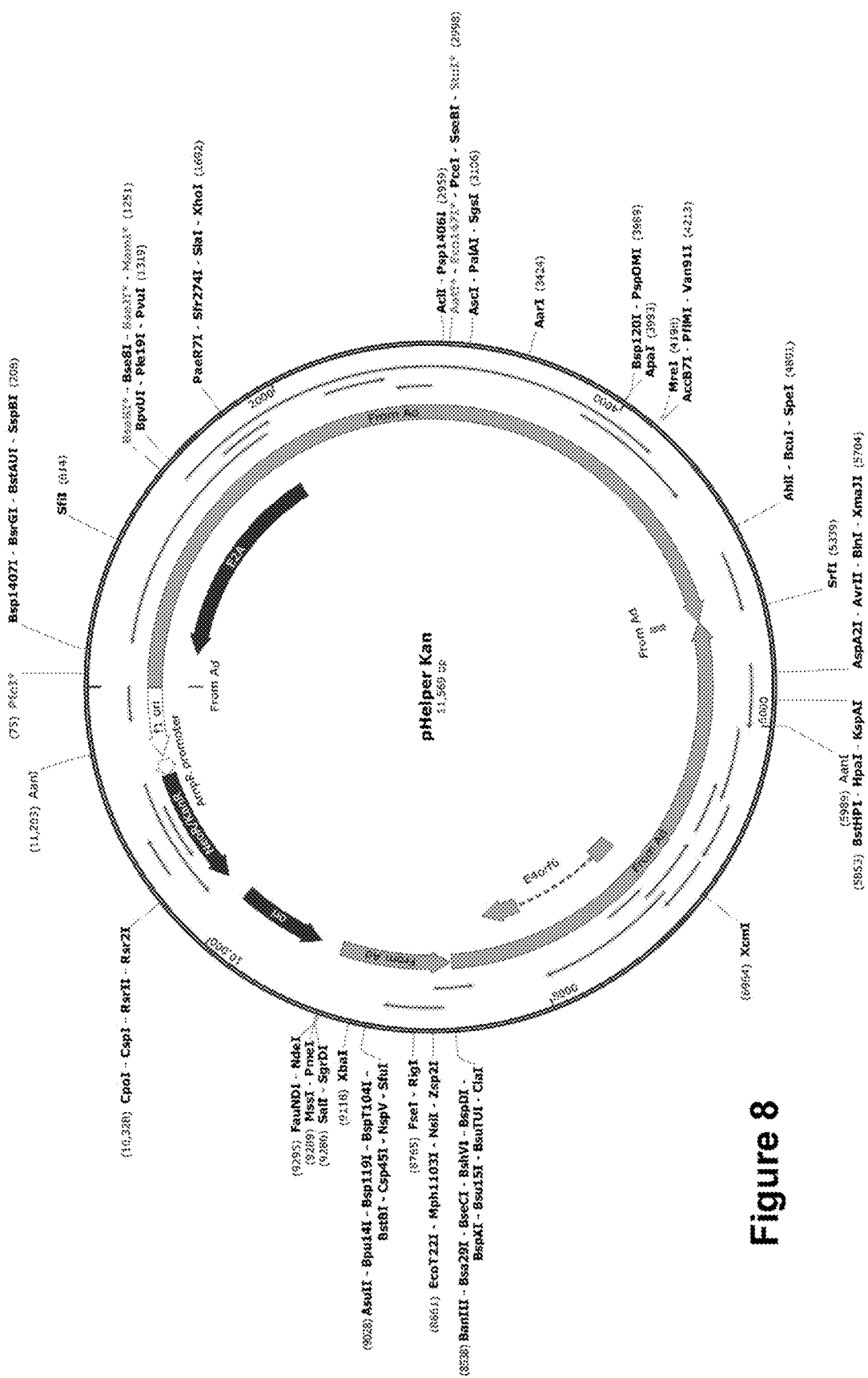
FIG. 8 shows a map of the non-AAV helper plasmid vector pHelper-Kan (SEQ ID NO:6).

Plasmid pHelper-Kan (SEQ ID NO:6; FIG. 8) is a non-AAV helper function-providing polynucleotide that may be used in accordance with the present invention to provide non-AAV helper functions.

Coding Strand of Plasmid pHelper-Kan (SEQ ID NO: 6):
ggtacccaac tccatgctta acagtcccca ggtacagccc accctgcgtc gcaaccagga acagctctac agcttcctgg agcgccactc gccctacttc cgcagccaca gtgcgcagat taggagcgcc acttcttttt gtcacttgaa aaacatgtaa aataatgta ctaggagaca ctttcaataa aggcaaatgt ttttatttgt acactctcgg gtgattattt acccccccacc cttgccgtct gcgccgttta aaatcaaag gggttctgcc gcgcatcgct atgcgccact ggcagggaca cgttgcgata ctggtgttta gtgctccact taaactcagg cacaaccatc cgcggcagct cggtgaagtt ttcactccac aggctgcgca ccatcaccaa cgcgtttagc aggtcgggcg ccgatatctt gaagtcgcag ttggggcctc cgccctgcgc gcgcgagttg cgatacacag ggttgcagca ctggaacact atcagcgccg ggtggtgcac gctggccagc acgctcttgt cggagatcag atccgcgtcc aggtcctccg cgttgctcag ggcgaacgga gtcaactttg gtagctgcct tcccaaaaag ggtgcatgcc caggctttga gttgcactcg caccgtagtg gcatcagaag gtgaccgtgc ccggtctggg cgttaggata cagcgcctgc atgaaagcct tgatctgctt aaaagccacc tgagcctttg cgccttcaga gaagaacatg ccgcaagact tgccggaaaa ctgattggcc ggacaggccg cgtcatgcac gcagcacctt gcgtcggtgt tggagatctg caccacattt cggccccacc ggttcttcac gatcttggcc ttgctagact gctccttcag cgcgcgctgc ccgttttcgc tcgtcacatc catttcaatc acgtgctcct tatttatcat aatgctcccg tgtagacact taagctcgcc ttcgatctca gcgcagcggt gcagccacaa cgcgcagccc gtgggctcgt ggtgcttgta ggttacctct gcaaacgact gcaggtacgc ctgcaggaat cgcccccatca tcgtcacaaa ggtcttgttg ctggtgaagg tcagctgcaa cccgcggtgc tcctcgttta gccaggtctt gcatacggcc gccagagctt ccacttggtc aggcagtagc ttgaagtttg cctttagatc gttatccacg tggtacttgt ccatcaacgc gcgcgcagcc tccatgccct tctcccacgc agacacgatc ggcaggctca gcgggtttat caccgtgctt tcactttccg cttcactgga ctcttccttt tcctcttgcg tccgcatacc ccgcgccact gggtcgtctt cattcagccg ccgcaccgtg cgcttacctc ccttgccgtg cttgattagc accggtgggt tgctgaaacc caccatttgt agcgccacat cttctctttc ttcctcgctg tccacgatca cctctgggga tggcgggcgc tcgggcttgg gagaggggcg cttcttttc tttttggacg caatggccaa atccgccgtc gaggtcgatg ccgcgggct gggtgtgcgc ggcaccagcg catcttgtga cgagtcttct tcgtcctcgg actcgagacg ccgcctcagc cgcttttttg ggggcgcgcg gggaggcggc ggcgacggcg acggggacga cacgtcctcc atggttggtg gacgtcgcgc cgcaccgcgt ccgcgctcgg gggtggtttc gcgctgctcc tcttcccgac tggccatttc cttctcctat aggcagaaaa agatcatgga gtcagtcgag aaggaggaca gcctaaccgc ccccttgag ttcgccacca ccgcctccac cgatgccgcc aacgcgccta ccaccttccc cgtcgaggca ccccgcttg aggaggagga -continued

```
agtgattatc gagcaggacc caggttttgt aagcgaagac gacgaggatc gctcagtacc aacagaggat aaaaagcaag accaggacga cgcagaggca aacgaggaac aagtcgggcg gggggaccaa aggcatggcg actacctaga tgtgggagac gacgtgctgt tgaagcatct gcagcgccag tgcgccatta tctgcgacgc gttgcaagag cgcagcgatg tgccctcgc catagcggat gtcagccttg cctacgaacg ccacctgttc tcaccgcgcg tacccccaa acgccaagaa aacggcacat gcgagcccaa cccgcgcctc aacttctacc ccgtatttgc cgtgccagag gtgcttgcca cctatcacat cttttttccaa aactgcaaga taccctatc ctgccgtgcc aaccgcagcc gagcggacaa gcagctggcc ttgcggcagg gcgctgtcat acctgatatc gcctcgctcg acgaagtgcc aaaaatcttt gagggtcttg gacgcgacga gaaacgcgcg gcaaacgctc tgcaacaaga aaacagcgaa aatgaaagtc actgtggagt gctggtggaa cttgagggtg acaacgcgcg cctagccgtg ctgaaacgca gcatcgaggt cacccacttt gcctacccgg cacttaacct accccccaag gttatgagca cagtcatgag cgagctgatc gtgcgccgtg cacgacccct ggagagggat gcaaacttgc aagaacaaac cgaggagggc ctacccgcag ttggcgatga gcagctggcg cgctggcttg agacgcgcga gcctgccgac ttggaggagc gacgcaagct aatgatggcc gcagtgcttg ttaccgtgga gcttgagtgc atgcagcggt tctttgctga cccggagatg cagcgcaagc tagaggaaac gttgcactac accttcgcc agggctacgt gcgccaggcc tgcaaaattt ccaacgtgga gctctgcaac ctggtctcct accttggaat tttgcacgaa aaccgcctcg ggcaaaacgt gcttcattcc acgctcaagg gcgaggcgcg ccgcgactac gtccgcgact gcgtttactt atttctgtgc tacacctggc aaacggccat gggcgtgtgg cagcaatgcc tggaggagcg caacctaaag gagctgcaga gctgctaaa gcaaaacttg aaggacctat ggacggcctt caacgagcgc tccgtggccg cgcacctggc ggacattatc ttccccgaac gcctgcttaa aaccctgcaa cagggtctgc cagacttcac cagtcaaagc atgttgcaaa actttaggaa ctttatccta gagcgttcag gaattctgcc cgccacctgc tgtgcgcttc ctagcgactt tgtgcccatt aagtaccgtg aatgccctcc gccgctttgg ggtcactgct accttctgca gctagccaac taccttgcct accactccga catcatggaa gacgtgagcg gtgacggcct actggagtgt cactgtcgct gcaacctatg caccccgcac cgctccctgg tctgcaattc gcaactgctt agcgaaagtc aaattatcgg taccttttgag ctgcagggtc cctcgcctga cgaaaagtcc gcggctccgg ggttgaaact cactccgggg ctgtggacgt cggcttacct tcgcaaattt gtacctgagg actaccacgc ccacgagatt aggttctacg aagaccaatc ccgcccgcca aatgcggagc ttaccgcctg cgtcattacc cagggccaca tccttggcca attgcaagcc atcaacaaag cccgccaaga gtttctgcta cgaaagggac ggggggttta cctggacccc cagtccggcg aggagctcaa cccaatcccc ccgccgccgc agccctatca gcagccgcgg gcccttgctt cccaggatgg cacccaaaaa gaagctgcag ctgccgccgc cgccacccac
```

-continued

```
ggacgaggag gaatactggg acagtcaggc agaggaggtt ttggacgagg aggaggagat gatggaagac tgggacagcc tagacgaagc ttccgaggcc gaagaggtgt cagacgaaac accgtcaccc tcggtcgcat tccctcgcc ggcgcccag aaattggcaa ccgttcccag catcgctaca acctccgctc ctcaggcgcc gccggcactg cctgttcgcc gacccaaccg tagatgggac accactggaa ccagggccgg taagtctaag cagccgccgc cgttagccca agagcaacaa cagcgccaag gctaccgctc gtggcgcggg cacaagaacg ccatagttgc ttgcttgcaa gactgtgggg gcaacatctc cttcgcccgc cgctttcttc tctaccatca cggcgtggcc ttcccccgta acatcctgca ttactaccgt catctctaca gcccctactg caccggcggc agcggcagcg gcagcaacag cagcggtcac acagaagcaa aggcgaccgg atagcaagac tctgacaaag cccaagaaat ccacagcggc ggcagcagca ggaggaggag cgctgcgtct ggcgcccaac gaacccgtat cgacccgcga gcttagaaat aggattttc ccactctgta tgctatattt caacaaagca ggggccaaga acaagagctg aaaataaaaa acaggtctct gcgctccctc acccgcagct gcctgtatca caaaagcgaa gatcagcttc ggcgcacgct ggaagacgcg gaggctctct tcagcaaata ctgcgcgctg actcttaagg actagtttcg cgccttct caaatttaag cgcgaaaact acgtcatctc cagcggccac acccggcgcc agcacctgtc gtcagcgcca ttatgagcaa ggaaattccc acgccctaca tgtggagtta ccagccacaa atgggacttg cggctggagc tgcccaagac tactcaaccc gaataaacta catgagcgcg ggaccccaca tgatatcccg ggtcaacgga atccgcgccc accgaaaccg aattctcctc gaacaggcgg ctattaccac cacacctcgt aataaccta atccccgtag ttggcccgct gccctggtgt accaggaaag tcccgctccc accactgtgg tacttcccag agacgcccag gccgaagttc agatgactaa ctcaggggcg cagcttgcgg gcggctttcg tcacagggtg cggtcgcccg ggcgttttag ggcggagtaa cttgcatgta ttgggaattg tagttttttt aaaatgggaa gtgacgtatc gtgggaaaac ggaagtgaag atttgaggaa gttgtgggtt ttttggcttt cgtttctggg cgtaggttcg cgtgcggttt tctgggtgtt ttttgtggac tttaaccgtt acgtcatttt ttagtcctat atatactcgc tctgtacttg gccctttta cactgtgact gattgagctg gtgccgtgtc gagtggtgtt ttttaatagg tttttttact ggtaaggctg actgttatgg ctgccgctgt ggaagcgctg tatgttgttc tggagcggga gggtgctatt ttgcctaggc aggagggttt ttcaggtgtt tatgtgtttt tctctcctat taattttgtt atacctccta tgggggctgt aatgttgtct ctacgcctgc gggtatgtat tccccgggc tatttcggtc gctttttagc actgaccgat gttaaccaac ctgatgtgtt taccgagtct tacattatga ctccggacat gaccgaggaa ctgtcggtgg tgcttttaa tcacggtgac cagttttttt acggtcacgc cggcatggcc gtagtccgtc ttatgcttat aagggttgtt tttcctgttg taagacaggc ttctaatgtt taaatgtttt tttttttgtt
```

-continued

```
attttatttt gtgtttaatg caggaacccg cagacatgtt tgagagaaaa atggtgtctt tttctgtggt ggttccggaa cttacctgcc tttatctgca tgagcatgac tacgatgtgc ttgctttttt gcgcgaggct ttgcctgatt ttttgagcag caccttgcat tttatatcgc cgcccatgca acaagcttac atagggcta cgctggttag catagctccg agtatgcgtg tcataatcag tgtgggttct tttgtcatgg ttcctggcgg ggaagtggcc gcgctggtcc gtgcagacct gcacgattat gttcagctgg ccctgcgaag ggacctacgg gatcgcggta tttttgttaa tgttccgctt ttgaatctta tacaggtctg tgaggaacct gaattttgc aatcatgatt cgctgcttga ggctgaaggt ggagggcgct ctggagcaga tttttacaat ggccggactt aatattcggg atttgcttag agacatattg ataaggtggc gagatgaaaa ttatttgggc atggttgaag gtgctggaat gtttatagag gagattcacc ctgaagggtt tagcctttac gtccacttgg acgtgagggc agtttgcctt ttggaagcca ttgtgcaaca tcttacaaat gccattatct gttctttggc tgtagagttt gaccacgcca ccgagggga gcgcgttcac ttaatagatc ttcattttga ggttttggat aatcttttgg aataaaaaaa aaaaaacatg gttcttccag ctcttcccgc tcctcccgtg tgtgactcgc agaacgaatg tgtaggttgg ctgggtgtgg cttattctgc ggtggtggat gttatcaggg cagcggcgca tgaaggagtt tacatagaac ccgaagccag ggggcgcctg gatgctttga gagagtggat atactacaac tactacacag agcgagctaa gcgacgagac cggagacgca gatctgtttg tcacgcccgc acctggtttt gcttcaggaa atatgactac gtccggcgtt ccatttggca tgacactacg accaacacga tctcggttgt ctcggcgcac tccgtacagt agggatcgcc tacctccttt tgagacagag acccgcgcta ccatactgga ggatcatccg ctgctgcccg aatgtaacac tttgacaatg cacaacgtga gttacgtgcg aggtcttccc tgcagtgtgg gatttacgct gattcaggaa tgggttgttc cctgggatat ggttctgacg cgggaggagc ttgtaatcct gaggaagtgt atgcacgtgt gcctgtgttg tgccaacatt gatatcatga cgagcatgat gatccatggt tacgagtcct gggctctcca ctgtcattgt tccagtcccg gttccctgca gtgcatagcc ggcgggcagg ttttggccag ctggtttagg atggtggtgg atggcgccat gtttaatcag aggtttatat ggtaccggga ggtggtgaat tacaacatgc caaaagaggt aatgtttatg tccagcgtgt ttatgagggg tcgccactta atctacctgc gcttgtggta tgatggccac gtgggttctg tggtccccgc catgagcttt ggatacagcg ccttgcactg tgggattttg aacaatattg tggtgctgtg ctgcagttac tgtgctgatt taagtgagat cagggtgcgc tgctgtgccc ggaggacaag gcgtctcatg ctgcgggcgg tgcgaatcat cgctgaggag accactgcca tgttgtattc ctgcaggacg gagcggcggc ggcagcagtt tattcgcgcg ctgctgcagc accaccgccc tatcctgatg cacgattatg actctacccc catgtaggcg tggacttccc cttcgccgcc cgttgagcaa ccgcaagttg gacagcagcc tgtggctcag cagctggaca gcgacatgaa cttaagcgag ctgcccgggg agtttattaa
```

```
tatcactgat gagcgtttgg ctcgacagga aaccgtgtgg aatataacac
ctaagaatat gtctgttacc catgatatga tgcttttaa ggccagccgg
ggagaaagga ctgtgtactc tgtgtgttgg gagggaggtg gcaggttgaa
tactagggtt ctgtgagttt gattaaggta cggtgatcaa tataagctat
gtggtggtgg ggctatacta ctgaatgaaa aatgacttga aattttctgc
aattgaaaaa taaacacgtt gaaacataac atgcaacagg ttcacgattc
tttattcctg ggcaatgtag gagaaggtgt aagagttggt agcaaaagtt
tcagtggtgt attttccact ttcccaggac catgtaaaag acatagagta
agtgcttacc tcgctagttt ctgtggattc actagaatcg atgtaggatg
ttgcccctcc tgacgcggta ggagaagggg agggtgccct gcatgtctgc
cgctgctctt gctcttgccg ctgctgagga gggggcgca tctgccgcag
caccggatgc atctgggaaa agcaaaaaag gggctcgtcc ctgtttccgg
aggaatttgc aagcggggtc ttgcatgacg gggaggcaaa cccccgttcg
ccgcagtccg gccggcccga gactcgaacc ggggtcctg cgactcaacc
cttggaaaat aaccctccgg ctacagggag cgagccactt aatgctttcg
ctttccagcc taaccgctta cgccgcgcgc ggccagtggc caaaaaagct
agcgcagcag ccgccgcgcc tggaaggaag ccaaaaggag cgctcccccg
ttgtctgacg tcgcacacct gggttcgaca cgcgggcggt aaccgcatgg
atcacggcgg acggccggat ccggggttcg aaccccggtc gtccgccatg
ataccccttgc gaatttatcc accagaccac ggaagagtgc ccgcttacag
gctctccttt tgcacggtct agagcgtcaa cgactgcgca cgcctcaccg
gccagagcgt cccgaccatg gagcacttt tgccgctgcg caacatctgg
aaccgcgtcc gcgactttcc gcgcgcctcc accaccgccg ccggcatcac
ctggatgtcc aggtacatct acggattacg tcgacgttta aaccatatga
tcagctcact caaaggcggt aatacggtta tccacagaat caggggataa
cgcaggaaag aacatgtgag caaaaggcca gcaaaaggcc aggaaccgta
aaaaggccgc gttgctggcg ttttttccata ggctccgccc ccctgacgag
catcacaaaa atcgacgctc aagtcagagg tggcgaaacc cgacaggact
ataaagatac caggcgtttc ccctggaag ctccctcgtg cgctctcctg
ttccgaccct gccgcttacc ggatacctgt ccgcctttct cccttcggga
agcgtggcgc tttctcatag ctcacgctgt aggtatctca gttcggtgta
ggtcgttcgc tccaagctgg gctgtgtgca cgaaccccc gttcagcccg
accgctgcgc cttatccggt aactatcgtc ttgagtccaa cccggtaaga
cacgacttat cgccactggc agcagccact ggtaacagga ttagcagagc
gaggtatgta ggcggtgcta cagagttctt gaagtggtgg cctaactacg
gctacactag aagaacagta tttggtatct gcgctctgct gaagccagtt
accttcggaa aaagagttgg tagctcttga tccggcaaac aaaccaccgc
tggtagcggt ggtttttttg tttgcaagca gcagattacg cgcagaaaaa
aaggatctca agaagatcct ttgatctttt ctacggggtc tgacgctcag
tggaacgaaa actcacgtta agggattttg gtcatgagat tatcaaaaag
```

-continued
```
gatcttcacc tagatcettt taaattaaaa atgaagtttt aaatcaatct aaagtatata tgagtaaact tggtctgaca gtcagaagaa ctcgtcaaga aggcgataga aggcgatgcg ctgcgaatcg ggagcggcga taccgtaaag cacgaggaag cggtcagccc attcgccgcc aagctcttca gcaatatcac gggtagccaa cgctatgtcc tgatagcggt ccgccacacc cagccggcca cagtcgatga atccagaaaa gcggccattt tccaccatga tattcggcaa gcaggcatcg ccatgggtca cgacgagatc ctcgccgtcg ggcatgctcg ccttgagcct ggcgaacagt tcggctggcg cgagccctg atgctcttcg tccagatcat cctgatcgac aagaccggct tccatccgag tacgtgctcg ctcgatgcga tgtttcgctt ggtggtcgaa tgggcaggta gccggatcaa gcgtatgcag ccgccgcatt gcatcagcca tgatggatac tttctcggca ggagcaaggt gagatgacag gagatcctgc cccggcactt cgcccaatag cagccagtcc cttcccgctt cagtgacaac gtcgagtaca gctgcgcaag gaacgcccgt cgtggccagc cacgatagcc gcgctgcctc gtcttgcagt tcattcaggg caccgacag gtcggtcttg acaaaaagaa ccgggcgccc ctgcgctgac agccggaaca cggcggcatc agagcagccg attgtctgtt gtgcccagtc atagccgaat agcctctcca cccaagcggc cggagaacct gcgtgcaatc catcttgttc aatcatactc ttcctttttc aatattattg aagcatttat cagggttatt gtctcatgag cggatacata tttgaatgta tttagaaaaa taaacaaata ggggttccgc gcacatttcc ccgaaaagtg ccacctaaat tgtaagcgtt aatattttgt taaaattcgc gttaaatttt tgttaaatca gctcattttt taaccaatag gccgaaatcg gcaaaatccc ttataaatca aaagaataga ccgagatagg gttgagtgtt gttccagttt ggaacaagag tccactatta aagaacgtgg actccaacgt caaagggcga aaaaccgtct atcagggcga tggcccacta cgtgaaccat cacctaatc aagtttttg gggtcgaggt gccgtaaagc actaaatcgg aaccctaaag ggagcccccg atttagagct tgacggggaa agccggcgaa cgtggcgaga aaggaaggga agaaagcgaa aggagcgggc gctagggcgc tggcaagtgt agcggtcacg ctgcgcgtaa ccaccacacc cgccgcgctt aatgcgccgc tacagggcgc gatggatcc
```

In SEQ ID NO:6, residues 1-5343 of pHelper-Kan are derived from adenovirus, and include a polynucleotide encoding the E2A protein (residues 258-1847); residues 5344-8535 are derived from adenovirus, and include a polynucleotide encoding the E4orf6 protein; residues 9423-10011 correspond to ori sequences; residues 10182-10976 encode a kanamycin resistance determinant expressed by a bla promoter sequence (residues 10977-11081); residues 11107-11561 correspond to f1 ori sequences (FIG. 8).

C. Illustrative rAAV Plasmid Vectors

Figure 9:
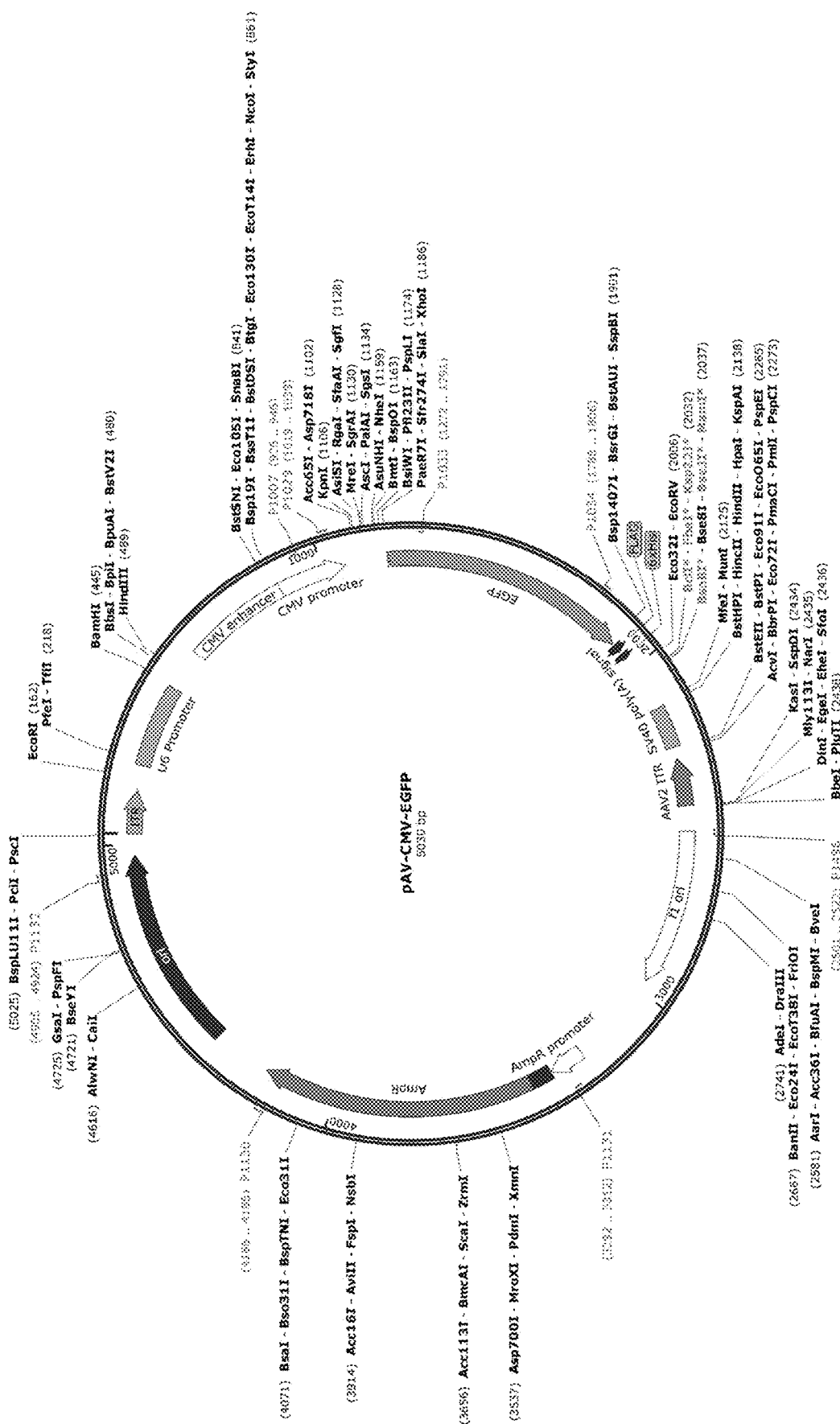
FIG. 9 shows a map of the rAAV plasmid vector pAV-CMV-EGFP (SEQ ID NO:7).

As discussed above, AAV helper function-providing polynucleotides and non-AAV helper function-providing polynucleotides are typically employed in concert with an rAAV plasmid vector to comprise a triple plasmid transfection system. Multiple commercially available rAAV plasmid vectors (e.g., pAV-CMV-EGFP, pGOI, etc. (Cell Biolabs, Inc., Invitrogen and Stratagene)) may be used in accordance with the present invention. An illustrative rAAV plasmid vector that may be used in accordance with the present invention is pAV-CMV-EGFP (SEQ ID NO:7; FIG. 9) which comprises a 5' ITR, a U6 promoter, CMV enhancer and promoter sequences, a polynucleotide encoding the enhanced green fluorescent protein (EGFP) (Gambotto, A. et al. (2000) "*Immunogenicity Of Enhanced Green Fluorescent Protein (EGFP) In BALB/C Mice: Identification Of An H2-Kd-Restricted CTL Epitope*," Gene Ther. 7(23):2036-2040; Tsien, R. Y. (1998) "*The Green Fluorescent Protein*," Annu. Rev. Biochem. 67:509-544; Cinelli, R. A. et al. (2000) "*The Enhanced Green Fluorescent Protein As A Tool For The Analysis Of Protein Dynamics And Localization: Local Fluorescence Study At The Single-Molecule Level*," Photochem. Photobiol. 71(6):771-776; Chopra A. (2008) "*Recombinant Adenovirus With Enhanced Green Fluorescent Protein*," In: MOLECULAR IMAGING AND CONTRAST AGENT Database (MICAD), National Center for Biotechnology Information, Bethesda Md.), FLAG-tag and 6× His-tag sites for facilitating recovery or localization of expressed proteins, an SV40 poly(A) site and a 3' ITR.

```
Coding Strand of Plasmid pAV-CMV-EGFP (SEQ ID NO: 7):
cctgcaggca gctgcgcgct cgctcgctca ctgaggccgc ccgggcgtcg ggcgaccttt ggtcgcccgg ccctccagtg agcgagcgcg cagagaggga gtggccaact ccatcactag gggttcctgc ggccgcacgc gtctagttat taatagtaat cgaattcgtg ttactcataa ctagtaaggt cgggcaggaa gagggcctat ttcccatgat tccttcatat ttgcatatac gatacaaggc tgttagagag ataattagaa ttaatttgac tgtaaacaca agatattag tacaaaatac gtgacgtaga aagtaataat ttcttgggta gtttgcagtt ttaaaattat gttttaaaat ggactatcat atgcttaccg taacttgaaa gtatttcgat ttcttgggtt tatatatctt gtggaaagga cgcgggatcc actggaccag gcagcagcgt cagaagactt ttttggaaaa gcttgactag taatactgta atagtaatca attacggggt cattagttca tagcccatat atggagttcc gcgttacata acttacggta aatggcccgc ctggctgacc gcccaacgac ccccgcccat tgacgtcaat aatgacgtat gttcccatag taacgccaat agggactttc cattgacgtc aatgggtgga gtatttacgg taaactgccc acttggcagt acatcaagtg tatcatatgc caagtacgcc ccctattgac gtcaatgacg gtaaatggcc cgcctggcat tatgcccagt acatgacctt atgggacttt cctacttggc agtacatcta cgtattagtc atcgctatta ccatggtgat gcggttttgg cagtacatca atgggcgtgg atagcggttt gactcacggg gatttccaag tctccacccc attgacgtca atgggagttt gttttgcacc aaaatcaacg ggactttcca aaatgtcgta acaactccgc cccattgacg caaatggggc gtaggcgtgt acggtgggag gtctatataa gcagagctgg tttagtgaac cgtcagatcc gctagagatc cggtaccgag gagatctgcc gccgcgatcg ccggcgcgcc agatctcacg cttaactagc tagcggaccg acgcgtacgc ggccgctcga gatggtgagc aagggcgagg agctgttcac cggggtggtg cccatcctgg tcgagctgga cggcgacgta aacggccaca gttcagcgt gtccggcgag ggcgagggcg atgccaccta cggcaagctg accctgaagt tcatctgcac caccggcaag ctgcccgtgc cctggcccac cctcgtgacc accctgacct acggcgtgca gtgcttcagc cgctaccccg accacatgaa gcagcacgac ttcttcaagt ccgccatgcc cgaaggctac gtccaggagc gcaccatctt cttcaaggac gacggcaact acaagacccg cgccgaggtg aagttcgagg gcgacaccct ggtgaaccgc atcgagctga agggcatcga cttcaaggag gacggcaaca tcctggggca caagctggag tacaactaca acagccacaa cgtctatatc atggccgaca agcagaagaa cggcatcaag gtgaacttca gatccgcca caacatcgag gacggcagcg tgcagctcgc cgaccactac cagcagaaca cccccatcgg cgacggcccc gtgctgctgc ccgacaacca ctacctgagc acccagtccg ccctgagcaa agaccccaac gagaagcgcg atcacatggt cctgctggag ttcgtgaccg ccgccgggat cactctcggc atggacgagc tgtacaagta agtcgaggat tataaggatg acgacgataa attcgtcgag
```

-continued

```
caccaccacc accaccacta ataaggttta tccgatccac cggatctaga taagatatcc gatccaccgg atctagataa ctgatcataa tcagccatac cacatttgta gaggttttac ttgctttaaa aaacctccca cacctccccc tgaacctgaa acataaaatg aatgcaattg ttgttgttaa cttgtttatt gcagcttata atggttacaa ataaagcaat agcatcacaa atttcacaaa taaagcattt ttttcactgc attctagttg tggtttgtcc aaactcatca atgtatctta acgcggtaac cacgtgcgga ccgagcggcc gcaggaaccc ctagtgatgg agttggccac tccctctctg cgcgctcgct cgctcactga ggccgggcga ccaaaggtcg cccgacgccc gggctttgcc cgggcggcct cagtgagcga gcgagcgcgc agctgcctgc aggggcgcct gatgcggtat tttctcctta cgcatctgtg cggtatttca caccgcatac gtcaaagcaa ccatagtacg cgccctgtag cggcgcatta agcgcggcgg gtgtggtggt tacgcgcagc gtgaccgcta cacctgccag cgccttagcg cccgctcctt tcgctttctt cccttccttt ctcgccacgt tcgccggctt tccccgtcaa gctctaaatc gggggctccc tttagggttc cgatttagtg ctttacggca cctcgacccc aaaaaacttg atttgggtga tggttcacgt agtgggccat cgccctgata gacggttttt cgccctttga cgttggagtc cacgttcttt aatagtggac tcttgttcca aactggaaca acactcaacc ctatctcggg ctattctttt gatttataag ggattttgcc gatttcggcc tattggttaa aaaatgagct gatttaacaa aaatttaacg cgaattttaa caaaatatta acgtttacaa ttttatggtg cactctcagt acaatctgct ctgatgccgc atagttaagc cagccccgac acccgccaac acccgctgac gcgccctgac gggcttgtct gctcccggca tccgcttaca gacaagctgt gaccgtctcc gggagctgca tgtgtcagag gttttcaccg tcatcaccga aacgcgcgag acgaaagggc ctcgtgatac gcctattttt ataggttaat gtcatgataa taatggtttc ttagacgtca ggtggcactt ttcggggaaa tgtgcgcgga acccctattt gtttatttt ctaaatacat tcaaatatgt atccgctcat gagacaataa ccctgataaa tgcttcaata atattgaaaa aggaagagta tgagtattca acatttccgt gtcgccctta ttcccttttt tgcggcattt tgccttcctg ttttttgctca cccagaaacg ctggtgaaag taaaagatgc tgaagatcag ttgggtgcac gagtgggtta catcgaactg gatctcaaca gcggtaagat ccttgagagt tttcgccccg aagaacgttt tccaatgatg agcactttta aagttctgct atgtggcgcg gtattatccc gtattgacgc cgggcaagag caactcggtc gccgcataca ctattctcag aatgacttgg ttgagtactc accagtcaca gaaaagcatc ttacggatgg catgacagta agagaattat gcagtgctgc cataaccatg agtgataaca ctgcggccaa cttacttctg acaacgatcg gaggaccgaa ggagctaacc gcttttttgc acaacatggg ggatcatgta actcgccttg atcgttggga accggagctg aatgaagcca taccaaacga cgagcgtgac accacgatgc ctgtagcaat ggcaacaacg ttgcgcaaac tattaactgg cgaactactt actctagctt
```

```
cccggcaaca attaatagac tggatggagg cggataaagt tgcaggacca cttctgcgct cggcccttcc ggctggctgg tttattgctg ataaatctgg agccggtgag cgtgggtctc gcggtatcat tgcagcactg gggccagatg gtaagccctc ccgtatcgta gttatctaca cgacggggag tcaggcaact atggatgaac gaaatagaca gatcgctgag ataggtgcct cactgattaa gcattggtaa ctgtcagacc aagtttactc atatatactt tagattgatt taaaacttca tttttaattt aaaaggatct aggtgaagat cctttttgat aatctcatga ccaaaatccc ttaacgtgag ttttcgttcc actgagcgtc agacccgta gaaaagatca aaggatcttc ttgagatcct ttttttctgc gcgtaatctg ctgcttgcaa acaaaaaaac caccgctacc agcggtggtt tgtttgccgg atcaagagct accaactctt tttccgaagg taactggctt cagcagagcg cagataccaa atactgtcct tctagtgtag ccgtagttag gccaccactt caagaactct gtagcaccgc ctacatacct cgctctgcta atcctgttac cagtggctgc tgccagtggc gataagtcgt gtcttaccgg gttggactca agacgatagt taccggataa ggcgcagcgg tcgggctgaa cggggggttc gtgcacacag cccagcttgg agcgaacgac ctacaccgaa ctgagatacc tacagcgtga gctatgagaa agcgccacgc ttcccgaagg gagaaaggcg gacaggtatc cggtaagcgg cagggtcgga acaggagagc gcacgaggga gcttccaggg ggaaacgcct ggtatcttta tagtcctgtc gggtttcgcc acctctgact tgagcgtcga ttttttgtgat gctcgtcagg ggggcggagc ctatggaaaa acgccagcaa cgcggccttt ttacggttcc tggccttttg ctggcctttt gctcacatgt
```

In SEQ ID NO:7, residues 1-128 of pAV-CMV-EGFP correspond to the 5' ITR; residues 201-441 are U6 promoter sequences; residues 562-865 are human cytomegalovirus (CMV) immediate early enhancer sequences; residues 866-1068 comprise the CMV immediate early promoter; residues 1192-1911 comprise a mammalian codon-optimized polynucleotide that encodes the EGFP; residues 1918-1941 encode the FLAG-tag; residues 1951-1968 encode the 6× His-tag; residues 2139-2260 encode the SV40 poly(A) sequence; residues 2293-2433 correspond to the 3' ITR; residues 2508-22963 correspond to F1 ori sequences; residues 3350-4210 encode an ampicillin resistance determinant and its signal sequence (residues 3350-3418) expressed by a bla promoter sequence (residues 3245-3349); residues 4381-4969 correspond to an ori sequence (FIG. 9).

Figure 10:
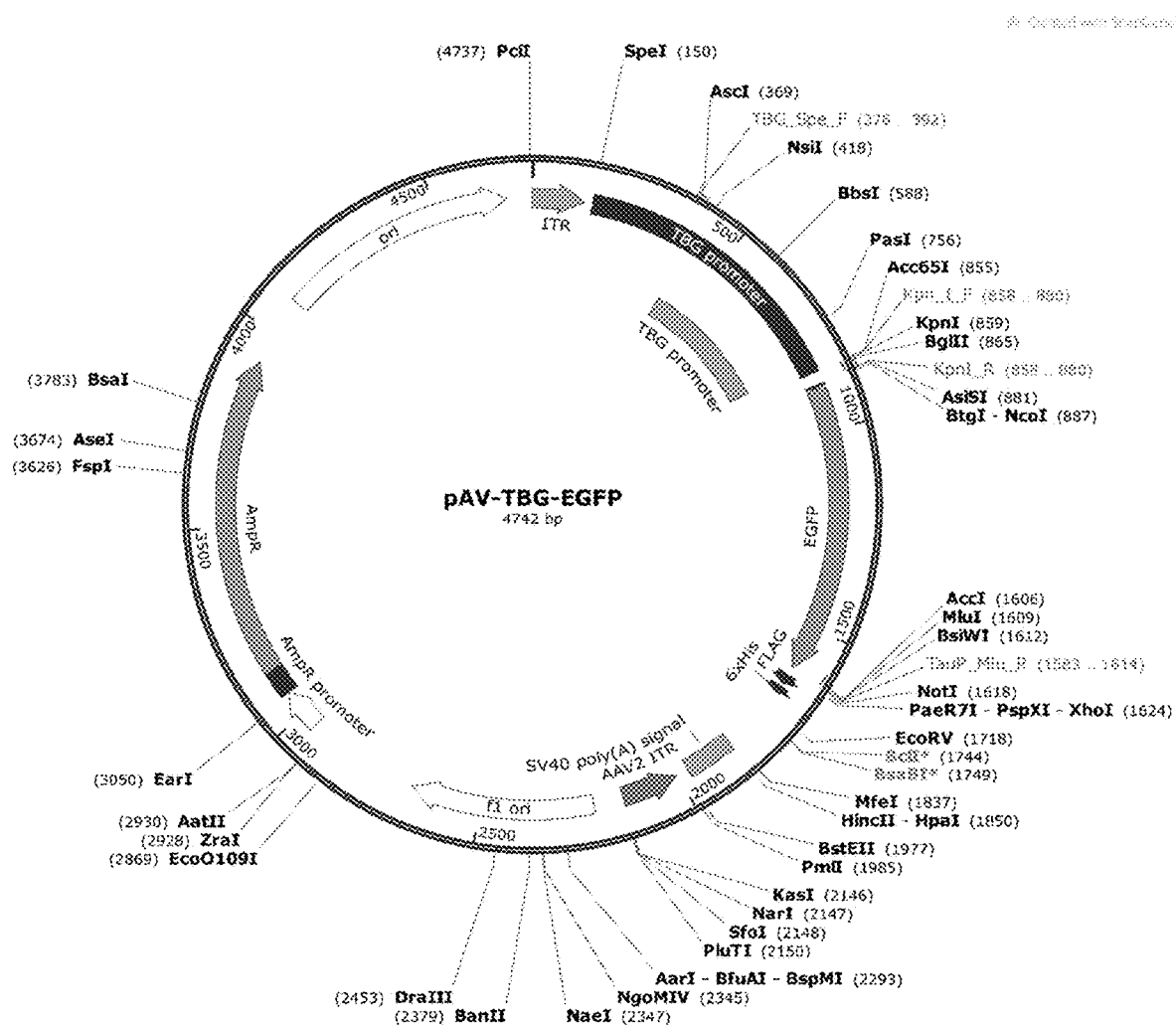
FIG. 10 shows a map of the rAAV plasmid vector pAV-TBG-EGFP (SEQ ID NO:8).

A second illustrative rAAV plasmid vector that may be used in accordance with the present invention is pAV-TBG-EGFP (SEQ ID NO:8; FIG. 10) which comprises a 5' ITR, a thyroid hormone-binding globulin (TBG) promoter, a polynucleotide encoding the enhanced green fluorescent protein (EGFP), FLAG-tag and 6× His-tag sites for facilitating recovery or localization of expressed proteins, an SV40 poly(A) site and a 3' ITR.

```
Coding Strand of Plasmid pAV-TBG-EGFP (SEQ ID NO: 8):
cctgcaggca gctgcgcgct cgctcgctca ctgaggccgc ccgggcgtcg ggcgaccttt ggtcgcccgg cctcagtgag cgagcgagcg cgcagagagg gagtggccaa ctccatcact aggggttcct gcggccggtc gcgtctagta ctagtaggtt aatttttaaa aagcagtcaa aagtccaagt ggcccttggc agcatttact ctctctgttt gctctggtta ataatctcag gagcacaaac attccagatc caggttaatt tttaaaaagc agtcaaaagt ccaagtggcc cttggcagca tttactctct ctgtttgctc tggttaataa tctcaggagc acaaacattc cagatccggc gcgcagggc tggaagctac ctttgacatc atttcctctg cgaatgcatg tataatttct acagaaccta ttagaaagga
```

-continued

```
tcacccagcc tctgcttttg tacaactttc ccttaaaaaa ctgccaattc cactgctgtt tggcccaata gtgagaactt tttcctgctg cctcttggtg cttttgccta tggcccctat tctgcctgct gaagacactc ttgccagcat ggacttaaac ccctccagct ctgacaatcc tctttctctt ttgttttaca tgaagggtct ggcagccaaa gcaatcactc aaagttcaaa ccttatcatt ttttgctttg ttcctcttgg ccttggtttt gtacatcagc tttgaaaata ccatcccagg gttaatgctg gggttaattt ataactaaga gtgctctagt tttgcaatac aggacatgct ataaaaatgg aaagatgttg ctttctgaga gacaggtacc gaggagatct gccgccgcga tcgccaccat ggtgagcaag ggcgaggagc tgttcaccgg ggtggtgccc atcctggtcg agctggacgg cgacgtaaac ggccacaagt tcagcgtgtc cggcgagggc gagggcgatg ccacttacgg caagctgacc ctgaagttca tctgcaccac cggcaagctg cccgtgccct ggcccaccct cgtgaccacc ctgacctacg gcgtgcagtg cttcagccgc taccccgacc acatgaagca gcacgacttc ttcaagtccg ccatgcccga aggctacgtc caggagcgca ccatcttctt caaggacgac ggcaactaca agacccgcgc cgaggtgaag ttcgagggcg acaccctggt gaaccgcatc gagctgaagg gcatcgactt caaggaggac ggcaacatcc tggggcacaa gctggagtac aactacaaca gccacaacgt ctatatcatg gccgacaagc agaagaacgg catcaaggtg aacttcaaga tccgccacaa catcgaggac ggcagcgtgc agctcgccga ccactaccag cagaacaccc ccatcggcga cggccccgtg ctgctgcccg acaaccacta cctgagcacc cagtccgccc tgagcaaaga ccccaacgag aagcgcgatc acatggtcct gctggagttc gtgaccgccg ccgggatcac tctcggcatg gacgagctgt acaagtagac gcgtacgcgg ccgctcgagg attataagga tgacgacgat aaattcgtcg agcaccacca ccaccaccac taataaggtt tatccgatcc accggatcta gataagatat ccgatccacc ggatctagat aactgatcat aatcagccat accacatttg tagaggtttt acttgcttta aaaaacctcc cacacctccc cctgaacctg aaacataaaa tgaatgcaat tgttgttgtt aacttgttta ttgcagctta taatggttac aaataaagca atagcatcac aaatttcaca aataaagcat ttttttcact gcattctagt tgtggtttgt ccaaactcat caatgtatct taacgcggta accacgtgcg gacccaacgg ccgcaggaac ccctagtgat ggagttggcc actccctctc tgcgcgctcg ctcgctcact gaggccgggc gaccaaaggt cgcccgacgc ccgggctttg cccgggcggc ctcagtgagc gagcgagcgc gcagctgcct gcaggggcgc ctgatgcggt attttctcct tacgcatctg tgcggtattt cacaccgcat acgtcaaagc aaccatagta cgcgccctgt agcggcacat taagcgcggc gggtgtggtg gttacgcgca gcgtgaccgc tacacctgcc agcgccttag cgcccgctcc tttcgctttc ttcccttcct ttctcgccac gttcgccggc tttccccgtc aagctctaaa tcggggggctc cctttagggt tccgatttag tgctttacgg cacctcgacc ccaaaaaact tgatttgggt gatggttcac gtagtgggcc atcgccctga tagacggttt ttcgcccttt gacgttggag
```

-continued

```
tccacgttct ttaatagtgg actcttgttc caaactggaa caacactcaa
ctctatctcg ggctattctt ttgatttata agggattttg ccgatttcgg
tctattggtt aaaaaatgag ctgatttaac aaaaatttaa cgcgaatttt
aacaaaatat taacgtttac aattttatgg tgcactctca gtacaatctg
ctctgatgcc gcatagttaa gccagccccg acaccgcca acaccgctg
acgcgccctg acgggcttgt ctgctcccgg catccgctta cagacaagct
gtgaccgtct ccgggagctg catgtgtcag aggttttcac cgtcatcacc
gaaacgcgcg agacgaaagg gcctcgtgat acgcctattt ttataggtta
atgtcatgat aataatggtt tcttagacgt caggtggcac ttttcgggga
aatgtgcgcg gaaccctat ttgtttattt ttctaaatac attcaaatat
gtatccgctc atgagacaat aaccctgata aatgcttcaa taatattgaa
aaaggaagag tatgagtatt caacatttcc gtgtcgccct tattccctt
tttgcggcat tttgccttcc tgttttgct cacccagaaa cgctggtgaa
agtaaaagat gctgaagatc agttgggtgc acgagtgggt tacatcgaac
tggatctcaa cagcggtaag atccttgaga gttttcgccc cgaagaacgt
tttccaatga tgagcacttt taaagttctg ctatgtggcg cggtattatc
ccgtattgac gccgggcaag agcaactcgg tcgccgcata cactattctc
agaatgactt ggttgagtac tcaccagtca cagaaaagca tcttacggat
ggcatgacag taagagaatt atgcagtgct gccataacca tgagtgataa
cactgcggcc aacttacttc tgacaacgat cggaggaccg aaggagctaa
ccgcttttt gcacaacatg ggggatcatg taactcgcct tgatcgttgg
gaaccggagc tgaatgaagc cataccaaac gacgagcgtg acaccacgat
gcctgtagca atggcaacaa cgttgcgcaa actattaact ggcgaactac
ttactctagc ttcccggcaa caattaatag actggatgga gcggataaa
gttgcaggac cacttctgcg ctcggccctt ccggctggct ggtttattgc
tgataaatct ggagccggtg agcgtgggtc tcgcggtatc attgcagcac
tggggccaga tggtaagccc tcccgtatcg tagttatcta cacgacgggg
agtcaggcaa ctatggatga acgaaataga cagatcgctg ataggtgc
ctcactgatt aagcattggt aactgtcaga ccaagtttac tcatatatac
tttagattga tttaaaactt cattttaat ttaaaggat ctaggtgaag
atcctttttg ataatctcat gaccaaaatc ccttaacgtg agttttcgtt
ccactgagcg tcagaccccg tagaaaagat caaaggatct tcttgagatc
ctttttttct gcgcgtaatc tgctgcttgc aaacaaaaa accaccgcta
ccagcggtgg tttgtttgcc ggatcaagag ctaccaactc tttttccgaa
ggtaactggc ttcagcagag cgcagatacc aaatactgtt cttctagtgt
agccgtagtt aggccaccac ttcaagaact ctgtagcacc gcctacatac
ctcgctctgc taatcctgtt accagtggct gctgccagtg gcgataagtc
gtgtcttacc gggttggact caagacgata gttaccggat aaggcgcagc
ggtcgggctg aacggggggt tcgtgcacac agcccagctt ggagcgaacg
acctacaccg aactgagata cctacagcgt gagctatgag aaagcgccac
```

-continued

```
gcttcccgaa gggagaaagg cggacaggta tccggtaagc ggcagggtcg gaacaggaga gcgcacgagg gagcttccag ggggaaacgc ctggtatctt tatagtcctg tcgggtttcg ccacctctga cttgagcgtc gattttttgtg atgctcgtca gggggggcgga gcctatgaa aaacgccagc aacgcggcct ttttacggtt cctggccttt tgctggcctt ttgctcacat gt
```

In SEQ ID NO:8, residues 1-130 of pAV-TBG-EGFP correspond to the 5' ITR; residues 150-854 are TBG promoter sequences, with residues 415-824 comprising the TBG promoter; residues 886-1608 encode the EGFP; residues 1630-1653 encode the FLAG-tag; residues 1663-1680 encode the 6× His-tag; residues 1851-1972 encode the poly(A) sequence; residues 2005-2145 corresponds to the 3' ITR; residues 2220-2675 correspond to F1 ori sequences; residues 3062-3922 encode an ampicillin resistance determinant and its signal sequence (residues 3062-3130) expressed by a bla promoter sequence (residues 2957-3061); residues 4093-4681 correspond to an ori sequence (FIG. 10).

As used herein, the term "native AAV serotype promoter sequence" is intended to denote a promoter sequence that natively controls the transcription of an AAV rep gene or is natively present within such rep gene. For example:

AAV1 P5 promoter sequences natively control the transcription of the rep gene of AAV1 and AAV1 P40 promoter sequences are natively found within the rep gene of AAV1. Thus, the AAV1 P5 promoter sequences and the AAV1 P40 promoter sequences are native AAV serotype promoter sequences of the rep gene of AAV1;

AAV2 P5 promoter sequences natively control the transcription of the rep gene of AAV2 and the AAV2 P40 promoter sequences are natively found within the rep gene of AAV2. Thus, the AAV2 P5 promoter sequences and the AAV2 P40 promoter sequences are native AAV serotype promoter sequences of the rep gene of AAV2;

AAV5 P5 promoter sequences natively control the transcription of the rep gene of AAV5 and the AAV5 P40 promoter sequences are natively found within the rep gene of AAV5. Thus, the AAV5 P5 promoter sequences and the AAV5 P40 promoter sequences are native AAV serotype promoter sequences of the rep gene of AAV5;

AAV6 P5 promoter sequences natively control the transcription of the rep gene of AAV6 and the AAV6 P40 promoter sequences are natively found within the rep gene of AAV6. Thus, the AAV6 P5 promoter sequences and the AAV6 P40 promoter sequences are native AAV serotype promoter sequences of the rep gene of AAV6; and AAV7 P5 promoter sequences natively control the transcription of the rep gene of AAV7 and the AAV7 P40 promoter sequences are natively found within the rep gene of AAV7. Thus, the AAV7 P5 promoter sequences and the AAV7 P40 promoter sequences are native AAV serotype promoter sequences of the rep gene of AAV7;

Native AAV P5 and P40 promoter sequences for AAV serotypes 1-8 are shown in Table 1. Such sequences, or subsequences thereof that are capable of mediating transcription, may be used in accordance with the methods of the present invention.

TABLE 1

| SEQ ID NO | AAV Promoter | Native Serotype | Sequence |
| --- | --- | --- | --- |
| SEQ ID NO: 9 | P5 | AAV1 | ggtcctgtat tagctgtcac gtgagtgctt ttgcgacatt ttgcgacacc acgtggccat ttagggtata tatggccgag tgagcgagca ggatctccat tttgaccgcg aaatttgaac gagcagcagc c |
| SEQ ID NO: 10 | P5 | AAV2 | ggtcctgtat tagaggtcac gtgagtgttt tgcgacattt tgcgacacca tgtggtcacg ctgggtattt aagcccgagt gagcacgcag ggtctccatt ttgaagcggg aggtttgaac gcgcagccgc c |
| SEQ ID NO: 11 | P5 | AAV3 | ccagctgcgt cagcagtcag gtgacccttt tgcgacagtt tgcgacacca cgtggccgct gagggtatat attctcgagt gagcgaacca ggagctccat tttgaccgcg aaatttgaac gagcagcagc c |
| SEQ ID NO: 12 | P5 | AAV4 | ggtccctgta ttagcagtca cgtgagtgtc gtatttcgcg gagcgtagcg gagcgcatac caagctgcca cgtcacagcc acgtggtccg tttgcgacag tttgcgacac catgtggtca ggagggtata taaccgcgag tgagccagcg aggagctcca ttttgcccgc gaattttgaa cgagcagcag cc |
| SEQ ID NO: 13 | P5 | AAV5 | atgtgatgtg ttttatccaa taggaagaaa gcgcgcgtat gagttctcgc gagacttccg gggtataaaa gaccgagtga acgagcccgc cgccattctt tgctctggac tgctagagga ccctcgctgc c |

TABLE 1-continued

| SEQ ID NO | AAV Promoter | Native Serotype | Sequence |
|---|---|---|---|
| SEQ ID NO: 14 | P5 | AAV6 | ggtcctgtat tagaggtcac gtgagtgttt tgcgacattt tgcgacacca tgtggtcacg ctgggtattt aagcccgagt gagcacgcag ggtctccatt ttgaagcggg aggtttgaac gcgcagcgcc |
| SEQ ID NO: 15 | P5 | AAV7 | ggtcctgtat tagctgtcac gtgagtgctt ttgcgacatt ttgcgacacc acgtggccat ttgaggtata tatggccgag tgagcgagca ggatctccat tttgaccgcg aaatttgaac gagcagcagc c |
| SEQ ID NO: 16 | P5 | AAV8 | ggtcctgtat tagctgtcac gtgagtgctt ttgcggcatt ttgcgacacc acgtggccat ttgaggtata tatggccgag tgagcgagca ggatctccat tttgaccgcg aaatttgaac gagcagcagc c |
| SEQ ID NO: 17 | P40 | AAV1 | ggtgacaaag caggaagtca aagagttctt ccgctgggcg caggatcacg tgaccgaggt ggcgcatgag ttctacgtca gaaagggtgg agccaacaaa agacccgccc ccgatgacgc ggataaaagc gagcccaagc gggcctgccc ctcagtcgcg gatccatcga cgtcagacgc |
| SEQ ID NO: 18 | P40 | AAV2 | ggtcaccaag caggaagtca aagacttttt ccggtgggca aaggatcacg tggttgaggt ggagcatgaa ttctacgtca aaaagggtgg agccaagaaa agacccgccc ccagtgacgc agatataagt gagcccaaac gggtgcgcag gtcagttgcg cagccatcga cgtcagacgc |
| SEQ ID NO: 19 | P40 | AAV3 | ggtcaccaaa caggaagtaa aggacttttt ccggtgggct tccgatcacg tgactgacgt ggctcatgag ttctacgtca gaaagggtgg agctaagaaa cgccccgcct ccaatgacgc ggatgtaagc gagccaaaac gggagtgcac gtcacttgcg cagccgacaa cgtcagacgc |
| SEQ ID NO: 20 | P40 | AAV4 | ggtcaccaag caggaagtca aagacttttt ccggtgggcg tcagatcacg tgaccgaggt gactcacgag ttttacgtca gaaagggtgg agctagaaag aggcccgccc ccaatgacgc agatataagt gagcccaagc gggcctgtcc gtcagttgcg cagccatcga cgtcagacgc |
| SEQ ID NO: 21 | P40 | AAV5 | gattactaag caggaagtca aggacttttt tgcttgggca aaggtcaatc aggtgccggt gactcacgag tttaaagttc cagggaatt ggcgggaact aaaggggcgg agaaatctct aaaacgccca ctgggtgacg tcaccaatac tagctataaa agtctggaga agcgggcctg gagcatgagg ctctcatttg ttcccgagac gcctcgcagt tcagacg |
| SEQ ID NO: 22 | P40 | AAV6 | ggtgacaaag caggaagtca aagagttctt ccgctgggcg caggatcacg tgaccgaggt ggcgcatgag ttctacgtca gaaagggtgg agccaacaag agacccgccc ccgatgacgc ggataaaagc gagcccaagc gggcctgccc ctcagtcgcg gatccatcga cgtcagacgc |
| SEQ ID NO: 23 | P40 | AAV8 | ggtgacgaag caggaagtca aagagttctt ccgctgggcc agtgatcacg tgaccgaggt ggcgcatgag ttctacgtca gaaagggcgg agccagcaaa agacccgccc ccgatgacgc ggatataagc gagcccaagc gggcctgccc ctcagtcgcg gatccatcga cgtcagacgc |
| SEQ ID NO: 24 | P40 | AAV8 | ggtgacaaag caggaagtca aagagttctt ccgctgggcc agtgatcacg tgaccgaggt ggcgcatgag ttttacgtca gaaagggcgg agccagcaaa agacccgccc ccgatgacgc ggataaaagc gagcccaagc gggcctgccc ctcagtcgcg gatccatcga cgtcagacgc |

In contrast, the term "non-native AAV serotype promoter sequence" is intended to denote a promoter sequence that does not natively control a rep gene of an AAV and is not natively found within such rep gene. Illustrative, non-limiting examples of non-native AAV serotype promoter sequences include: the AAV1 P5 promoter when used to direct the expression of an AAV2, AAV5, AAV6, or AAV7 rep gene; the AAV2 P5 promoter when used to direct the expression of an AAV1, AAV5, AAV6, or AAV7 rep gene; the AAV5 P5 promoter when used to direct the expression of an AAV1, AAV2, AAV6, or AAV7 rep gene; the AAV6 P5 promoter when used to direct the expression of an AAV1, AAV2, AAV5, or AAV7 rep gene; the AAV7 P5 promoter when used to direct the expression of an AAV1, AAV2, AAV5, or AAV6 rep gene; the AAV1 P40 promoter, when present within an AAV2, AAV5, AAV6, or AAV7 rep gene; the AAV2 P40 promoter, when present within an AAV1, AAV5, AAV6, or AAV7 rep gene; the AAV5 P40 promoter, when present within an AAV1, AAV2, AAV6, or AAV7 rep gene; the AAV6 P40 promoter, when present within an AAV1, AAV2, AAV5, or AAV7 rep gene; the AAV7 P40 promoter, when present within an AAV1, AAV2, AAV5, or AAV6 rep gene, etc.

In one embodiment, one or more of such AAV serotype promoter sequences can be genetically engineered into recombinant AAV helper plasmids that are designed to provide the Rep and Cap proteins to replace or augment the existing P5 or P40 promoters of such plasmids. Such modification is preferably accomplished using well-known methods of recombinant DNA technology.

The identity of the serotype of promoter sequences is indicated herein by denoting the involved promoter (e.g., P5, P40, etc.), the serotype of the rep gene with which it is natively associated, and the name of the vector. Thus, for example, a pAAV-RC2 plasmid that comprises a P5 promoter sequence that is natively associated with AAV2 is denoted as P5(2)-RC2; a pAAV-RC2 plasmid that comprises a P5 promoter sequence that is natively associated with AAV3 is denoted as P5(3)-RC2; a pAAV-RC5 plasmid that comprises a P40 promoter sequence that is natively associated with AAV7 is denoted as P40(7)-RC5; a pAAV-RC2 plasmid that comprises a P5 promoter sequence that is natively associated with AAV3 and a P40 promoter sequence that is natively associated with AAV8 is denoted as P5(3)/P40(8)-RC2; etc.

In one embodiment, the introduced AAV serotype promoter sequence will replace an initially present AAV serotype promoter sequence. In other embodiments, the introduced AAV serotype promoter sequence will be present in addition to such initially present AAV serotype promoter sequence, and will be positioned 5' to, or 3' to, such initially present AAV serotype promoter sequence. The introduced nucleotide sequence may be positioned adjacent to, or apart from, such initially present AAV serotype promoter sequence.

The substitution or addition of one or more of such AAV serotype promoter sequences invention increases rAAV production titers. As used herein, the term "production titer" is intended to denote the amount of concentration of infectious rAAV in a preparation. Such amounts or concentrations are preferably determined by titering the AAV or rAAV in such preparation. The production titers of the rAAV preparations of the present invention are preferably titered after subjecting producing cells (e.g., HEK293 transformed with an rAAV plasmid vector, an AAV helper vector providing Rep and Cap proteins, and an Ad helper vector providing required adenovirus transcription and translation factors) to three rounds of freeze/thawing, followed by sonication to release the rAAV particles. The preparation is then centrifuged. The employed AAV helper vector is localized to the supernatant. An aliquot of the preparation is treated with proteinase K, and the number of AAV genomes is determined. An aliquot of the preparation is infected into HeLa-32C2 cells (which express AAV2 Rep and Cap proteins), and infectious titer is measured using the infectious center assay (ICA) (François, A. et al. (2018) "*Accurate Titration of Infectious AAV Particles Requires Measurement of Biologically Active Vector Genomes and Suitable Controls*," Molec. Ther. Meth. Clin. Develop. 10:223-236) or more preferably, as the median tissue culture infective dose (TCID50) (Zen, Z. et al. (2004) "*Infectious Titer Assay For Adeno Associated Virus Vectors With Sensitivity Sufficient To Detect Single Infectious Events*," Hum. Gene Ther. 15:709-715).

As used herein, an rAAV production titer is said to be "increased" by the methods of the present invention if the production titer obtained from the use of the methods of the present invention is at least 10% greater, more preferably at least 20% greater, still more preferably at least 30% greater, still more preferably at least 40% greater, still more preferably at least 50% greater, still more preferably at least 60% greater, still more preferably at least 70% greater, still more preferably at least 80% greater, still more preferably at least 90% greater, still more preferably at least 2-fold greater, still more preferably at least 110% greater, still more preferably at least 120% greater, still more preferably at least 130% greater, still more preferably at least 140% greater, still more preferably at least 2.5-fold greater, still more preferably at least 160% greater, still more preferably at least 170% greater, still more preferably at least 180% greater, still more preferably at least 190% greater, and still more preferably at least 3-fold greater than the titer obtained from a similarly conducted production in which the additionally provided ions were not provided.

The rAAV whose production titer may be increased using the methods of the present invention may comprise any transgene cassette that permits the rAAV to be packaged into an rAAV plasmid vector that may be encapsidated within an AAV capsid particle. Without limitation, such transgene cassette(s) may be of human, primate (including chimpanzee, gibbon, gorilla, orangutan, etc.), cercopithecine (including baboon, cynomolgus monkey, velvet monkey, etc.), canine, glirine (including rat, mouse, hamster, guinea pig, etc.), feline, ovine, caprine, or equine origin.

In preferred embodiments, such an rAAV or rAAV plasmid vector will encode a protein (e.g., an enzyme, hormone, antibody, receptor, ligand, etc.), or comprise a transcribed nucleic acid, that is relevant to a genetic or heritable disease or condition, such that it may be used in gene therapy to treat such disease or condition.

The methods of the present invention may be used to increase the production titer of rAAV and rAAV plasmid vectors in cells that have been additionally transfected with:
(1) an AAD helper vector possessing a non-native AAV serotype promoter sequence and capable of expressing proteins or RNA molecules that are not natively provided by such rAAV or rAAV plasmid vectors, but are required for their production. As discussed above, such proteins or RNA molecules include the genes encoding the Rep52 and Rep78 proteins that are required for vector transcription control and replication, and for the packaging of viral genomes into the viral capsule, and cap genes that encode VP capsid proteins required to form infectious particles; and (2) an Ad helper vector that can provide the non-AAV helper proteins (e.g., E1a, E1b, E2a, VA and E4) or RNA molecules that are not provided by such rAAV or rAAV plasmid vectors, but are required for their production.

In one embodiment for producing the rAAV of the present invention, all of such genes and RNA molecules are provided on the same helper virus (or more preferably, helper vector) so as to comprise, in concert with an rAAV, a double plasmid transfection system. More preferably, however, for producing the rAAV of the present invention, the AAV helper function-providing polynucleotide that provides the required rep and cap genes and such non-native AAV serotype promoter sequences are provided on a vector that is separate from the vector that comprises the non-AAV helper function-providing polynucleotide, so that such vectors or plasmids, in concert with the rAAV, comprise a triple plasmid transfection system.

The invention thus derives in part from the recognition that the production of rAAV may be increased by causing the expression of Rep and Cap proteins to be directed by promoter sequences that are not native promoter sequences. Thus, by modifying a particular rAAV to replace its native P5 and/or P40 AAV serotype promoter sequence(s) with a non-native P5 and/or P40 AAV serotype promoter sequence (or by incorporating a non-native P5 and/or P40 AAV serotype promoter sequence into such rAAV), the methods of the present invention may be employed to increase the production titer of rAAV belonging to any serotype, including the AAV1, AAV2, AAV5, AAV6, AAV7, AAV8, AAV9 and AAV10 serotypes, and including hybrid serotypes (e.g., AAV2/5 and rAAV2/5, which is a hybrid of AAV serotypes 2 and 5 and thus has the trophism of both such serotypes).

The methods of the present invention may be employed to increase the production titers of rAAV that are to be produced using "helper" RNA or proteins provided by an adenovirus, a herpes simplex virus, a cytomegalovirus, a vaccinia virus or a papillomavirus.

The methods of the present invention may be employed to increase the production titers of rAAV produced by cells in adherent monolayer culture or in suspension culture, and may be used with any method capable of producing rAAV. Preferably, however, rAAV is produced by transfecting baby hamster kidney (BHK) cells, or more preferably, human embryonic kidney (HEK) cells grown in tissue culture with the plasmid vectors described above. The BHK cell line BHK-21 (ATCC CCL-10), which lacks endogenous retroviruses is a preferred BHK cell line. The HEK cell line HEK293 (ATCC CRL-1573) and its derivatives, such as HEK293T (ATCC CRL-3216, which is a highly transfectable derivative of the HEK293 cell line into which the temperature-sensitive gene for SV40 T-antigen was inserted) or HEK293T/17 (ATCC® CRL-11268, which was selected for its ease of transfection) are particularly preferred. The HEK293T/17 SF cell line (ATCC ACS-4500) is a derivative of the 293T/17 cell line (ATCC CRL-11268), adapted to serum-free medium and suspension, and may be employed if desired.

The preferred base medium of the present invention for culturing such cells is Eagle's Minimum Essential Medium (ATCC Catalog No. 30-2003) or Dulbecco's Modified Eagle's Medium (DMEM; Mediatech, Manassas, Va.). Fetal bovine serum (e.g., FBS; HyClone Laboratories, South Logan, Utah) is added to a final concentration of 10% in order to make the complete growth medium. Eagle's Minimum Essential Medium and Dulbecco's Modified Eagle's Medium are complex media that contain amino acids, vitamins, and optionally glucose, in addition to various inorganic salts. The media differ in that Dulbecco's modified Eagle's medium contains approximately four times as much of the vitamins and amino acids present in the original formula of Eagle's Minimum Essential Medium, and two to four times as much glucose. Additionally, it contains iron in the form of ferric sulfate and phenol red for pH indication (Yao, T et al. (2017) "*Animal-Cell Culture Media: History, Characteristics, And Current Issues*," Reproduc. Med. Biol. 16(2): 99-117).

Cells to be used for such transfection are preferably passaged twice weekly to maintain them in exponential growth phase. For small-scale transfections, an aliquot of, for example, $1 \times 10^6$ HEK293 or BHK cells per well on a multi-well plate, or $1.5 \times 10^7$ HEK293 cells per 15-cm dish, may be employed. For large-scale production HEK293 or BHK cells may be collected from multiple confluent 15-cm plates, and split into two 10-layer cell stacks (Corning, Corning, N.Y.) containing 1 liter of complete culturing medium. In one embodiment, such cells are grown for 4 days in such medium before transfection. The day before transfection, the two cell stacks may be trypsinized and the cells (e.g., approximately $6 \times 10^8$ cells) may be resuspended in 200 ml of medium. Preferably, the cells are allowed to attach for 24 hours before transfection. Confluency of the cell stacks may be monitored using a Diaphot inverted microscope (Nikon, Melville, N.Y.) from which the phase-contrast hardware had been removed in order to accommodate the cell stack on the microscope stage.

In particular, the present invention thus provides a method for increasing the production titer of a recombinantly-modified adeno-associated virus (rAAV) that comprises a transgene cassette, wherein the method comprises culturing cells that have been transfected with:

(1) the rAAV;
(2) a recombinantly-modified adeno-associated virus (AAV) helper vector that comprises an AAV helper function-providing polynucleotide, wherein such polynucleotide comprises a non-native AAV serotype P5 or P40 promoter sequence in replacement of, or in addition to, a native AAV serotype promoter sequence; and
(3) a vector that comprises a non-AAV helper function-providing polynucleotide;

wherein the culturing is conducted in a culture medium under conditions sufficient to permit the production of the rAAV, and wherein the presence of the non-native AAV serotype P5 or P40 promoter sequence causes the cells to produce the rAAV at an increased production titer relative to that which would be attained if the AAV helper function-providing polynucleotide contained native serotype P5 and P40 promoters.

The present invention further provides a method for increasing the production titer of a recombinantly-modified adeno-associated virus (rAAV) that comprises a transgene cassette, wherein the method comprises culturing cells that have been transfected with:

(1) the rAAV; and
(2) a recombinantly-modified adeno-associated virus (AAV) helper vector that comprises:
   (a) an AAV helper function-providing polynucleotide, wherein such polynucleotide comprises a non-native AAV serotype P5 or P40 promoter sequence in replacement of, or in addition to, a native AAV serotype promoter sequence; and
   (b) a non-AAV helper function-providing polynucleotide;

wherein the culturing is conducted in a culture medium under conditions sufficient to permit the production of the rAAV, and wherein the presence of the non-native AAV serotype P5 or P40 promoter sequence causes the cells to produce the rAAV at an increased production titer relative to that which would be attained if the AAV helper function-providing polynucleotide contained native serotype P5 and P40 promoters.

In preferred embodiments, the transgene cassette of such rAAV encodes a protein, or comprises a transcribed nucleic acid, that is therapeutic for a genetic or heritable disease or condition.

II. Pharmaceutical Compositions of the Present Invention

The invention additionally includes pharmaceutical compositions that comprise a pharmaceutically acceptable preparation of rAAV produced in accordance with the methods of the present invention, and a pharmaceutically acceptable carrier. The rAAV of such pharmaceutical compositions comprises a transgene cassette that encodes a protein, or comprises a transcribed nucleic acid, that is therapeutic for a genetic or heritable disease or condition, and is present in such pharmaceutical composition in an amount effective to ("effective amount")

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Suitable pharmaceutical excipients are described in U.S. Pat. Nos. 8,852,607; 8,192,975; 6,764,845; 6,759,050; and 7,598,070.

Generally, the ingredients of compositions of the invention are supplied either separately or mixed together in unit dosage form, for example, as a dry lyophilized powder or water-free concentrate, or as an aqueous solution in a hermetically sealed container such as a vial, an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline, or other diluent can be provided so that the ingredients may be mixed prior to administration.

The invention also provides a pharmaceutical pack or kit comprising one or more containers such pharmaceutical composition. Optionally associated with such container(s) can be a notice in the form prescribed by a governmental agency regulating the manufacture, use or sale of pharmaceuticals or biological products, which notice reflects approval by the agency of manufacture, use or sale for human administration.

The rAAV of such pharmaceutical compositions is preferably packaged in a hermetically sealed container, such as a vial, an ampoule or sachette indicating the quantity of the molecule, and optionally including instructions for use. In one embodiment, the rAAV of such kit is supplied as a dry sterilized lyophilized powder or water-free concentrate in a hermetically sealed container and can be reconstituted, e.g., with water, saline, or other diluent to the appropriate concentration for administration to a subject. The lyophilized material should be stored at between 2° C. and 8° C. in their original container and the material should be administered within 12 hours, preferably within 6 hours, within 5 hours, within 3 hours, or within 1 hour after being reconstituted. In another embodiment, the rAAV of such kit is supplied as an aqueous solution in a hermetically sealed container and can be diluted, e.g., with water, saline, or other diluent, to the appropriate concentration for administration to a subject. The kit can further comprise one or more other prophylactic and/or therapeutic agents useful for the treatment of the disease or condition, in one or more containers; and/or the kit can further comprise one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

III. Uses of the Invention

The methods of the present invention may be used to facilitate the production of rAAV, and may particularly be used to facilitate the production of rAAV that comprise transgene cassettes that encode a protein (e.g., an enzyme, hormone, antibody, receptor, ligand, etc.), or of rAAV that comprise a transcribed nucleic acid, that is relevant to a genetic or heritable disease or condition, such that it may be used in gene therapy to treat such disease or condition. Examples of such diseases and conditions include: achromatopsia (ACHM); alpha-1 antitrypsin (AAT) deficiency; Alzheimer's Disease; aromatic L-amino acid decarboxylase (AADC) deficiency; choroideremia (CHM); cancer; Duchenne muscular dystrophy; dysferlin deficiency; follistatin gene deficiency (BMDSIBM); hemophilia A; hemophilia B; hepatitis A; hepatitis B; hepatitis C; Huntington's disease; idiopathic Parkinson's disease; late-infantile neuronal ceroid lipofuscinosis (LINCL, an infantile form of Batten disease); Leber congenital amaurosis (LCA); Leber's hereditary optic neuropathy (LHON); limb girdle muscular dystrophy 1B (LGMD1B); limb girdle muscular dystrophy 1C (LGMD1C); limb girdle muscular dystrophy 2A (LGMD2A); limb girdle muscular dystrophy 2B (LGMD2B); limb girdle muscular dystrophy 2I (LGMD2I); limb girdle muscular dystrophy 2L (LGMD2L); lipoprotein lipase (LPL) deficiency; metachromatic leukodystrophy; neurological disability; neuromotor deficit; neuroskeletal impairment; Parkinson's disease; rheumatoid arthritis; Sanfilippo A syndrome; spinal muscular atrophy (SMA); X-linked retinoschisis (XLRS); α-sarcoglycan deficiency (LGMD2D); β-sarcoglycan deficiency (LGMD2E); γ-sarcoglycan deficiency (LGMD2C) and δ-sarcoglycan deficiency (LGMD2F).

IV. Embodiments of the Invention

The invention concerns a recombinantly-modified adeno-associated virus (AAV) helper vector that comprises an AAV helper function-providing polynucleotide, and uses and compositions thereof. It is particularly directed to the following embodiments E1-E16:

E1. A recombinantly-modified adeno-associated virus (AAV) helper vector that comprises an AAV helper function-providing polynucleotide, wherein the polynucleotide comprises a non-native AAV serotype P5 or P40 promoter sequence.

E2. The recombinantly-modified adeno-associated virus (AAV) helper vector of E1, wherein the AAV helper function-providing polynucleotide vector comprises a non-native AAV serotype P5 promoter sequence.

E3. The recombinantly-modified adeno-associated virus (AAV) helper vector of any one of E1 or E2, wherein the AAV helper function-providing polynucleotide vector comprises a non-native AAV serotype P40 promoter sequence.

E4. The recombinantly-modified adeno-associated virus (AAV) helper vector of any one of E1-E3, wherein the vector is a plasmid vector.

E5. The recombinantly-modified adeno-associated virus (AAV) helper vector of E1, wherein the non-native AAV serotype P5 or P40 promoter sequence replaces a native AAV serotype promoter sequence.

E6. The recombinantly-modified adeno-associated virus (AAV) helper vector of any one of E1-E5, wherein the vector additionally comprises a non-AAV helper function-providing polynucleotide.

E7. A method for increasing the production titer of a recombinantly-modified adeno-associated virus (rAAV) that comprises a transgene cassette, wherein the method comprises culturing cells that have been transfected with:
(1) an rAAV plasmid vector that comprises the transgene cassette flanked by the inverted terminal repeated sequences;
(2) the recombinantly-modified adeno-associated virus (AAV) helper vector of E6;
wherein the culturing is conducted in a culture medium under conditions sufficient to permit the production of the rAAV and wherein the presence of the non-native AAV serotype P5 or P40 promoter sequence causes the cells to produce the rAAV at an increased production titer relative to that which would be attained if the AAV helper function-providing polynucleotide contained native serotype P5 and P40 promoters.

E8. A method for increasing the production titer of a recombinantly-modified adeno-associated virus (rAAV) that comprises a transgene cassette, wherein the method comprises culturing cells that have been transfected with:
(1) an rAAV plasmid vector that comprises the transgene cassette flanked by the inverted terminal repeated sequences;
(2) the recombinantly-modified adeno-associated virus (AAV) helper vector of any one of E1-E6; and
(3) an additional vector, especially a plasmid vector, that comprises a non-AAV helper function-providing polynucleotide;
wherein the culturing is conducted in a culture medium under conditions sufficient to permit the production of the rAAV, and wherein the presence of the non-native AAV serotype P5 or P40 promoter sequence causes the cells to produce the rAAV at an increased production titer relative to that which would be attained if the AAV helper function-providing polynucleotide contained native serotype P5 and P40 promoters.

E9. The method of any one of E7-E8, wherein:
(A) the AAV helper function-providing polynucleotide of the vector encodes an AAV1 Cap protein, and the non-native AAV serotype promoter sequence is a promoter sequence of an AAV of serotype AAV3, AAV4, AAV5, AAV6, AAV7 or AAV8, or a hybrid of one or more of the serotypes;

(B) the AAV helper function-providing polynucleotide of the vector encodes an AAV2 Cap protein, and the non-native AAV serotype promoter sequence is a promoter sequence of an AAV of serotype AAV1, AAV3, AAV4, AAV5, AAV6, AAV7 or AAV8, or a hybrid of one or more of the serotypes;

(C) the AAV helper function-providing polynucleotide of the vector encodes an AAV3 Cap protein, and the non-native AAV serotype promoter sequence is a promoter sequence of an AAV of serotype AAV1, AAV4, AAV5, AAV6, AAV7 or AAV8, or a hybrid of one or more of the serotypes;

(D) the AAV helper function-providing polynucleotide of the vector encodes an AAV4 Cap protein, and the non-native AAV serotype promoter sequence is a promoter sequence of an AAV of serotype AAV1, AAV3, AAV5, AAV6, AAV7 or AAV8, or a hybrid of one or more of the serotypes;

(E) the AAV helper function-providing polynucleotide of the vector encodes an AAV5 Cap protein, and the non-native AAV serotype promoter sequence is a promoter sequence of an AAV of serotype AAV1, AAV3, AAV4, AAV6, AAV7 or AAV8, or a hybrid of one or more of the serotypes;

(F) the AAV helper function-providing polynucleotide of the vector encodes an AAV6 Cap protein, and the non-native AAV serotype promoter sequence is a promoter sequence of an AAV of serotype AAV1, AAV3, AAV4, AAV5, AAV7 or AAV8, or a hybrid of one or more of the serotypes;

(G) the AAV helper function-providing polynucleotide of the vector encodes an AAV7 Cap protein, and the non-native AAV serotype promoter sequence is a promoter sequence of an AAV of serotype AAV1, AAV3, AAV4, AAV5, AAV6 or AAV8, or a hybrid of one or more of the serotypes; or (H) the AAV helper function-providing polynucleotide of the vector encodes an AAV8 Cap protein, and the non-native AAV serotype promoter sequence is a promoter sequence of an AAV of serotype AAV1, AAV3, AAV4, AAV5, AAV6 or AAV7, or a hybrid of one or more of the serotypes.

E10. The method of any one of E7-E9, wherein the cells are human embryonic kidney cells, baby hamster kidney cells or sf9 insect cells.

E11. The method of E10, wherein the cells are HEK293 human embryonic kidney cells.

E12. The method of E10, wherein the cells are BHK21 baby hamster kidney cells.

E13. The method of any one of E7-E12, wherein the transgene cassette encodes a protein, or comprises a transcribed nucleic acid, that is therapeutic for a genetic or heritable disease or condition.

E14. A preparation of the recombinantly-modified adeno-associated virus (rAAV) produced by the method of E13.

E15. A pharmaceutical composition that comprises the recombinantly-modified adeno-associated virus (rAAV) produced by the method of E13, and a pharmaceutically acceptable carrier.

E16. The preparation of recombinantly-modified adeno-associated virus (rAAV) of E14, or the pharmaceutical composition of E15, for use in the treatment of the genetic or heritable disease or condition.

EXAMPLES

Having now generally described the invention, the same will be more readily understood through reference to the following examples, which are provided by way of illustration and are not intended to be limiting of the present invention unless specified.

Example 1

Comparison of rAAV Production Titers by Cells Transfected with AAV RC2 Helper Plasmid Vectors Having a Non-Native AAV Serotype P5 Promoter Sequence In order to demonstrate the ability of non-native AAV serotype promoter sequences to affect the production titer of rAAV, derivatives of AAV helper plasmid AAV RC2 (having an AAV2 rep gene and a cap gene that encodes Cap protein of the AAV2 serotype) were constructed that comprised a non-native AAV serotype promoter sequence (FIG. 11) in lieu of the native AAV2 serotype P5 promoter of such plasmid (FIG. 12A; downward striped rectangle). The P19 and P40 promoters of the constructs were not changed, and thus were both native AAV2 serotype promoter sequences (FIG. 12A; solid black rectangles).

The following constructs were employed; the sequences of the promoter regions are shown in Table 1:
(1) Parent-RC2—pAAV-RC2 (SEQ ID NO:2), which contains the AAV2 rep gene and a partial portion of the full AAV2 serotype P5 promoter sequence (SEQ ID NO:10), and the AAV2 cap gene, whose expression is controlled by a native AAV2 P40 promoter sequence (SEQ ID NO:18);
(2) P5(1)-RC2—a derivative of plasmid vector pAAV-RC2 in which native AAV serotype P5 promoter sequences had been replaced with the P5 promoter sequences of AAV serotype 1 (SEQ ID NO:9);
(3) P5(2)-RC2—a derivative of plasmid vector pAAV-RC2 in which the partial AAV2 serotype P5 promoter sequences of Parent-RC2 had been replaced with the full-length P5 promoter sequences of AAV serotype 2 (SEQ ID NO:10);
(4) P5(3)-RC2—a derivative of plasmid vector pAAV-RC2 in which native AAV2 serotype P5 promoter sequences had been replaced with the P5 promoter sequences of AAV serotype 3 (SEQ ID NO:11);
(5) P5(4)-RC2—a derivative of plasmid vector pAAV-RC2 in which native AAV2 serotype P5 promoter sequences had been replaced with the P5 promoter sequences of AAV serotype 4 (SEQ ID NO:12);
(6) P5(5)-RC2—a derivative of plasmid vector pAAV-RC2 in which native AAV2 serotype P5 promoter sequences had been replaced with the P5 promoter sequences of AAV serotype 5 (SEQ ID NO:13);
(7) P5(6)-RC2—a derivative of plasmid vector pAAV-RC2 in which native AAV2 serotype P5 promoter sequences had been replaced with the P5 promoter sequences of AAV serotype 6 (SEQ ID NO:14);
(8) P5(7)-RC2—a derivative of plasmid vector pAAV-RC2 in which native AAV2 serotype P5 promoter sequences had been replaced with the P5 promoter sequences of AAV serotype 7 (SEQ ID NO:15); and
(9) P5(8)-RC2—a derivative of plasmid vector pAAV-RC2 in which native AAV2 serotype P5 promoter sequences had been replaced with the P5 promoter sequences of AAV serotype 8 (SEQ ID NO:16).

FIG. 12B shows the production titers of rAAV obtained using such AAV helper plasmid vectors. The production titers of rAAV were obtained using a triple plasmid transfection system with an rAAV (pGOI; BBa_K404119), and an Ad helper plasmid (pHelper) that provided the required adenoviral functions. Plasmid pGOI is an rAAV plasmid vector that comprises, in the 5' to 3' direction, a 5' ITR, a CMV promoter, a β-globin intron, a polynucleotide encoding the yellow fluorescent protein mVenus (Nagai, T. et al. (2002) "*A Variant Of Yellow Fluorescent Protein With Fast And Efficient Maturation For Cell-Biological Applications,*" Nat. Biotechnol. 20(1):87-90), the polyA domain of human growth hormone and a 3' ITR. FIG. 12B reveals that the serotype of the P5 promoter affects rAAV production titers, and indicates that replacing the native AAV2 P5 promoter of the plasmid vector pAAV-RC2 with an AAV5 serotype P5 promoter greatly decreased rAAV production titer, whereas replacing the native AAV2 P5 promoter of the plasmid vector pAAV-RC2 with a P5 promoter of AAV serotype 1, 3, 5, 7 or 8 greatly increased rAAV production titer.

Example 2

Comparison of rAAV Production Titers by Cells Transfected with AAV RC2 Helper Plasmid Vectors Having a Non-Native AAV Serotype P40 Promoter Sequence In order to further demonstrate the ability of non-native AAV serotype promoter sequences to affect the production titer of rAAV, derivatives of AAV helper plasmid AAV RC2 (having an AAV2 rep gene and a cap gene that encodes Cap protein of the AAV2 serotype) were constructed that comprised a non-native AAV serotype promoter sequence (FIG. 11) in lieu of the native serotype P40 promoter of such plasmid (FIG. 13A; upward striped rectangle). The P5 and P19 promoters of the constructs were not changed, and thus were both native AAV2 serotype promoter sequences (FIG. 13A; solid black rectangles).

The following constructs were employed; the sequences of the promoter regions are shown in Table 1:
(1) Parent-RC2—pAAV-RC2 (SEQ ID NO:2), which contains the AAV2 rep gene and a partial portion of the full AAV2 serotype P5 promoter sequence (SEQ ID NO:10), and the AAV2 cap gene, whose expression is controlled by a native AAV2 P40 promoter sequence (SEQ ID NO:18);
(2) P40(1)-RC2—a derivative of plasmid vector pAAV-RC2 in which native AAV2 serotype P40 promoter sequences had been replaced with the P40 promoter sequences of AAV serotype 1 (SEQ ID NO:17);
(3) P40(2)-RC2—a derivative of plasmid vector pAAV-RC2 in which the AAV2 serotype P40 promoter sequences of Parent-RC2 had been replaced with the P40 promoter sequences of AAV serotype 2 (SEQ ID NO:18);
(4) P40(3)-RC2—a derivative of plasmid vector pAAV-RC2 in which native AAV2 serotype P40 promoter sequences had been replaced with the P40 promoter sequences of AAV serotype 3 (SEQ ID NO:19);
(5) P40(4)-RC2—a derivative of plasmid vector pAAV-RC2 in which native AAV2 serotype P40 promoter sequences had been replaced with the P40 promoter sequences of AAV serotype 4 (SEQ ID NO:20);
(6) P40(5)-RC2—a derivative of plasmid vector pAAV-RC2 in which native AAV2 serotype P40 promoter sequences had been replaced with the P40 promoter sequences of AAV serotype 5 (SEQ ID NO:21);
(7) P40(6)-RC2—a derivative of plasmid vector pAAV-RC2 in which native AAV2 serotype P40 promoter sequences had been replaced with the P40 promoter sequences of AAV serotype 6 (SEQ ID NO:22);

(8) P40(7)-RC2—a derivative of plasmid vector pAAV-RC2 in which native AAV2 serotype P40 promoter sequences had been replaced with the P40 promoter sequences of AAV serotype 7 (SEQ ID NO:23); and (9) P40(8)-RC2—a derivative of plasmid vector pAAV-RC2 in which native AAV2 serotype P40 promoter sequences had been replaced with the P40 promoter sequences of AAV serotype 8 (SEQ ID NO:24).

FIG. 13B shows the production titers of rAAV obtained using such AAV helper plasmid vectors. Production titers of rAAV were obtained essentially as described in Example 1. The results of the investigation reveal that the serotype of the P40 promoter also affects rAAV production titers, and indicate that replacing the native AAV2 P40 promoter of the plasmid vector pAAV-RC2 with an AAV5 serotype P40 promoter greatly decreased rAAV production titer, whereas replacing the native AAV2 P40 promoter of the plasmid vector pAAV-RC2 with an AAV1 serotype P40 promoter or with an AAV8 serotype P40 promoter greatly increased rAAV production titer.

Example 3

Comparison of rAAV Production Titers by Cells Transfected with AAV RC2 Helper Plasmid Vectors Having Non-Native AAV Serotype P5 and P40 Promoter Sequences In order to further demonstrate the ability of non-native AAV serotype promoter sequences to affect the production titer of rAAV, derivatives of AAV helper plasmid AAV RC2 (having an AAV2 rep gene and a cap gene that encodes Cap protein of the AAV2 serotype) were constructed that comprised non-native AAV serotype promoter sequences (FIG. 11) in lieu of the native AAV2 serotype P5 (FIG. 14A; downward striped rectangle) and P40 (FIG. 14A; upward striped rectangle) promoters of such plasmid. The AAV2 P19 promoter of the constructs were not changed, and thus was the native AAV2 serotype promoter sequence (FIG. 14A; solid black rectangle).

The following constructs were employed; the sequences of the promoter regions are shown in Table 1:

(1) Parent-RC2—pAAV-RC2 (SEQ ID NO:2), which contains the AAV2 rep gene and a partial portion of the full AAV2 serotype P5 promoter sequence (SEQ ID NO:10), and the AAV2 cap gene, whose expression is controlled by a native AAV2 P40 promoter sequence (SEQ ID NO:18);

(2) P5(2)-RC2—a derivative of plasmid vector pAAV-RC2 in which the partial AAV2 serotype P5 promoter sequences of Parent-RC2 had been replaced with the full-length P5 promoter sequences of AAV serotype 2 (SEQ ID NO:10);

(3) P5(3)-RC2—a derivative of plasmid vector pAAV-RC2 in which native AAV2 serotype P5 promoter sequences had been replaced with the P5 promoter sequence of AAV3 (SEQ ID NO:11);

(4) P5(5)-RC2—a derivative of plasmid vector pAAV-RC2 in which native AAV2 serotype P5 promoter sequences had been replaced with the P5 promoter sequence of AAV5 (SEQ ID NO:13);

(5) P40(1)-RC2—a derivative of plasmid vector pAAV-RC2 in which native AAV2 serotype P40 promoter sequences had been replaced with the P40 promoter sequences of AAV1 (SEQ ID NO:17);

(6) P5(2)/P40(1)-RC2—a derivative of plasmid vector pAAV-RC2 in which native AAV2 serotype P5 promoter sequences had been replaced with the P5 promoter sequence of AAV2 (SEQ ID NO:10) and in which native P40 promoter sequences had been replaced with the P40 promoter sequence of AAV1 (SEQ ID NO:17);

(7) P5(3)/P40(1)-RC2—a derivative of plasmid vector pAAV-RC2 in which native AAV2 serotype P5 promoter sequences had been replaced with the P5 promoter sequence of AAV3 (SEQ ID NO:11) and in which native P40 promoter sequences had been replaced with the P40 promoter sequence of AAV1 (SEQ ID NO:17); and (8) P5(5)/P40(1)-RC2—a derivative of plasmid vector pAAV-RC2 in which native AAV2 serotype P5 promoter sequences had been replaced with the P5 promoter sequence of AAV5 (SEQ ID NO:13) and in which native P40 promoter sequences had been replaced with the P40 promoter sequence of AAV1 (SEQ ID NO:17).

Production titers of rAAV were obtained essentially as described in Example 1. FIG. 14B shows the production titers of rAAV obtained using such AAV helper plasmid vectors. As shown in FIG. 14B, the replacement of the native P5 and P40 promoters of pAAV-RC2 with the P5 promoter sequence of AAV3 or AAV5 and the P40 promoter sequence of AAV1 synergistically increased rAAV production titers.

Example 4

Comparison of rAAV Production Titers by Cells Transfected with AAV RC6 Helper Plasmid Vectors Having Non-Native AAV Serotype P5 and P40 Promoter Sequences In order to further demonstrate the ability of non-native AAV serotype promoter sequences to affect the production titer of rAAV, derivatives of AAV helper plasmid AAV RC6 (having an AAV2 rep gene and a cap gene that encodes Cap protein of the AAV6 serotype) were constructed that comprised non-native AAV serotype promoter sequences (FIG. 11) in lieu of the native AAV2 serotype P5 (FIG. 15A; downward striped rectangle) and P40 (FIG. 15A; downward striped rectangle) promoters of such plasmid. The AAV2 P19 promoter of the constructs were not changed, and thus was the native AAV2 serotype promoter sequence (FIG. 15A; solid black rectangle).

The following constructions were employed; the sequences of the promoter regions are shown in Table 1:

(1) Parent-RC6—pAAV-RC6 (SEQ ID NO:4), which contains the AAV2 rep gene and its native AAV2 serotype P5 promoter sequence (SEQ ID NO:10), and the AAV6 cap gene, whose expression is controlled by a native AAV2 P40 promoter sequence (SEQ ID NO:18);

(2) P5(1)-RC6—a derivative of plasmid vector pAAV-RC6 in which native AAV2 serotype P5 promoter sequences had been replaced with the P5 promoter sequence of AAV1 (SEQ ID NO:9);

(3) P5(2)-RC6—a derivative of plasmid vector pAAV-RC6 in which native AAV2 serotype P5 promoter sequences had been replaced with the P5 promoter sequence of AAV2 (SEQ ID NO:10);

(4) P5(3)-RC6—a derivative of plasmid vector pAAV-RC6 in which native AAV2 serotype P5 promoter sequences had been replaced with the P5 promoter sequence of AAV3 (SEQ ID NO:11);

(5) P5(7)-RC6—a derivative of plasmid vector pAAV-RC6 in which native AAV2 serotype P5 promoter sequences had been replaced with the P5 promoter sequence of AAV7 (SEQ ID NO:15); and (6) P5(8)-RC6—a derivative of plasmid vector pAAV-RC6 in which native AAV2 serotype P5 promoter sequences had been replaced with the P5 promoter sequence of AAV8 (SEQ ID NO:16).

FIG. 15B shows the production titers of rAAV obtained using such AAV helper plasmid vectors. Production titers of rAAV were obtained essentially as described in Example 1.

The results of the investigation are shown in FIGS. 15B and 15C, and reveal that the production titers of rAAV obtained using such AAV helper plasmid vectors. As shown in such Figures, the replacement of the native P5 and P40 promoters of pAAV-RC6 with the P5 promoter sequence of AAV serotype 1, 2, 3, 7 or 8 increased rAAV production titers.

Example 5

Comparison of rAAV Production Titers by Cells Transfected with AAV RC1, AAV RC5 or AAV RC7 Helper Plasmid Vectors Having Non-Native AAV Serotype P5 and P40 Promoter Sequences In order to further demonstrate the ability of non-native AAV serotype promoter sequences to affect the production titer of rAAV, derivatives of AAV helper plasmid AAV RC1 (having an AAV2 rep gene and a cap gene that encodes Cap protein of the AAV1 serotype), derivatives of AAV helper plasmid AAV RC5 (having an AAV2 rep gene and a cap gene that encodes Cap protein of the AAV5 serotype) and derivatives of AAV helper plasmid AAV RC7 (having an AAV2 rep gene and a cap gene that encodes Cap protein of the AAV7 serotype) were constructed that comprised non-native AAV serotype promoter sequences (FIG. 11) in lieu of the native AAV2 serotype P5 (FIG. 16A; downward striped rectangle) and/or P40 (FIG. 16A; upward striped rectangle) promoter sequences of such plasmids.

The following constructions were employed; the sequences of the promoter regions are shown in Table 1:
(1) Parent-RC1—pAAV-RC1 (SEQ ID NO:1), which contains the AAV2 rep gene and its native AAV2 serotype P5 promoter sequence (SEQ ID NO:10), and the AAV1 cap gene, whose expression is controlled by a native AAV2 P40 promoter sequence (SEQ ID NO:18);
(2) Parent-RC5—pAAV-RC5 (SEQ ID NO:3), which contains the AAV2 rep gene and its native AAV2 serotype P5 promoter sequence (SEQ ID NO:10), and the AAV5 cap gene, whose expression is controlled by a native AAV2 P40 promoter sequence (SEQ ID NO:18);
(3) Parent-RC7—pAAV-RC7 (SEQ ID NO:5), which contains the AAV2 rep gene and its native AAV2 serotype P5 promoter sequence (SEQ ID NO:10), and the AAV7 cap gene, whose expression is controlled by a native AAV2 P40 promoter sequence (SEQ ID NO:18);
(4) P5(2)-RC1—a derivative of plasmid vector pAAV-RC1 in which native AAV1 serotype P5 promoter sequences had been replaced with the P5 promoter sequence of AAV2 (SEQ ID NO:10);
(5) P5(7)-RC1—a derivative of plasmid vector pAAV-RC1 in which native AAV1 serotype P5 promoter sequences had been replaced with the P5 promoter sequence of AAV7 (SEQ ID NO:15);
(6) P5(8)-RC1—a derivative of plasmid vector pAAV-RC1 in which native AAV1 serotype P5 promoter sequences had been replaced with the P5 promoter sequence of AAV8 (SEQ ID NO:16);
(7) P5(7)-RC5—a derivative of plasmid vector pAAV-RC5 in which native AAV5 serotype P5 promoter sequences had been replaced with the P5 promoter sequence of AAV7 (SEQ ID NO:15);
(8) P5(2)-RC7—a derivative of plasmid vector pAAV-RC7 in which native AAV7 serotype P5 promoter sequences had been replaced with the P5 promoter sequence of AAV2 (SEQ ID NO:10).
(9) P5(7)-RC7—a derivative of plasmid vector pAAV-RC7 in which native AAV7 serotype P5 promoter sequences had been replaced with the P5 promoter sequence of AAV7 (SEQ ID NO:15); and
(10) P5(8)-RC7—a derivative of plasmid vector pAAV-RC7 in which native AAV7 serotype P5 promoter sequences had been replaced with the P5 promoter sequence of AAV8 (SEQ ID NO:16).

Production titers of rAAV were obtained essentially as described in Example 1. The results of the investigation are shown in FIG. 16B, and reveals that the replacement of the native P5 promoter sequences of pAAV-RC1, pAAV-RC5, and pAAV-RC7 with P5 promoter sequence of AAV serotype 2, 7 or 8 increased rAAV production titers.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for increasing the production titer of a recombinantly-modified adeno-associated virus (rAAV) that comprises a transgene cassette that is flanked by inverted terminal repeated sequences, wherein said method comprises culturing human embryonic kidney cells or baby hamster kidney cells transfected with:

(1) an rAAV plasmid vector that comprises said transgene cassette flanked by said inverted terminal repeated sequences; and (2) an rAAV helper vector that comprises an AAV helper function-providing polynucleotide, wherein said polynucleotide comprises an AAV P5 promoter sequence, an AAV P40 promoter sequence, an AAV Cap encoding sequence, and an AAV Rep encoding sequence;

wherein said AAV Rep encoding sequence is under the transcriptional control of said AAV P5 promoter sequence, and expresses said AAV Rep52 protein and said AAV Rep78 protein in said transfected cells;

wherein said AAV Cap encoding sequence is under the transcriptional control of said AAV P40 promoter sequence, and expresses said AAV Cap protein in said transfected cells; and wherein said AAV P5 promoter sequence is not native to said AAV Rep encoding sequence and/or said AAV P40 promoter sequence is not native to said AAV Cap encoding sequence; and (3) an Ad helper plasmid vector that comprises a polynucleotide encoding viral transcription and translation factors required for the replication and packaging of rAAV;

wherein said culturing is conducted in a culture medium under conditions sufficient to permit the production of said rAAV and wherein:

(A) (1) said Rep encoding sequence of said rAAV helper vector is an AAV2 Rep encoding sequence that is under the transcriptional control of the P5 promoter of AAV1, the P5 promoter of AAV3, the P5 promoter of AAV5, the P5 promoter of AAV7 or the P5 promoter of AAV8, and (2) said Cap encoding sequence of said rAAV helper vector is an AAV2 Cap encoding sequence that is under the transcriptional control of the P40 promoter of AAV2; or (B) (1) said Rep encoding sequence of said rAAV helper vector is an AAV2 Rep encoding sequence that is under the transcriptional control of the P5 promoter of AAV2, and (2) said Cap encoding sequence of said rAAV helper vector is an AAV2 Cap encoding sequence that is under the transcriptional control of the P40 promoter of AAV1 or the P40 promoter of AAV8; or (C) (1) said Rep encoding sequence of said rAAV helper vector is an AAV2 Rep encoding sequence that is under the transcriptional control of the P5 promoter of AAV3 or the P5 promoter of AAV5, and (2) said Cap encoding sequence of said rAAV helper vector is an AAV2 Cap encoding sequence that is under the transcriptional control of the P40 promoter of AAV1; or (D) (1) said Rep encoding sequence of said rAAV helper vector is an AAV2 Rep encoding sequence that is under the transcriptional control of the P5 promoter of AAV1, the P5 promoter of AAV2, the P5 promoter of AAV3, the P5 promoter of AAV7 or the P5 promoter of AAV8, and (2) said Cap encoding sequence of said rAAV helper vector is an AAV6 Cap encoding sequence that is under the transcriptional control of the P40 promoter of AAV2; or (E) (1) said Rep encoding sequence of said rAAV helper vector is an AAV2 Rep encoding sequence that is under the transcriptional control of the P5 promoter of AAV2, the P5 promoter of AAV7 or the P5 promoter of AAV8, and (2) said Cap encoding sequence of said rAAV helper vector is an AAV1 Cap encoding sequence, an AAV5 Cap encoding sequence or an AAV7 Cap encoding sequence that is under the transcriptional control of the P40 promoter of AAV2;

wherein the transfection of said cells with said rAAV plasmid vector, said Ad helper plasmid, and said rAAV helper vector that comprises:

(1) said AAV P5 promoter sequence that is not native to said AAV Rep coding sequence of said rAAV helper vector, and/or (2) said AAV P40 promoter sequence that is not native to said AAV Cap coding sequence of said rAAV helper vector causes said transfected cells to produce said rAAV at a production titer that is increased relative to that which would be attained if said AAV P5 promoter sequence of said rAAV helper vector were native to said Rep encoding sequence of said rAAV helper vector and said AAV P40 promoter sequence of said rAAV helper vector were native to said Cap encoding sequence of said rAAV helper vector.

2. The method of claim 1, wherein said rAAV helper vector comprises:
 (1) said AAV2 Rep encoding sequence that is under the transcriptional control of the P5 promoter of AAV1, the P5 promoter of AAV3, the P5 promoter of AAV5, the P5 promoter of AAV7 or the P5 promoter of AAV8, and
 (2) said AAV2 Cap encoding sequence that is under the transcriptional control of the P40 promoter of AAV2.

3. The method of claim 1, wherein said rAAV helper vector comprises:
 (1) said AAV2 Rep encoding sequence that is under the transcriptional control of the P5 promoter of AAV2, and
 (2) said AAV2 Cap encoding sequence that is under the transcriptional control of the P40 promoter of AAV1 or the P40 promoter of AAV8.

4. The method of claim 1, wherein said rAAV helper vector comprises:
 (1) said AAV2 Rep encoding sequence that is under the transcriptional control of the P5 promoter of AAV3 or the P5 promoter of AAV5, and
 (2) said AAV2 Cap encoding sequence that is under the transcriptional control of the P40 promoter of AAV1.

5. The method of claim 1, wherein said rAAV helper vector comprises:
 (1) said AAV2 Rep encoding sequence that is under the transcriptional control of the P5 promoter of AAV1, the P5 promoter of AAV2, the P5 promoter of AAV3, the P5 promoter of AAV7 or the P5 promoter of AAV8, and
 (2) said AAV6 Cap encoding sequence that is under the transcriptional control of the P40 promoter of AAV2.

6. The method of claim 1, wherein said rAAV helper vector comprises:
 (1) said AAV2 Rep encoding sequence that is under the transcriptional control of the P5 promoter of AAV2, the P5 promoter of AAV7 or the P5 promoter of AAV8, and
 (2) said AAV1, said AAV5 or said AAV7 Cap encoding sequence that is under the transcriptional control of the P40 promoter of AAV2.

7. The method of claim 1, wherein said method comprises culturing the human embryonic kidney cells.

8. The method of claim 7, wherein said human embryonic kidney cells are HEK 293 human embryonic kidney cells.

9. The method of claim 1, wherein said method comprises culturing the baby hamster kidney cells.

10. The method of claim 9, wherein said baby hamster kidney cells are BHK21 baby hamster kidney cells.

11. The method of claim 1, wherein said transgene cassette encodes a protein, or comprises a polynucleotide domain that is transcribed into an RNA molecule, wherein said protein or said RNA molecule is therapeutic for a disease or a condition that is genetic or heritable.

12. The method of claim 11, wherein said transgene cassette encodes the protein that is therapeutic for said disease or said condition that is genetic or heritable.

13. The method of claim 11, wherein said transgene cassette comprises the polynucleotide domain that is transcribed into the RNA molecule that is therapeutic for said disease or said condition that is genetic or heritable.

14. The method of claim 11, wherein said disease or said condition that is genetic or heritable is: achromatopsia (ACHM); alpha-1 antitrypsin (AAT) deficiency; Alzheimer's Disease; aromatic L-amino acid decarboxylase (AADC) deficiency; choroideremia (CHM); cancer; Duchenne muscular dystrophy; dysferlin deficiency; follistatin gene deficiency (BMDSIBM); hemophilia A; hemophilia B; hepatitis A; hepatitis B; hepatitis C; Huntington's disease; idiopathic Parkinson's disease; late-infantile neuronal ceroid lipofuscinosis (LINCL, an infantile form of Batten disease); Leber congenital amaurosis (LCA); Leber's hereditary optic neuropathy (LHON); limb girdle muscular dystrophy 1B (LGMD1B); limb girdle muscular dystrophy 1C (LGMD1C); limb girdle muscular dystrophy 2A (LGMD2A); limb girdle muscular dystrophy 2B (LGMD2B); limb girdle muscular dystrophy 2I (LGMD2I); limb girdle muscular dystrophy 2L (LGMD2L); lipoprotein lipase (LPL) deficiency; metachromatic leukodystrophy; neurological disability; neuromotor deficit; neuroskeletal impairment; Parkinson's disease; rheumatoid arthritis; Sanfilippo A syndrome; spinal muscular atrophy (SMA); X-linked retinoschisis (XLRS); α-sarcoglycan deficiency (LGMD2D); β-sarcoglycan deficiency (LGMD2E); γ-sarcoglycan deficiency (LGMD2C); or δ-sarcoglycan deficiency (LGMD2F).

15. A method for increasing the production titer of a recombinantly-modified adeno-associated virus that comprises a transgene cassette that is flanked by inverted terminal repeated sequences, wherein said method comprises culturing human embryonic kidney cells or baby hamster kidney cells transfected with:
 (1) an rAAV plasmid vector that comprises said transgene cassette flanked by said inverted terminal repeated sequences; and
 (2) an rAAV helper vector that comprises:
  (a) an AAV helper function-providing polynucleotide portion that comprises an AAV P5 promoter sequence, an AAV P40 promoter sequence, an AAV Cap encoding sequence, and an AAV Rep encoding sequence;
   wherein said AAV Rep encoding sequence is under the transcriptional control of said AAV P5 promoter sequence, and expresses said AAV Rep52 protein and said AAV Rep78 protein in said transfected cells;
   wherein said AAV Cap encoding sequence is under the transcriptional control of said AAV P40 promoter sequence, and expresses said AAV Cap protein in said transfected cells; and
   wherein said AAV P5 promoter sequence is not native to said AAV Rep encoding sequence and/or said AAV P40 promoter sequence is not native to said AAV Cap encoding sequence; and
  (b) a non-AAV helper function-providing polynucleotide portion that encodes viral transcription and translation factors required for the replication and packaging of rAAV;
wherein said culturing is conducted in a culture medium under conditions sufficient to permit the production of said rAAV and wherein:
 (A) (1) said Rep encoding sequence of said rAAV helper vector is an AAV2 Rep encoding sequence that is under the transcriptional control of the P5 promoter of AAV1, the P5 promoter of AAV3, the P5 promoter of AAV5, the P5 promoter of AAV7 or the P5 promoter of AAV8, and (2) said Cap encoding sequence of said rAAV helper vector is an AAV2 Cap encoding sequence that is under the transcriptional control of the P40 promoter of AAV2; or (B) (1) said Rep encoding sequence of said rAAV helper vector is an AAV2 Rep encoding sequence that is under the transcriptional control of the P5 promoter of AAV2, and (2) said Cap encoding sequence of said rAAV helper vector is an AAV2 Cap encoding sequence that is under the transcriptional control of the P40 promoter of AAV1 or the P40 promoter of AAV8; or (C) (1) said Rep encoding sequence of said rAAV helper vector is an AAV2 Rep encoding sequence that is under the transcriptional control of the P5 promoter of AAV3 or the P5 promoter of AAV5, and (2) said Cap encoding sequence of said rAAV helper vector is an AAV2 Cap encoding sequence that is under the transcriptional control of the P40 promoter of AAV1; or (D) (1) said Rep encoding sequence of said rAAV helper vector is an AAV2 Rep encoding sequence that is under the transcriptional control of the P5 promoter of AAV1, the P5 promoter of AAV2, the P5 promoter of AAV3, the P5 promoter of AAV7 or the P5 promoter of AAV8, and (2) said Cap encoding sequence of said rAAV helper vector is an AAV6 Cap encoding sequence that is under the transcriptional control of the P40 promoter of AAV2; or (E) (1) said Rep encoding sequence of said rAAV helper vector is an AAV2 Rep encoding sequence that is under the transcriptional control of the P5 promoter of AAV2, the P5 promoter of AAV7 or the P5 promoter of AAV8, and (2) said Cap encoding sequence of said rAAV helper vector is an AAV1 Cap encoding sequence, an AAV5 Cap encoding sequence or an AAV7 Cap encoding sequence that is under the transcriptional control of the P40 promoter of AAV2;

wherein the transfection of said cells with said rAAV plasmid vector, said Ad helper plasmid, and said rAAV helper vector that comprises:

(1) said AAV P5 promoter sequence that is not native to said AAV Rep coding sequence of said rAAV helper vector, and/or (2) said AAV P40 promoter sequence that is not native to said AAV Cap coding sequence of said rAAV helper vector causes said transfected cells to produce said rAAV at a production titer that is increased relative to that which would be attained if said AAV P5 promoter sequence of said rAAV helper vector were native to said Rep encoding sequence of said rAAV helper vector and said AAV P40 promoter sequence of said rAAV helper vector were native to said Cap encoding sequence of said rAAV helper vector.

16. The method of claim 15, wherein said rAAV helper vector comprises:

(1) said AAV2 Rep encoding sequence that is under the transcriptional control of the P5 promoter of AAV1, the P5 promoter of AAV3, the P5 promoter of AAV5, the P5 promoter of AAV7 or the P5 promoter of AAV8, and (2) said AAV2 Cap encoding sequence that is under the transcriptional control of the P40 promoter of AAV2.

17. The method of claim 15, wherein said rAAV helper vector comprises:

(1) said AAV2 Rep encoding sequence that is under the transcriptional control of the P5 promoter of AAV2, and (2) said AAV2 Cap encoding sequence that is under the transcriptional control of the P40 promoter of AAV1 or the P40 promoter of AAV8.

18. The method of claim 15, wherein said rAAV helper vector comprises:

(1) said AAV2 Rep encoding sequence that is under the transcriptional control of the P5 promoter of AAV3 or the P5 promoter of AAV5, and (2) said AAV2 Cap encoding sequence that is under the transcriptional control of the P40 promoter of AAV1.

19. The method of claim 15, wherein said rAAV helper vector comprises:

(1) said AAV2 Rep encoding sequence that is under the transcriptional control of the P5 promoter of AAV1, the P5 promoter of AAV2, the P5 promoter of AAV3, the P5 promoter of AAV7 or the P5 promoter of AAV8, and (2) said AAV6 Cap encoding sequence that is under the transcriptional control of the P40 promoter of AAV2.

20. The method of claim 15, wherein said rAAV helper vector comprises:

(1) said AAV2 Rep encoding sequence that is under the transcriptional control of the P5 promoter of AAV2, the P5 promoter of AAV7 or the P5 promoter of AAV8, and (2) said AAV1, AAV5 or AAV7 Cap encoding sequence that is under the transcriptional control of the P40 promoter of AAV2.

21. The method of claim 15, wherein said method comprises culturing the human embryonic kidney cells.

22. The method of claim 21, wherein said human embryonic kidney cells are HEK 293 human embryonic kidney cells.

23. The method of claim 15, wherein said method comprises culturing the baby hamster kidney cells.

24. The method of claim 23, wherein said baby hamster kidney cells are BHK21 baby hamster kidney cells.

25. The method of claim 15, wherein said transgene cassette encodes a protein, or comprises a polynucleotide domain that is transcribed into an RNA molecule, wherein said protein or said RNA molecule is therapeutic for a disease or a condition that is genetic or heritable.

26. The method of claim 25, wherein said transgene cassette encodes a protein that is therapeutic for said disease or said condition that is genetic or heritable.

27. The method of claim 25, wherein said transgene cassette comprises a polynucleotide domain that is transcribed into an RNA molecule that is therapeutic for said disease or said condition that is genetic or heritable.

28. The method of claim 27, wherein said disease or said condition that is genetic or heritable is: achromatopsia; alpha-1 antitrypsin deficiency; Alzheimer's Disease; aromatic L-amino acid decarboxylase deficiency; choroideremia; cancer; Duchenne muscular dystrophy; dysferlin deficiency; follistatin gene deficiency; hemophilia A; hemophilia B; hepatitis A; hepatitis B; hepatitis C; Huntington's disease; idiopathic Parkinson's disease; late-infantile neuronal ceroid lipofuscinosis, an infantile form of Batten disease; Leber congenital amaurosis; Leber's hereditary optic neuropathy; limb girdle muscular dystrophy 1B; limb girdle muscular dystrophy 1C; limb girdle muscular dystrophy 2A; limb girdle muscular dystrophy 2B; limb girdle muscular dystrophy 2I; limb girdle muscular dystrophy 2L; lipoprotein lipase deficiency; metachromatic leukodystrophy; neurological disability; neuromotor deficit; neuroskeletal impairment; Parkinson's disease; rheumatoid arthritis; Sanfilippo A syndrome; spinal muscular atrophy; X-linked retinoschisis; α-sarcoglycan deficiency; β-sarcoglycan deficiency; γ-sarcoglycan deficiency; or δ-sarcoglycan deficiency.

* * * * *

SEQUENCE LISTING

<160> NUMBER OF SEQ ID NOS: 24

<210> SEQ ID NO 1
<211> LENGTH: 7431
<212> TYPE: DNA
<213> ORGANISM: Artificial Sequence
<220> FEATURE:
<223> OTHER INFORMATION: Coding Strand of Plasmid pAAV-RC1

<400> SEQUENCE: 1
catggttttg ggacgtttcc tgagtcagat tcgcgaaaaa ctgattcaga gaatttaccg      60

-continued

```
cgggatcgag ccgactttgc caaactggtt cgcggtcaca aagaccagaa atggcgccgg      120
aggcgggaac aaggtggtgg atgagtgcta catccccaat tacttgctcc ccaaaaccca      180
gcctgagctc cagtgggcgt ggactaatat ggaacagtat ttaagcgcct gtttgaatct      240
cacggagcgt aaacggttgg tggcgcagca tctgacgcac gtgtcgcaga cgcaggagca      300
gaacaaagag aatcagaatc ccaattctga tgcgccggtg atcagatcaa aaacttcagc      360
caggtacatg gagctggtcg ggtggctcgt ggacaagggg attacctcgg agaagcagtg      420
gatccaggag gaccaggcct catacatctc cttcaatgcg gcctccaact cgcggtccca      480
aatcaaggct gccttggaca atgcgggaaa gattatgagc ctgactaaaa ccgcccccga      540
ctacctggtg ggccagcagc ccgtggagga catttccagc aatcggattt ataaaatttt      600
ggaactaaac gggtacgatc cccaatatgc ggcttccgtc tttctgggat gggccacgaa      660
aaagttcggc aagaggaaca ccatctggct gtttgggcct gcaactaccg ggaagaccaa      720
catcgcggag gccatagccc acactgtgcc cttctacggg tgcgtaaaact ggaccaatga      780 gaactttccc ttcaacgact gtgtcgacaa gatggtgatc tggtgggagg aggggaagat      840
gaccgccaag gtcgtggagt cggccaaagc cattctcgga ggaagcaagg tgcgcgtgga      900
ccagaaatgc aagtcctcgg cccagataga cccgactccc gtgatcgtca cctccaacac      960
caacatgtgc gccgtgattg acgggaactc aacgaccttc gaacaccagc agccgttgca     1020
agaccggatg ttcaaatttg aactcacccg ccgtctggat catgactttg gaaggtcac      1080 caagcaggaa gtcaaagact ttttccggtg ggcaaaggat cacgtggttg aggtggagca     1140
tgaattctac gtcaaaaagg gtggagccaa gaaaagaccc gccccagtg acgcagatat      1200 aagtgagccc aaacgggtgc gcgagtcagt tgcgcagcca tcgacgtcag acgcggaagc     1260
ttcgatcaac tacgcagaca ggtaccaaaa caaatgttct cgtcacgtgg gcatgaatct     1320
gatgctgttt ccctgcagac aatgcgagag aatgaatcag aattcaaata tctgcttcac     1380
tcacggacag aaagactgtt tagagtgctt tcccgtgtca gaatctcaac ccgtttctgt     1440
cgtcaaaaag gcgtatcaga aactgtgcta cattcatcat atcatgggaa aggtgccaga     1500
cgcttgcact gcctgcgatc tggtcaatgt ggatttggat gactgcatct ttgaacaata     1560
aatgatttaa atcaggtatg gctgccgatg gttatcttcc agattggctc gaggacaacc     1620
tctctgaggg cattcgcgag tggtgggact tgaaacctgg agccccgaag cccaaagcca     1680
accagcaaaa gcaggacgac ggccggggtc tggtgcttcc tggctacaag tacctcggac     1740
ccttcaacgg actcgacaag ggggagcccg tcaacgcggc ggacgcagcg ccctcgagc      1800 acgacaaggc ctacgaccag cagctcaaag cgggtgacaa tccgtacctg cggtataacc     1860
acgccgacgc cgagtttcag gagcgtctgc aagaagatac gtcttttggg ggcaacctcg     1920
ggcgagcagt cttccaggcc aagaagcggg ttctcgaacc tctcggtctg gttgaggaag     1980
gcgctaagac ggctcctgga aagaaacgtc cggtagagca gtcgccacaa gagccagact     2040
cctcctcggg catcggcaag acaggccagc agcccgctaa aaagagactc aattttggtc     2100
agactggcga ctcagagtca gtccccgatc acaacctct cggagaacct ccagcaaccc     2160
ccgctgctgt gggaccctact acaatggctt caggcgtgg cgcaccaatg gcagacaata     2220
acgaaggcgc cgacggagtg ggtaatgcct caggaaattg gcattgcgat tccacatggc     2280
tgggcgacag agtcatcacc accagcaccc gcacctgggc cttgcccacc tacaataacc     2340
acctctacaa gcaaatctcc agtgcttcaa cgggggccag caacgacaac cactacttcg     2400
gctacagcac cccctggggg tatttttgatt tcaacagatt ccactgccac ttttcaccac     2460
```

```
gtgactggca gcgactcatc aacaacaatt ggggattccg gcccaagaga ctcaacttca    2520
aactcttcaa catccaagtc aaggaggtca cgacgaatga tggcgtcaca accatcgcta    2580
ataaccttac cagcacggtt caagtcttct cggactcgga gtaccagctt ccgtacgtcc    2640
tcggctctgc gcaccagggc tgcctcctc cgttcccggc ggacgtgttc atgattccgc     2700
aatacggcta cctgacgctc aacaatggca gccaagccgt gggacgttca tccttttact    2760
gcctggaata tttcccttct cagatgctga gaacgggcaa caactttacc ttcagctaca    2820
cctttgagga agtgcctttc cacagcagct acgcgcacag ccagagcctg accggctga    2880 tgaatcctct catcgaccaa tacctgtatt acctgaacag aactcaaaat cagtccggaa    2940
gtgcccaaaa caaggacttg ctgtttagcc gtgggtctcc agctggcatg tctgttcagc    3000
ccaaaaactg gctacctgga ccctgttatc ggcagcagcg cgtttctaaa acaaaaacag    3060
acaacaacaa cagcaatttt acctggactg gtgcttcaaa atataacctc aatgggcgtg    3120
aatccatcat caaccctggc actgctatgg cctcacacaa agacgacgaa gacaagttct    3180
ttcccatgag cggtgtcatg attttttggaa aagagagcgc cggagcttca aacactgcat    3240
tggacaatgt catgattaca gacgaagagg aaattaaagc cactaaccct gtggccaccg    3300
aaagatttgg gaccgtggca gtcaatttcc agagcagcag cacagaccct gcgaccggag    3360
atgtgcatgc tatgggagca ttacctggca tggtgtggca agatagagac gtgtacctgc    3420
agggtcccat ttgggccaaa attcctcaca cagatggaca ctttcacccg tctcctctta    3480
tgggcggctt tggactcaag aacccgcctc ctcagatcct catcaaaaac acgcctgttc    3540
ctgcgaatcc tccggcggag ttttcagcta caaagtttgc ttcattcatc acccaatact    3600
ccacaggaca agtgagtgtg gaaattgaat gggagctgca gaaagaaaac agcaagcgct    3660
ggaatcccga agtgcagtac acatccaatt atgcaaaatc tgccaacgtt gattttactg    3720
tggacaacaa tggactttat actgagcctc gccccattgg cacccgttac cttacccgtc    3780
ccctgtaagg cgcgccaccg gttgcttgtt aatcaataaa ccgtttaatt cgtttcagtt    3840
gaactttggt ctctgcgtat ttctttctta tctagtttcc atgctctagg atccactagt    3900
aacggccgcc agtgtgctgg aattcggctt tgtagttaat gattaacccg ccatgctact    3960
tatctacgta gccatgctct agaggtcctg tattagaggt cacgtgagtg ttttgcgaca    4020
ttttgcgaca ccatgtggtc acgctgggta tttaagcccg agtgagcacg cagggtctcc    4080
attttgaagc gggaggtttg aacgcgcagc cgccaagccg aattctgcag atatccaaac    4140
actggcggcc gctcgactag agcggccgcc accgcgtgg agctccagct tttgttccct    4200
ttagtgaggg ttaattgcgc gcttggcgta atcatggtca tagctgtttc ctgtgtgaaa    4260
ttgttatccg ctcacaattc cacacaacat acgagccgga agcataaagt gtaaagcctg    4320
gggtgcctaa tgagtgagct aactcacatt aattgcgttg cgctcactgc ccgctttcca    4380
gtcgggaaac ctgtcgtgcc agctgcatta atgaatcggc caacgcgcgg ggagaggcgg    4440
tttgcgtatt gggcgctctt ccgcttcctc gctcactgac tcgctgcgct cggtcgttcg    4500
gctgcggcga gcggtatcag ctcactcaaa ggcggtaata cggttatcca cagaatcagg    4560
ggataacgca ggaaagaaca tgtgagcaaa aggccagcaa aaggccagga accgtaaaaa    4620
ggccgcgttg ctggcgtttt tccataggct ccgcccccct gacgagcatc acaaaaatcg    4680
acgctcaagt cagaggtggc gaaacccgac aggactataa agataccagg cgtttccccc    4740
tggaagctcc ctcgtgcgct ctcctgttcc gaccctgccg cttaccggat acctgtccgc    4800
```

```
ctttctccct tcgggaagcg tggcgctttc tcatagctca cgctgtaggt atctcagttc    4860
ggtgtaggtc gttcgctcca agctgggctg tgtgcacgaa ccccccgttc agcccgaccg    4920
ctgcgcctta tccggtaact atcgtcttga gtccaacccg gtaagacacg acttatcgcc    4980
actggcagca gccactggta acaggattag cagagcgagg tatgtaggcg gtgctacaga    5040
gttcttgaag tggtggccta actacggcta cactagaaga acagtatttg gtatctgcgc    5100
tctgctgaag ccagttacct tcggaaaaag agttggtagc tcttgatccg gcaaacaaac    5160
caccgctggt agcggtggtt ttttgtttg caagcagcag attacgcgca gaaaaaaagg    5220
atctcaagaa gatcctttga tcttttctac ggggtctgac gctcagtgga acgaaaactc    5280
acgttaaggg attttggtca tgagattatc aaaaaggatc ttcacctaga tccttttaaa    5340
ttaaaaatga agttttaaat caatctaaag tatatatgag taaacttggt ctgacagtta    5400
ccaatgctta atcagtgagg cacctatctc agcgatctgt ctatttcgtt catccatagt    5460
tgcctgactc cccgtcgtgt agataactac gatacgggag ggcttaccat ctggccccag    5520
tgctgcaatg ataccgcgag acccacgctc accggctcca gatttatcag caataaacca    5580
gccagccgga agggccgagc gcagaagtgg tcctgcaact ttatccgcct ccatccagtc    5640
tattaattgt tgccgggaag ctagagtaag tagttcgcca gttaatagtt tgcgcaacgt    5700
tgttgccatt gctacaggca tcgtggtgtc acgctcgtcg tttggtatgg cttcattcag    5760
ctccggttcc caacgatcaa ggcgagttac atgatccccc atgttgtgca aaaaagcggt    5820
tagctccttc ggtcctccga tcgttgtcag aagtaagttg gccgcagtgt tatcactcat    5880
ggttatggca gcactgcata attctcttac tgtcatgcca tccgtaagat gcttttctgt    5940
gactggtgag tactcaacca agtcattctg agaatagtgt atgcggcgac cgagttgctc    6000
ttgcccggcg tcaatacggg ataataccgc gccacatagc agaactttaa aagtgctcat    6060
cattggaaaa cgttcttcgg ggcgaaaact ctcaaggatc ttaccgctgt tgagatccag    6120
ttcgatgtaa cccactcgtg cacccaactg atcttcagca tcttttactt tcaccagcgt    6180
ttctgggtga gcaaaaacag gaaggcaaaa tgccgcaaaa aagggaataa gggcgacacg    6240
gaaatgttga atactcatac tcttcctttt tcaatattat tgaagcattt atcagggtta    6300
ttgtctcatg agcggataca tatttgaatg tatttagaaa aataaacaaa tagggggttcc    6360 gcgcacattt ccccgaaaag tgccacctaa attgtaagcg ttaatatttt gttaaaattc    6420
gcgttaaatt tttgttaaat cagctcattt tttaaccaat aggccgaaat cggcaaaatc    6480
ccttataaat caaagaaata gaccgagata gggttgagtg ttgttccagt ttggaacaag    6540
agtccactat taaagaacgt ggactccaac gtcaagggc gaaaaaccgt ctatcagggc    6600 gatgcccac tacgtgaacc atcaccctaa tcaagttttt tggggtcgag gtgccgtaaa    6660
gcactaaatc ggaaccctaa agggagcccc cgatttagag cttgacgggg aaagccggcg    6720
aacgtggcga gaaaggaagg gaagaaagcg aaaggagcgg gcgctagggc gctggcaagt    6780
gtagcggtca cgctgcgcgt aaccaccaca cccgccgcgc ttaatgcgcc gctacagggc    6840
gcgtcccatt cgccattcag gctgcgcaac tgttgggaag ggcgatcggt gcgggcctct    6900
tcgctattac gccagctggc gaaggggga tgtgctgcaa ggcgattaag ttgggtaacg    6960
ccagggtttt cccagtcacg acgttgtaaa acgacggcca gtgagcgcgc gtaatacgac    7020
tcactatagg gcgaattggg taccgggccc cccctcgagg tcgacggtat cggggagct    7080 cgcagggtct ccatttgaa gcgggaggtt tgaacgcgca gccgccatgc cggggtttta    7140
cgagattgtg attaaggtcc ccagcgacct tgacgagcat ctgcccggca tttctgacag    7200
```

```
ctttgtgaac tgggtggccg agaaggaatg ggagttgccg ccagattctg acatggatct    7260
gaatctgatt gagcaggcac ccctgaccgt ggccgagaag ctgcagcgcg actttctgac    7320
ggaatggcgc cgtgtgagta aggccccgga ggctcttttc tttgtgcaat ttgagaaggg    7380
agagagctac ttccacatgc acgtgctcgt ggaaaccacc ggggtgaaat c             7431

<210> SEQ ID NO 2
<211> LENGTH: 7415
<212> TYPE: DNA
<213> ORGANISM: Artificial Sequence
<220> FEATURE:
<223> OTHER INFORMATION: Coding Strand of Plasmid pAAV-RC2

<400> SEQUENCE: 2
ccgggccccc cctcgaggtc gacggtatcg ggggagctcg cagggtctcc attttgaagc      60
gggaggtttg aacgcgcagc cgccatgccg gggttttacg agattgtgat taaggtcccc     120
agcgaccttg acgagcatct gcccggcatt tctgacagct ttgtgaactg ggtggccgag     180
aaggaatggg agttgccgcc agattctgac atggatctga atctgattga gcaggcaccc     240
ctgaccgtgg ccgagaagct gcagcgcgac tttctgacgg aatggcgccg tgtgagtaag     300
gccccggagg ctcttttctt tgtgcaattt gagaagggag agagctactt ccacatgcac     360
gtgctcgtgg aaaccaccgg ggtgaaatcc atggttttgg acgtttcct gagtcagatt      420 cgcgaaaaac tgattcagag aatttaccgc gggatcgagc cgactttgcc aaactggttc     480
gcggtcacaa agaccagaaa tggcgccgga ggcgggaaca aggtggtgga tgagtgctac     540
atccccaatt acttgctccc caaaacccag cctgagctcc agtgggcgtg gactaatatg     600
gaacagtatt taagcgcctg tttgaatctc acggagcgta acggttggt ggcgcagcat      660 ctgacgcacg tgtcgcagac gcaggagcag aacaaagaga atcagaatcc caattctgat     720
gcgccggtga tcagatcaaa aacttcagcc aggtacatgg agctggtcgg tggctcgtg     780 gacaagggga ttacctcgga gaagcagtgg atccaggagg accaggcctc atacatctcc     840
ttcaatgcgg cctccaactc gcggtcccaa atcaaggctg ccttggacaa tgcgggaaag     900
attatgagcc tgactaaaac cgcccccgac tacctggtgg ccagcagcc cgtggaggac     960 atttccagca atcggattta taaaattttg gaactaaacg gtacgatcc ccaatatgcg     1020 gcttccgtct ttctgggatg ggccacgaaa agttcggca agaggaacac catctggctg      1080
tttgggcctg caactaccgg gaagaccaac atcgcggagg ccatagccca cactgtgccc     1140
ttctacgggt gcgtaaactg gaccaatgag aactttccct tcaacgactg tgtcgacaag     1200
atggtgatct ggtgggagga ggggaagatg accgccaagg tcgtggagtc ggccaaagcc     1260
attctcggag gaagcaaggt gcgcgtggac cagaaatgca gtcctcggcc cagatagac      1320 ccgactcccg tgatcgtcac ctccaacacc aacatgtgcg ccgtgattga cgggaactca    1380
acgaccttcg aacaccagca gccgttgcaa gaccggatgt tcaaatttga actcaccgc     1440 cgtctggatc atgactttgg gaaggtcacc aagcaggaag tcaaagactt tttccggtgg    1500
gcaaaggatc acgtggttga ggtggagcat gaattctacg tcaaaagggg tggagccaag    1560
aaaagacccg cccccagtga cgcagatata agtgagccca acgggtgcg cgagtcagtt     1620 gcgcagccat cgacgtcaga cgcggaagct tcgatcaact acgcagacag gtaccaaaac    1680
aaatgttctc gtcacgtggg catgaatctg atgctgtttc cctgcagaca atgcgagaga    1740
atgaatcaga attcaaatat ctgcttcact cacggacaga aagactgttt agagtgcttt    1800
```

```
cccgtgtcag aatctcaacc cgtttctgtc gtcaaaaagg cgtatcagaa actgtgctac    1860
attcatcata tcatgggaaa ggtgccagac gcttgcactg cctgcgatct ggtcaatgtg    1920
gatttggatg actgcatctt tgaacaataa atgatttaaa tcaggtatgg ctgccgatgg    1980
ttatcttcca gattggctcg aggacactct ctctgaagga ataagacagt ggtggaagct    2040
caaacctggc ccaccaccac caaagcccgc agagcggcat aaggacgaca gcagggtct     2100
tgtgcttcct gggtacaagt acctcggacc cttcaacgga ctcgacaagg gagagccggt    2160
caacgaggca gacgccgcgg ccctcgagca cgacaaagcc tacgaccggc agctcgacag    2220
cggagacaac ccgtacctca agtacaacca cgccgacgcg gagtttcagg agcgccttaa    2280
agaagatacg tcttttgggg gcaacctcgg acgagcagtc ttccaggcga aaaagagggt    2340
tcttgaacct ctgggcctgg ttgaggaacc tgttaagacg gctccgggaa aaaagaggcc    2400
ggtagagcac tctcctgtgg agccagactc ctcctcggga accggaaagg cgggccagca    2460
gcctgcaaga aaaagattga attttggtca gactggagac gcagactcag tacctgaccc    2520
ccagcctctc ggacagccac cagcagcccc ctctggtctg ggaactaata cgatggctac    2580
aggcagtggc gcaccaatgg cagacaataa cgagggcgcc gacggagtgg gtaattcctc    2640
gggaaattgg cattgcgatt ccacatggat gggcgacaga gtcatcacca ccagcacccg    2700
aacctgggcc ctgcccacct acaacaacca cctctacaaa caaatttcca gccaatcagg    2760
agcctcgaac gacaatcact actttggcta cagcacccct tggggtatt ttgacttcaa     2820
cagattccac tgccacttt caccacgtga ctggcaaaga ctcatcaaca caactgggg      2880
attccgaccc aagagactca acttcaagct ctttaacatt caagtcaaag aggtcacgca    2940
gaatgacggt acgacgacga ttgccaataa ccttaccagc acggttcagg tgtttactga    3000
ctcggagtac cagctcccgt acgtcctcgg ctcggcgcat caaggatgcc tcccgccgtt    3060
cccagcagac gtcttcatgg tgccacagta tggatacctc accctgaaca acgggagtca    3120
ggcagtagga cgctcttcat tttactgcct ggagtacttt ccttctcaga tgctgcgtac    3180
cggaaacaac tttaccttca gctacacttt tgaggacgtt cctttccaca gcagctacgc    3240
tcacagccca agtctggacc gtctcatgaa tcctctcatc gaccagtacc tgtattactt    3300
gagcagaaca aacactccaa gtggaaccac cacgcagtca aggcttcagt tttctcaggc    3360
cggagcgagt gacattcggg accagtctag gaactggctt cctggaccct gttaccgcca    3420
gcagcgagta tcaaagacat ctgcggataa caacaacagt gaatactcgt ggactggagc    3480
taccaagtac cacctcaatg gcagagactc tctggtgaat ccgggcccgg ccatggcaag    3540
ccacaaggac gatgaagaaa agttttttcc tcagagcggg gttctcatct ttgggaagca    3600
aggctcagag aaaacaaatg tggacattga aaaggtcatg attacagacg aagaggaaat    3660
caggacaacc aatcccgtgg ctacggagca gtatggttct gtatctacca acctccagag    3720
aggcaacaga caagcagcta ccgcagatgt caacacacaa ggcgttcttc caggcatggt    3780
ctggcaggac agagatgtgt accttcaggg gcccatctgg gcaaagattc acacacggac    3840
cggacatttt cacccctctc cctcatgggc tggattcgga cttaaacacc tcctccaca    3900
gattctcatc aagaacaccc cggtacctgc gaatccttcg accaccttca gtgcggcaaa    3960
gtttgcttcc ttcatcacac agtactccac gggacaggtc agcgtggaga tcgagtggga    4020
gctgcagaag gaaaacagca aacgctggaa tcccgaaatt cagtacactt ccaactacaa    4080
caagtctgtt aatgtggact ttactgtgga cactaatggc gtgtattcag agcctcgccc    4140
cattggcacc agatacctga ctcgtaatct gtaattgctt gttaatcaat aaaccgttta    4200
```

```
attcgtttca gttgaacttt ggtctctgcg tatttctttc ttatctagtt tccatgctct   4260
aggatccact agtaacggcc gccagtgtgc tggaattcgg ctttgtagtt aatgattaac   4320
ccgccatgct acttatctac gtagccatgc tctagaggtc ctgtattaga ggtcacgtga   4380
gtgttttgcg acattttgcg acaccatgtg gtcacgctgg gtatttaagc ccagtgagc   4440 acgcagggtc tccattttga agcgggaggt ttgaacgcgc agccgccaag ccgaattctg   4500
cagatatcca aacactggcg gccgctcgac tagagcggcc gccaccgcgg tggagctcca   4560
gcttttgttc cctttagtga gggttaattg cgcgcttggc gtaatcatgg tcatagctgt   4620
ttcctgtgtg aaattgttat ccgctcacaa ttccacacaa catacgagcc ggaagcataa   4680
agtgtaaagc ctggggtgcc taatgagtga gctaactcac attaattgcg ttgcgctcac   4740
tgcccgcttt ccagtcggga aacctgtcgt gccagctgca ttaatgaatc ggccaacgcg   4800
cggggagagg cggtttgcgt attgggcgct cttccgcttc ctcgctcact gactcgctgc   4860
gctcggtcgt tcggctgcgg cgagcggtat cagctcactc aaaggcggta atacggttat   4920
ccacagaatc aggggataac gcaggaaaga acatgtgagc aaaaggccag caaaaggcca   4980
ggaaccgtaa aaaggccgcg ttgctggcgt ttttccatag gctccgcccc cctgacgagc   5040
atcacaaaaa tcgacgctca agtcagaggt ggcgaaaccc gacaggacta taaagatacc   5100
aggcgtttcc ccctggaagc tccctcgtgc gctctcctgt tccgaccctg ccgcttaccg   5160
gatacctgtc cgcctttctc ccttcgggaa gcgtggcgct ttctcatagc tcacgctgta   5220
ggtatctcag ttcggtgtag gtcgttcgct ccaagctggg ctgtgtgcac gaaccccccg   5280
ttcagcccga ccgctgcgcc ttatccggta actatcgtct tgagtccaac ccggtaagac   5340
acgacttatc gccactggca gcagccactg gtaacaggat tagcagagcg aggtatgtag   5400
gcggtgctac agagttcttg aagtggtggc ctaactacgg ctacactaga agaacagtat   5460
ttggtatctg cgctctgctg aagccagtta ccttcggaaa aagagttggt agctcttgat   5520
ccggcaaaca aaccaccgct ggtagcggtg gtttttttgt ttgcaagcag cagattacgc   5580
gcagaaaaaa aggatctcaa gaagatcctt tgatctttc tacggggtct gacgctcagt   5640
ggaacgaaaa ctcacgttaa gggattttgg tcatgagatt atcaaaaagg atcttcacct   5700
agatcctttt aaattaaaaa tgaagtttta aatcaatcta agtatatat gagtaaactt   5760 ggtctgacag ttaccaatgc ttaatcagtg aggcacctat ctcagcgatc tgtctatttc   5820
gttcatccat agttgcctga ctccccgtcg tgtagataac tacgatacgg gagggcttac   5880
catctggccc cagtgctgca atgataccgc gagacccacg ctcaccggct ccagatttat   5940
cagcaataaa ccagccagcc ggaagggccg agcgcagaag tggtcctgca actttatccg   6000
cctccatcca gtctattaat tgttgccggg aagctagagt aagtagttcg ccagttaata   6060
gtttgcgcaa cgttgttgcc attgctacag gcatcgtggt gtcacgctcg tcgtttggta   6120
tggcttcatt cagctccggt tcccaacgat caaggcgagt tacatgatcc cccatgttgt   6180
gcaaaaaagc ggttagctcc ttcggtcctc cgatcgttgt cagaagtaag ttggccgcag   6240
tgttatcact catggttatg gcagcactgc ataattctct tactgtcatg ccatccgtaa   6300
gatgcttttc tgtgactggt gagtactcaa ccaagtcatt ctgagaatag tgtatgcggc   6360
gaccgagttg ctcttgcccg gcgtcaatac gggataatac cgcgccacat agcagaactt   6420
taaaagtgct catcattgga aaacgttctt cgggcgaaa actctcaagg atcttaccgc   6480
tgttgagatc cagttcgatg taacccactc gtgcacccaa ctgatcttca gcatctttta   6540
```

```
ctttcaccag cgtttctggg tgagcaaaaa caggaaggca aaatgccgca aaaagggaa       6600 taagggcgac acggaaatgt tgaatactca tactcttcct ttttcaatat tattgaagca     6660
tttatcaggg ttattgtctc atgagcggat acatatttga atgtatttag aaaaataaac    6720 aaatagggg tccgcgcaca tttccccgaa aagtgccacc taaattgtaa gcgttaatat     6780
tttgttaaaa ttcgcgttaa attttttgtta aatcagctca ttttttaacc aataggccga  6840
aatcggcaaa atcccttata aatcaaaaga atagaccgag ataggggttga gtgttgttcc  6900 agtttggaac aagagtccac tattaaagaa cgtggactcc aacgtcaaag ggcgaaaaac   6960
cgtctatcag ggcgatggcc cactacgtga accatcaccc taatcaagtt ttttggggtc   7020
gaggtgccgt aaagcactaa atcggaaccc taaagggagc ccccgattta gagcttgacg   7080
gggaaagccg cgaacgtgg cgagaaagga agggaagaaa gcgaaaggag cgggcgctag    7140
ggcgctggca agtgtagcgg tcacgctgcg cgtaaccacc acacccgccg cgcttaatgc  7200
gccgctacag ggcgcgtccc attcgccatt caggctgcgc aactgttggg aagggcgatc   7260
ggtgcgggcc tcttcgctat tacgccagct ggcgaaaggg gatgtgctg caaggcgatt     7320 aagttgggta acgccagggt ttcccagtc acgacgttgt aaaacgacgg ccagtgagcg   7380
cgcgtaatac gactcactat agggcgaatt gggta                              7415
```

<210> SEQ ID NO 3
<211> LENGTH: 7395
<212> TYPE: DNA
<213> ORGANISM: Artificial Sequence
<220> FEATURE:
<223> OTHER INFORMATION: Coding Strand of Plasmid pAAV-RC5

<400> SEQUENCE: 3

```
catggttttg ggacgtttcc tgagtcagat tcgcgaaaaa ctgattcaga gaatttaccg       60
cgggatcgag ccgactttgc caaactggtt cgcggtcaca aagaccagaa atggcgccgg    120
aggcgggaac aaggtggtgg atgagtgcta catccccaat tacttgctcc ccaaaaccca   180
gcctgagctc cagtgggcgt ggactaatat ggaacagtat ttaagcgcct gtttgaatct   240
cacggagcgt aaacggttgg tggcgcagca tctgacgcac gtgtcgcaga cgcaggagca   300
gaacaaagag aatcagaatc ccaattctga tgcgccggtg atcagatcaa aaacttcagc   360
caggtacatg gagctggtcg ggtggctcgt ggacaagggg attacctcgg agaagcagtg   420
gatccaggag gaccaggcct catacatctc cttcaatgcg gcctccaact cgcggtccca   480
aatcaaggct gccttggaca atgcgggaaa gattatgagc ctgactaaaa ccgcccccga   540
ctacctggtg ggccagcagc ccgtggagga catttccagc aatcggattt ataaaatttt   600
ggaactaaac gggtacgatc cccaatatgc ggcttccgtc tttctgggat gggcacgaa    660 aaagttcggc aagaggaaca ccatctggct gtttgggcct gcaactaccg ggaagaccaa   720
catcgcggag gccatagccc cacactgtgcc cttctacggg tgcgtaaaact ggaccaatga   780 gaactttccc ttcaacgact gtgtcgacaa gatggtgatc tggtgggagg aggggaagat   840
gaccgccaag gtcgtggagt cggccaaagc cattctcgga ggaagcaagg tgcgcgtgga   900
ccagaaatgc aagtcctcgg cccagataga cccgactccc gtgatcgtca cctccaacac   960
caacatgtgc gccgtgattg acgggaactc aacgaccttc gaacaccagc agccgttgca  1020
agaccggatg ttcaaatttg aactcacccg ccgtctggat catgactttg gaaggtcac   1080 caagcaggaa gtcaaagact ttttccgtgt ggcaaaggat cacgtggttg aggtggcagca  1140 tgaattctac gtcaaaaagg gtggagccaa gaaaagaccc gccccagtg acgcagatat   1200
```

-continued

```
aagtgagccc aaacgggtgc gcgagtcagt tgcgcagcca tcgacgtcag acgcggaagc    1260
ttcgatcaac tacgcagaca ggtaccaaaa caaatgttct cgtcacgtgg gcatgaatct    1320
gatgctgttt ccctgcagac aatgcgagag aatgaatcag aattcaaata tctgcttcac    1380
tcacggacag aaagactgtt tagagtgctt cccgtgtca gaatctcaac ccgtttctgt     1440
cgtcaaaaag gcgtatcaga aactgtgcta cattcatcat atcatgggaa aggtgccaga    1500
cgcttgcact gcctgcgatc tggtcaatgt ggatttggat gactgcatct ttgaacaata    1560
aatgatttaa atcaggtatg tcttttgttg atcaccctcc agattggttg aagaagttg     1620 gtgaaggtct tcgcgagttt ttgggccttg aagcgggccc accgaaacca aacccaatc     1680 agcagcatca agatcaagcc cgtggtcttg tgctgcctgg ttataactat ctcggacccg    1740
gaaacggtct cgatcgagga gagcctgtca cagggcaga cgaggtcgcg cgagagcacg     1800
acatctcgta caacgagcag cttgaggcgg gagacaaccc ctacctcaag tacaaccacg    1860
cggacgccga gtttcaggag aagctcgccg acgacacatc cttcggggga aacctcggaa    1920
aggcagtctt tcaggccaag aaaagggttc tcgaacctt tggcctggtt gaagagggtg     1980
ctaagacggc ccctaccgga aagcggatag acgaccactt tccaaaaaga aagaaggctc    2040
ggaccgaaga ggactccaag ccttccacct cgtcagacgc cgaagctgga cccagcggat    2100
cccagcagct gcaaatccca gcccaaccag cctcaagttt gggagctgat acaatgtctg    2160
cgggaggtgg cggcccattg ggcgacaata accaaggtgc cgatggagtg ggcaatgcct    2220
cgggagattg gcattgcgat tccacgtgga tgggggacag agtcgtcacc aagtccaccc    2280
gaacctgggt gctgcccagc tacaacaacc accagtaccg agagatcaaa agcggctccg    2340 tcgacgaag caacgccaac gcctactttg gatacagcac cccctggggg tactttgact     2400
ttaaccgctt ccacagccac tggagccccc gagactggca aagactcatc aacaactact    2460
ggggcttcag accccggtcc ctcagagtca aaatcttcaa cattcaagtc aaagaggtca    2520
cggtgcagga ctccaccacc accatcgcca acaacctcac ctccaccgtc caagtgttta    2580
cggacgacga ctaccagctg ccctacgtcg tcggcaacgg gaccgaggga tgcctgccgg    2640
ccttccctcc gcaggtcttt acgctgccgc agtacggtta cgcgacgctg aaccgcgaca    2700
acacagaaaa tcccaccgag aggagcagct tcttctgcct agagtacttt cccagcaaga    2760
tgctgagaac gggcaacaac tttgagttta cctacaactt tgaggaggtg cccttccact    2820
ccagcttcgc tcccagtcag aacctgttca agctggccaa cccgctggtg gaccagtact    2880
tgtaccgctt cgtgagcaca aataacactg gcggagtcca gttcaacaag aacctggccg    2940
ggagatacgc caacacctac aaaaactggt tcccggggcc catgggccga cccagggct     3000 ggaacctggg ctccggggtc aaccgcgcca gtgtcagcgc cttcgccacg accaatagga    3060
tggagctcga gggcgcgagt taccaggtgc ccccgcagcc gaacggcatg accaacaacc    3120
tccagggcag caacacctat gccctggaga acactatgat cttcaacagc cagccgcga    3180 acccgggcac caccgccacg tacctcgagg gcaacatgct catcaccagc gagagcgaga    3240
cgcagccggt gaaccgcgtg gcgtacaacg tcggcgggca gatggccacc aacaaccaga    3300
gctccaccac tgcccccgcg accggcacgt acaacctcca ggaaatcgtg cccggcagcg    3360
tgtggatgga gagggacgtg tacctccaag gacccatctg gccaagatc ccagagacgg     3420 gggcgcactt tcaccctctc ccggccatgg gcggattcgg actcaaacac ccaccgcca     3480 tgatgctcat caagaacacg cctgtgcccg gaaatatcac cagcttctcg gacgtgcccg    3540
```

| | |
|---|---|
| tcagcagctt catcacccag tacagcaccg ggcaggtcac cgtggagatg gagtgggagc | 3600 |
| tcaagaagga aaactccaag aggtggaacc cagagatcca gtacacaaac aactacaacg | 3660 |
| acccccagtt tgtggacttt gccccggaca gcaccgggga atacagaacc accagaccta | 3720 |
| tcggaacccg ataccttacc cgaccccttt aaggcgcgcc accggttgct tgttaatcaa | 3780 |
| taaaccgttt aattcgtttc agttgaactt tggtctctgc gtatttcttt cttatctagt | 3840 |
| ttccatgctc taggatccac tagtaacggc cgccagtgtg ctggaattcg ctttgtagt | 3900 |
| taatgattaa cccgccatgc tacttatcta cgtagccatg ctctagaggt cctgtattag | 3960 |
| aggtcacgtg agtgttttgc gacattttgc gacaccatgt ggtcacgctg ggtatttaag | 4020 |
| cccgagtgag cacgcagggt ctccattttg aagcgggagg tttgaacgcg cagccgccaa | 4080 |
| gccgaattct gcagatatcc aaacactggc ggccgctcga ctagagcggc cgccaccgcg | 4140 |
| gtggagctcc agcttttgtt ccctttagtg agggttaatt gcgcgcttgg cgtaatcatg | 4200 |
| gtcatagctg tttcctgtgt gaaattgtta tccgctcaca attccacaca acatacgagc | 4260 |
| cggaagcata aagtgtaaag cctggggtgc ctaatgagtg agctaactca cattaattgc | 4320 |
| gttgcgctca ctgcccgctt tccagtcggg aaacctgtcg tgccagctgc attaatgaat | 4380 |
| cggccaacgc gcggggagag gcggtttgcg tattgggcgc tcttccgctt cctcgctcac | 4440 |
| tgactcgctg cgctcggtcg ttcggctgcg gcgagcggta tcagctcact caaaggcggt | 4500 |
| aatacggtta tccacagaat caggggataa cgcaggaaag aacatgtgag caaaaggcca | 4560 |
| gcaaaaggcc aggaaccgta aaaaggccgc gttgctggcg ttttccata ggctccgccc | 4620 |
| ccctgacgag catcacaaaa atcgacgctc aagtcagagg tggcgaaacc cgacaggact | 4680 |
| ataaagatac caggcgtttc ccctggaag ctccctcgtg cgctctcctg ttccgaccct | 4740 |
| gccgcttacc ggatacctgt ccgcctttct cccttcggga agcgtggcgc tttctcatag | 4800 |
| ctcacgctgt aggtatctca gttcggtgta ggtcgttcgc tccaagctgg gctgtgtgca | 4860 |
| cgaacccccc gttcagcccg accgctgcgc cttatccggt aactatcgtc ttgagtccaa | 4920 |
| cccggtaaga cacgacttat cgccactggc agcagccact ggtaacagga ttagcagagc | 4980 |
| gaggtatgta ggcggtgcta cagagttctt gaagtggtgg cctaactacg gctacactag | 5040 |
| aagaacagta tttggtatct gcgctctgct gaagccagtt accttcggaa aaagagttgg | 5100 |
| tagctcttga tccggcaaac aaaccaccgc tggtagcggt ggttttttg tttgcaagca | 5160 |
| gcagattacg cgcagaaaaa aaggatctca agaagatcct ttgatctttt ctacggggtc | 5220 |
| tgacgctcag tggaacgaaa actcacgtta agggattttg gtcatgagat tatcaaaaag | 5280 |
| gatcttcacc tagatccttt taaattaaaa atgaagtttt aaatcaatct aaagtatata | 5340 |
| tgagtaaact tggtctgaca gttaccaatg cttaatcagt gaggcaccta tctcagcgat | 5400 |
| ctgtctattt cgttcatcca tagttgcctg actccccgtc gtgtagataa ctacgatacg | 5460 |
| ggagggctta ccatctggcc ccagtgctgc aatgataccg cgagacccac gctcaccggc | 5520 |
| tccagattta tcagcaataa accagccagc cggaagggcc gagcgcagaa gtggtcctgc | 5580 |
| aactttatcc gcctccatcc agtctattaa ttgttgccgg gaagctagag taagtagttc | 5640 |
| gccagttaat agtttgcgca acgttgttgc cattgctaca ggcatcgtgg tgtcacgctc | 5700 |
| gtcgtttggt atggcttcat tcagctccgg ttcccaacga tcaaggcgag ttacatgatc | 5760 |
| ccccatgttg tgcaaaaaag cggttagctc cttcggtcct ccgatcgttg tcagaagtaa | 5820 |
| gttggccgca gtgttatcac tcatggttat ggcagcactg cataattctc ttactgtcat | 5880 |
| gccatccgta agatgctttt ctgtgactgg tgagtactca accaagtcat tctgagaata | 5940 |

| | |
|---|---|
| gtgtatgcgg cgaccgagtt gctcttgccc ggcgtcaata cgggataata ccgcgccaca | 6000 |
| tagcagaact ttaaaagtgc tcatcattgg aaaacgttct cgggcgaa aactctcaag | 6060 |
| gatcttaccg ctgttgagat ccagttcgat gtaacccact cgtgcaccca actgatcttc | 6120 |
| agcatctttt actttcacca gcgtttctgg gtgagcaaaa acaggaaggc aaaatgccgc | 6180 |
| aaaaaaggga taagggcga cacggaaatg ttgaatactc atactcttcc ttttttcaata | 6240 |
| ttattgaagc atttatcagg gttattgtct catgagcgga tacatatttg aatgtattta | 6300 |
| gaaaaataaa caaatagggg ttccgcgcac atttccccga aaagtgccac ctaaattgta | 6360 |
| agcgttaata ttttgttaaa attcgcgtta aattttttgtt aaatcagctc atttttttaac | 6420 |
| caataggccg aaatcggcaa aatcccttat aaatcaaaag aatagaccga gatagggttg | 6480 |
| agtgttgttc cagtttggaa caagagtcca ctattaaaga acgtggactc caacgtcaaa | 6540 |
| gggcgaaaaa ccgtctatca gggcgatggc ccactacgtg aaccatcacc ctaatcaagt | 6600 |
| tttttgggt cgaggtgccg taaagcacta atcggaacc ctaaagggag ccccccgattt | 6660 |
| agagcttgac ggggaaagcc ggcgaacgtg gcgagaagg aagggaagaa agcgaaagga | 6720 |
| gcgggcgcta gggcgctggc aagtgtagcg gtcacgctgc gcgtaaccac cacacccgcc | 6780 |
| gcgcttaatg cgccgctaca gggcgcgtcc cattcgccat tcaggctgcg caactgttgg | 6840 |
| gaagggcgat cggtgcggc ctcttcgcta ttacgccagc tggcgaaagg gggatgtgct | 6900 |
| gcaaggcgat taagttgggt aacgccaggg ttttcccagt cacgacgttg taaaacgacg | 6960 |
| gccagtgagc gcgcgtaata cgactcacta tagggcgaat tgggtaccgg ccccccctc | 7020 |
| gaggtcgacg gtatcggggg agctcgcagg gtctccattt tgaagcggga ggtttgaacg | 7080 |
| cgcagccgcc atgccgggt tttacgagat tgtgattaag gtccccagcg accttgacga | 7140 |
| gcatctgccc ggcatttctg acagctttgt gaactgggtg gccgagaagg aatgggagtt | 7200 |
| gccgccagat tctgacatgg atctgaatct gattgagcag gcaccctga ccgtggccga | 7260 |
| gaagctgcag cgcgactttc tgacggaatg gcgccgtgtg agtaaggccc cggaggctct | 7320 |
| tttctttgtg caatttgaga agggagagag ctacttccac atgcacgtgc tcgtggaaac | 7380 |
| caccggggtg aaatc | 7395 |

<210> SEQ ID NO 4
<211> LENGTH: 7431
<212> TYPE: DNA
<213> ORGANISM: Artificial Sequence
<220> FEATURE:
<223> OTHER INFORMATION: Coding Strand of Plasmid pAAV-RC6

<400> SEQUENCE: 4

| | |
|---|---|
| catggttttg gacgtttcc tgagtcagat tcgcgaaaaa ctgattcaga gaatttaccg | 60 |
| cgggatcgag ccgactttgc caaactggtt cgcggtcaca aagaccagaa atggcgccgg | 120 |
| aggcgggaac aaggtggtgg atgagtgcta catccccaat tacttgctcc ccaaaaccca | 180 |
| gcctgagctc cagtgggcgt ggactaatat ggaacagtat ttaagcgcct gtttgaatct | 240 |
| cacgagcgt aaacggttgg tggcgcagca tctgacgcac gtgtcgcaga cgcaggagca | 300 |
| gaacaaagag aatcagaatc ccaattctga tgcgccggtg atcagatcaa aaacttcagc | 360 |
| caggtacatg gagctggtcg ggtggctcgt ggacaagggg attacctcgg agaagcagtg | 420 |
| gatccaggag gaccaggcct catacatctc cttcaatgcg gcctccaact cgcggtccca | 480 |
| aatcaaggct gccttggaca tgcgggaaa gattatgagc ctgactaaaa ccgcccccga | 540 |

```
ctacctggtg ggccagcagc ccgtggagga catttccagc aatcggattt ataaaatttt      600
ggaactaaac gggtacgatc cccaatatgc ggcttccgtc tttctgggat gggccacgaa      660
aaagttcggc aagaggaaca ccatctggct gtttgggcct gcaactaccg ggaagaccaa      720
catcgcggag gccatagccc acactgtgcc cttctacggg tgcgtaaact ggaccaatga      780
gaactttccc ttcaacgact gtgtcgacaa gatggtgatc tggtgggagg aggggaagat      840
gaccgccaag gtcgtggagt cggccaaagc cattctcgga ggaagcaagg tgcgcgtgga      900
ccagaaatgc aagtcctcgg cccagataga cccgactccc gtgatcgtca cctccaacac      960
caacatgtgc gccgtgattg acgggaactc aacgaccttc gaacaccagc agccgttgca     1020
agaccggatg ttcaaatttg aactcacccg ccgtctggat catgactttg ggaaggtcac     1080
caagcaggaa gtcaaagact ttttccggtg ggcaaaggat cacgtggttg aggtggagca     1140
tgaattctac gtcaaaaagg gtggagccaa gaaaagaccc gcccccagtg acgcagatat     1200
aagtgagccc aaacgggtgc gcgagtcagt tgcgcagcca tcgacgtcag acgcggaagc     1260
ttcgatcaac tacgcagaca ggtaccaaaa caaatgttct cgtcacgtgg gcatgaatct     1320
gatgctgttt ccctgcagac aatgcgagag aatgaatcag aattcaaata tctgcttcac     1380
tcacggacag aaagactgtt tagagtgctt tcccgtgtca gaatctcaac ccgtttctgt     1440
cgtcaaaaag gcgtatcaga aactgtgcta cattcatcat atcatgggaa aggtgccaga     1500
cgcttgcact gcctgcgatc tggtcaatgt ggatttggat gactgcatct ttgaacaata     1560
aatgatttaa atcaggtatg gctgccgatg ttatcttcc agattggctc gaggacaacc     1620
tctctgaggg cattcgcgag tggtgggact tgaaacctgg agccccgaaa cccaaagcca     1680
accagcaaaa gcaggacgac ggccggggtc tggtgcttcc tggctacaag tacctcggac     1740
ccttcaacgg actcgacaag ggggagcccg tcaacgcggc ggatgcagcg ccctcgagc     1800 acgacaaggc ctacgaccag cagctcaaag cgggtgacaa tccgtacctg cggtataacc     1860
acgccgacgc cgagtttcag gagcgtctgc aagaagatac gtcttttggg ggcaacctcg     1920
ggcgagcagt cttccaggcc aagaagaggg ttctcgaacc ttttggtctg gttgaggaag     1980
gtgctaagac ggctcctgga aagaaacgtc cggtagagca gtcgccacaa gagccagact     2040
cctcctcggg cattggcaag acaggccagc agcccgctaa aaagagactc aattttggtc     2100
agactggcga ctcagagtca gtccccgacc cacaacctct cggagaacct ccagcaaccc     2160
ccgctgctgt gggacctact acaatggctt caggcggtgg cgcaccaatg gcagacaata     2220
acgaaggcgc cgacggagtg ggtaatgcct caggaaattg gcattgcgat tccacatggc     2280
tgggcgacag agtcatcacc accagcaccc gaacatgggc cttgcccacc tataacaacc     2340
acctctacaa gcaaatctcc agtgcttcaa cggggggccag caacgacaac cactacttcg     2400
gctacagcac ccccctgggg tattttgatt tcaacagatt ccactgccat ttctcaccac     2460
gtgactggca gcgactcatc aacaacaatt gggggattccg gcccaagaga ctcaacttca     2520
agctcttcaa catccaagtc aaggaggtca cgacgaatga tggcgtcacg accatcgcta     2580
ataaccttac cagcacggtt caagtcttct cggactcgga gtaccagttg ccgtacgtcc     2640
tcggctctgc gcaccaggc tgcctccctc cgttcccggc ggacgtgttc atgattccgc     2700
agtacggcta cctaacgctc aacaatggca gccaggcagt gggacggtca tcctttttact     2760 gcctggaata tttcccatcg cagatgctga aacgggcaa taactttacc ttcagctaca     2820
ccttcgagga cgtgccttc cacagcagct acgcgcacag ccagagcctg gaccggctga     2880
tgaatcctct catcgaccag tacctgtatt acctgaacag aactcagaat cagtccggaa     2940
```

```
gtgcccaaaa caaggacttg ctgtttagcc gggggtctcc agctggcatg tctgttcagc    3000
ccaaaaactg gctacctgga ccctgttacc ggcagcagcg cgtttctaaa acaaaaacag    3060
acaacaacaa cagcaacttt acctggactg gtgcttcaaa atataacctt aatgggcgtg    3120
aatctataat caaccctggc actgctatgg cctcacacaa agacgacaaa gacaagttct    3180
ttcccatgag cggtgtcatg attttggaa aggagagcgc cggagcttca aacactgcat     3240
tggacaatgt catgatcaca gacgaagagg aaatcaaagc cactaacccc gtggccaccg    3300
aaagatttgg gactgtggca gtcaatctcc agagcagcag cacagaccct gcgaccggag    3360
atgtgcatgt tatgggagcc ttacctggaa tggtgtggca agacagagac gtatacctgc    3420
agggtcctat ttgggccaaa attcctcaca cggatggaca ctttcacccg tctcctctca    3480
tgggcggctt tggacttaag cacccgcctc ctcagatcct catcaaaaac acgcctgttc    3540
ctgcgaatcc tccggcagag ttttcggcta caaagtttgc ttcattcatc acccagtatt    3600
ccacaggaca agtgagcgtg gagattgaat gggagctgca gaaagaaaac agcaaacgct    3660
ggaatcccga agtgcagtat acatctaact atgcaaaatc tgccaacgtt gatttcactg    3720
tggacaacaa tggactttat actgagcctc gccccattgg cacccgttac ctcacccgtc    3780
ccctgtaagg cgcgccaccg gttgcttgtt aatcaataaa ccgtttaatt cgtttcagtt    3840
gaactttggt ctctgcgtat ttcttttctta tctagtttcc atgctctagg atccactagt    3900
aacggccgcc agtgtgctgg aattcggctt tgtagttaat gattaacccg ccatgctact    3960
tatctacgta gccatgctct agaggtcctg tattagaggt cacgtgagtg ttttgcgaca    4020
ttttgcgaca ccatgtggtc acgctgggta tttaagcccg agtgagcacg cagggtctcc    4080
attttgaagc gggaggtttg aacgcgcagc cgccaagccg aattctgcag atatccaaac    4140
actggcggcc gctcgactag agcggccgcc accgcggtgg agctccagct tttgttccct    4200
ttagtgaggg ttaattgcgc gcttggcgta atcatggtca tagctgtttc ctgtgtgaaa    4260
ttgttatccg ctcacaattc cacacaacat acgagccgga agcataaagt gtaaagcctg    4320
gggtgcctaa tgagtgagct aactcacatt aattgcgttg cgctcactgc ccgctttcca    4380
gtcgggaaac ctgtcgtgcc agctgcatta atgaatcggc caacgcgcgg ggagaggcgg    4440
tttgcgtatt gggcgctctt ccgcttcctc gctcactgac tcgctgcgct cggtcgttcg    4500
gctgcggcga gcggtatcag ctcactcaaa ggcggtaata cggttatcca cagaatcagg    4560
ggataacgca ggaaagaaca tgtgagcaaa aggccagcaa aaggccagga accgtaaaaa    4620
ggccgcgttg ctggcgtttt tccataggct ccgcccccct gacgagcatc acaaaaatcg    4680
acgctcaagt cagaggtggc gaaacccgac aggactataa agataccagg cgtttccccc    4740
tggaagctcc ctcgtgcgct ctcctgttcc gaccctgccg cttaccggat acctgtccgc    4800
ctttctccct tcgggaagcg tggcgctttc tcatagctca cgctgtaggt atctcagttc    4860
ggtgtaggtc gttcgctcca agctgggctg tgtgcacgaa ccccccgttc agcccgaccg    4920
ctgcgcctta tccggtaact atcgtcttga gtccaacccg gtaagacacg acttatcgcc    4980
actggcagca gccactggta acaggattag cagagcgagg tatgtaggcg gtgctacaga    5040
gttcttgaag tggtggccta actacggcta cactagaaga acagtatttg gtatctgcgc    5100
tctgctgaag ccagttacct tcggaaaaag agttggtagc tcttgatccg gcaaacaaac    5160
caccgctggt agcggtggtt tttttgtttg caagcagcag attacgcgca gaaaaaaagg    5220
atctcaagaa gatcctttga tcttttctac ggggtctgac gctcagtgga acgaaaactc    5280
```

```
acgttaaggg attttggtca tgagattatc aaaaaggatc ttcacctaga tccttttaaa    5340
ttaaaaatga agtttaaat caatctaaag tatatatgag taaacttggt ctgacagtta     5400
ccaatgctta atcagtgagg cacctatctc agcgatctgt ctatttcgtt catccatagt    5460
tgcctgactc cccgtcgtgt agataactac gatacgggag gcttaccat ctggccccag     5520
tgctgcaatg ataccgcgag acccacgctc accggctcca gatttatcag caataaacca    5580
gccagccgga agggccgagc gcagaagtgg tcctgcaact ttatccgcct ccatccagtc    5640
tattaattgt tgccgggaag ctagagtaag tagttcgcca gttaatagtt tgcgcaacgt    5700
tgttgccatt gctacaggca tcgtggtgtc acgctcgtcg tttggtatgg cttcattcag    5760
ctccggttcc caacgatcaa ggcgagttac atgatccccc atgttgtgca aaaaagcggt    5820
tagctccttc ggtcctccga tcgttgtcag aagtaagttg gccgcagtgt tatcactcat    5880
ggttatggca gcactgcata attctcttac tgtcatgcca tccgtaagat gcttttctgt    5940
gactggtgag tactcaacca agtcattctg agaatagtgt atgcggcgac cgagttgctc    6000
ttgcccggcg tcaatacggg ataataccgc gccacatagc agaactttaa aagtgctcat    6060
cattggaaaa cgttcttcgg ggcgaaaact ctcaaggatc ttaccgctgt tgagatccag    6120
ttcgatgtaa cccactcgtg cacccaactg atcttcagca tcttttactt tcaccagcgt    6180
ttctgggtga gcaaaaacag gaaggcaaaa tgccgcaaaa aagggaataa gggcgacacg    6240
gaaatgttga atactcatac tcttcctttt tcaatattat tgaagcattt atcagggtta    6300
ttgtctcatg agcggataca tatttgaatg tatttagaaa aataaacaaa tagggggttcc   6360
gcgcacattt ccccgaaaag tgccacctaa attgtaagcg ttaatatttt gttaaaattc    6420
gcgttaaatt tttgttaaat cagctcattt tttaaccaat aggccgaaat cggcaaaatc    6480
ccttataaat caaagaata gaccgagata gggttgagtg ttgttccagt ttggaacaag     6540
agtccactat taagaacgt ggactccaac gtcaagggc gaaaaccgt ctatcagggc       6600
gatgcccac tacgtgaacc atcaccctaa tcaagttttt tggggtcgag gtgccgtaaa     6660
gcactaaatc ggaacccta agggagcccc cgatttagag cttgacgggg aaagccggcg     6720
aacgtggcga gaaaggaagg gaagaaagcg aaaggagcgg gcgctagggc gctggcaagt    6780
gtagcggtca cgctgcgcgt aaccaccaca cccgccgcgc ttaatgcgcc gctacagggc    6840
gcgtcccatt cgccattcag gctgcgcaac tgttgggaag ggcgatcggt gcgggcctct    6900
tcgctattac gccagctggc gaaagggggga tgtgctgcaa ggcgattaag ttgggtaacg    6960
ccagggtttt cccagtcacg acgttgtaaa acgacggcca gtgagcgcgc gtaatacgac    7020
tcactatagg gcgaattggg taccgggccc cccctcgagg tcgacggtat cggggggagct    7080
cgcagggtct ccattttgaa gcgggaggtt tgaacgcgca gccgccatgc cggggttta     7140
cgagattgtg attaaggtcc ccagcgacct tgacgagcat ctgcccggca tttctgacag    7200
ctttgtgaac tgggtggccg agaaggaatg ggagttgccg ccagattctg acatggatct    7260
gaatctgatt gagcaggcac ccctgaccgt ggccgagaag ctgcagcgcg actttctgac    7320
ggaatggcgc cgtgtgagta aggcccccgga ggctctttc tttgtgcaat ttgagaaggg    7380
agagagctac ttccacatgc acgtgctcgt ggaaaccacc ggggtgaaat c             7431
```

<210> SEQ ID NO 5
<211> LENGTH: 7434
<212> TYPE: DNA
<213> ORGANISM: Artificial Sequence
<220> FEATURE:
<223> OTHER INFORMATION: Coding Strand of Plasmid pAAV-RC7

<400> SEQUENCE: 5

```
catggttttg ggacgtttcc tgagtcagat tcgcgaaaaa ctgattcaga gaatttaccg      60
cgggatcgag ccgactttgc caaactggtt cgcggtcaca aagaccagaa atggcgccgg     120
aggcgggaac aaggtggtgg atgagtgcta catccccaat tacttgctcc ccaaaaccca     180
gcctgagctc cagtgggcgt ggactaatat ggaacagtat ttaagcgcct gtttgaatct     240
cacggagcgt aaacggttgg tggcgcagca tctgacgcac gtgtcgcaga cgcaggagca     300
gaacaaagag aatcagaatc ccaattctga tgcgccggtg atcagatcaa aaacttcagc     360
caggtacatg gagctggtcg ggtggctcgt ggacaagggg attacctcgg agaagcagtg     420
gatccaggag gaccaggcct catacatctc cttcaatgcg gcctccaact cgcggtccca     480
aatcaaggct gccttggaca atgcgggaaa gattatgagc ctgactaaaa ccgcccccga     540
ctacctggtg ggccagcagc ccgtggagga catttccagc aatcggattt ataaaatttt     600
ggaactaaac gggtacgatc cccaatatgc ggcttccgtc tttctgggat gggccacgaa     660
aaagttcggc aagaggaaca ccatctggct gtttgggcct gcaactaccg ggaagaccaa     720
catcgcggag gccatagccc acactgtgcc cttctacggg tgcgtaaact ggaccaatga     780
gaactttccc ttcaacgact gtgtcgacaa gatggtgatc tggtgggagg aggggaagat     840
gaccgccaag gtcgtggagt cggccaaagc cattctcgga ggaagcaagg tgcgcgtgga     900
ccagaaatgc aagtcctcgg cccagataga cccgactccc gtgatcgtca cctccaacac     960
caacatgtgc gccgtgattg acgggaactc aacgacttc gaacaccagc agccgttgca    1020
agaccggatg ttcaaatttg aactcacccg ccgtctggat catgactttg ggaaggtcac    1080
caagcaggaa gtcaaagact ttttccggtg ggcaaaggat cacgtggttg aggtggagca    1140
tgaattctac gtcaaaaagg gtggagccaa gaaaagaccc gcccccagtg acgcagatat    1200
aagtgagccc aaacgggtgc gcgagtcagt tgcgcagcca tcgacgtcag acgcggaagc    1260
ttcgatcaac tacgcagaca ggtaccaaaa caaatgttct cgtcacgtgg gcatgaatct    1320
gatgctgttt ccctgcagac aatgcgagag aatgaatcag aattcaaata tctgcttcac    1380
tcacggacag aaagactgtt tagagtgctt tcccgtgtca gaatctcaac ccgtttctgt    1440
cgtcaaaaag gcgtatcaga aactgtgcta cattcatcat atcatgggaa aggtgccaga    1500
cgcttgcact gcctgcgatc tggtcaatgt ggatttggat gactgcatct ttgaacaata    1560
aatgatttaa atcaggtatg gctgccgatg gttatcttcc agattggctc gaggacaacc    1620
tctctgaggg cattcgcgag tggtgggacc tgaaacctgg agccccgaaa cccaaagcca    1680
accagcaaaa gcaggacaac ggccggggtc tggtgcttcc tggctacaag tacctcggac    1740
ccttcaacgg actcgacaag ggggagcccg tcaacgcggc ggacgcagcg gcctcgagc    1800
acgacaaggc ctacgaccag cagctcaaag cgggtgacaa tccgtacctg cggtataacc    1860
acgccgacgc cgagtttcag gagcgtctgc aagaagatac gtcatttggg gcaacctcg    1920
ggcgagcagt cttccaggcc aagaagcggg ttctcgaacc tctcggtctg gttgaggaag    1980
gcgctaagac ggctcctgca aagaagagac cggtagagcc gtcacctcag cgttcccccg    2040
actcctccac gggcatcggc aagaaaggcc agcagcccgc cagaaagaga ctcaatttcg    2100
gtcagactgg cgactcagag tcagtccccg accctcaacc tctcggagaa cctccagcag    2160
cgccctctag tgtgggatct ggtacagtgg ctgcaggcgg tggcgcacca atggcagaca    2220
ataacgaagg tgccgacgga gtgggtaatg cctcaggaaa ttggcattgc gattccacat    2280
```

-continued

```
ggctgggcga cagagtcatt accaccagca cccgaacctg ggccctgccc acctacaaca   2340
accacctcta caagcaaatc tccagtgaaa ctgcaggtag taccaacgac aacacctact   2400
tcggctacag cacccctgg gggtattttg actttaacag attccactgc cacttctcac   2460
cacgtgactg gcagcgactc atcaacaaca actggggatt ccggcccaag aagctgcggt   2520
tcaagctctt caacatccag gtcaaggagg tcacgacgaa tgacggcgtt acgaccatcg   2580
ctaataacct taccagcacg attcaggtat tctcggactc ggaataccag ctgccgtacg   2640
tcctcggctc tgcgcaccag ggctgcctgc ctccgttccc ggcggacgtc ttcatgattc   2700
ctcagtacgg ctacctgact ctcaacaatg cagtcagtc tgtgggacgt tcctccttct   2760
actgcctgga gtacttcccc tctcagatgc tgagaacggg caacaacttt gagttcagct   2820
acagcttcga ggacgtgcct ttccacagca gctacgcaca cagccagagc ctggaccggc   2880
tgatgaatcc cctcatcgac cagtacttgt actacctggc cagaacacag agtaacccag   2940
gaggcacagc tggcaatcgg gaactgcagt tttaccaggg cgggccttca actatggccg   3000
aacaagccaa gaattggtta cctggaccttt gcttccggca caaagagtc tccaaaacgc   3060 tggatcaaaa caacaacagc aactttgctt ggactggtgc caccaaatat cacctgaacg   3120
gcagaaactc gttggttaat cccggcgtcg ccatggcaac tcacaaggac gacgaggacc   3180
gcttttcccc atccagcgga gtcctgattt ttggaaaaac tggagcaact aacaaaacta   3240
cattggaaaa tgtgttaatg acaaatgaag aagaaattcg tcctactaat cctgtagcca   3300
cggaagaata cgggatagtc agcagcaact acaagcggc taatactgca gcccagacac   3360
aagttgtcaa caaccaggga gccttacctg gcatggtctg gcagaaccgg gacgtgtacc   3420
tgcagggtcc catctgggcc aagattcctc acacggatgg caactttcac ccgtctcctt   3480
tgatgggcgg ctttggactt aaacatccgc ctcctcagat cctgatcaag aacactcccg   3540
ttcccgctaa tcctccggag gtgtttactc ctgccaagtt tgcttcgttc atcacacagt   3600
acagcaccgg acaagtcagc gtggaaatcg agtgggagct gcagaaggaa aacagcaagc   3660
gctggaaccc ggagattcag tacacctcca actttgaaaa gcagactggt gtggactttg   3720
ccgttgacag ccagggtgtt tactctgagc ctcgccctat tggcactcgt tacctcaccc   3780
gtaatctgta aggcgcgcca ccggttgctt gttaatcaat aaaccgttta attcgtttca   3840
gttgaacttt ggtctctgcg tatttctttc ttatctagtt tccatgctct aggatccact   3900
agtaacggcc gccagtgtgc tggaattcgg ctttgtagtt aatgattaac ccgccatgct   3960
acttatctac gtagccatgc tctagaggtc ctgtattaga ggtcacgtga gtgttttgcg   4020
acattttgcg acaccatgtg gtcacgctgg gtatttaagc ccgagtgagc acgcagggtc   4080
tccattttga agcgggaggt ttgaacgcgc agccgccaag ccgaattctg cagatatcca   4140
aacactggcg gccgctcgac tagagcggcc gccaccgcgg tggagctcca gcttttgttc   4200
cctttagtga gggttaattg cgcgcttggc gtaatcatgg tcatagctgt ttcctgtgtg   4260
aaattgttat ccgctcacaa ttccacacaa catacgagcc ggaagcataa agtgtaaagc   4320
ctggggtgcc taatgagtga gctaactcac attaattgcg ttgcgctcac tgcccgcttt   4380
ccagtcggga aacctgtcgt gccagctgca ttaatgaatc ggccaacgcg cggggagagg   4440
cggtttgcgt attgggcgct cttccgcttc ctcgctcact gactcgctgc gctcggtcgt   4500
tcggctgcgg cgagcggtat cagctcactc aaaggcggta atacggttat ccacagaatc   4560
aggggataac gcaggaaaga acatgtgagc aaaaggccag caaaaggcca ggaaccgtaa   4620
aaaggccgcg ttgctggcgt ttttccatag gctccgcccc cctgacgagc atcacaaaaa   4680
```

```
tcgacgctca agtcagaggt ggcgaaaccc gacaggacta taaagatacc aggcgtttcc    4740
ccctggaagc tccctcgtgc gctctcctgt tccgaccctg ccgcttaccg gatacctgtc    4800
cgcctttctc ccttcgggaa gcgtggcgct ttctcatagc tcacgctgta ggtatctcag    4860
ttcggtgtag tcgttcgct  ccaagctggg ctgtgtgcac gaaccccccg ttcagcccga    4920
ccgctgcgcc ttatccggta actatcgtct tgagtccaac ccggtaagac acgacttatc    4980
gccactggca gcagccactg gtaacaggat tagcagagcg aggtatgtag gcggtgctac    5040
agagttcttg aagtggtggc ctaactacgg ctacactaga agaacagtat ttggtatctg    5100
cgctctgctg aagccagtta ccttcggaaa aagagttggt agctcttgat ccggcaaaca    5160
aaccaccgct ggtagcggtg gtttttttgt ttgcaagcag cagattacgc gcagaaaaaa    5220
aggatctcaa gaagatcctt tgatcttttc tacggggtct gacgctcagt ggaacgaaaa    5280
ctcacgttaa gggattttgg tcatgagatt atcaaaaagg atcttcacct agatcctttt    5340
aaattaaaaa tgaagtttta atcaatcta  agtatatat  gagtaaactt ggtctgacag    5400
ttaccaatgc ttaatcagtg aggcacctat ctcagcgatc tgtctatttc gttcatccat    5460
agttgcctga ctccccgtcg tgtagataac tacgatacgg gagggcttac catctggccc    5520
cagtgctgca atgataccgc gagacccacg ctcaccggct ccagatttat cagcaataaa    5580
ccagccagcc ggaagggccg agcgcagaag tggtcctgca actttatccg cctccatcca    5640
gtctattaat tgttgccggg aagctagagt aagtagttcg ccagttaata gtttgcgcaa    5700
cgttgttgcc attgctacag gcatcgtggt gtcacgctcg tcgtttggta tggcttcatt    5760
cagctccggt tcccaacgat caaggcgagt tacatgatcc cccatgttgt gcaaaaaagc    5820
ggttagctcc ttcggtcctc cgatcgttgt cagaagtaag ttggccgcag tgttatcact    5880
catggttatg gcagcactgc ataattctct tactgtcatg ccatccgtaa gatgcttttc    5940
tgtgactggt gagtactcaa ccaagtcatt ctgagaatag tgtatgcggc gaccgagttg    6000
ctcttgcccg gcgtcaatac gggataatac cgcgccacat agcagaactt taaaagtgct    6060
catcattgga aaacgttctt cggggcgaaa actctcaagg atcttaccgc tgttgagatc    6120
cagttcgatg taacccactc gtgcacccaa ctgatcttca gcatctttta ctttcaccag    6180
cgtttctggg tgagcaaaaa caggaaggca aaatgccgca aaaaagggaa taagggcgac    6240
acggaaatgt tgaatactca tactcttcct ttttcaatat tattgaagca tttatcaggg    6300
ttattgtctc atgagcggat acatatttga atgtatttag aaaaataaac aaataggggt    6360
tccgcgcaca tttccccgaa aagtgccacc taaattgtaa gcgttaatat tttgttaaaa    6420
ttcgcgttaa attttgttaa atcagctca  ttttttaacc aataggccga atcggcaaa     6480 atcccttata aatcaaaaga atagaccgag atagggttga gtgttgttcc agtttggaac    6540
aagagtccac tattaaagaa cgtggactcc aacgtcaaag ggcgaaaaac cgtctatcag    6600
ggcgatggcc cactacgtga accatcaccc taatcaagtt ttttggggtc gaggtgccgt    6660
aaagcactaa atcggaaccc taaagggagc ccccgattta gagcttgacg gggaaagccg    6720
gcgaacgtgg cgagaaagga agggaagaaa gcgaaaggag cgggcgctag gcgctggca    6780 agtgtagcgg tcacgctgcg cgtaaccacc acacccgccg cgcttaatgc gccgctacag    6840
ggcgcgtccc attcgccatt caggctgcgc aactgttggg aagggcgatc ggtgcgggcc    6900
tcttcgctat tacgccagct ggcgaaaggg ggatgtgctg caaggcgatt aagttgggta    6960
acgccagggt tttcccagtc acgacgttgt aaaacgacgg ccagtgagcg cgcgtaatac    7020
```

| | |
|---|---|
| gactcactat agggcgaatt gggtaccggg cccccctcg aggtcgacgg tatcggggga | 7080 |
| gctcgcaggg tctccatttt gaagcgggag gtttgaacgc gcagccgcca tgccggggtt | 7140 |
| ttacgagatt gtgattaagg tccccagcga ccttgacgag catctgcccg gcatttctga | 7200 |
| cagctttgtg aactgggtgg ccgagaagga atgggagttg ccgccagatt ctgacatgga | 7260 |
| tctgaatctg attgagcagg caccctgac cgtggccgag aagctgcagc gcgactttct | 7320 |
| gacggaatgg cgccgtgtga gtaaggcccc ggaggctctt ttctttgtgc aatttgagaa | 7380 |
| gggagagagc tacttccaca tgcacgtgct cgtggaaacc accggggtga aatc | 7434 |

<210> SEQ ID NO 6
<211> LENGTH: 11569
<212> TYPE: DNA
<213> ORGANISM: Artificial Sequence
<220> FEATURE:
<223> OTHER INFORMATION: Coding Strand of Plasmid pHelper-Kan

<400> SEQUENCE: 6

| | |
|---|---|
| ggtacccaac tccatgctta acagtcccca ggtacagccc accctgcgtc gcaaccagga | 60 |
| acagctctac agcttcctgg agcgccactc gccctacttc cgcagccaca gtgcgcagat | 120 |
| taggagcgcc acttcttttt gtcacttgaa aaacatgtaa aataatgta ctaggagaca | 180 |
| ctttcaataa aggcaaatgt ttttatttgt acactctcgg gtgattattt acccccacc | 240 |
| cttgccgtct cgccgttta aaatcaaag gggttctgcc gcgcatcgct atgcgccact | 300 |
| ggcagggaca cgttgcgata ctggtgttta gtgctccact taaactcagg cacaaccatc | 360 |
| cgcggcagct cggtgaagtt ttcactccac aggctgcgca ccatcaccaa cgcgtttagc | 420 |
| aggtcgggcg ccgatatctt gaagtcgcag ttggggcctc cgccctgcgc gcgcgagttg | 480 |
| cgatacacag ggttgcagca ctggaacact atcagcgccg ggtggtgcac gctgccagc | 540 |
| acgctcttgt cggagatcag atccgcgtcc aggtcctccg cgttgctcag ggcgaacgga | 600 |
| gtcaactttg gtagctgcct tcccaaaaag ggtgcatgcc caggctttga gttgcactcg | 660 |
| caccgtagtg gcatcagaag gtgaccgtgc ccggtctggg cgttaggata cagcgcctgc | 720 |
| atgaaagcct tgatctgctt aaaagccacc tgagcctttg cgccttcaga gaagaacatg | 780 |
| ccgcaagact tgccggaaaa ctgattggcc ggacaggccg cgtcatgcac gcagcacctt | 840 |
| gcgtcggtgt tggagatctg caccacattt cggcccacc ggttcttcac gatcttggcc | 900 |
| ttgctagact gctccttcag cgcgcgctgc ccgttttcgc tcgtcacatc catttcaatc | 960 |
| acgtgctcct tatttatcat aatgctcccg tgtagacact taagtcgcc ttcgatctca | 1020 |
| gcgcagcggt gcagccacaa cgcgcagccc gtgggctcgt ggtgcttgta ggttacctct | 1080 |
| gcaaacgact gcaggtacgc ctgcaggaat cgccccatca tcgtcacaaa ggtcttgttg | 1140 |
| ctggtgaagg tcagctgcaa cccgcggtgc tcctcgttta gccaggtctt gcatacggcc | 1200 |
| gccagagctt ccacttggtc aggcagtagc ttgaagtttg cctttagatc gttatccacg | 1260 |
| tggtacttgt ccatcaacgc gcgcgcagcc tccatgccct tctcccacgc agacacgatc | 1320 |
| ggcaggctca gcgggtttat caccgtgctt tcactttccg cttcactgga ctcttccttt | 1380 |
| tcctcttgcg tccgcatacc ccgcgccact gggtcgtctt cattcagccg ccgcaccgtg | 1440 |
| cgcttacctc ccttgccgtg cttgattagc accggtgggt tgctgaaacc caccatttgt | 1500 |
| agcgccacat cttctctttc ttcctcgctg tccacgatca cctctgggga tggcgggcgc | 1560 |
| tcgggcttgg gagaggggcg cttcttttc tttttggacg caatggccaa atccgccgtc | 1620 |
| gaggtcgatg gccgcgggct gggtgtgcgc ggcaccagcg catcttgtga cgagtcttct | 1680 |

```
tcgtcctcgg actcgagacg ccgcctcagc cgcttttttg ggggcgcgcg gggaggcggc   1740
ggcgacggcg acggggacga cacgtcctcc atggttggtg gacgtcgcgc cgcaccgcgt   1800
ccgcgctcgg gggtggtttc gcgctgctcc tcttcccgac tggccatttc cttctcctat   1860
aggcagaaaa agatcatgga gtcagtcgag aaggaggaca gcctaaccgc ccccttgag    1920
ttcgccacca ccgcctccac cgatgccgcc aacgcgccta ccaccttccc cgtcgaggca   1980
cccccgcttg aggaggagga agtgattatc gagcaggacc caggttttgt aagcgaagac   2040
gacgaggatc gctcagtacc aacagaggat aaaaagcaag accaggacga cgcagaggca   2100
aacgaggaac aagtcgggcg gggggaccaa aggcatggcg actacctaga tgtgggagac   2160
gacgtgctgt tgaagcatct gcagcgccag tgcgccatta tctgcgacgc gttgcaagag   2220
cgcagcgatg tgcccctcgc catagcggat gtcagccttg cctacgaacg ccacctgttc   2280
tcaccgcgcg taccccccaa acgccaagaa aacggcacat gcgagcccaa cccgcgcctc   2340
aacttctacc ccgtatttgc cgtgccagag gtgcttgcca cctatcacat ctttttccaa   2400
aactgcaaga taccctatc ctgccgtgcc aaccgcagcc gagcggacaa gcagctggcc    2460
ttgcggcagg gcgctgtcat acctgatatc gcctcgctcg acgaagtgcc aaaaatcttt   2520
gagggtcttg gacgcgacga gaaacgcgcg gcaaacgctc tgcaacaaga aaacagcgaa   2580
aatgaaagtc actgtggagt gctggtggaa cttgagggtg acaacgcgcg cctagccgtg   2640
ctgaaacgca gcatcgaggt caccactttt gcctaccggg cacttaacct acccccaag    2700
gttatgagca cagtcatgag cgagctgatc gtgcgccgtg cacgacccct ggagagggat   2760
gcaaacttgc aagaacaaac cgaggagggc ctacccgcag ttggcgatga gcagctggcg   2820
cgctggcttg agacgcgcga gcctgccgac ttggaggagc gacgcaagct aatgatggcc   2880
gcagtgcttg ttaccgtgga gcttgagtgc atgcagcggt tctttgctga cccggagatg   2940
cagcgcaagc tagaggaaac gttgcactac accttcgcc agggctacgt gcgccaggcc    3000
tgcaaaattt ccaacgtgga gctctgcaac ctggtctcct accttggaat tttgcacgaa   3060
aaccgcctcg gcaaaaacgt gcttcattcc acgtcaagg gcgaggcgcg ccgcgactac    3120
gtccgcgact gcgtttactt atttctgtgc tacacctgga aaacggccat gggcgtgtgg   3180
cagcaatgcc tggaggagcg caacctaaag gagctgcaga gctgctaaa gcaaaacttg    3240
aaggacctat ggacggcctt caacgagcgc tccgtggccg cgcacctggc ggacattatc   3300
ttccccgaac gcctgcttaa aaccctgcaa cagggtctgc cagacttcac cagtcaaagc   3360
atgttgcaaa actttaggaa ctttatccta gagcgttcag gaattctgcc cgccacctgc   3420
tgtgcgcttc ctagcgactt tgtgcccatt aagtaccgtg aatgccctcc gccgctttgg   3480
ggtcactgct accttctgca gctagccaac taccttgcct accactccga catcatggaa   3540
gacgtgagcg gtgacggcct actggagtgt cactgtcgct gcaacctatg caccccgcac   3600
cgctccctgg tctgcaattc gcaactgctt agcgaaagtc aaattatcgg tacctttgag   3660
ctgcagggtc cctcgcctga cgaaaagtcc gcggctccgg ggttgaaact cactccgggg   3720
ctgtggacgt cggcttacct tcgcaaattt gtacctgagg actaccacgc ccacgagatt   3780
aggttctacg aagaccaatc ccgccgccaa atgcgcgagc ttaccgcctg cgtcattacc   3840
cagggccaca tccttggcca attgcaagcc atcaacaaag cccgccaaga gtttctgcta   3900
cgaaagggac gggggttta cctggacccc cagtccggcg aggagctcaa cccaatcccc   3960
ccgccgccgc agccctatca gcagccgcgg gcccttgctt cccaggatgg cacccaaaaa   4020
```

-continued

```
gaagctgcag ctgccgccgc cgccacccac ggacgaggag gaatactggg acagtcaggc    4080
agaggaggtt ttggacgagg aggaggagat gatggaagac tgggacagcc tagacgaagc    4140
ttccgaggcc gaagaggtgt cagacgaaac accgtcaccc tcggtcgcat tccctcgcc     4200 ggcgccccaa aaattggcaa ccgttcccag catcgctaca acctccgctc ctcaggcgcc    4260
gccggcactg cctgttcgcc gacccaaccg tagatgggac accactggaa ccagggccgg    4320
taagtctaag cagccgccgc cgttagccca agagcaacaa cagcgccaag gctaccgctc    4380
gtggcgcggg cacaagaacg ccatagttgc ttgcttgcaa gactgtgggg gcaacatctc    4440
cttcgcccgc cgctttcttc tctaccatca cggcgtggcc ttccccgta acatcctgca     4500 ttactaccgt catctctaca gccctactg caccggcggc agcggcagcg gcagcaacag     4560
cagcggtcac acagaagcaa aggcgaccgg atagcaagac tctgacaaag cccaagaaat    4620
ccacagcggc ggcagcagca ggaggaggag cgctgcgtct ggcgcccaac gaacccgtat    4680
cgacccgcga gcttagaaat aggatttttc ccactctgta tgctatattt caacaaagca    4740
ggggccaaga acaagagctg aaaataaaaa acaggtctct gcgctccctc acccgcagct    4800
gcctgtatca caaagcgaa gatcagcttg gcgcacgct ggaagacgcg gaggctctct       4860
tcagcaaata ctgcgcgctg actcttaagg actagtttcg cgccctttct caaatttaag    4920
cgcgaaaact acgtcatctc cagcggccac accggcgcc agcacctgtc gtcagcgcca     4980
ttatgagcaa ggaaattccc acgccctaca tgtggagtta ccagccacaa atgggacttg    5040
cggctggagc tgcccaagac tactcaaccc gaataaacta catgagcgcg ggaccccaca    5100
tgatatcccg ggtcaacgga atccgcgccc accgaaaccg aattctcctc gaacaggcgg    5160
ctattaccac cacacctcgt aataaccta atcccgtag ttggcccgct gccctggtgt       5220
accaggaaag tcccgctccc accactgtgg tacttcccag agacgcccag gccgaagttc    5280
agatgactaa ctcaggggcg cagcttgcgg gcggctttcg tcacagggtg cggtcgcccg    5340
ggcgttttag ggcggagtaa cttgcatgta ttgggaattg tagttttttt aaaatgggaa    5400
gtgacgtatc gtgggaaaac ggaagtgaag atttgaggaa gttgtgggtt ttttggcttt    5460
cgtttctggg cgtaggttcg cgtgcggttt tctgggtgtt ttttgtggac tttaaccgtt    5520
acgtcatttt ttagtcctat atatactcgc tctgtacttg gccctttta cactgtgact     5580 gattgagctg gtgccgtgtc gagtggtgtt tttaatagg tttttttact ggtaaggctg      5640
actgttatgg ctgccgctgt ggaagcgctg tatgttgttc tggagcggga gggtgctatt    5700
ttgcctaggc aggagggttt ttcaggtgtt tatgtgtttt tctctcctat taattttgtt    5760
atacctccta tgggggctgt aatgttgtct ctacgcctgc gggtatgtat tccccgggc     5820 tatttcggtc gcttttagc actgaccgat gttaaccaac ctgatgtgtt taccgagtct     5880
tacattatga ctccggacat gaccgaggaa ctgtcggtgg tgcttttaa tcacggtgac      5940 cagttttttt acgtcacgc cggcatggcc gtagtccgtc ttatgcttat aagggttgtt     6000
tttcctgttg taagacaggc ttctaatgtt taaatgtttt tttttttgtt attttatttt    6060
gtgtttaatg caggaacccg cagacatgtt tgagagaaaa atggtgtctt tttctgtggt    6120
ggttccggaa cttacctgcc tttatctgca tgagcatgac tacgatgtgc ttgctttttt    6180
gcgcgaggct ttgcctgatt ttttgagcag caccttgcat tttatatcgc cgcccatgca    6240
acaagcttac ataggggcta cgctggttag catagctccg agtatgcgtg tcataatcag    6300
tgtgggttct tttgtcatgg ttcctggcgg ggaagtggcc gcgctggtcc gtgcagacct    6360
gcacgattat gttcagctgg ccctgcgaag ggacctacgg gatcgcggta ttttttgttaa   6420
```

```
tgttccgctt ttgaatctta tacaggtctg tgaggaacct gaattttgc aatcatgatt      6480
cgctgcttga ggctgaaggt ggagggcgct ctggagcaga tttttacaat ggccggactt      6540
aatattcggg atttgcttag agacatattg ataaggtggc gagatgaaaa ttatttgggc      6600
atggttgaag gtgctggaat gtttatagag gagattcacc ctgaagggtt tagcctttac      6660
gtccacttgg acgtgagggc agtttgcctt ttggaagcca ttgtgcaaca tcttacaaat      6720
gccattatct gttctttggc tgtagagttt gaccacgcca ccggagggga gcgcgttcac      6780
ttaatagatc ttcattttga ggttttggat aatctttgg aataaaaaaa aaaaaacatg       6840
gttcttccag ctcttcccgc tcctcccgtg tgtgactcgc agaacgaatg tgtaggttgg      6900
ctgggtgtgg cttattctgc ggtggtggat gttatcaggg cagcggcgca tgaaggagtt      6960
tacatagaac ccgaagccag ggggcgcctg gatgctttga gagtggat atactacaac        7020
tactacacag agcgagctaa gcgacgagac cggagacgca gatctgtttg tcacgcccgc      7080
acctggtttt gcttcaggaa atatgactac gtccggcgtt ccatttggca tgacactacg      7140
accaacacga tctcggttgt ctcggcgcac tccgtacagt agggatcgcc tacctccttt      7200
tgagacagag acccgcgcta ccatactgga ggatcatccg ctgctgcccg aatgtaacac      7260
tttgacaatg cacaacgtga gttacgtgcg aggtcttccc tgcagtgtgg gatttacgct      7320
gattcaggaa tggttgttc cctgggatat ggttctgacg cgggaggagc ttgtaatcct       7380
gaggaagtgt atgcacgtgt gcctgtgttg tgccaacatt gatatcatga cgagcatgat      7440
gatccatggt tacgagtcct gggctctcca ctgtcattgt tccagtcccg gttccctgca     7500
gtgcatagcc ggcgggcagg ttttggccag ctggtttagg atggtggtgg atggcgccat     7560
gtttaatcag aggtttatat ggtaccggga ggtggtgaat tacaacatgc caaaagaggt     7620
aatgtttatg tccagcgtgt ttatgagggg tcgccactta atctacctgc gcttgtggta      7680
tgatggccac gtgggttctg tggtccccgc catgagcttt ggatacagcg ccttgcactg      7740
tgggattttg aacaatattg tggtgctgtg ctgcagttac tgtgctgatt taagtgagat      7800
cagggtgcgc tgctgtgccc ggaggacaag gcgtctcatg ctgcgggcgg tgcgaatcat      7860
cgctgaggag accactgcca tgttgtattc ctgcaggacg gagcggcggc ggcagcagtt      7920
tattcgcgcg ctgctgcagc accaccgccc tatcctgatg cacgattatg actctacccc     7980
catgtaggcg tggacttccc cttcgccgcc cgttgagcaa ccgcaagttg dacagcagcc      8040
tgtggctcag cagctggaca gcgacatgaa cttaagcgag ctgcccgggg agtttattaa     8100
tatcactgat gagcgtttgg ctcgacagga aaccgtgtgg aatataacac ctaagaatat     8160
gtctgttacc catgatatga tgctttttaa ggccagccgg ggagaaagga ctgtgtactc     8220
tgtgtgttgg gagggaggtg gcaggttgaa tactagggtt ctgtgagttt gattaaggta     8280
cggtgatcaa tataagctat gtggtggtgg ggctatacta ctgaatgaaa aatgacttga     8340
aattttctgc aattgaaaaa taaacacgtt gaaacataac atgcaacagg ttcacgattc      8400
tttattcctg ggcaatgtag gagaaggtgt aagagttggt agcaaaagtt tcagtggtgt      8460
atttccact ttcccaggac catgtaaaag acatagagta agtgcttacc tcgctagttt       8520
ctgtggattc actagaatcg atgtaggatg ttgcccctcc tgacgcggta ggagaagggg     8580
agggtgccct gcatgtctgc cgctgctctt gctcttgccg ctgctgagga gggggggcgca    8640
tctgccgcag caccgatgc atctgggaaa agcaaaaaag gggctcgtcc ctgtttccgg      8700
aggaatttgc aagcggggtc ttgcatgacg gggaggcaaa ccccgttcg ccgcagtccg       8760
```

```
gccggcccga gactcgaacc gggggtcctg cgactcaacc cttggaaaat aaccctccgg    8820
ctacagggag cgagccactt aatgctttcg ctttccagcc taaccgctta cgccgcgcgc    8880
ggccagtggc caaaaaagct agcgcagcag ccgccgcgcc tggaaggaag ccaaaaggag    8940
cgctcccccg ttgtctgacg tcgcacacct gggttcgaca cgcgggcggt aaccgcatgg    9000
atcacggcgg acggccggat ccggggttcg aaccccggtc gtccgccatg atacccttgc    9060
gaatttatcc accagaccac ggaagagtgc ccgcttacag gctctccttt tgcacggtct    9120
agagcgtcaa cgactgcgca cgcctcaccg gccagagcgt cccgaccatg gagcactttt    9180
tgccgctgcg caacatctgg aaccgcgtcc gcgactttcc gcgcgcctcc accaccgccg    9240
ccggcatcac ctggatgtcc aggtacatct acggattacg tcgacgttta aaccatatga    9300
tcagctcact caaaggcggt aatacggtta tccacagaat caggggataa cgcaggaaag    9360
aacatgtgag caaaaggcca gcaaaaggcc aggaaccgta aaaaggccgc gttgctggcg    9420 ttttttccata ggctccgccc ccctgacgag catcacaaaa atcgacgctc aagtcagagg    9480
tggcgaaacc cgacaggact ataaagatac caggcgtttc cccctggaag ctccctcgtg    9540
cgctctcctg ttccgaccct gccgcttacc ggatacctgt ccgcctttct cccttcggga    9600
agcgtggcgc tttctcatag ctcacgctgt aggtatctca gttcggtgta ggtcgttcgc    9660
tccaagctgg gctgtgtgca cgaaccccc gttcagcccg accgctgcgc cttatccggt    9720
aactatcgtc ttgagtccaa cccggtaaga cacgacttat cgccactggc agcagccact    9780
ggtaacagga ttagcagagc gaggtatgta ggcggtgcta cagagttctt gaagtggtgg    9840
cctaactacg gctacactag aagaacagta tttggtatct gcgctctgct gaagccagtt    9900
accttcggaa aaagagttgg tagctcttga tccggcaaac aaaccaccgc tggtagcggt    9960
ggtttttttg tttgcaagca gcagattacg cgcagaaaaa aaggatctca agaagatcct   10020
ttgatctttt ctacggggtc tgacgctcag tggaacgaaa actcacgtta agggattttg   10080
gtcatgagat tatcaaaaag gatcttcacc tagatccttt taaattaaaa atgaagtttt   10140
aaatcaatct aaagtatata tgagtaaact tggtctgaca gtcagaagaa ctcgtcaaga   10200
aggcgataga aggcgatgcg ctgcgaatcg ggagcggcga taccgtaaag cacgaggaag   10260
cggtcagccc attcgccgcc aagctcttca gcaatatcac gggtagccaa cgctatgtcc   10320
tgatagcggt ccgccacacc cagccggcca cagtcgatga atccagaaaa gcggccattt   10380
tccaccatga tattcggcaa gcaggcatcg ccatgggtca cgacgagatc ctcgccgtcg   10440
ggcatgctcg ccttgagcct ggcgaacagt tcggctggcg cgagccctg atgctcttcg    10500 tccagatcat cctgatcgac aagaccggct tccatccgag tacgtgctcg ctcgatgcga   10560
tgtttcgctt ggtggtcgaa tgggcaggta gccggatcaa gcgtatgcag ccgccgcatt   10620
gcatcagcca tgatggatac tttctcggca ggagcaaggt gagatgacag gagatcctgc   10680
cccggcactt cgcccaatag cagccagtcc cttcccgctt cagtgacaac gtcgagtaca   10740
gctgcgcaag gaacgcccgt cgtggccagc cacgatagcc gcgctgcctc gtcttgcagt   10800
tcattcaggg caccggacag gtcggtcttg acaaaaagaa ccgggcgccc ctgcgctgac   10860
agccggaaca cggcggcatc agagcagccg attgtctgtt gtgcccagtc atagccgaat   10920
agcctctcca cccaagcggc cggagaacct gcgtgcaatc catcttgttc aatcatactc   10980 ttccttttc aatattattg aagcatttat cagggttatt gtctcatgag cggatacata   11040
tttgaatgta tttagaaaaa taaacaaata ggggttccgc gcacatttcc ccgaaaagtg   11100
ccacctaaat tgtaagcgtt aatattttgt taaaattcgc gttaaatttt tgttaaatca   11160
```

```
gctcatttt  taaccaatag  gccgaaatcg  gcaaaatccc  ttataaatca  aaagaataga   11220
ccgagatagg  gttgagtgtt  gttccagttt  ggaacaagag  tccactatta  aagaacgtgg   11280
actccaacgt  caaagggcga  aaaaccgtct  atcagggcga  tggcccacta  cgtgaaccat   11340
caccctaatc  aagttttttg  gggtcgaggt  gccgtaaagc  actaaatcgg  aaccctaaag   11400 ggagccccg  atttagagct  tgacggggaa  agccggcgaa  cgtggcgaga  aggaaggga    11460 agaaagcgaa  aggagcgggc  gctagggcgc  tggcaagtgt  agcggtcacg  ctgcgcgtaa   11520
ccaccacacc  cgccgcgctt  aatgcgccgc  tacagggcgc  gatggatcc               11569
```

<210> SEQ ID NO 7
<211> LENGTH: 5030
<212> TYPE: DNA
<213> ORGANISM: Artificial Sequence
<220> FEATURE:
<223> OTHER INFORMATION: Coding Strand of Plasmid pAV-CMV-EGFP

<400> SEQUENCE: 7

```
cctgcaggca  gctgcgcgct  cgctcgctca  ctgaggccgc  ccgggcgtcg  ggcgaccttt     60
ggtcgcccgg  ccctccagtg  agcgagcgcg  cagagaggga  gtggccaact  ccatcactag    120
gggttcctgc  ggccgcacgc  gtctagttat  taatagtaat  cgaattcgtg  ttactcataa    180
ctagtaaggt  cgggcaggaa  gagggcctat  ttcccatgat  tccttcatat  ttgcatatac    240
gatacaaggc  tgttagagag  ataattagaa  ttaatttgac  tgtaaacaca  aagatattag    300
tacaaaatac  gtgacgtaga  aagtaataat  ttcttgggta  gtttgcagtt  ttaaaattat    360
gttttaaaat  ggactatcat  atgcttaccg  taacttgaaa  gtatttcgat  ttcttgggtt    420
tatatatctt  gtggaaagga  cgcgggatcc  actggaccag  gcagcagcgt  cagaagactt    480
ttttggaaaa  gcttgactag  taatactgta  atagtaatca  attacgggggt  cattagttca   540 tagcccatat  atggagttcc  gcgttacata  acttacggta  aatggcccgc  ctggctgacc    600
gcccaacgac  ccccgcccat  tgacgtcaat  aatgacgtat  gttcccatag  taacgccaat    660
agggactttc  cattgacgtc  aatgggtgga  gtatttacgg  taaactgccc  acttggcagt    720
acatcaagtg  tatcatatgc  caagtacgcc  ccctattgac  gtcaatgacg  gtaaatggcc    780
cgcctggcat  tatgcccagt  acatgacctt  atgggacttt  cctacttggc  agtacatcta    840
cgtattagtc  atcgctatta  ccatggtgat  gcggttttgg  cagtacatca  atgggcgtgg    900
atagcggttt  gactcacggg  gatttccaag  tctccacccc  attgacgtca  atgggagttt    960
gttttgcacc  aaaatcaacg  ggactttcca  aaatgtcgta  acaactccgc  cccattgacg   1020
caaatgggcg  gtaggcgtgt  acggtgggag  gtctatataa  gcagagctgg  tttagtgaac   1080
cgtcagatcc  gctagagatc  cggtaccgag  agatctgcc  gccgcgatcg  ccggcgcgcc   1140
agatctcacg  cttaactagc  tagcggaccg  acgcgtacgc  ggccgctcga  tggtgagc    1200 aagggcgagg  agctgttcac  cggggtggtg  cccatcctgg  tcgagctgga  cggcgacgta   1260
aacggccaca  agttcagcgt  gtccggcgag  ggcgagggcg  atgccaccta  cggcaagctg   1320
accctgaagt  tcatctgcac  caccggcaag  ctgcccgtgc  cctggcccac  cctcgtgacc   1380
accctgacct  acggcgtgca  gtgcttcagc  cgctaccccg  accacatgaa  gcagcacgac   1440
ttcttcaagt  ccgccatgcc  cgaaggctac  gtccaggagc  gcaccatctt  cttcaaggac   1500
gacggcaact  acaagacccg  cgccgaggtg  aagttcgagg  gcgacaccct  ggtgaaccgc   1560
atcgagctga  agggcatcga  cttcaaggag  gacggcaaca  tcctggggca  caagctggag   1620
```

```
tacaactaca acagccacaa cgtctatatc atggccgaca agcagaagaa cggcatcaag    1680
gtgaacttca agatccgcca caacatcgag gacggcagcg tgcagctcgc cgaccactac    1740
cagcagaaca cccccatcgg cgacggcccc gtgctgctgc ccgacaacca ctacctgagc    1800
acccagtccg ccctgagcaa agaccccaac gagaagcgcg atcacatggt cctgctggag    1860
ttcgtgaccg ccgccgggat cactctcggc atggacgagc tgtacaagta agtcgaggat    1920
tataaggatg acgacgataa attcgtcgag caccaccacc accaccacta taaggtttta    1980
tccgatccac cggatctaga taagatatcc gatccaccgg atctagataa ctgatcataa    2040
tcagccatac cacatttgta gaggttttac ttgctttaaa aaacctccca cacctccccc    2100
tgaacctgaa acataaaatg aatgcaattg ttgttgttaa cttgtttatt gcagcttata    2160
atggttacaa ataaagcaat agcatcacaa atttcacaaa taaagcattt ttttcactgc    2220
attctagttg tggtttgtcc aaactcatca atgtatctta acgcggtaac cacgtgcgga    2280
ccgagcggcc gcaggaaccc ctagtgatgg agttggccac tccctctctg cgcgctcgct    2340
cgctcactga ggccgggcga ccaaaggtcg cccgacgccc gggctttgcc cggcggcct    2400 cagtgagcga gcgagcgcgc agctgcctgc aggggcgcct gatgcggtat tttctcctta    2460
cgcatctgtg cggtatttca caccgcatac gtcaaagcaa ccatagtacg cgccctgtag    2520
cggcgcatta agcgcggcgg gtgtggtggt tacgcgcagc gtgaccgcta cacctgccag    2580
cgccttagcg cccgctcctt tcgctttctt cccttccttt ctcgccacgt tcgccggctt    2640
tccccgtcaa gctctaaatc gggggctccc tttagggttc cgatttagtg ctttacggca    2700
cctcgacccc aaaaaacttg atttgggtga tggttcacgt agtgggccat cgccctgata    2760
gacggttttt cgccctttga cgttggagtc cacgttcttt aatagtggac tcttgttcca    2820
aactggaaca cactcaacc ctatctcggg ctattctttt gatttataag gattttgcc    2880 gatttcggcc tattggttaa aaaatgagct gatttaacaa aaatttaacg cgaattttaa    2940
caaaatatta cgtttacaa ttttatggtg cactctcagt acaatctgct ctgatgccgc    3000
atagttaagc cagccccgac acccgccaac acccgctgac gcgccctgac gggcttgtct    3060
gctcccggca tccgcttaca gacaagctgt gaccgtctcc gggagctgca tgtgtcagag    3120
gttttcaccg tcatcaccga aacgcgcgag acgaaagggc ctcgtgatac gcctatttt    3180 ataggttaat gtcatgataa taatggtttc ttagacgtca ggtggcactt ttcggggaaa    3240
tgtgcgcgga accctatttt gtttattttt ctaaatacat tcaaatatgt atccgctcat    3300
gagacaataa ccctgataaa tgcttcaata atattgaaaa aggaagagta tgagtattca    3360
acatttccgt gtcgccctta ttcccttttt tgcggcattt gccttcctg ttttgctca    3420 cccagaaacg ctggtgaaag taaaagatgc tgaagatcag ttgggtgcac gagtgggtta    3480
catcgaactg gatctcaaca gcggtaagat ccttgagagt tttcgccccg aagaacgttt    3540
tccaatgatg agcacttta aagttctgct atgtggcgcg gtattatcc gtattgacgc    3600 cgggcaagag caactcggtc gccgcataca ctattctcag aatgacttgg ttgagtactc    3660
accagtcaca gaaaagcatc ttacggatgg catgacagta agagaattat gcagtgctgc    3720
cataaccatg agtgataaca ctgcggccaa cttacttctg acaacgatcg gaggaccgaa    3780
ggagctaacc gctttttgc acaacatggg ggatcatgta actcgccttg atcgttggga    3840
accggagctg aatgaagcca taccaaacga cgagcgtgac accacgatgc ctgtagcaat    3900
ggcaacaacg ttgcgcaaac tattaactgg cgaactactt actctagctt cccggcaaca    3960
attaatagac tggatggagg cggataaagt tgcaggacca cttctgcgct cggcccttcc    4020
```

```
ggctggctgg tttattgctg ataaatctgg agccggtgag cgtgggtctc gcggtatcat    4080
tgcagcactg gggccagatg gtaagccctc ccgtatcgta gttatctaca cgacggggag    4140
tcaggcaact atggatgaac gaaatagaca gatcgctgag ataggtgcct cactgattaa    4200
gcattggtaa ctgtcagacc aagtttactc atatatactt tagattgatt taaaacttca    4260
tttttaattt aaaaggatct aggtgaagat cctttttgat aatctcatga ccaaaatccc    4320
ttaacgtgag ttttcgttcc actgagcgtc agacccgta gaaaagatca aaggatcttc     4380
ttgagatcct ttttttctgc gcgtaatctg ctgcttgcaa acaaaaaaac caccgctacc    4440
agcggtggtt tgtttgccgg atcaagagct accaactctt tttccgaagg taactggctt    4500
cagcagagcg cagataccaa atactgtcct tctagtgtag ccgtagttag gccaccactt    4560
caagaactct gtagcaccgc ctacatacct cgctctgcta atcctgttac cagtggctgc    4620
tgccagtggc gataagtcgt gtcttaccgg gttggactca agacgatagt taccggataa    4680
ggcgcagcgg tcgggctgaa cggggggttc gtgcacacag cccagcttgg agcgaacgac    4740
ctacaccgaa ctgagatacc tacagcgtga gctatgagaa agcgccacgc ttcccgaagg    4800
gagaaaggcg gacaggtatc cggtaagcgg cagggtcgga acaggagagc gcacgaggga    4860
gcttccaggg ggaaacgcct ggtatcttta tagtcctgtc gggtttcgcc acctctgact    4920
tgagcgtcga ttttgtgat gctcgtcagg ggggcggagc ctatgaaaaa acgccagcaa     4980
cgcggccttt ttacggttcc tggccttttg ctggcctttt gctcacatgt               5030

<210> SEQ ID NO 8
<211> LENGTH: 4742
<212> TYPE: DNA
<213> ORGANISM: Artificial Sequence
<220> FEATURE:
<223> OTHER INFORMATION: Coding Strand of Plasmid pAV-TBG-EGFP

<400> SEQUENCE: 8
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact    120
aggggttcct gcggccggtc gcgtctagta ctagtaggtt aatttttaaa aagcagtcaa    180
aagtccaagt ggcccttggc agcatttact ctctctgttt gctctggtta ataatctcag    240
gagcacaaac attccagatc caggttaatt tttaaaaagc agtcaaaagt ccaagtggcc    300
cttggcagca tttactctct ctgtttgctc tggttaataa tctcaggagc acaaacattc    360
cagatccggc gcgccagggc tggaagctac ctttgacatc atttcctctg cgaatgcatg    420
tataatttct acagaaccta ttagaaagga tcacccagcc tctgcttttg tacaactttc    480
ccttaaaaaa ctgccaattc cactgctgtt tggcccaata gtgagaactt ttcctgctg     540 cctcttggtg cttttgccta tggccctat tctgcctgct gaagacactc ttgccagcat    600
ggacttaaac ccctccagct ctgacaatcc tcttctctct tgttttaca tgaagggtct    660 ggcagccaaa gcaatcactc aaagttcaaa ccttatcatt ttttgctttg ttcctcttgg    720
ccttggtttt gtacatcagc tttgaaaata ccatcccagg gttaatgctg gggttaattt    780
ataactaaga gtgctctagt tttgcaatac aggacatgct ataaaaatgg aaagatgttg    840
ctttctgaga gacaggtacc gaggagatct gccgccgcga tcgccaccat ggtgagcaag    900
ggcgaggagc tgttcaccgg ggtggtgccc atcctggtcg agctggacgg cgacgtaaac    960
ggccacaagt tcagcgtgtc cggcgagggc gagggcgatg ccacttacgg caagctgacc   1020
```

```
ctgaagttca tctgcaccac cggcaagctg cccgtgccct ggcccaccct cgtgaccacc    1080
ctgacctacg gcgtgcagtg cttcagccgc tacccccgacc acatgaagca gcacgacttc   1140
ttcaagtccg ccatgcccga aggctacgtc caggagcgca ccatcttctt caaggacgac   1200
ggcaactaca agacccgcgc cgaggtgaag ttcgagggcg acaccctggt gaaccgcatc    1260
gagctgaagg gcatcgactt caaggaggac ggcaacatcc tggggcacaa gctggagtac   1320
aactacaaca gccacaacgt ctatatcatg gccgacaagc agaagaacgg catcaaggtg    1380
aacttcaaga tccgccacaa catcgaggac ggcagcgtgc agctcgccga ccactaccag    1440
cagaacaccc ccatcggcga cggccccgtg ctgctgcccg acaaccacta cctgagcacc    1500
cagtccgccc tgagcaaaga ccccaacgag aagcgcgatc acatggtcct gctggagttc    1560
gtgaccgccg ccgggatcac tctcggcatg gacgagctgt acaagtagac gcgtacgcgg    1620
ccgctcgagg attataagga tgacgacgat aaattcgtcg agcaccacca ccaccaccac    1680
taataaggtt tatccgatcc accggatcta gataagatat ccgatccacc ggatctagat    1740
aactgatcat aatcagccat accacatttg tagaggtttt acttgcttta aaaaacctcc    1800
cacacctccc cctgaacctg aaacataaaa tgaatgcaat tgttgttgtt aacttgttta    1860
ttgcagctta atggttac aaataaagca atagcatcac aaatttcaca aataaagcat    1920
ttttttcact gcattctagt tgtggtttgt ccaaactcat caatgtatct taacgcggta    1980
accacgtgcg gacccaacgg ccgcaggaac ccctagtgat ggagttggcc actccctctc    2040
tgcgcgctcg ctcgctcact gaggccgggc gaccaaaggt cgcccgacgc ccgggctttg    2100
cccgggcggc ctcagtgagc gagcgagcgc gcagctgcct gcaggggcgc ctgatgcggt    2160
attttctcct tacgcatctg tgcggtattt cacaccgcat acgtcaaagc aaccatagta    2220
cgcgccctgt agcggcacat taagcgcggc gggtgtggtg gttacgcgca gcgtgaccgc    2280
tacacctgcc agcgccttag cgcccgctcc tttcgctttc ttcccttcct ttctcgccac    2340
gttcgccggc tttccccgtc aagctctaaa tcggggctc cctttagggt tccgatttag    2400
tgctttacgg cacctcgacc ccaaaaaact tgatttgggt gatggttcac gtagtgggcc    2460
atcgccctga tagacggttt ttcgcccttt gacgttggag tccacgttct ttaatagtgg    2520
actcttgttc caaactggaa caacactcaa ctctatctcg gctattcctt tgatttata    2580 agggattttg ccgatttcgg tctattggtt aaaaaatgag ctgatttaac aaaaatttaa    2640
cgcgaatttt aacaaaatat taacgtttac aattttatgg tgcactctca gtacaatctg    2700
ctctgatgcc gcatagttaa gccagccccg acacccgcca cacccgctg acgcgccctg    2760 acgggcttgt ctgctcccgg catccgctta cagacaagct gtgaccgtct ccgggagctg    2820
catgtgtcag aggttttcac cgtcatcacc gaaacgcgcg agacgaaagg gcctcgtgat    2880
acgcctattt ttataggtta atgtcatgat aataatggtt tcttagacgt caggtggcac    2940
ttttcgggga aatgtgcgcg gaaccccctat ttgtttatttt ttctaaatac attcaaatat    3000
gtatccgctc atgagacaat aaccctgata aatgcttcaa taatattgaa aaaggaagag    3060
tatgagtatt caacatttcc gtgtcgccct tattcccttt tttgcggcat tttgccttcc    3120 tgttttgct cacccagaaa cgctggtgaa agtaaaagat gctgaagatc agttgggtgc    3180
acgagtgggt tacatcgaac tggatctcaa cagcggtaag atccttgaga gttttcgccc    3240
cgaagaacgt tttccaatga tgagcacttt taaagttctg ctatgtggcg cggtattatc    3300
ccgtattgac gccgggcaag agcaactcgg tcgccgcata cactattctc agaatgactt    3360
ggttgagtac tcaccagtca cagaaaagca tcttacggat ggcatgacag taagagaatt    3420
```

```
atgcagtgct gccataacca tgagtgataa cactgcggcc aacttacttc tgacaacgat    3480
cggaggaccg aaggagctaa ccgcttttt gcacaacatg ggggatcatg taactcgcct    3540
tgatcgttgg gaaccggagc tgaatgaagc cataccaaac gacgagcgtg acaccacgat    3600
gcctgtagca atgccaacaa cgttgcgcaa actattaact ggcgaactac ttactctagc    3660
ttcccggcaa caattaatag actggatgga ggcggataaa gttgcaggac cacttctgcg    3720
ctcggccctt ccggctggct ggtttattgc tgataaatct ggagccggtg agcgtgggtc    3780
tcgcggtatc attgcagcac tggggccaga tggtaagccc tcccgtatcg tagttatcta    3840
cacgacgggg agtcaggcaa ctatggatga acgaaataga cagatcgctg agataggtgc    3900
ctcactgatt aagcattggt aactgtcaga ccaagtttac tcatatatac tttagattga    3960
tttaaaactt catttttaat ttaaaaggat ctaggtgaag atccttttg ataatctcat    4020 gaccaaaatc ccttaacgtg agttttcgtt ccactgagcg tcagacccg tagaaaagat    4080 caaaggatct tcttgagatc ctttttttct gcgcgtaatc tgctgcttgc aaacaaaaaa    4140
accaccgcta ccagcggtgg tttgtttgcc ggatcaagag ctaccaactc tttttccgaa    4200
ggtaactggc ttcagcagag cgcagatacc aaatactgtt cttctagtgt agccgtagtt    4260
aggccaccac ttcaagaact ctgtagcacc gcctacatac ctcgctctgc taatcctgtt    4320
accagtggct gctgccagtg gcgataagtc gtgtcttacc gggttggact caagacgata    4380
gttaccggat aaggcgcagc ggtcgggctg aacggggggt tcgtgcacac agcccagctt    4440
ggagcgaacg acctacaccg aactgagata cctacagcgt gagctatgag aaagcgccac    4500
gcttcccgaa gggagaaagg cggacaggta tccggtaagc ggcagggtcg gaacaggaga    4560
gcgcacgagg gagcttccag ggggaaacgc ctggtatctt tatagtcctg tcgggtttcg    4620
ccacctctga cttgagcgtc gatttttgtg atgctcgtca ggggggcgga gcctatggaa    4680
aaacgccagc aacgcggcct ttttacggtt cctggccttt tgctggcctt ttgctcacat    4740
gt                                                                  4742

<210> SEQ ID NO 9
<211> LENGTH: 131
<212> TYPE: DNA
<213> ORGANISM: adeno-associated virus 1
<220> FEATURE:
<221> NAME/KEY: misc_feature
<222> LOCATION: (1)..(131)
<223> OTHER INFORMATION: P5 Promoter of AAV1

<400> SEQUENCE: 9
ggtcctgtat tagctgtcac gtgagtgctt ttgcgacatt ttgcgacacc acgtggccat     60
ttagggtata tatggccgag tgagcgagca ggatctccat tttgaccgcg aaatttgaac    120
gagcagcagc c                                                         131

<210> SEQ ID NO 10
<211> LENGTH: 131
<212> TYPE: DNA
<213> ORGANISM: adeno-associated virus 2
<220> FEATURE:
<221> NAME/KEY: misc_feature
<222> LOCATION: (1)..(131)
<223> OTHER INFORMATION: P5 Promoter of AAV2

<400> SEQUENCE: 10
ggtcctgtat tagaggtcac gtgagtgttt tgcgacattt tgcgacacca tgtggtcacg     60
```
ctgggtattt aagcccgagt gagcacgcag ggtctccatt ttgaagcggg aggtttgaac    120
gcgcagccgc c                                                        131

<210> SEQ ID NO 11
<211> LENGTH: 131
<212> TYPE: DNA
<213> ORGANISM: adeno-associated virus 3
<220> FEATURE:
<221> NAME/KEY: 'misc_feature
<222> LOCATION: (1)..(131)
<223> OTHER INFORMATION: P5 Promoter of AAV3

<400> SEQUENCE: 11
ccagctgcgt cagcagtcag gtgaccettt tgcgacagtt tgcgacacca cgtggccgct    60
gagggtatat attctcgagt gagcgaacca ggagctccat tttgaccgcg aaatttgaac   120
gagcagcagc c                                                        131

<210> SEQ ID NO 12
<211> LENGTH: 192
<212> TYPE: DNA
<213> ORGANISM: adeno-associated virus 4
<220> FEATURE:
<221> NAME/KEY: misc_feature
<222> LOCATION: (1)..(192)
<223> OTHER INFORMATION: P5 Promoter of AAV4

<400> SEQUENCE: 12
ggtccctgta ttagcagtca cgtgagtgtc gtatttcgcg gagcgtagcg gagcgcatac    60
caagctgcca cgtcacagcc acgtggtccg tttgcgacag tttgcgacac catgtggtca   120
ggagggtata taaccgcgag tgagccagcg aggagctcca ttttgcccgc gaattttgaa   180
cgagcagcag cc                                                       192

<210> SEQ ID NO 13
<211> LENGTH: 131
<212> TYPE: DNA
<213> ORGANISM: adeno-associated virus 5
<220> FEATURE:
<221> NAME/KEY: misc_feature
<222> LOCATION: (1)..(131)
<223> OTHER INFORMATION: P5 Promoter of AAV5

<400> SEQUENCE: 13
atgtgatgtg ttttatccaa taggaagaaa gcgcgcgtat gagttctcgc gagacttccg    60
gggtataaaa gaccgagtga acgagcccgc cgccattctt tgctctggac tgctagagga   120
ccctcgctgc c                                                        131

<210> SEQ ID NO 14
<211> LENGTH: 130
<212> TYPE: DNA
<213> ORGANISM: adeno-associated virus 6
<220> FEATURE:
<221> NAME/KEY: misc_feature
<222> LOCATION: (1)..(130)
<223> OTHER INFORMATION: P5 Promoter of AAV6

<400> SEQUENCE: 14
ggtcctgtat tagaggtcac gtgagtgttt tgcgacattt tgcgacacca tgtggtcacg    60
ctgggtattt aagcccgagt gagcacgcag ggtctccatt ttgaagcggg aggtttgaac   120
gcgcagcgcc                                                          130

```
<210> SEQ ID NO 15
<211> LENGTH: 131
<212> TYPE: DNA
<213> ORGANISM: adeno-associated virus 7
<220> FEATURE:
<221> NAME/KEY: misc_feature
<222> LOCATION: (1)..(131)
<223> OTHER INFORMATION: P5 Promoter of AAV7

<400> SEQUENCE: 15
ggtcctgtat tagctgtcac gtgagtgctt ttgcgacatt ttgcgacacc acgtggccat        60
ttgaggtata tatggccgag tgagcgagca ggatctccat tttgaccgcg aaatttgaac       120
gagcagcagc c                                                            131

<210> SEQ ID NO 16
<211> LENGTH: 131
<212> TYPE: DNA
<213> ORGANISM: adeno-associated virus 8
<220> FEATURE:
<221> NAME/KEY: misc_feature
<222> LOCATION: (1)..(131)
<223> OTHER INFORMATION: P5 Promoter of AAV8

<400> SEQUENCE: 16
ggtcctgtat tagctgtcac gtgagtgctt ttgcggcatt ttgcgacacc acgtggccat        60
ttgaggtata tatggccgag tgagcgagca ggatctccat tttgaccgcg aaatttgaac       120
gagcagcagc c                                                            131

<210> SEQ ID NO 17
<211> LENGTH: 180
<212> TYPE: DNA
<213> ORGANISM: adeno-associated virus 1
<220> FEATURE:
<221> NAME/KEY: misc_feature
<222> LOCATION: (1)..(180)
<223> OTHER INFORMATION: P40 Promoter of AAV1

<400> SEQUENCE: 17
ggtgacaaag caggaagtca aagagttctt ccgctgggcg caggatcacg tgaccgaggt        60
ggcgcatgag ttctacgtca gaaagggtgg agccaacaaa agacccgccc ccgatgacgc       120
ggataaaagc gagcccaagc gggcctgccc ctcagtcgcg gatccatcga cgtcagacgc       180

<210> SEQ ID NO 18
<211> LENGTH: 180
<212> TYPE: DNA
<213> ORGANISM: adeno-associated virus 2
<220> FEATURE:
<221> NAME/KEY: misc_feature
<222> LOCATION: (1)..(180)
<223> OTHER INFORMATION: P40 Promoter of AAV2

<400> SEQUENCE: 18
ggtcaccaag caggaagtca aagactttt ccggtgggca aaggatcacg tggttgaggt        60
ggagcatgaa ttctacgtca aaagggtgg agccaagaaa agacccgccc ccagtgacgc       120
agatataagt gagcccaaac gggtgcgcga gtcagttgcg cagccatcga cgtcagacgc       180

<210> SEQ ID NO 19
<211> LENGTH: 180
<212> TYPE: DNA
<213> ORGANISM: adeno-associated virus 3
<220> FEATURE:
<221> NAME/KEY: misc_feature
<222> LOCATION: (1)..(180)
```

<223> OTHER INFORMATION: P40 Promoter of AAV3

<400> SEQUENCE: 19

```
ggtcaccaaa caggaagtaa aggactttt ccggtgggct tccgatcacg tgactgacgt      60
ggctcatgag ttctacgtca gaaagggtgg agctaagaaa cgccccgcct ccaatgacgc     120
ggatgtaagc gagccaaaac gggagtgcac gtcacttgcg cagccgacaa cgtcagacgc    180
```

<210> SEQ ID NO 20
<211> LENGTH: 180
<212> TYPE: DNA
<213> ORGANISM: adeno-associated virus 4
<220> FEATURE:
<221> NAME/KEY: misc_feature
<222> LOCATION: (1)..(180)
<223> OTHER INFORMATION: P40 Promoter of AAV4

<400> SEQUENCE: 20

```
ggtcaccaag caggaagtca aagactttt ccggtgggcg tcagatcacg tgaccgaggt      60
gactcacgag ttttacgtca gaaagggtgg agctagaaag aggcccgccc ccaatgacgc    120
agatataagt gagcccaagc gggcctgtcc gtcagttgcg cagccatcga cgtcagacgc    180
```

<210> SEQ ID NO 21
<211> LENGTH: 227
<212> TYPE: DNA
<213> ORGANISM: adeno-associated virus 5
<220> FEATURE:
<221> NAME/KEY: misc_feature
<222> LOCATION: (1)..(227)
<223> OTHER INFORMATION: P40 Promoter of AAV5

<400> SEQUENCE: 21

```
gattactaag caggaagtca aggactttt tgcttgggca aaggtcaatc aggtgccggt      60
gactcacgag tttaaagttc cagggaatt ggcgggaact aaaggggcgg agaaatctct    120
aaaacgccca ctgggtgacg tcaccaatac tagctataaa agtctggaga agcgggcctg    180
gagcatgagg ctctcatttg ttcccgagac gcctcgcagt tcagacg                  227
```

<210> SEQ ID NO 22
<211> LENGTH: 180
<212> TYPE: DNA
<213> ORGANISM: adeno-associated virus 6
<220> FEATURE:
<221> NAME/KEY: misc_feature
<222> LOCATION: (1)..(180)
<223> OTHER INFORMATION: P40 Promoter of AAV6

<400> SEQUENCE: 22

```
ggtgacaaag caggaagtca aagagttctt ccgctgggcg caggatcacg tgaccgaggt      60
ggcgcatgag ttctacgtca gaaagggtgg agccaacaag agacccgccc ccgatgacgc    120
ggataaaagc gagcccaagc gggcctgccc ctcagtcgcg gatccatcga cgtcagacgc    180
```

<210> SEQ ID NO 23
<211> LENGTH: 180
<212> TYPE: DNA
<213> ORGANISM: adeno-associated virus 7
<220> FEATURE:
<221> NAME/KEY: misc_feature
<222> LOCATION: (1)..(180)
<223> OTHER INFORMATION: P40 Promoter of AAV7

<400> SEQUENCE: 23

```
ggtgacgaag caggaagtca aagagttctt ccgctgggcc agtgatcacg tgaccgaggt      60
```

```
ggcgcatgag ttctacgtca gaaagggcgg agccagcaaa agacccgccc ccgatgacgc      120
ggatataagc gagcccaagc gggcctgccc ctcagtcgcg gatccatcga cgtcagacgc      180

<210> SEQ ID NO 24
<211> LENGTH: 180
<212> TYPE: DNA
<213> ORGANISM: adeno-associated virus 8
<220> FEATURE:
<221> NAME/KEY: misc_feature
<222> LOCATION: (1)..(180)
<223> OTHER INFORMATION: P40 Promoter of AAV8

<400> SEQUENCE: 24
ggtgacaaag caggaagtca aagagttctt ccgctgggcc agtgatcacg tgaccgaggt       60
ggcgcatgag ttttacgtca gaaagggcgg agccagcaaa agacccgccc ccgatgacgc      120
ggataaaagc gagcccaagc gggcctgccc ctcagtcgcg gatccatcga cgtcagacgc      180
```